United States Patent
Liu et al.

(10) Patent No.: US 12,195,495 B2
(45) Date of Patent: *Jan. 14, 2025

(54) NUCLEOSIDE ANALOGUE, PREPARATION METHOD AND APPLICATION

(71) Applicant: GENEMIND BIOSCIENCES COMPANY LIMITED, Shenzhen (CN)

(72) Inventors: Bin Liu, Shenzhen (CN); Luyang Zhao, Shenzhen (CN); Yuxiang Chen, Shenzhen (CN); Bo Yang, Shenzhen (CN); Jie Jian, Shenzhen (CN); Fang Chen, Shenzhen (CN); Qin Yan, Shenzhen (CN)

(73) Assignee: GeneMind Biosciences Co., Ltd., Shenzhen (CN)

( * ) Notice: Subject to any disclaimer, the term of this patent is extended or adjusted under 35 U.S.C. 154(b) by 0 days.

This patent is subject to a terminal disclaimer.

(21) Appl. No.: 17/964,696

(22) Filed: Oct. 12, 2022

(65) Prior Publication Data

US 2023/0114671 A1 Apr. 13, 2023

Related U.S. Application Data

(63) Continuation of application No. 16/882,849, filed on May 26, 2020, now Pat. No. 11,512,106, which is a continuation of application No. PCT/CN2018/118259, filed on Nov. 29, 2018.

(30) Foreign Application Priority Data

Nov. 30, 2017 (CN) .......................... 201711239701.0

(51) Int. Cl.
| | |
|---|---|
| *C07H 19/06* | (2006.01) |
| *C07H 19/16* | (2006.01) |
| *C12Q 1/68* | (2018.01) |
| *C12Q 1/6869* | (2018.01) |

(52) U.S. Cl.
CPC ............. *C07H 19/06* (2013.01); *C07H 19/16* (2013.01); *C12Q 1/6869* (2013.01)

(58) Field of Classification Search
CPC ....... C07H 19/06; C07H 19/16; C12Q 1/6869
See application file for complete search history.

(56) References Cited

U.S. PATENT DOCUMENTS

| | | | |
|---|---|---|---|
| 7,566,537 B2 | 7/2009 | Balasubramanian et al. | |
| 9,163,053 B2 * | 10/2015 | Siddiqi | ................ C12Q 1/6876 |
| 11,512,106 B2 * | 11/2022 | Liu | ......................... C07H 19/10 |
| 2009/0061437 A1 | 3/2009 | Efcavitch et al. | |
| 2017/0130051 A1 | 5/2017 | Marma et al. | |

FOREIGN PATENT DOCUMENTS

| | | |
|---|---|---|
| WO | 2007062160 A2 | 5/2007 |
| WO | 2008137661 A1 | 11/2008 |
| WO | 2008144315 A1 | 11/2008 |
| WO | 2008144544 A1 | 11/2008 |
| WO | 2009124254 A1 | 10/2009 |
| WO | 2017058953 A1 | 4/2017 |
| WO | 2017087887 A1 | 5/2017 |
| WO | 2018121587 A1 | 7/2018 |

OTHER PUBLICATIONS

Supplementary European Search Report in related EP18884565.5, dated Mar. 10, 2022, 10 pages.
Jon P. Anderson et al, Incorporation of reporter-labeled nucleotides by DNA polymerases, Bio Techniques 38:257-264 Feb. 2005).

* cited by examiner

*Primary Examiner* — Jezia Riley
(74) *Attorney, Agent, or Firm* — Kagan Binder, PLLC

(57) ABSTRACT

The present invention relates to a nucleoside analog having the structure of the following formula, a method for preparing the nucleoside analog, and an application of the nucleoside analog in nucleic acid sequencing, etc.

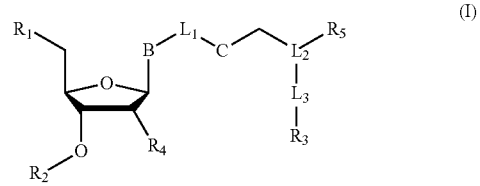

wherein $L_1$, $L_2$, and $L_3$ are each independently a covalent bond or a covalently linked group; B is a base or a base derivative; $R_1$ is —OH or a phosphate group; $R_2$ is H or a cleavable group; $R_3$ is a detectable group or a targeting group; $R_5$ is a polymerase reaction inhibitory group; $R_4$ is H or —OR$_6$, wherein $R_6$ is H or a cleavable group; and C is a cleavable group or a cleavable bond.

16 Claims, 6 Drawing Sheets four-color fluorescently labeled nucleic acids

NUCLEOSIDE ANALOGUE, PREPARATION METHOD AND APPLICATION

CROSS-REFERENCE TO RELATED APPLICATION

This application is a Continuation of Ser. No. 16/882,849, filed May 26, 2020, and titled "NUCLEOSIDE ANALOG, PREPARATION METHOD AND APPLICATION", which in turn claims priority to International Application No. PCT/CN2018/118259, filed Nov. 29, 2018, and titled "NUCLEOSIDE ANALOG, PREPARATION METHOD AND APPLICATION", which in turn claims priority from Chinese Application having serial number 201711239701.0, filed on Nov. 30, 2017, all of which are incorporated herein by reference in their entireties.

FIELD

The present disclosure relates to compounds, and more particularly to nucleoside analogs, the preparation method and application thereof.

BACKGROUND

DNA sequencing is a basic means of biological and pharmaceutical research. Nucleic acid sequencing may be carried out by techniques like sequencing-by-synthesis (SBS) or sequencing-by-ligation (SBL).

Today's SBS nucleic acid sequencing platforms on the market, including the second- and third-generation sequencing platforms, mostly use an DNA polymerase to bind nucleotide analogs to a template based on the base complementary pairing principle (base extension), and then detect signals from the nucleotide analogs bound to the template or detect changes in physical and chemical signals caused by the binding of the nucleotide analogs to the template to realize the nucleic acid sequencing.

Therefore, how to obtain nucleotide analogs that have stable structures and high reaction efficiency, may generate stable detectable signals, as well as may effectively inhibit the binding of the next nucleotide to the template has been a problem to be solved or improved.

SUMMARY

In a first aspect of the present disclosure, there is provided a nucleoside or nucleotide analog compound, having a structural formula (I):

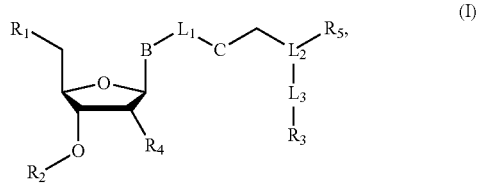

wherein $L_1$, $L_2$, and $L_3$ are each independently a covalent bond or a covalently linked group; B is a base or a base derivative; $R_1$ is —OH or a phosphate group; $R_2$ is H or a cleavable group; $R_3$ is a detectable group or a targeting group; $R_5$ is a polymerase reaction inhibitory group; $R_4$ is H or —$OR_6$, wherein $R_6$ is H or a cleavable group; and C is a cleavable group or a cleavable bond.

It is found through experimental tests that when applied in a sequencing process, the above compound (also called as nucleotide with a reversible termination group and a detectable label or nucleotide analog) is linked to a 3' end of a newly synthesized strand (complementary to the template strand) under the reaction of an enzyme to pair with a base of the template in each cycle of sequencing. Moreover, such nucleotide analog bears an inhibitory group or a related structure, which may prevent the next base, nucleotide or nucleotide analog from binding to the template strand, thereby preventing multiple base pairing from occurring on the same one template strand in a single reaction of a single cycle. Therefore, the above compound may be effectively used in the nucleic acid sequencing and applicable to a variety of sequencing platforms, including but not limited to, HiSeq/MiSeq/NextSeq/NovaSeq platforms of Illumina, BGISEQ50/500 of BGI and Sequel platform of PacBio.

Generally, when using a compound which bears a fluorescent molecule as a detectable group/label for the base extension and/or polymerase chain reaction (PCR) and/or sequencing, for a sequencing platform which uses an imaging system to acquire signals, such as to acquire images of an extension product, the appearance of the fluorescent molecule/extension product/template-primer complex on the image is a spot. Therefore, any factors that affect the luminescence behavior of the fluorescent molecule will directly affect the application results of the compound.

In designing the structure of the above compound, the inventors found that, with respect to the intramolecular quenching caused by the influence of the reduction potential of a base in a dNTP on the luminescence behavior of a fluorescent molecule in the same one dNTP, the farther the distance between the base and the fluorescent dye of the compound is, the less the intramolecular quenching occurs; while with respect to the intermolecular quenching caused by the influence of a dNTP or nucleic acid stand on a fluorescent molecule of another dNTP, it is mainly related to a degree of freedom of the dNTP, which is mainly determined by the stiffness and flexibility as well as the length of a linker between the base and the fluorescent molecule in the dNTP. In general, the shorter the linker, the stronger the rigidity and the lower the degree of freedom, and the less the intermolecular quenching occurs.

As both the intramolecular quenching and the intermolecular quenching are considered and verified, the compound of the above structure designed by the inventors is particularly suitable for SBS platforms.

In a second aspect of the present disclosure, there is provided a dNTP analog. According to embodiments of the present disclosure, the dNTP analog includes at least one selected from a group including: a dATP analog, being the compound having the structural formula (I) as described above, where B is a base A; a dCTP analog, being the compound having the structural formula (I) as described above, where B is a base C; a dGTP analog, being the compound having the structural formula (I) as described above, where B is a base G; and a dTTP analog, being the compound having the structural formula (I) as described above, where B is a base T.

In some embodiments, the dNTP analog includes one, two, three or all four of the dATP analog, the dCTP analog, the dGTP analog and the dTTP analog.

In a third aspect of the present disclosure, there is provided an NIT analog. According to embodiments of the present disclosure, the NIT analog includes at least one selected from a group including: an ATP analog, being the compound having the structural formula (I) as described above, where B is a base A; a CTP analog, being the compound having the structural formula (I) as described above, where B is a base C; a GTP analog, being the compound having the structural formula (I) as described above, where B is a base G; and a UTP analog, being the compound having the structural formula (I) as described above, where B is a base U.

In some embodiments, the NIT analog includes one, two, three or all four of the ATP analog, the CTP analog, the GTP analog and the UTP analog.

In a fourth aspect of the present disclosure, there is provided a dNTP analog mixture. According to embodiments of the present disclosure, the dNTP analog mixture includes: a dATP analog, being the compound having the structural formula (I) as described above, where B is a base A; a dCTP analog, being the compound having the structural formula (I) as described above, where B is a base C; a dGTP analog, being the compound having the structural formula (I) as described above, where B is a base G; and a dTTP analog, being the compound having the structural formula (I) as described above, where B is a base T, and at least three of the dATP analog, the dCTP analog, the dGTP analog and the dTTP analog each have a different detectable group or targeting group from each other.

In a fifth aspect of the present disclosure, there is provided a dNTP analog mixture. According to embodiments of the present disclosure, the dNTP analog mixture includes a combination of any two nucleotide analogs selected from a group including: a dATP analog, being the compound having the structural formula (I) as described above, where B is a base A; a dCTP analog, being the compound having the structural formula (I) as described above, where B is a base C; a dGTP analog, being the compound having the structural formula (I) as described above, where B is a base G; and a dTTP analog, being the compound having the structural formula (I) as described above, where B is a base T, wherein the two nucleotide analogs in the combination each have a different detectable group or targeting group from each other.

In a sixth aspect of the present disclosure, there is provided an NTP analog mixture. According to embodiments of the present disclosure, the NTP analog mixture includes: an ATP analog, being the compound having the structural formula (I) as described above, where B is a base A; a CTP analog, being the compound having the structural formula (I) as described above, where B is a base C; a GTP analog, being the compound having the structural formula (I) as described above, where B is a base G; and a UTP analog, being the compound having the structural formula (I) as described above, where B is a base U, wherein three of the ATP analog, the CTP analog, the GTP analog and the UTP analog each have a different detectable group or targeting group from each other.

In a seventh aspect of the present disclosure, there is provided an NTP analog mixture. According to embodiments of the present disclosure, the NTP analog mixture includes a combination of any two nucleotide analogs selected from a group including: an ATP analog, being the compound having the structural formula (I) as described above, where B is a base A; a CTP analog, being the compound having the structural formula (I) as described above, where B is a base C; a GTP analog, being the compound having the structural formula (I) as described above, where B is a base G; and a UTP analog, being the compound having the structural formula (I) as described above, where B is a base U, wherein the two nucleotide analogs in the combination each have a different detectable group from each other.

In an eighth aspect of the present disclosure, there is provided use of the dNTP analog, the NIT analog, the dNTP analog mixture or the NIT analog mixture as described in any embodiment hereinbefore in nucleic acid sequencing, a controlled polymerase chain reaction or a base extension reaction.

In a ninth aspect of the present disclosure, there is provided a kit for nucleic acid sequencing or a controlled polymerase chain reaction. According to embodiments of the present disclosure, the kit includes: the dNTP analog, the NIT analog, the dNTP analog mixture or the NTP analog mixture as described in any embodiment hereinbefore. The kit may be used for DNA and/or RNA sequencing.

In a tenth aspect of the present disclosure, there is provided a nucleic acid sequencing method. According to embodiments of the present disclosure, the method includes: (a) placing a mixture of a first template-primer complex, one or more nucleotide analogs and a DNA polymerase under a condition suitable for base extension to enable the nucleotide analog to bind to the first template-primer complex, obtaining an extension product; and the nucleotide analog is selected from the dNTP analog, the NTP analog, the dNTP analog mixture and the NTP analog mixture as described in any embodiment hereinbefore. By using the nucleotide analogs with the above structural characteristics, this method can effectively convert biochemical changes into stable photoelectric signals and acquire them, so as to realize the effective and accurate determination of base sequence of the template.

In an eleventh aspect of the present disclosure, there is provided a primer extending method. According to embodiments of the present disclosure, the primer extending method includes: placing a polymerase, a template-primer complex and one or more nucleotide analogs into a reactor to enable the nucleotide analog to bind to the template-primer complex, obtaining an extension product, wherein the nucleotide analog is selected from any compound having the structural formula (I) as described above. With the method, the primer can be extended effectively and accurately.

In a twelfth aspect of the present disclosure, there is provided a reaction mixture. According to embodiments of the present disclosure, the reaction mixture includes: a template to be tested; a primer paired with at least a part of a strand of the template to be tested; a DNA polymerase; and the dNTP analog, the NTP analog, the dNTP analog mixture or the NTP analog mixture as described in any embodiment hereinbefore.

In a thirteenth aspect of the present disclosure, there is provided a method for preparing the compound having the structural formula (I) as described in any above embodiment. According to embodiments of the present disclosure, the method includes:

synthesizing N-succinimidyl-3-(2-pyridyldithiol) propionate (SPDP) using dithiodipyridine and mercaptopropionic acid; synthesizing a first linker using (10-1)

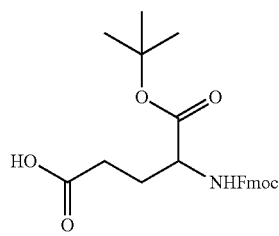

and ethyl chloroformate, the first linker being (10-7)

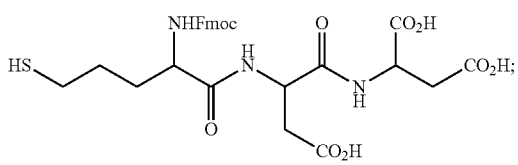

connecting a dNTP to the SPDP to obtain dNTP-SPDP; and synthesizing the target compound using the first linker and the dNTP-SPDP.

In a fourteenth aspect of the present disclosure, there is provided a method for preparing the compound having the structural formula (I) as described in any above embodiment. According to embodiments of the present disclosure, the method includes: synthesizing dNTP-MPSSK having a following structure:

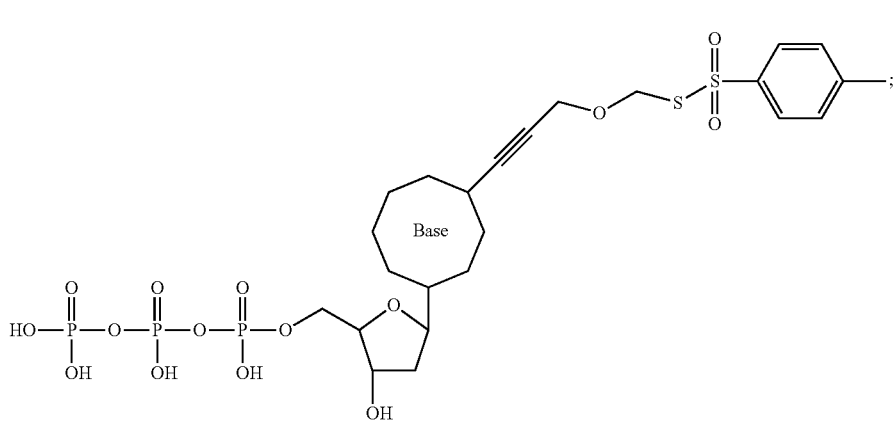

synthesizing a second linker using (31-4)

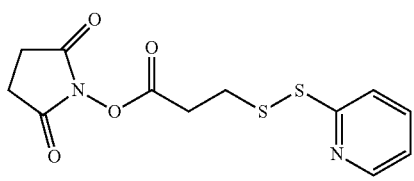

and a hexapeptide, the second linker being (11-10)

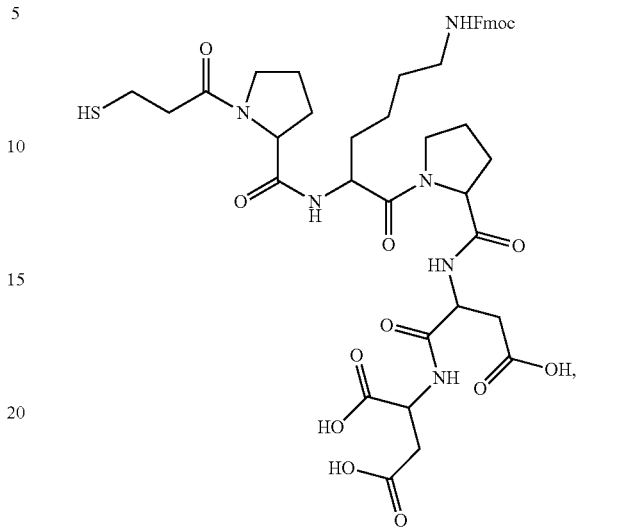

and the hexapeptide being H-Pro-Lys(Fmoc)-Pro-Asp-Asp-OH; and mixing the second linker and the dNTP-MPSSK to obtain the compound.

DETAILED DESCRIPTION

Figure 1:
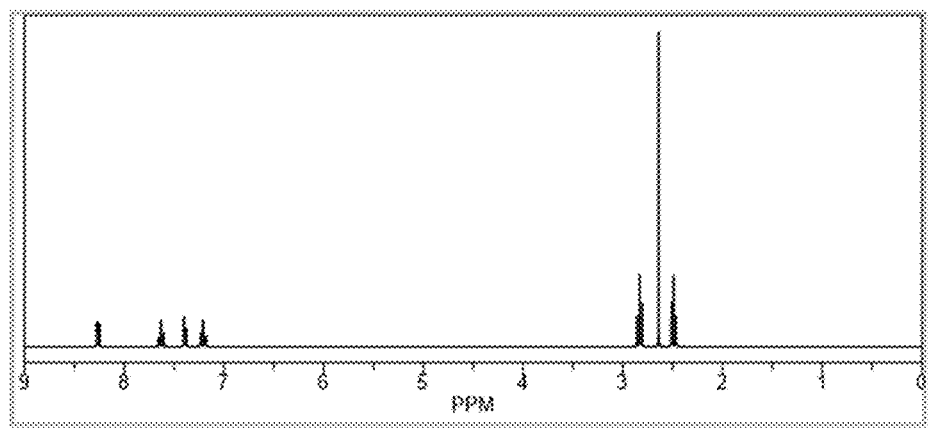
FIG. 1 is an NMR spectrum of SPDP according to an embodiment of the present disclosure.

Reference will be made in detail to embodiments of the present disclosure, examples of which are illustrated in the accompanying drawings. The embodiments described herein with reference to drawings are explanatory, illustrative, and used to generally understand the present disclosure, and shall not be construed to limit the present disclosure.

Unless specified otherwise, reagents, detecting instruments and the like used in the embodiments may be formulated or prepared by those skilled in the art or are commercially available.

Unless specified otherwise, terms "Base" and "B" used herein are equivalent and refer to nucleobase(s), including adenine (A), thymine (T), cytosine (C), guanine (G), uracil (U), and derivatives thereof.

The term "controlled polymerase chain reaction" refers to a polymerase chain reaction that may be controlled to proceed continuously or discontinuously, such as a nucleic acid sequencing based on the SBS principle.

Unless specified otherwise, all scientific and technological terms used herein have the same meaning as commonly understood by those skilled in the art. All patents and publications involved are incorporated herein by reference in their entirety. In the case where one or more of the combined scientific and technological literatures, patent literatures, and similar materials are different from or contradictory to the present disclosure (including but not limited to the defined terms, the term applications, the described technologies, etc.), the present disclosure shall prevail.

Unless specified otherwise, the following definitions shall be applied herein. Chemical elements are consistent with Periodic Table of Elements in CAS version and Handbook of Chemistry and Physics, 75$^{th}$ edition, 1994. Further, general principles of organic chemistry may refer to the descriptions in "Organic Chemistry, Thomas Sorrell, University Science Books, Sausalito: 1999" and "March's Advanced Organic Chemistry by Michael B. Smith and Jerry March, John Wiley & Sons, New York: 2007", the entire contents of which are incorporated herein by reference.

Unless specified otherwise or there is a clear conflict in context, terms "a", "an", and "the" used herein are intended to include plural forms, such as including "at least one" or "one or more" of the indicated elements.

It should be understood that, terms "optionally substituted" and "substituted or unsubstituted" are used interchangeably. In general, the term "substituted" means that one or more hydrogen atoms in a given structure are substituted by a particular substituent. Unless specified otherwise, the term "an optionally substituted group" means that the group may be substituted at any substitutable position thereof. When more than one position of a given structural formula can be substituted by one or more substituents selected from specific groups, the given structural formula may be substituted by the same or different substituents at individual positions.

In the present disclosure, the expressions such as "each of . . . independently", " . . . each independently" and "independently" are interchangeable, and should be understood broadly, which not only means that in different groups, the specific options expressed by the same symbol do not affect each other, but also means that in a same one group, the specific options expressed by the same symbol do not affect each other.

Herein, the substituents of a compound are described in accordance with types and/or ranges of groups, including each independent sub-combination of individual members in these types and/or ranges of groups. For example, the term "$C_{1-6}$ alkyl" specifically refers to independently disclosed methyl, ethyl, $C_3$ alkyl, $C_4$ alkyl, $C_5$ alkyl and $C_6$ alkyl.

Regarding a linking substituent, it should be understood that, when the structure clearly includes a linking group, Markush variables listed for that substituent should be understood as a linking group. For example, if the structure includes a linking group, and Markush variables defined with respect to the group includes "alkyl" or "aryl", the "alkyl" and "aryl" should be understood as an alkylene group or an arylene group, respectively.

The term "alkyl" or "alkyl group" as used herein refers to a saturated linear or branched monovalent hydrocarbyl group containing 1 to 20 carbon atoms, wherein the alkyl group may be optionally substituted by one or more substituents described in the present disclosure. Unless specified otherwise, the alkyl group contains 1 to 20 carbon atoms. In an embodiment, the alkyl group contains 1 to 12 carbon atoms. In another embodiment, the alkyl group contains 1 to 6 carbon atoms. In yet another embodiment, the alkyl group contains 1 to 4 carbon atoms. In yet another embodiment, the alkyl group contains 1 to 3 carbon atoms.

The term "alkyl" per se or as a part of a substituent refers to, unless specified otherwise, a straight (i.e., unbranched) or branched carbon (C) chain, which may be fully saturated, mono- or poly-unsaturated and include mono-, di- and multivalent radicals of a specified number of carbon atoms. Here, a saturated group includes, but is not limited to, methyl, ethyl, n-propyl, iso-propyl, n-butyl, tert-butyl, iso-butyl, (cyclohexyl) methyl, n-pentyl or its isomers, n-hexyl or its isomers, n-heptyl or its isomers, n-octyl or its isomers. Herein, an unsaturated group includes, but is not limited to, vinyl, 2-propenyl, crotyl, 2-isopentenyl, 2-(butadienyl), 2,3-pentadienyl, 3-(1,4-pentadienyl), pentenyl, 1-propynyl, and 3-propynyl.

The term "alkylene" per se or as a part of a substituent refer to a group derived from an alkyl and an unsaturated alkyl, and includes, but is not limited to, unsaturated alkyl derivatives of $C_{1-24}$ carbon chains, preferably $C_{1-10}$ carbon chains, such as —$CH_2CH_2CH_2CH_2$—.

The term "heteroalkyl" per se or as a part of a substituent refers to a straight or branched chain containing at least one carbon atom and at least one heteroatom like O, N, P, Si and S, preferably N and S. Here, heteroalkyl is not a cyclic group. Examples of heteroalkyl include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —S(O)—$CH_3$, —$CH_2$—$CH_2$—S(O)—$CH_3$, —CH=CH—N($CH_3$), —O—$CH_3$, —O—$CH_2$—$CH_3$, and —CN. For a group containing 2 heteroatoms, examples include —$CH_2$—NH—$OCH_3$ and —$CH_3$—O—$Si(CH_3)_3$. Herein, heteroalkyl also includes a group bearing a double or triple bond.

The term "heteroalkylene" per se or as a part of a substituent refers to a group derived from an alkyl and an unsaturated alkyl, examples of which include, but are not limited to, unsaturated derivatives of —$CH_2$—$CH_2$—S—$CH_2$—$CH_2$— and —$CH_2$—S—$CH_2$—$CH_2$—NH—$CH_2$—. The heteroatom in the heteroalkylene may occupy either or both of the chain termini, such as alkyleneoxy, alkylenedioxy, alkyleneamino, alkylenediamino.

The terms "cycloalkyl" and "heterocycloalkyl", by themselves or as a part of a substituent refer to cyclic versions of alkyl and heteroalkyl, respectively, but not refer to amyl herein. Examples of cycloalkyl include, but are not limited to, cyclopropyl, cyclobutyl, cyclopentyl, cyclohexyl, 1-cyclohexenyl, 3-cyclohexenyl, and cycloheptyl. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, 2-tetrahydrofuranyl, 3-tetrahydrofuranyl, etc.

The term "acyl" refers to —C(O)R, where R is a optionally substituent, and may be alkyl, cycloalkyl, heteroalkyl, and the like.

The term "aromatic group" refer to an unsaturated group, such as aryl, etc. The term "heteroaryl" refers to aryl groups (or rings) containing at least a heteroatom, such as O, N, P, Si or S. Examples of the heteroaryl include, but are not limited to, phenyl, naphthyl, imidazolyl, pyrimidinyl, and the like.

The terms "detectable label" or "detectable group" refer to a group/moiety/agent/compound that can specifically release a signal or can be specifically recognized, such as a fluorescent dye or a detectable dye. In some examples, a) A, T, G and C are labeled with ROX, Alexa532, Cy5 and IF700 dyes, respectively; b) A, T, G and C are each labeled with Cy5 dye, and distinguished from each other based on different adding time/orders.

The term "polymerase" refers to any natural or non-naturally occurring enzyme or other catalyst that is capable of catalyzing a polymerization reaction. In some examples, the polymerase is 9° N polymerase or variants thereof, E. coli DNA polymerase I, Bacteriophage T4 DNA polymerase, Sequenas enzyme, Taq DNA polymerase, Bacillus stearothermophilus DNA polymerase, Bst 2.0 DNA polymerase, phi29 DNA polymerase, or T7 DNA polymerase.

Terms "nucleotide" and "nucleotide analog" refer to a nucleoside-5'-polyphosphate compound or a related analog thereof, in which the base of the nucleotide includes A, T, G, C, U or respective analogs thereof, and the number of phosphate contained therein is 2, 3, 4, 5, 6, 7, 8 or more. The nucleotide may be modified at the base and/or phosphate moiety. In some examples, an application method of the nucleotide analogs is as follows: the nucleotide analogs bear an inhibitory group capable of virtually blocking the 3' end of a base, and are fluorescently labeled, which are applied to the second- or third-generation (single molecule) SBS, and the four fluorescent bases (A, T, G, C) are labeled with a same fluorescent group ATTO647N, which are added in four repetitions.

Compounds and Combination Thereof.

In some embodiments, there is provided a nucleoside or nucleotide analog compound, having a structural formula (I):

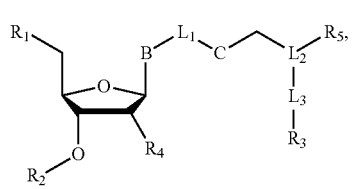
(I)

wherein $L_1$, $L_2$, and $L_3$ are each independently a covalent bond or a covalently linked group; B is a base or a base derivative; $R_1$ is —OH or a phosphate group; $R_2$ is H or a cleavable group; $R_3$ is a detectable group or a targeting group; $R_5$ is a polymerase reaction inhibitory group; $R_4$ is H, $NH_2$, or —$OR_6$, wherein $R_6$ is H or a cleavable group; and C is a cleavable group or a cleavable bond.

The so-called "targeting group" includes a group/moiety/structure/compound capable of reacting with a specific group or compound, thereby providing a detectable signal. The related reaction includes a coupling, specific binding and/or click chemistry reaction, etc. For example, the targeting group may be a biotinyl, which is capable of combining with a detectable group bearing streptavidin (streptomycin, SA); alternatively, the targeting group may be azide, which may react with a detectable group bearing DBCO (e.g., DBCO-fluorescent dye) through click chemistry, thereby providing a detectable signal to indicate whether the reaction at a specific site is realized, such as a nucleic acid sequencing reaction.

It is found through experimental tests that when applied in a sequencing process, the above compound (also called as nucleotide with a reversible termination group and a detectable label or nucleotide analog) is linked to a 3' end of a newly synthesized strand (complementary to the template strand) under the reaction of an enzyme to pair with a base of the template in each cycle of sequencing. Moreover, such nucleotide analog bears an inhibitory group or a related structure, which may prevent the next base, nucleotide or nucleotide analog from binding to the template strand, thereby preventing multiple bases pairing from occurring on the same one template strand in a single reaction of a single cycle. Therefore, the above compound may be effectively used in the nucleic acid sequencing.

The above nucleotide analog (i.e., the compound of formula (I)) is applicable to a variety of sequencing platforms, including, but not limited to, HiSeq/MiSeq/NextSeq/NovaSeq platforms of Illumina, BGISEQ50/500 of BGI and Sequel platform of PacBio.

According to some embodiments, C is a cleavable group, which comprises a trivalent radical having a structural formula (II) or a quadrivalent radical having a structural formula (III):

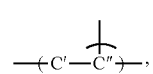
(II)

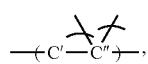
(III)

wherein C' is a bivalent radical comprising a disulfide bond and a carbon-oxygen bond, a disulfide bond, or a carbon-oxygen bond; and C" is an optionally substituted branched alkyl or an optionally substituted aryl. Tests show that nucleotide analog with such structure has a stronger stability and/or an increased spatial configuration, which could enhance the ability to bind to the enzyme, thus improving the reaction efficiency in sequencing.

According to some embodiments, the phosphate group is a monophosphate group, a biphosphate group, a triphosphate group or a polyphosphate group.

According to some embodiments, Bis cytosine, thymine, adenine, guanine, hypoxanthine, deazaadenine, deazaguanine, deazahypoxanthine, 7-methylguanine, 5,6-dihydrouracil, 5-methylcytosine or 5-hydroxymethylcytosine, or their respective derivatives.

According to some embodiments, B is divalent cytosine, divalent guanine, divalent adenine, divalent thymine, divalent uracil, divalent hypoxanthine, divalent xanthine, divalent deazaadenine, divalent deazaguanine, divalent deazahypoxanthine, divalent 7-methylguanine, divalent 5,6-dihydrouracil, divalent 5-methylcytosine or divalent 5-hydroxymethylcytosine, or their respective derivatives.

According to some embodiments, $R_6$ is H, an optionally substituted alkyl or amino.

According to some embodiments, $R_6$ is H or $C_{1-5}$ alkyl.

According to some embodiments, Reis at least one selected from a group including H,

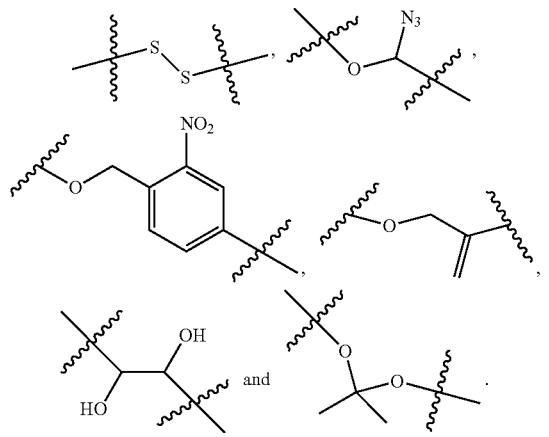

The "detectable group" (detectable agent) includes, but is not limited to, fluorescent or luminescent substances of Cy2 moiety, Cy3 moiety, Cy5 moiety, Cy7 moiety, Hoechst33258 moiety, Hoechst33342 moiety, Hoechst34580 moiety, PO-PRO-1 moiety, PO-PRO-1-DNA moiety, POPO-1 moiety, DAPI-DNA moiety, DAPI moiety, SYTO 45-DNA moiety, Alexa Fluor®350 moiety, Alexa Fluor) 450 moiety, Alexa Fluor® 430 moiety, Alexa Fluor® 488 moiety, Alexa Fluor® 532 moiety, Alexa Fluor® 546 moiety, Alexa Fluor® 555 moiety, Alexa Fluor® 568 moiety, Alexa Fluor® 594 moiety, Alexa Fluor® 610 moiety, Alexa Fluor) 633 moiety, Alexa Fluor® 635 moiety, Alexa Fluor) 635 moiety, Alexa Fluor) 647 moiety, Alexa Fluor® 660 moiety, Alexa Fluor) 680 moiety, Alexa Fluor® 700 moiety, Alexa Fluor® 750 moiety, Alexa Fluor® 790 moiety, APC (allophycocyanin), APC-Seta-750, AsRed2, ATTO390, ATTO425, ATTO430LS, ATTO465, ATTO488, ATTO490LS, ATTO495, ATTO514, ATTO520, ATTO532, ATTO550, ATTO565, ATTO590, ATTO594, ATTO645 and ATTO680.

In some examples, $R_3$ is a detectable group. In some examples, $R_3$ is a fluorescent dye. In some examples, $R_3$ is a targeting group. In some examples, $R_3$ is a reactive group of click chemistry. In some examples, $R_3$ is azido. In some examples, $R_3$ is biotinyl.

In some examples, $R_3$ is the fluorescent dye. In some examples, $R_3$ is Alexa Fluor350 moiety, Alexa Fluor®450 moiety, Alexa Fluor) 430 moiety, Alexa Fluor® 488 moiety, Alexa Fluor) 532 moiety, Alexa Fluor® 546 moiety, Alexa Fluor® 555 moiety, Alexa Fluor® 568 moiety, Alexa Fluor® 594 moiety, Alexa Fluor® 610 moiety, Alexa Fluor® 633 moiety, Alexa Fluor® 635 moiety, Alexa Fluor) 635 moiety, Alexa Fluor® 647 moiety, Alexa Fluor) 660 moiety, Alexa Fluor) 680 moiety, Alexa Fluor® 700 moiety, Alexa Fluor® 750 moiety, or Alexa. Fluor® 790 moiety.

In some examples, $R_3$ is FAM™ moiety, TET™ group, JOE™ group, VIC™ group, HEX™ group, NED™ group, PET® group, ROX™ group, TAMRA™ group, TET™ group, Texas Red® group, Rhodamine 6G (R6G) group, or Cy5 group.

In some examples, $R_3$ is

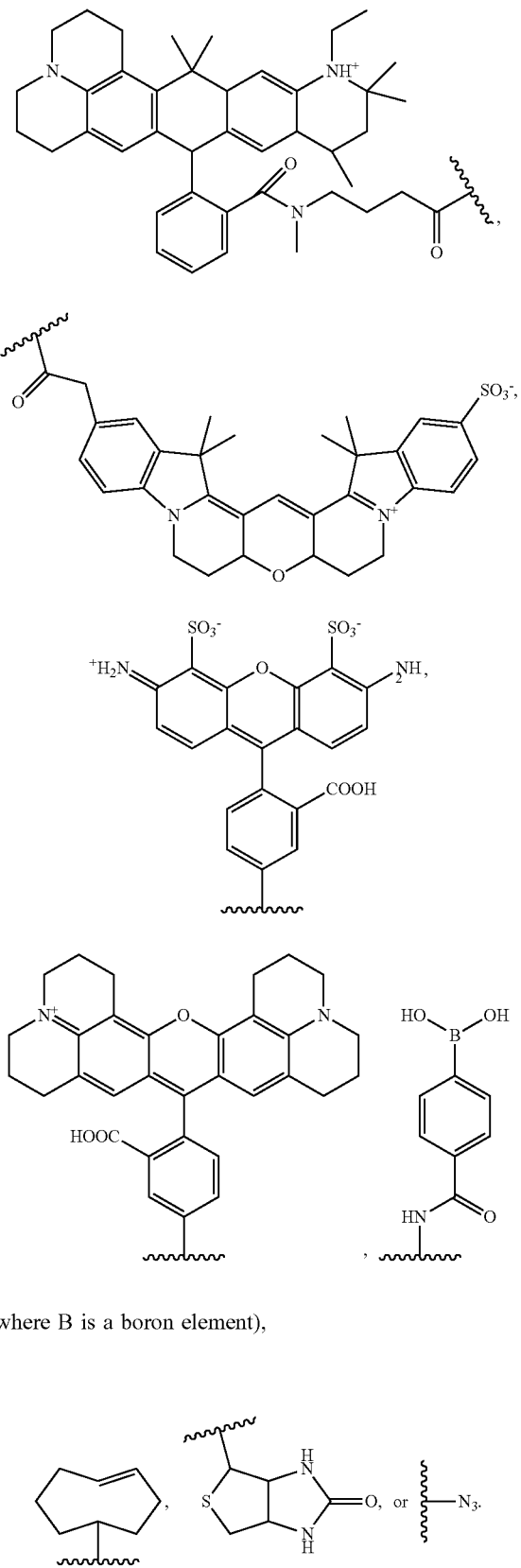

(where B is a boron element),

The following examples are detectable groups or compounds that can be or are easily bound (coupled or specifically bound) with the targeting group:
ROX-labeled dibenzocyclooctyne (DBCO)(ROX-DBCO or DBCO-ROX)
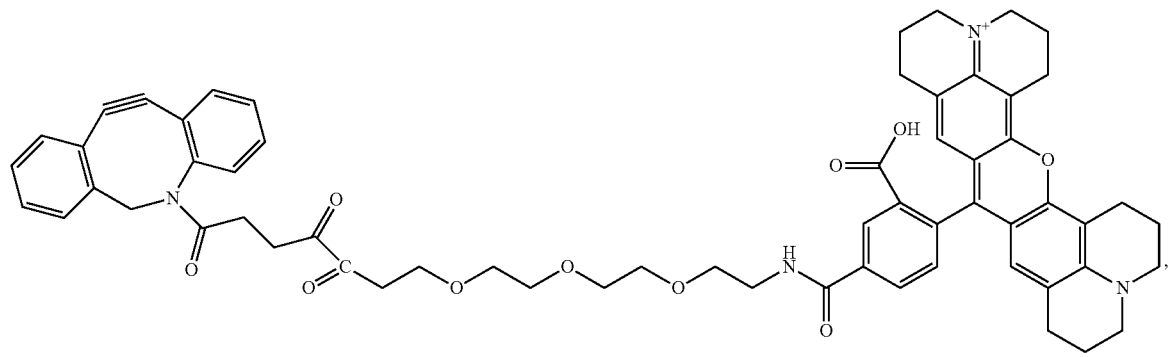 [SMILES: O=C(CCOCCOCCOCCNC(=O)c1ccc(C2=c3cc4c5c(c3Oc3c2cc2c6c3CCCN6CCC2)CCC[N+]=5CCC4)c(C(=O)O)c1)C(=O)CCC(=O)N1Cc2ccccc2C#Cc2ccccc21]
which, when bound with a dATP analog bearing azido as the targeting group, forms a structure as follows:
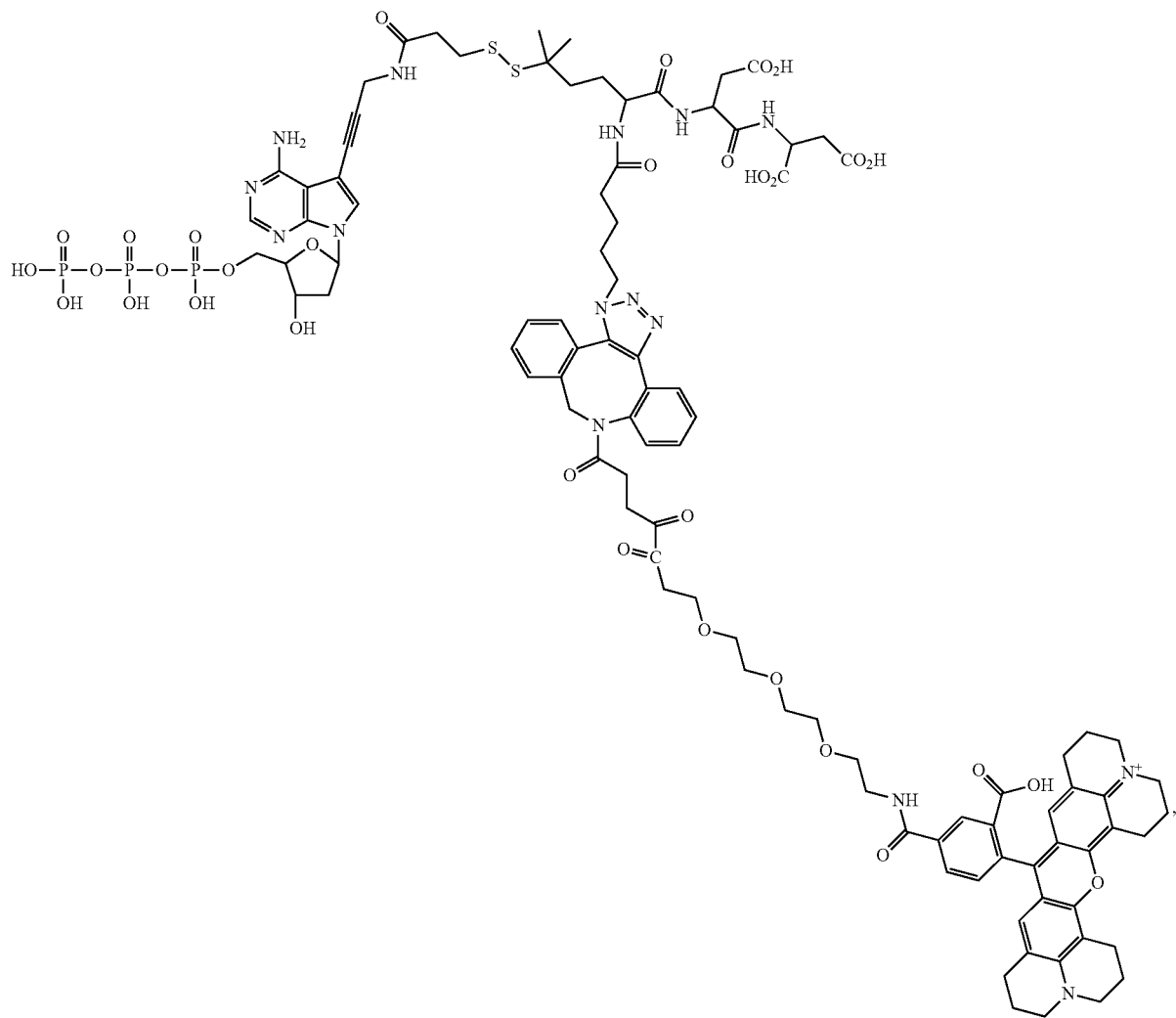 [SMILES: CC(C)(CCC(NC(=O)CCCCn1nnc2c1-c1ccccc1CN(C(=O)CCC(=O)C(=O)CCOCCOCCOCCNC(=O)c1ccc(C3=c4cc5c6c(c4Oc4c3cc3c7c4CCCN7CCC3)CCC[N+]=6CCC5)c(C(=O)O)c1)c1ccccc1-2)C(=O)NC(CC(=O)O)C(=O)NC(CC(=O)O)C(=O)O)SSCCC(=O)NCC#Cc1cn(C2CC(O)C(COP(=O)(O)OP(=O)(O)OP(=O)(O)O)O2)c2ncnc(N)c12]

ATTO Rho6G-labeled SHA(ATTO Rho6G-SHA or SHA-ATTO Rho6G)
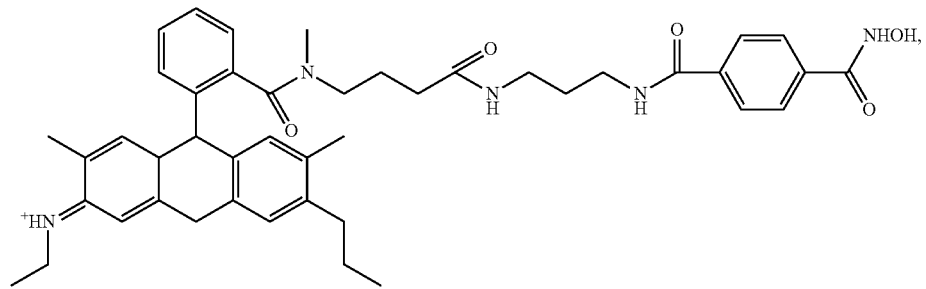
which, when bound with a dTTP analog, forms a structure as follows:
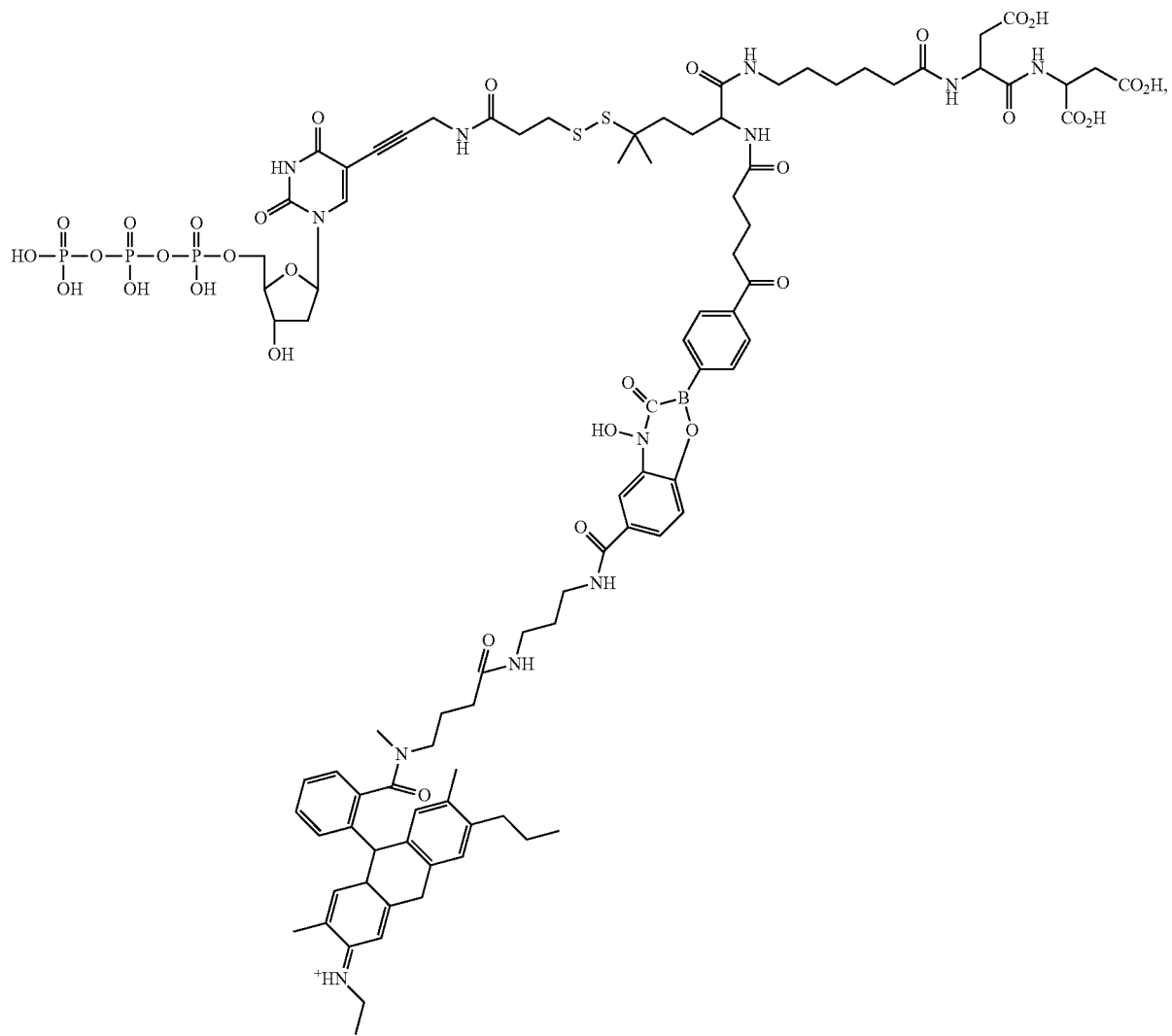 [SMILES: CCCc1cc2c(cc1C)C(c1ccccc1C(=O)N(C)CCCC(=O)NCCCNC(=O)c1ccc3c(c1)N(O)C(=O)B(c1ccc(C(=O)CCCC(=O)NC(CCC(C)(C)SSCCC(=O)NCC#Cc4cn(C5CC(O)C(COP(=O)(O)OP(=O)(O)OP(=O)(O)O)O5)c(=O)[nH]c4=O)C(=O)NCCCCCC(=O)NC(CC(=O)O)C(=O)NC(CC(=O)O)C(=O)O)cc1)O3)C1C=C(C)/C(=[NH+]/CC)C=C1C2]

ATTO647N-labeled tetrazine (ATTO647N-tetrazine or tetrazine-ATTO647N)
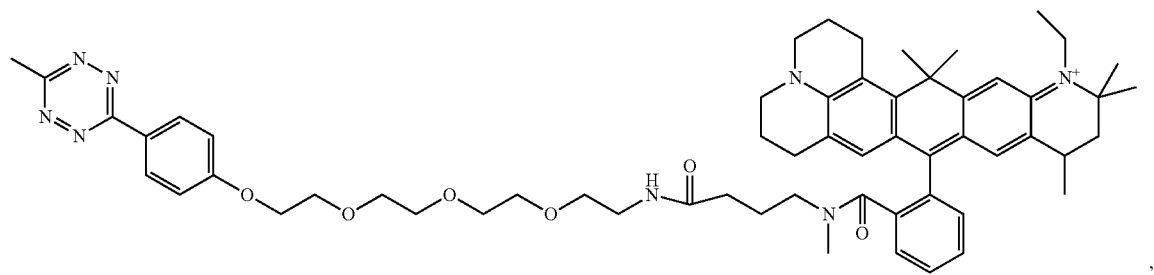
which, when bound with a dGTP analog, forms a structure as follows:
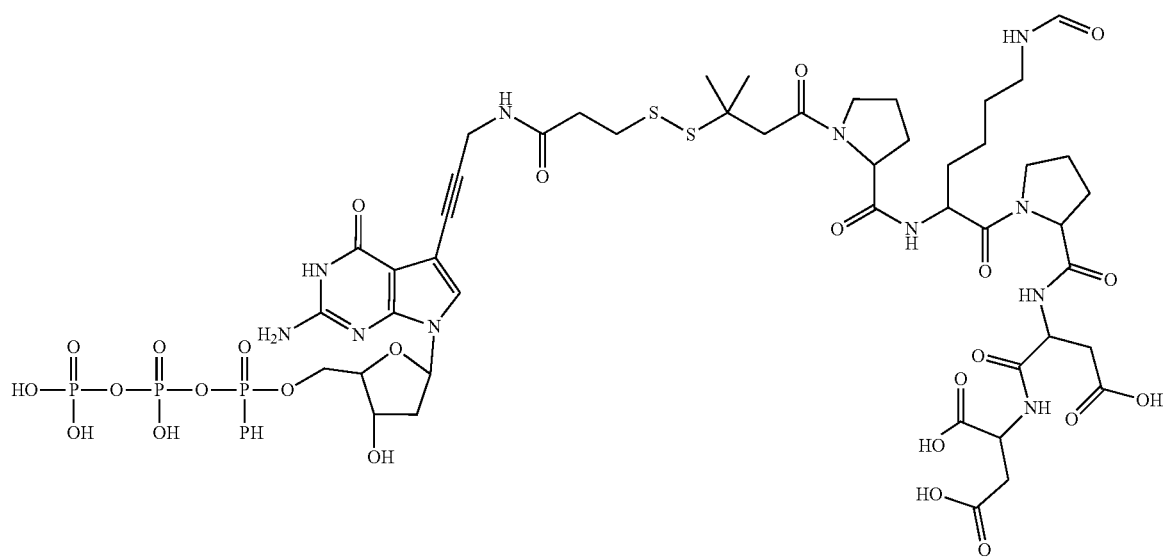

-continued

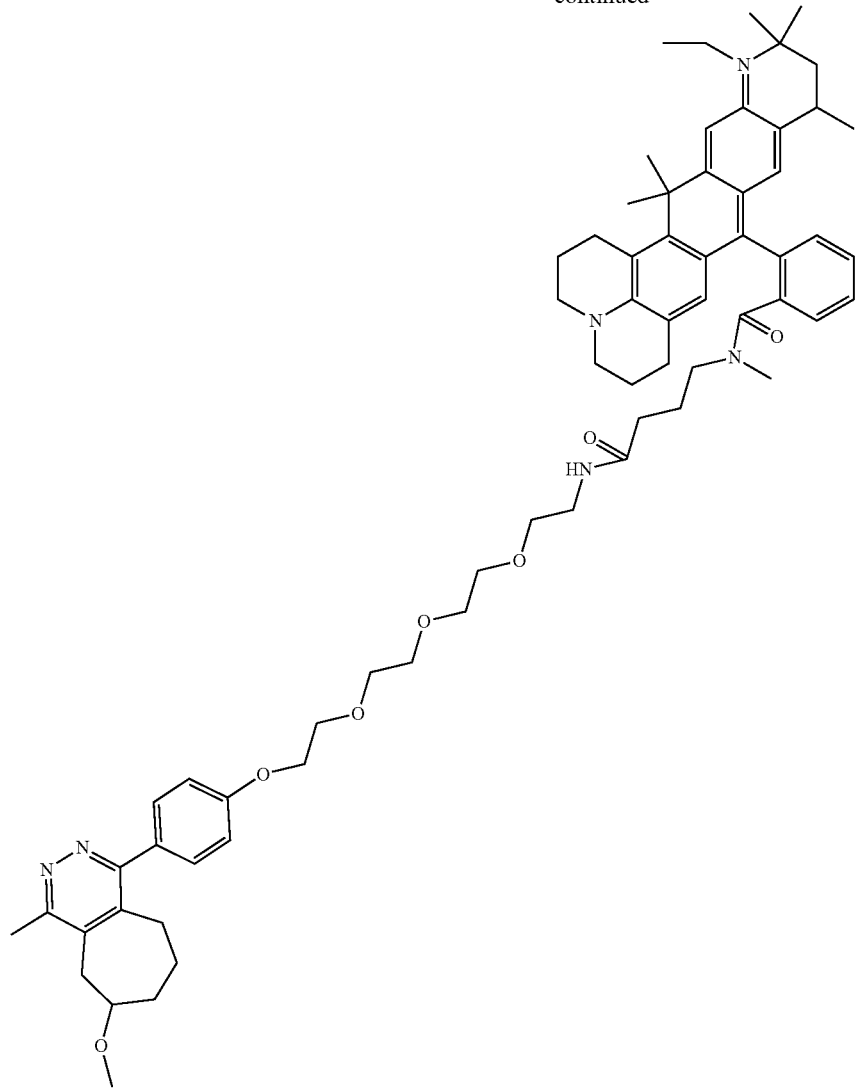

In some examples, $R_3$ is ATTO390 group, ATTO425 group, ATTO430LS group, ATTO465 group, ATTO 488 group, ATTO490LS group, ATTO495 group, ATTO514 group, ATTO520 group, ATTO532 group, ATTO550 group, ATTO565 group, ATTO590 group, ATTO594 group, ATTO610 group, ATTO620 group, ATTO633 group, ATTO635 group, ATTO647 group, ATTO647 group, ATTO647N group, ATTO655 group, ATTO665 group, ATTO700 group, ATTO725 group, ATTO740 group, ATTO680 group, ATTOOxa12 group, ATTORho3B group, ATTO Rho6G group, ATTO Rho11 group, ATTO Rho12 group, ATTO Rho13 group, ATTO Rho14 group, ATTO Rho101 group, or ATTO Thio12 group.

In some examples, $R_3$ is BO-PRO-1 group, BO-PRO-3 group, BOBO-1 group, BOBO-3 group, BODIPY630 650-X group, BODIPY650/665-X group, BODIPY FL group, BODIPYR6G group, BODIPY TMR-X group, BODIPY TR-X group, BODIPY TR-X pH7.0 group, BODIPYTR-X-phallacidin group, BODIPY-DiMe group, BODIPY-Phenyl group, BODIPY-TMSCC group, C3-Indocyanine group, C3-Oxacyanine group, C3-Thiacyanine-Dye (EtOH) group, C3-Thiacyanine-Dye (PrOH) group, C5-Indocyanine group, C5-Oxacyanine group, C5-Thiacyanine group, C7-Indocyanine group, C7-Oxacyanine group, C454T, C-Phycyanin group, Calcein group, Calcein-red-orange group, Calcium-Crimson group, Calcium Green-1 group, or Calcium Orange group.

In some examples, $R_3$ is CF450M group, CF405S group, CF488A group, CF543 group, CF555 group, CFP group, CFSE group, CF350 group, CF485 group, Chlorophyll-A group, Chlorophyll-B group, Chromeo488 group, Chromeo494 group, Chromeo505 group, Chromeo546 group, Chromeo642 group, Cryptolight CF1 group, Cryptolight CF2 group, Cryptolight CF3 group, Cryptolight CF4 group, Cryptolight CF5 group, Cryptolight CF6 group, Crystal Violet group, Cumarin153 group, Cy2 group, Cy3 group, Cy3.5 group, Cy3B group, Cy5ET group, Cy5 group, Cy5.5 group, Cy7 group, or DAPI group.

In some examples, $R_3$ is DsRed-Express group, DsRed-Express2 group, DsRed-Express T1 group, DY350XL group, DY-480 group, DY-480XL Megastokes group, DY485 group, DY485XL Megastokes group, DY490 group, DY490XL Megastokes group, DY-500 group, DY-500XL Megastokes group, DY-520 group, DY520 Megastokes group, DY-547 group, DY549P1 group, DY-554 group, DY-555 group, DY-557 group, DY-590 group, DY-615 group, DY-630 group, DY-631 group, DY-633 group, DY-635 group, DY-636 group, DY-647 group, DY-649P1 group, DY-650 group, DY651 group, DY-656 group, DY-673 group, DY-675 group, DY-676 group, DY-680 group, DY-681 group, DY-700 group, DY-701 group, DY-730 group, DY-731 group, DY-750 group, DY-751 group, DY-776 group, DY-782 group, Dye-28 group, Dye-33 group, Dye-45 group, Dye-304 group, or Dye-1041 group.

In some examples, $R_3$ is Dylight488 group, Dylight594 group, Dylight633 group, Dylight649 group, Dylight680 group, Hilyte Fluor488 group, Hilyte Fluor555 group, Hilyte Fluor647 group, Hilyte Fluor680 group, Hilyte Fluor750 group, HiLyte Plus555 group, HiLyte Plus647 group, HiLyte Plus750 group, Hoechst33258 group, or Hoechst33342 group.

In some examples, $R_3$ is PromoFluor-350 group, PromoFluor-405 group, PromoFluor-415 group, PromoFluor-488 group, PromoFluor-488 Premium group, PromoFluor-488LS group, PromoFluor-500LSS group, PromoFluor-505 group, PromoFluor-555 group, PromoFluor-590 group, PromoFluor-510LSS group, PromoFluor-514LSS group, PromoFluor-520LSS group, PromoFluor-532 group, PromoFluor-546 group, PromoFluor-610 group, PromoFluor-633 group, PromoFluor-647 group, PromoFluor-670 group, PromoFluor-680 group, PromoFluor-700 group, PromoFluor-750 group, PromoFluor-770 group, PromoFluor-780 group, or PromoFluor-840 group.

In some examples, $R_3$ is QD525 group, QD565 group, QD585 group, QD605 group, QD655 group, QD705 group, QD800 group, QD903 group, QDpbS950 group, QDot525 group, QDot545 group, QDot565 group, QDot585 group, QDot605 group, QDot625 group, QDot655 group, QDot705 group, QDot800 group, QpyMe2 group, QSY7 group, QSY9 group, QSY21 group, QSY35 group, Rhodamine700 perchlorate group, Rhodamine group, Rhodamine6G group, Rhodamine101 group, Rhodamine123 group, RhodamineB group, RhodamineGreen group, Rhodamine pH-Probe585-7.0 group, Rhodamine pH-Probe585-7.5 group, Rhodamine phalloidin group, Rhodamine Red-X group, or Rhodamine Tag pH-Probe 585-7.0 group.

In some examples, $R_3$ is SYBR Green group, SYPRO Ruby group, SYTO9 group, SYTO11 group, SYTO13 group, SYTO16 group, SYTO17 group, SYTO45 group, SYTO59 group, SYTO60 group, SYTO61 group, SYTO62 group, SYTO82 group, SYTORNASelect group, SYTOX Blue group, SYTOX Green group, SYTOX Orange group, SYTOX Red group, Texas red group, Texas red DHPE group, or Texas red-X group.

In some embodiments, $L_1$ is $L_1^A$-$L_1^B$-$L_1^C$-$L_1^D$-$L_1^E$, wherein $L_1^A$, $L_1^B$, $L_1^C$, $L_1^D$, and $L_1^E$ are each a covalent bond, substituted or unsubstituted alkylene, substituted or unsubstituted heteroalkylene, substituted or unsubstituted cycloalkylene, substituted or unsubstituted isocycloalkylalkenyl, or substituted or unsubstituted aryl alkenyl, and at least one of $L_1^A$, $L_1^B$, $L_1^C$, $L_1^D$ and $L_1^E$ is not a bond.

Alternatively, $L_1$ is $L_1^A$-$L_1^B$-$L_1^C$-$L_1^D$-$L_1^E$, wherein $L_1^A$, $L_1^B$, $L_1^C$, $L_1^D$, and $L_1^E$ are each a covalent bond, substituted or unsubstituted $C_1$-8 alkylene, substituted or unsubstituted 2-8 membered heteroalkylene, substituted or unsubstituted $C_{3-8}$cycloalkylene, substituted or unsubstituted 3-8 membered isocycloalkylene, or substituted or unsubstituted $C_{6-8}$ aryl alkenyl, and at least one of $L_1^A$, $L_1^B$, $L_1^C$, $L_1^D$ and $L_1^E$ is not a bond.

In some embodiments, $L_2$ is $L_2^A$-$L_2^B$-$L_2^C$-$L_2^D$, wherein $L_2^A$, $L_2^B$, $L_2^C$ and $L_2^D$ are each a covalent bond, substituted or unsubstituted alkyl, substituted or unsubstituted heteroalkylene, substituted or unsubstituted cycloalkyl, substituted or unsubstituted isocycloalkyl, substituted or unsubstituted aryl, and at least one of $L_2^A$, $L_2^B$, $L_2^C$ and $L_2^D$ is not a bond.

In some embodiments, $L_3$ is $L_3^A$-$L_3^B$-$L_3^C$-$L_3^D$ or $L_3^A L_3^B L_3^C L_3^D$ wherein $L_3^A$, $L_3^B$, $L_3^C$ and $L_3^D$ are each a covalent bond, substituted or unsubstituted alkyl, substituted or unsubstituted heteroalkylene, substituted or unsubstituted cycloalkyl, substituted or unsubstituted isocycloalkyl, substituted or unsubstituted aryl, and at least one of $L_3^A$, $L_3^B$, $L_3^C$ and $L_3^D$ is not a bond.

In some embodiments, $L_1$ may be selected from the following structures:

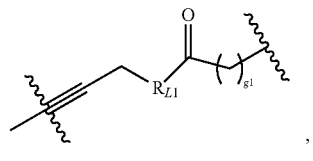

where g1 is an integer of 0 to 10, and $R_{L1}$ is NH or O; preferably, g1 is 1 or 4;

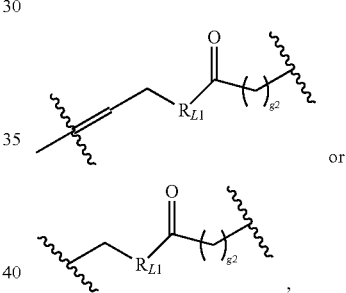

where g2 is 0, 1, 2, 3, 4 or 5, and $R_{L1}$ is NH or O; preferably, g2 is 1 or 4;

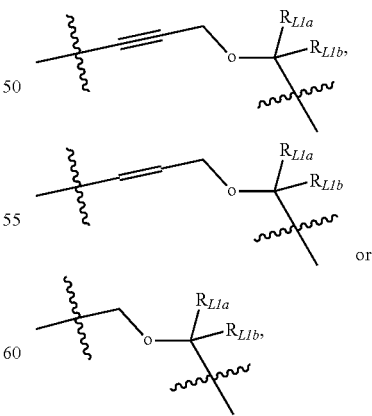

where $R_{L1a}$ and $R_{L1b}$ are each independently H, —$CH_3$, —$CX_3$, —$CHX_2$, —$CH_2X$, —CN, -Ph, $C_{1-6}$ alkyl, $C_{2-6}$ alkyl or $C_{3-6}$ cycloalkyl, wherein X is Cl, Br, or I; or

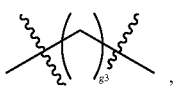

where g3 is 0, 1, 2, 3, or 4, preferably 1 or 2.

In some embodiments, $L_2$ may be selected from but not limited to the following structures:

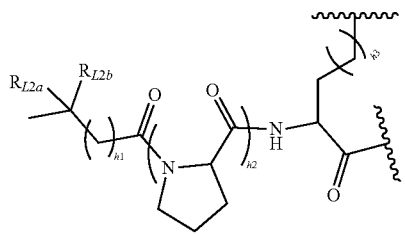

where $R_{L2a}$ and $R_{L2}$ are each independently H, $C_{1-5}$alkyl chain, 3-6 membered cycloalkyl or phenyl, preferably H, methyl, ethyl, 5-6 membered cycloalkyl or phenyl, and h1, h2 and h3 are each independently an integer of 0 to 6, preferably 0, 1 or 2;

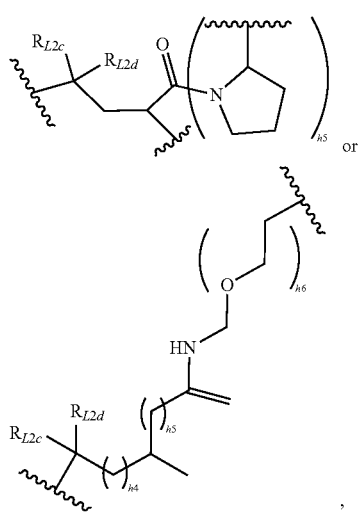

where $R_{L2c}$ and $R_{L2d}$ are each independently H or $C_{3-6}$ alkyl chain, and h4, h5 and h6 are each independently an integer of 0 to 6, preferably, h4 is 0, 1 or 2, h5 is preferably 5 or 6, and h6 is preferably 4, 5 or 6; or

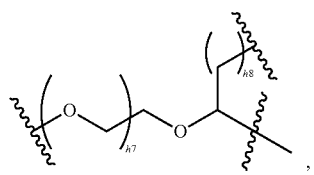

where h7 and h8 are each independently an integer of 1 to 6, preferably 1, 2 or 3.

Terms "cleavable group" or "cleavable bond" used herein means that this bond or group may be broken down (separated, hydrolyzed, stable bond broken) into a single monovalent or bivalent bond. The cleavage of the group or the bond may be caused by various external stimulations, such as enzymes, nucleophiles, reductants, light irradiation, oxidizing reagents, acid reagents, etc. Usually, under these stimulating factors (such astris(2-carboxyethyl) phosphine (TCEP), Tris(3-hydroxypropyl) phosphine (THPP), laser irradiation, Pd(0), etc.), the cleavable group or cleavable bond is broken down.

In some embodiments, the cleavable group or the cleavable bond may be selected from the followings:

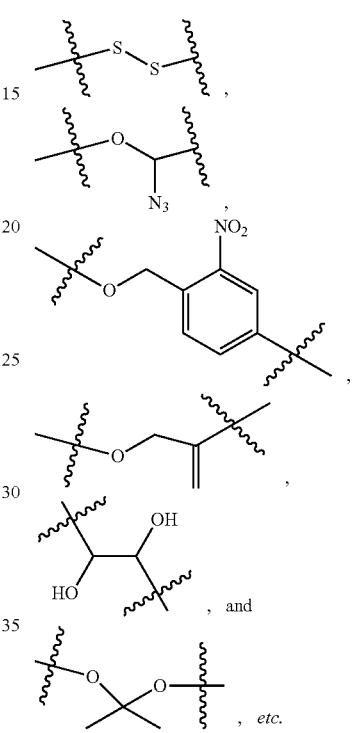

The term "photo-cleavable bond" or "photo-cleavable group" (e.g., o-nitrobenzyl) means that a connecting bond thereof may break down underlight stimulation.

The term "inhibitory group" (inhibition) refers to a group or a covalent bond that is capable of virtually blocking the 3' end of a base by for example steric hindrance and/or charge effect of a molecule. For example, under certain conditions, the inhibitory group interacts with manganese ions to make no free manganese ion participate in the polymerization pairing process. The so-called virtual block (virtually blocking or virtual inhibition) is compared to the blocking achieved by modifying the —$CH_2$— at the 2' and/or the —OH at the 3' of the five-carbon sugar of the nucleotide (nucleotide analog); with maintaining the natural state of the —$CH_2$— at the 2' and/or the —OH at the 3'position of the five-carbon sugar of the nucleotide (nucleotide analog), virtual blocking achieves blocking the incorporation of the next nucleotide (nucleotide analog) by for example steric hindrance and/or charge effect of a molecule.

The "inhibitory group" includes, but is not limited to, a charged group (e.g., a group bearing a positive charge, a group bearing a negative charge, or a group bearing both positive and negative charges). Alternatively, the "inhibitory group" includes two or more charged groups. The charged group may be selected from: —COOH, —$PO_4$, —$SO_4$, —$SO_3$, and —$SO_2$. In an embodiment, the following structure is preferred for $R_5$:

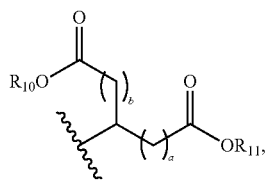

where $R_{10}$ and $R_{11}$ are each independently H or $C_{1-6}$ alkyl, a and b are each independently an integer of 1 to 5, preferably 1 or 2.

In some application examples, $R_5$ is

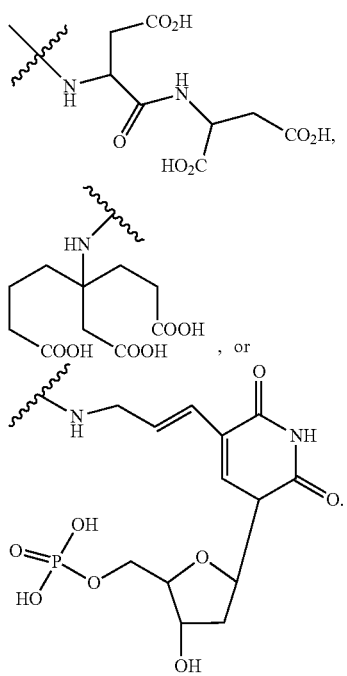

According to some embodiments, wherein when C' comprises a carbon-oxygen bond but no disulfide bond, C" comprises an azido or a nitroso; preferably, the azido or nitroso group is on the branch of C", for example, on the branch of alkyl or aryl; more preferably, the distance between the azido or nitroso group and the disulfide bond or the carbon-oxygen bond is no more than five atoms, i.e., the main chain of the linking group between the azido or nitroso group and the disulfide bond or the carbon-oxygen bond is no more than five atoms long; therefore, the compound with any of these characteristic not only has a strong stability and/or spatial configuration, but also shows better cleaving efficiency in sequencing.

According to some embodiments, wherein C' comprises a carbon-oxygen bond but no disulfide bond, and C" comprises an azido or a nitroso, enable the compound used in sequencing without the need for a capping step. The capping step includes adding a reagent to protect the reductive group such as —SH exposed after cleavage.

According to some embodiments, wherein C" further comprises at least one selected from a group comprising: an optionally substituted ethynyl, an optionally substituted amido alkyl, and an optionally substituted straight or branched alkyl.

According to some embodiments, wherein C" further comprises at least one selected from a group comprising: an optionally substituted amido alkyl, and an optionally substituted straight or branched alkyl.

According to some embodiments, wherein C comprises at least one selected from a group comprising:

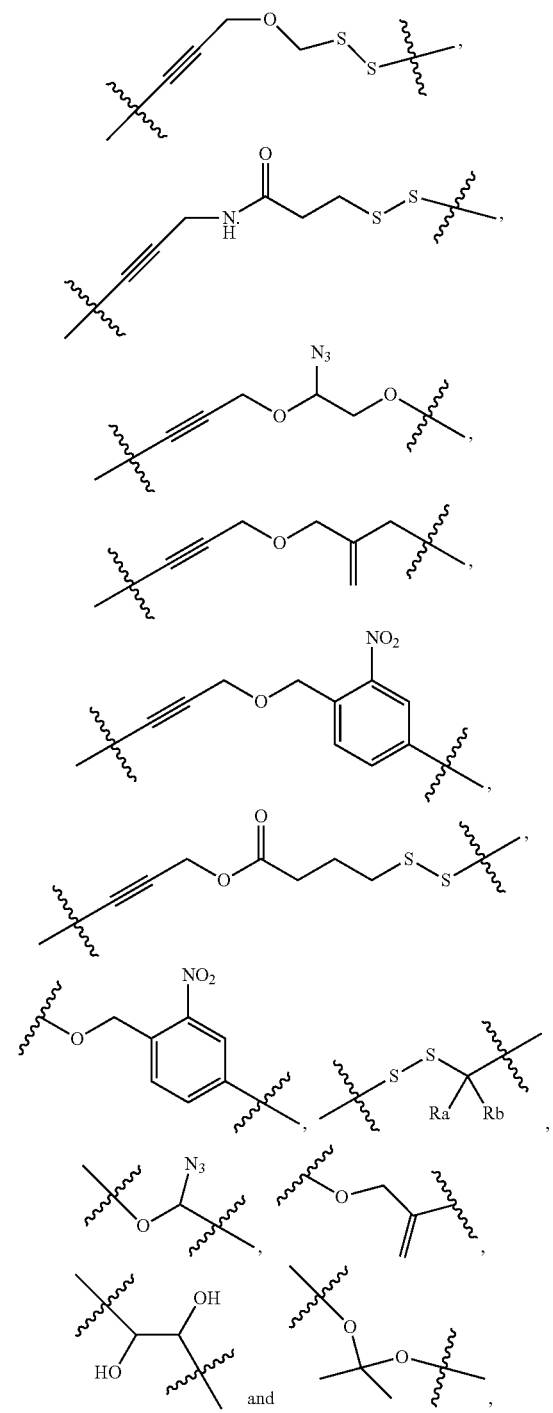

wherein Ra and Rb are each independently H, optionally substituted alkyl, optionally substituted heteroalkylene, optionally substituted cycloalkyl, optionally substituted isocycloalkyl, or optionally substituted aryl, at least one of Ra and Rb is not H.

According to some embodiments, C is a group containing at least one selected from the followings: an optionally substituted ethynyl, an optionally substituted disulfide bond, an optionally substituted amido alkyl, an optionally substituted aryl, an optionally substituted alkoxy, an optionally substituted azido, and an optionally substituted unbranched or branched alkyl.

According to some embodiments, C is a group containing at least one selected from the followings: ethynyl, a disulfide bond, amide group, alkyleneoxy, aryl, azido, or linear or branched alkylene each optionally substituted with hydroxyl.

According to some embodiments, C is at least one selected from the followings:

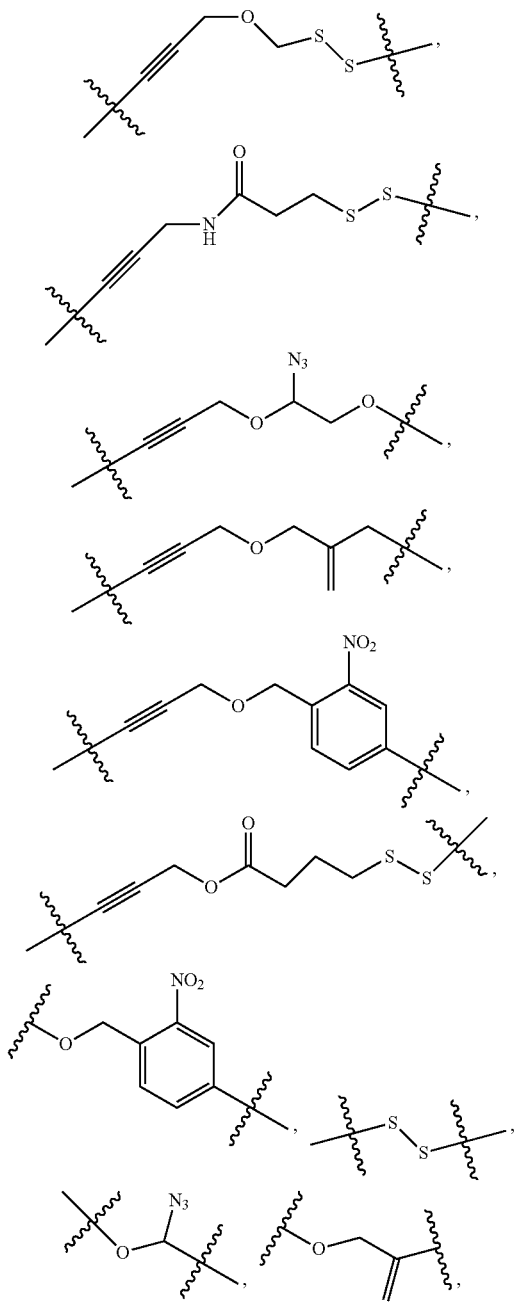

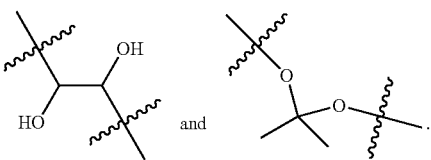

According to some embodiments, $L_1$, $L_2$ and $L_3$ are each independently at least one selected from the followings: an independent bond, an optionally substituted alkyl, an optionally substituted alkylene, an optionally substituted heteroalkylene, an optionally substituted cycloalkyl, an optionally substituted isocycloalkyl and an optionally substituted aryl alkenyl.

According to some embodiments, $L_1$, $L_2$ and $L_3$ are each independently selected from the followings: an independent bond, an optionally substituted $C_1$ alkyl, an optionally substituted $C_1$ alkylene, an optionally substituted $C_{2-8}$ heteroalkylene, an optionally substituted $C_{3-8}$ cycloalkylene, an optionally substituted $C_{3-8}$ isocycloalkylene, and an optionally substituted $C_6$-8 aryl alkenyl.

According to some embodiments, $L_1$ is at least one selected from the followings: an independent bond, an optionally substituted $C_{1-3}$ alkyl and an optionally substituted $C_{1-3}$ alkylene.

According to some embodiments, $L_1$ includes at least one selected from the followings:

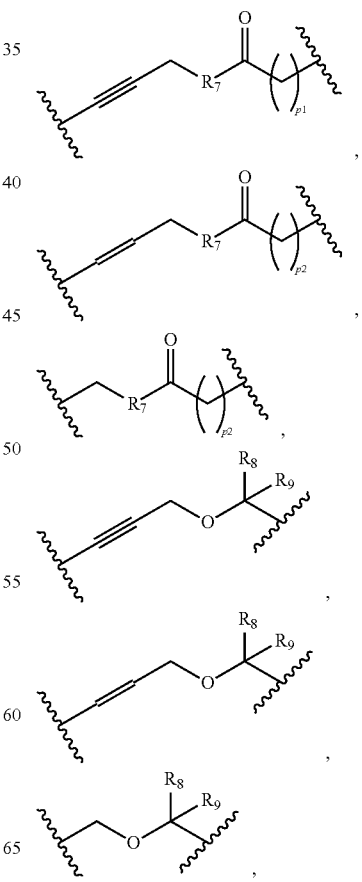

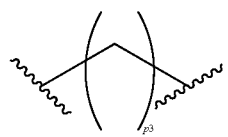

wherein each $R_7$ is independently an amide bond or O, each $p_1$ is independently an integer of 0 to 10, preferably for 4;

each $p_2$ is independently an integer of 0 to 5, preferably 1 or 4;

each $R_8$ and each $R_9$ are independently at least one selected from the followings: H, —CH$_3$, —CX$_3$, —CHX$_2$, —CH$_2$X, —CN, -Ph, $C_{1-6}$ alkyl, $C_{2-6}$ alkyl and $C_{3-6}$ cycloalkyl, wherein X is Cl, Br, or I;

each $p_3$ is independently an integer of 0 to 4, preferably 1 or 2.

According to some embodiments, $L_2$ includes at least one selected from the followings:

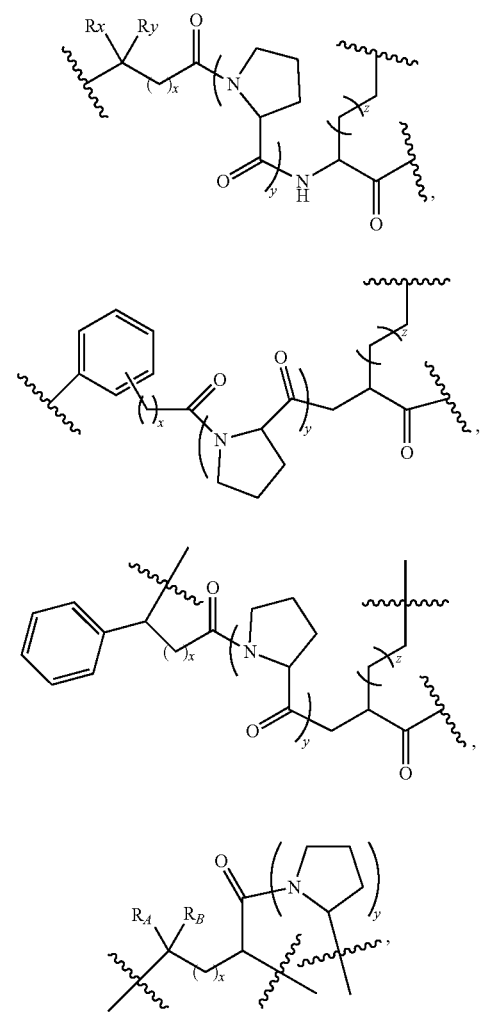

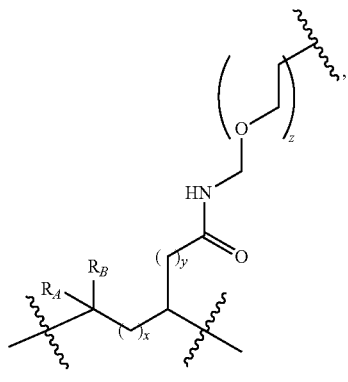

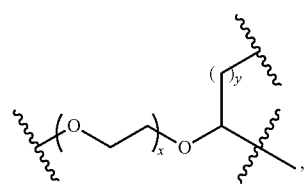

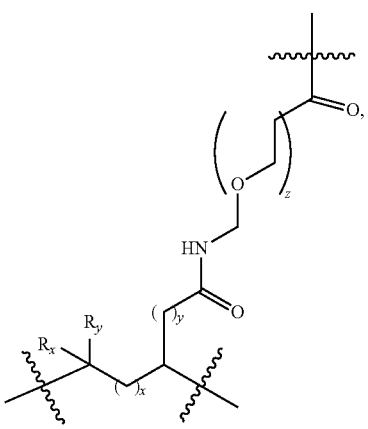

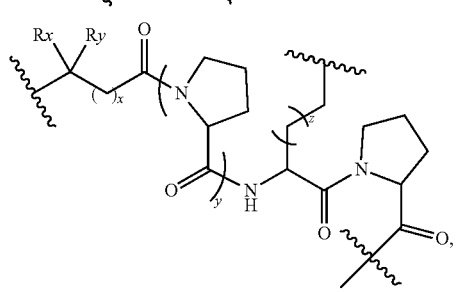

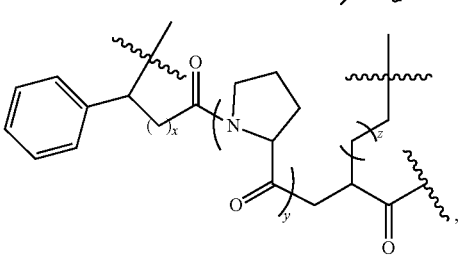

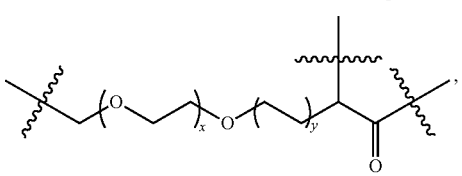

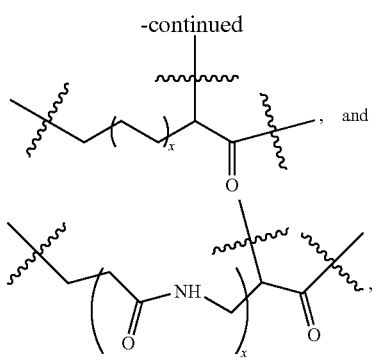

wherein $R_x$, $R_y$, $R_A$, and $R_B$ are each independently H, $C_{1-6}$ alkyl chain, $C_{3-10}$ cycloalkyl, or $C_{5-10}$ aryl, and x, y, and z are each independently an integer of 0 to 6.

According to some embodiments, $R_x$ and $R_y$ are each independently H, $C_{3-5}$ cycloalkyl, $C_{5-6}$ cycloalkyl, or phenyl.

According to some embodiments, $L_5$ is selected from the followings:

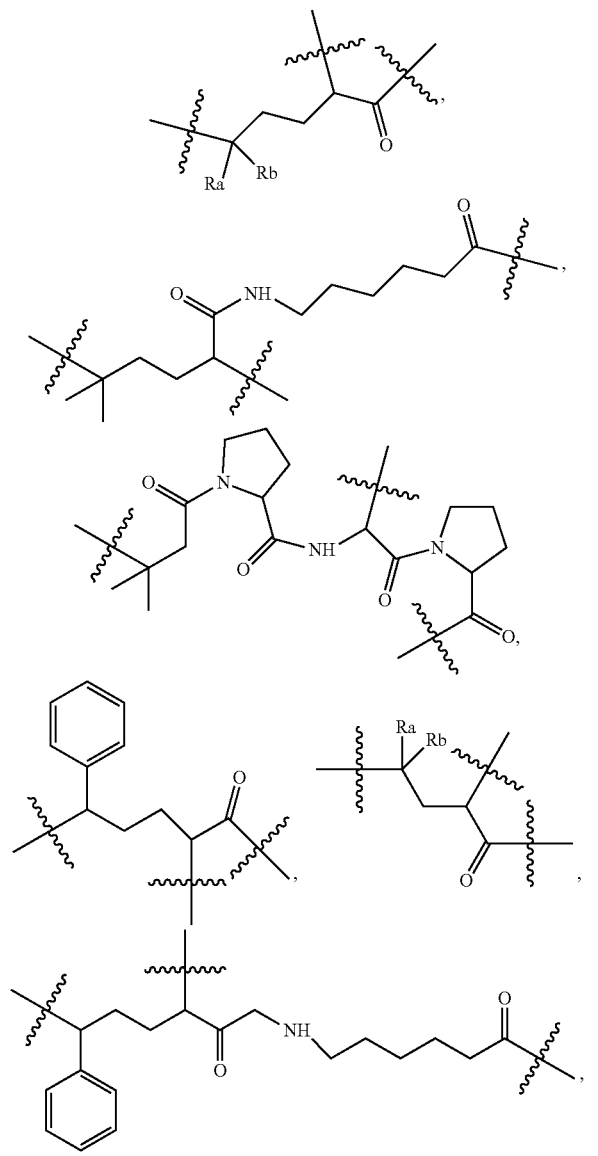

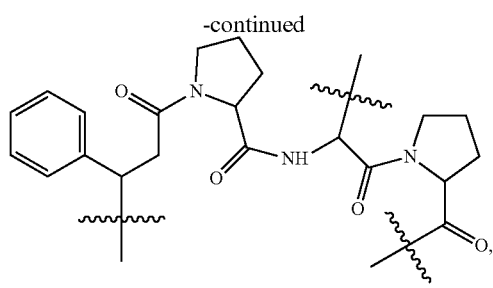

wherein Ra and Rb are each independently H, substituted or unsubstituted alkyl, substituted or unsubstituted heteroalkylene, substituted or unsubstituted cycloalkyl, substituted or unsubstituted isocycloalkyl, or substituted or unsubstituted aryl.

According to some embodiments, $L_3$ is selected from the followings:
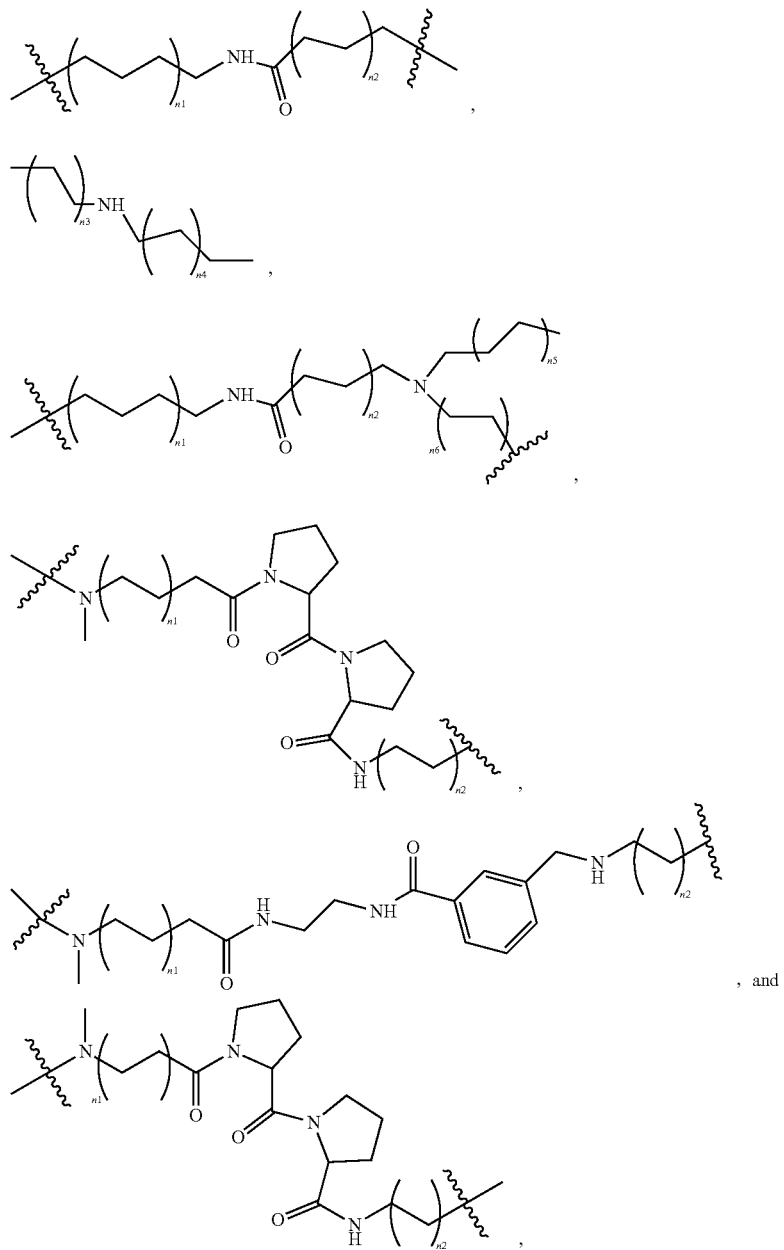
wherein n1, n2, n3, n4, n5, and n6 are each independently an integer of 0 to 7.
According to some embodiments, $L_3$ has a structure selected from the followings:
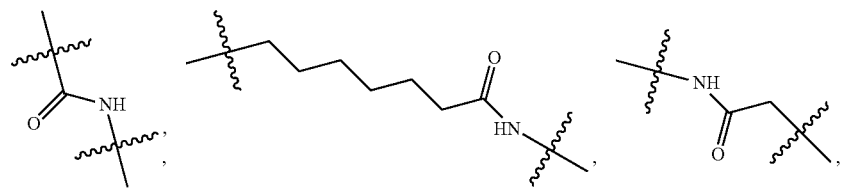

-continued
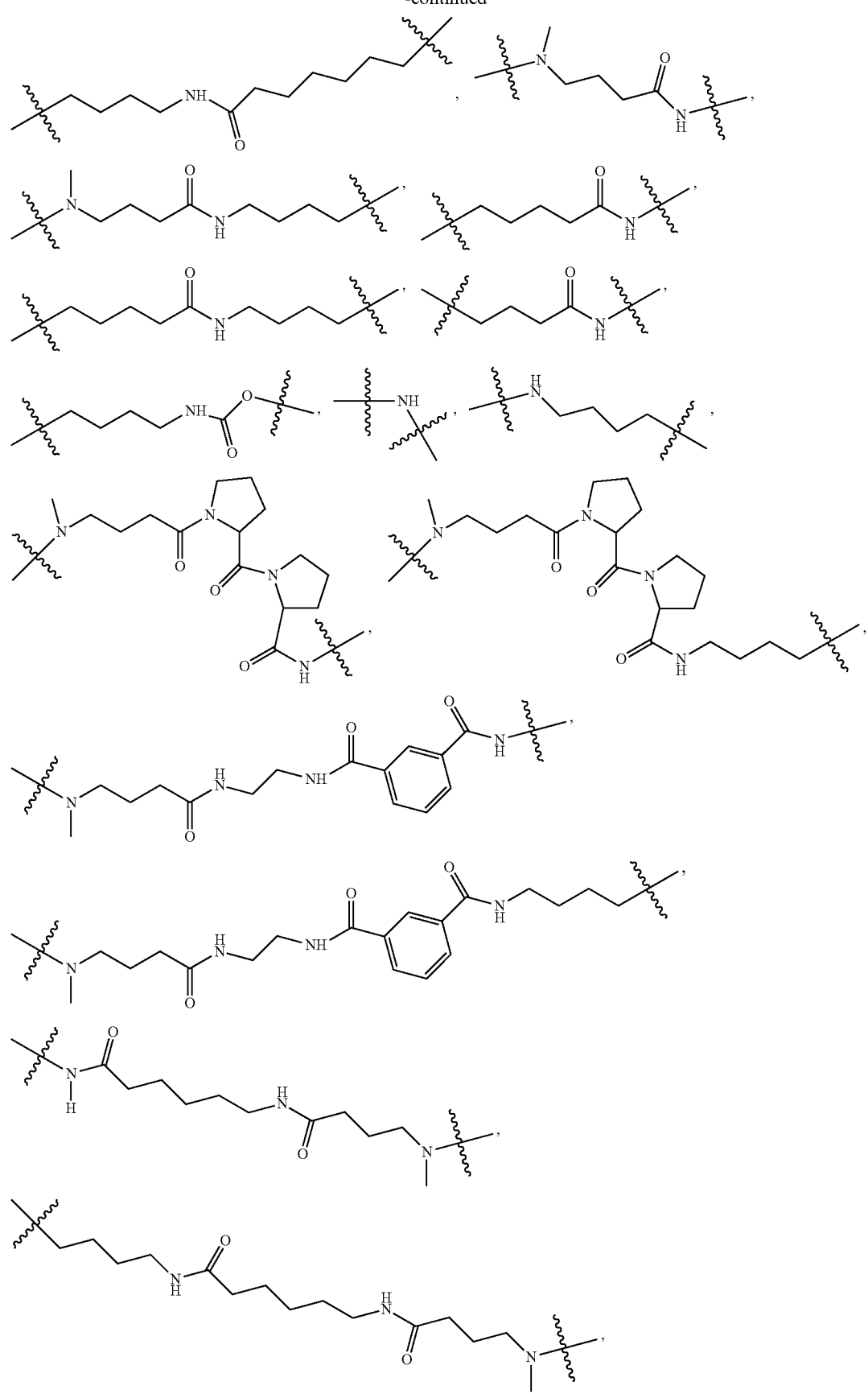

-continued

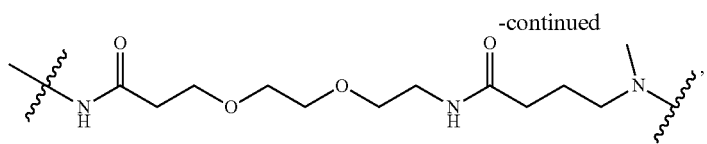

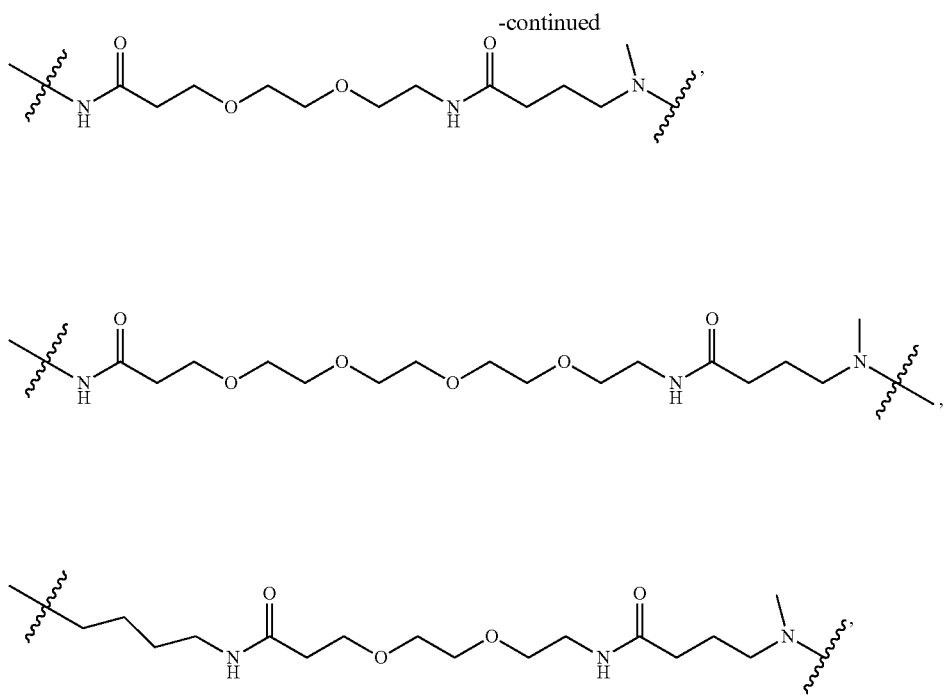

According to some embodiments, $R_3$ is at least one selected from the followings: a dye, a reactive group of click chemistry, azido and biotinyl.

According to some embodiments, $R_5$ includes at least one charged group, and the charged group includes —COOH, —$PO_4$, —$SO_4$, —$SO_3$, and —$SO_2$.

According to some embodiments, the compound has at least one structure selected from the followings:

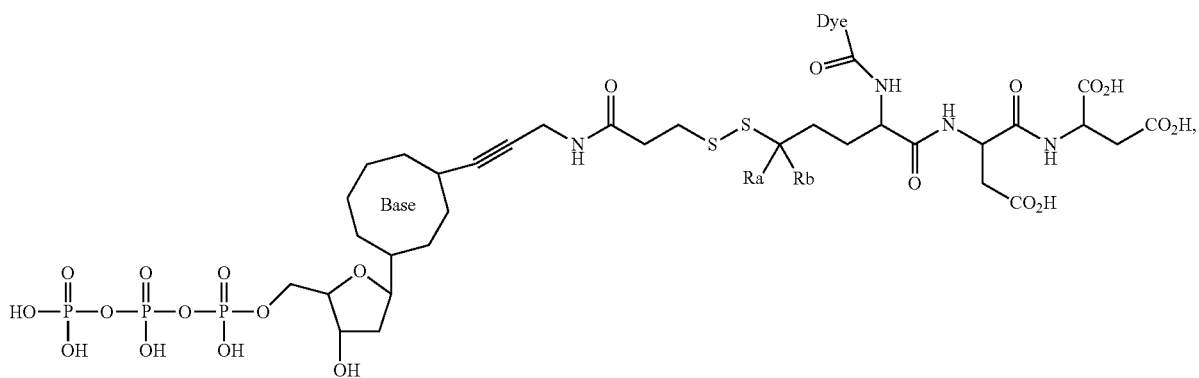

(1)

(2)
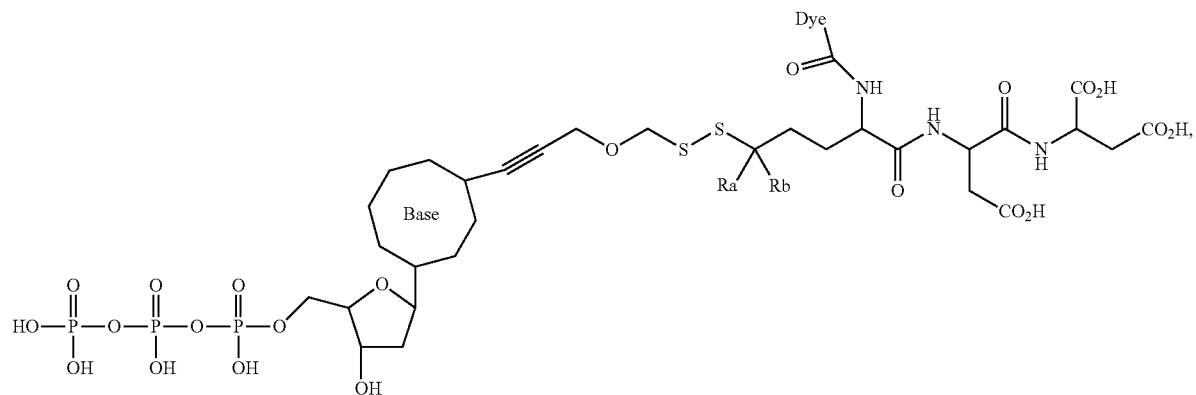
(35)
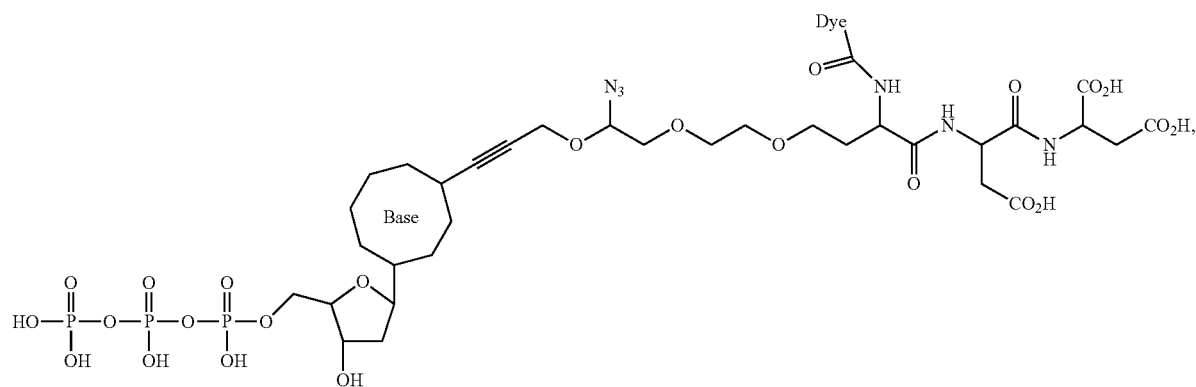
(36)
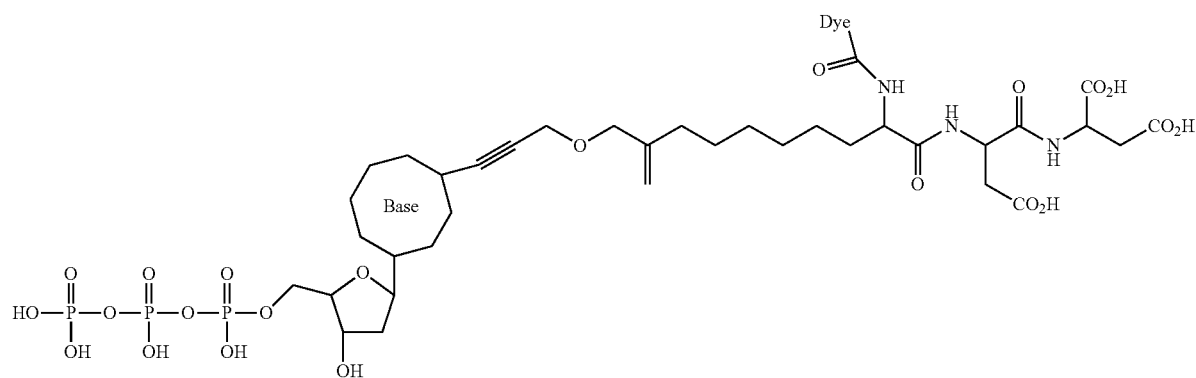
(37)
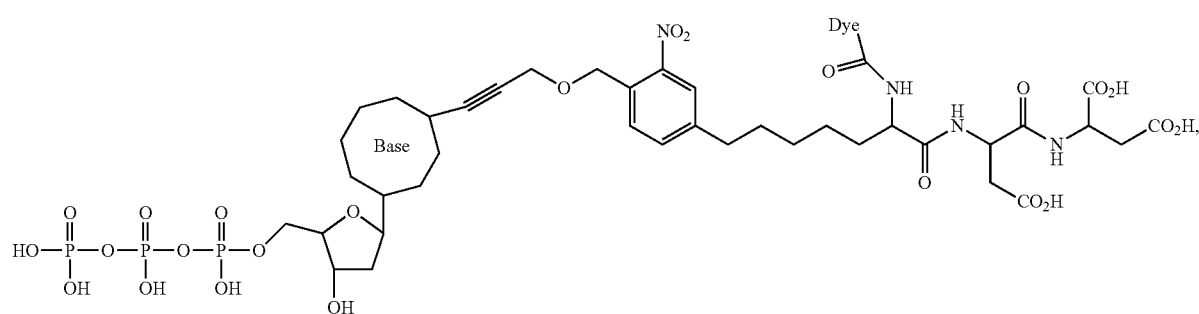

(38)
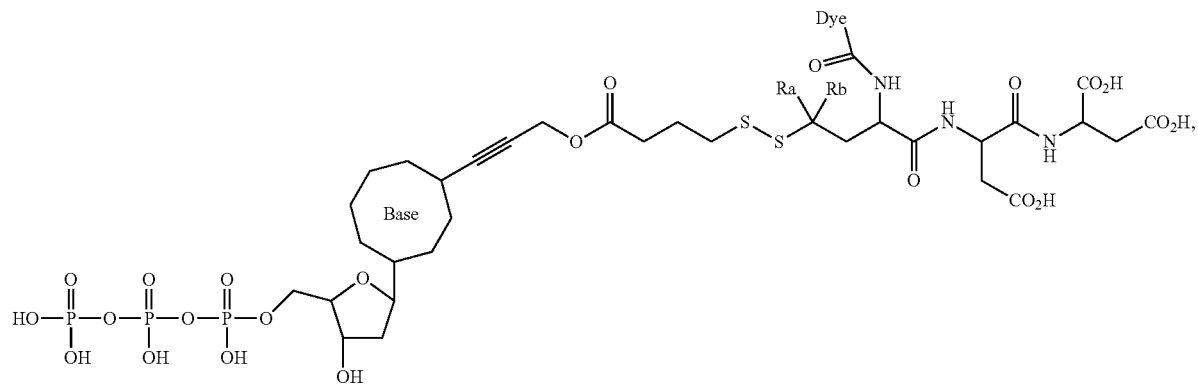
(39)
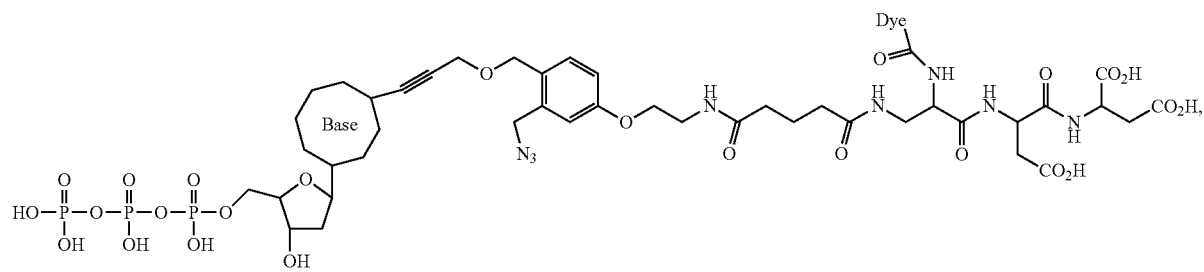
(11-13)
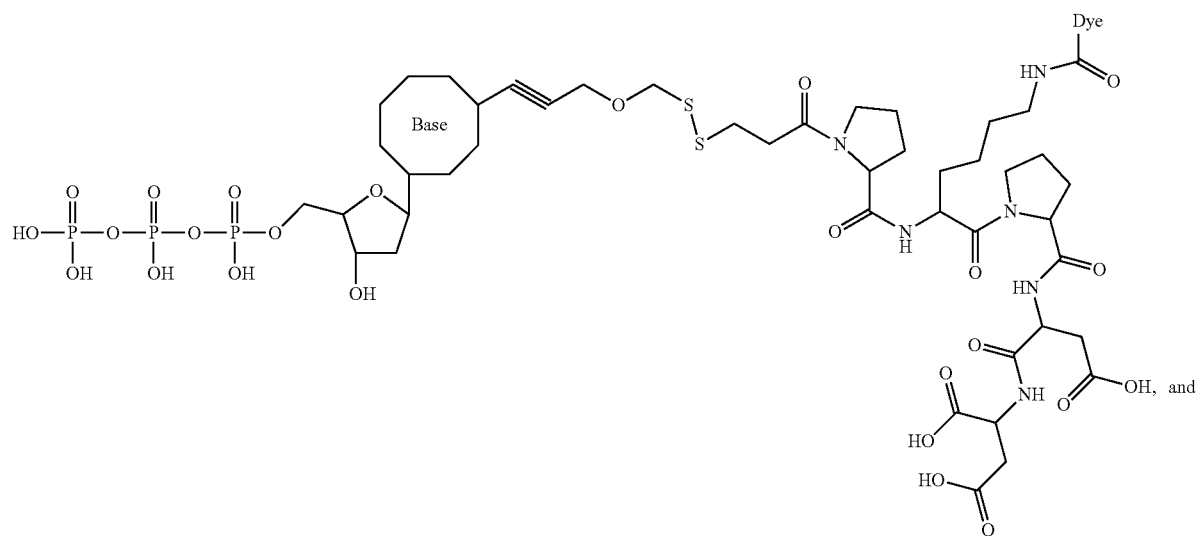
(93)
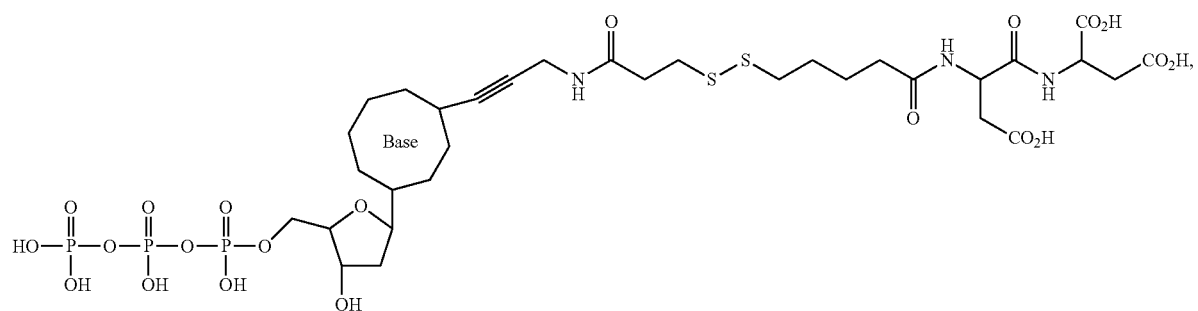

wherein each Ra and each Rb independently are at least one selected from the followings: H, an optionally substituted alkyl, an optionally substituted heteroalkylene, an optionally substituted cycloalkyl, an optionally substituted isocycloalkyl and an optionally substituted aryl.

According to some embodiments, each Ra and each Rb independently are H, $C_{3-6}$ alkyl, heteroalkyl having 3 to 6 skeleton atoms, $C_{2-6}$ alkenyl, heteroalkenyl having 3 to 6 skeleton atoms, $C_{3-6}$ cycloalkyl, 3-6 membered heterocyclic group, phenyl, heteroaryl having 5 to 6 skeleton atoms, wherein the $C_{1-6}$ alkyl, heteroalkyl having 3 to 6 skeleton atoms, $C_{2-6}$ alkenyl, heteroalkenyl having 3 to 6 skeleton atoms, $C_{3-6}$ cycloalkyl, 3-6 membered heterocyclic group, phenyl and heteroaryl having 5 to 6 skeleton atoms are each independently unsubstituted or substituted with 1 to 3 halogen, $C_{1-6}$ alkyl, $C_{2-6}$ alkenyl, CN, or $NO_2$.

According to some embodiments, the compound has at least one structure selected from the followings:

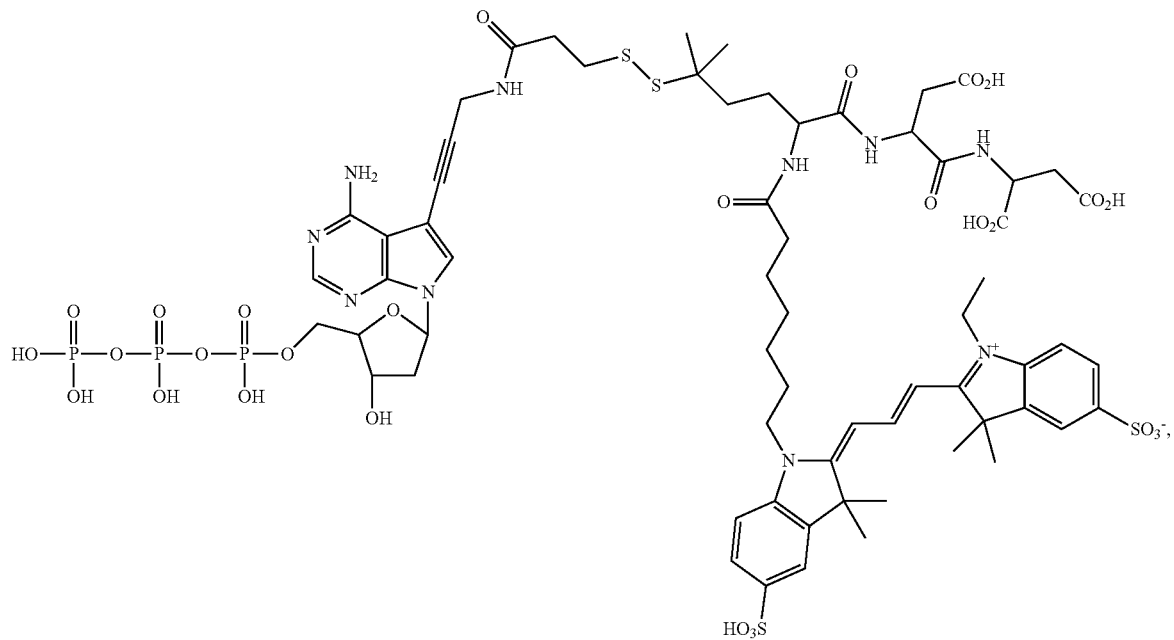

(3)

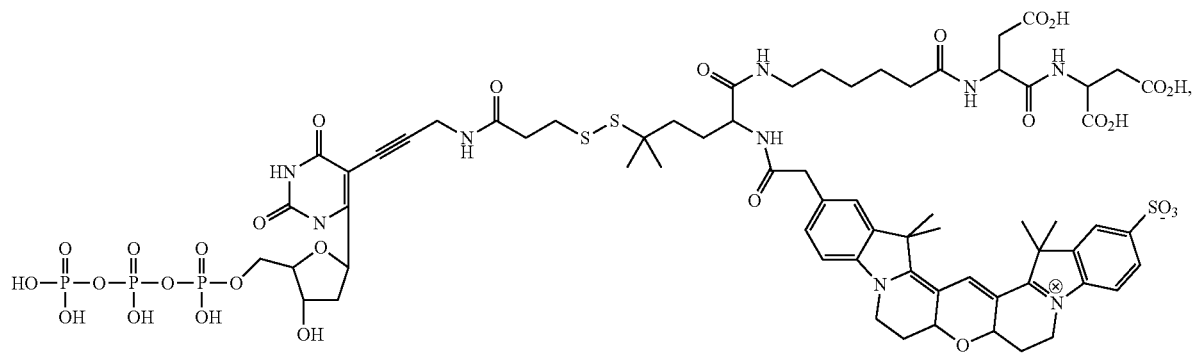

(4)

-continued
(5)
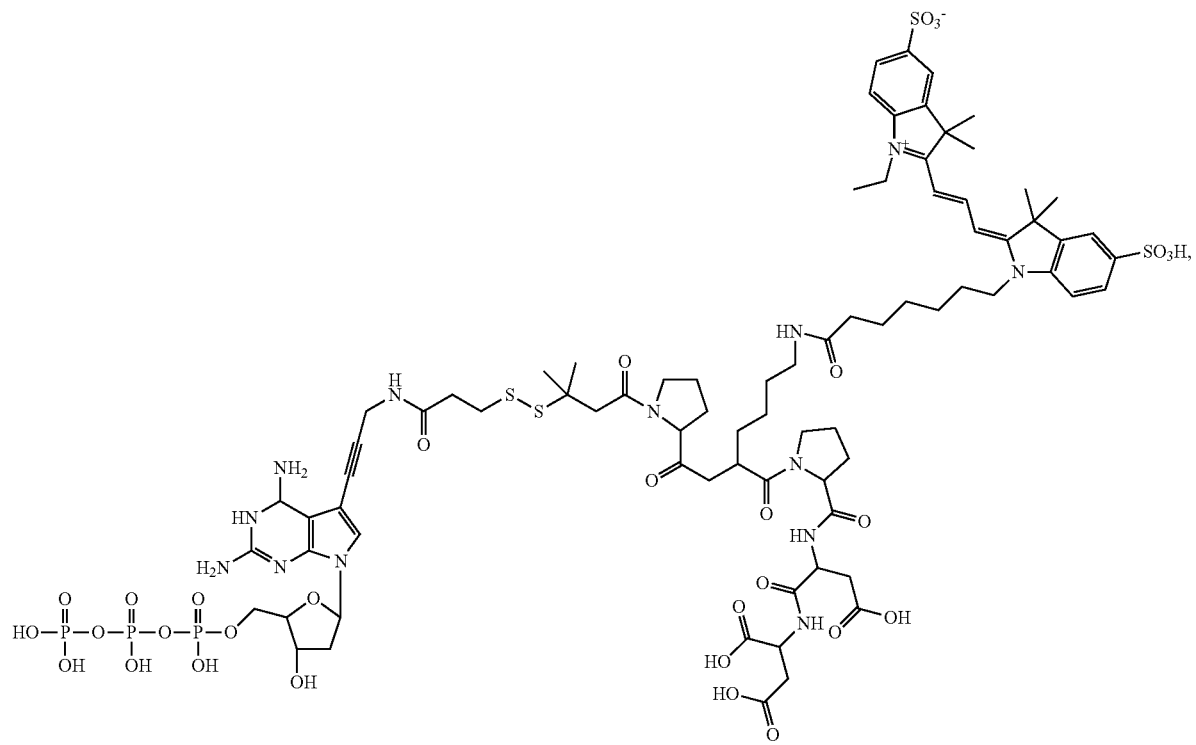
(6)
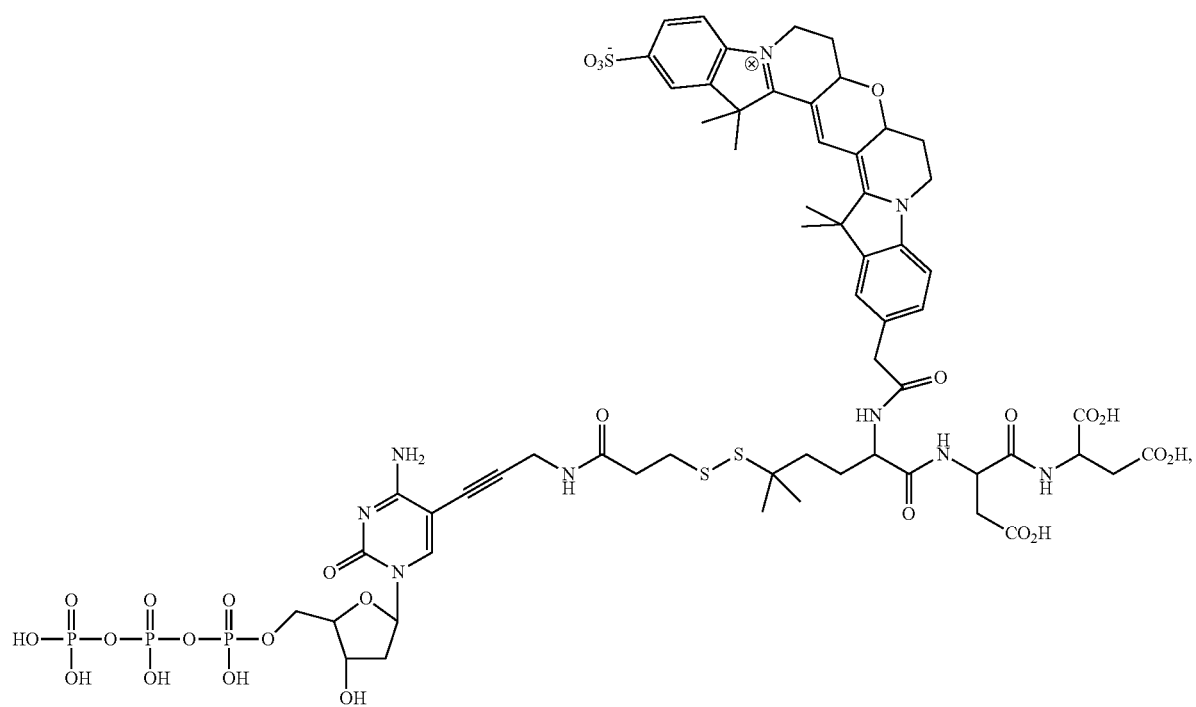

-continued
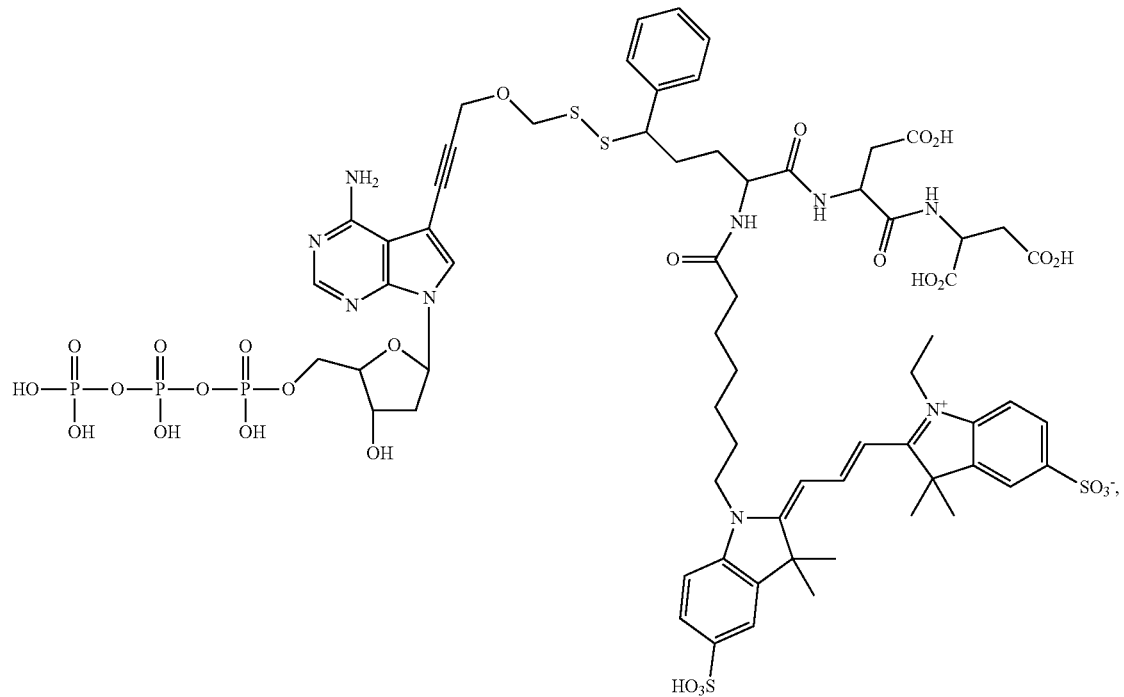
(7)
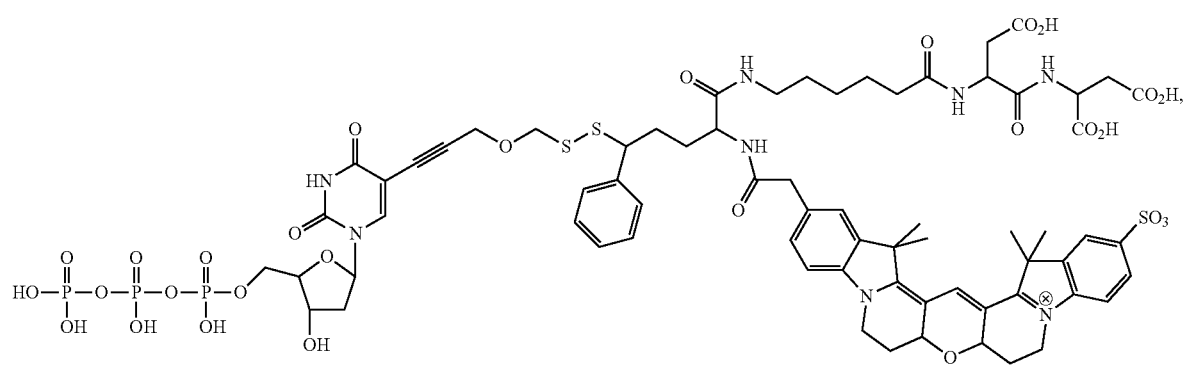
(8)

(9)
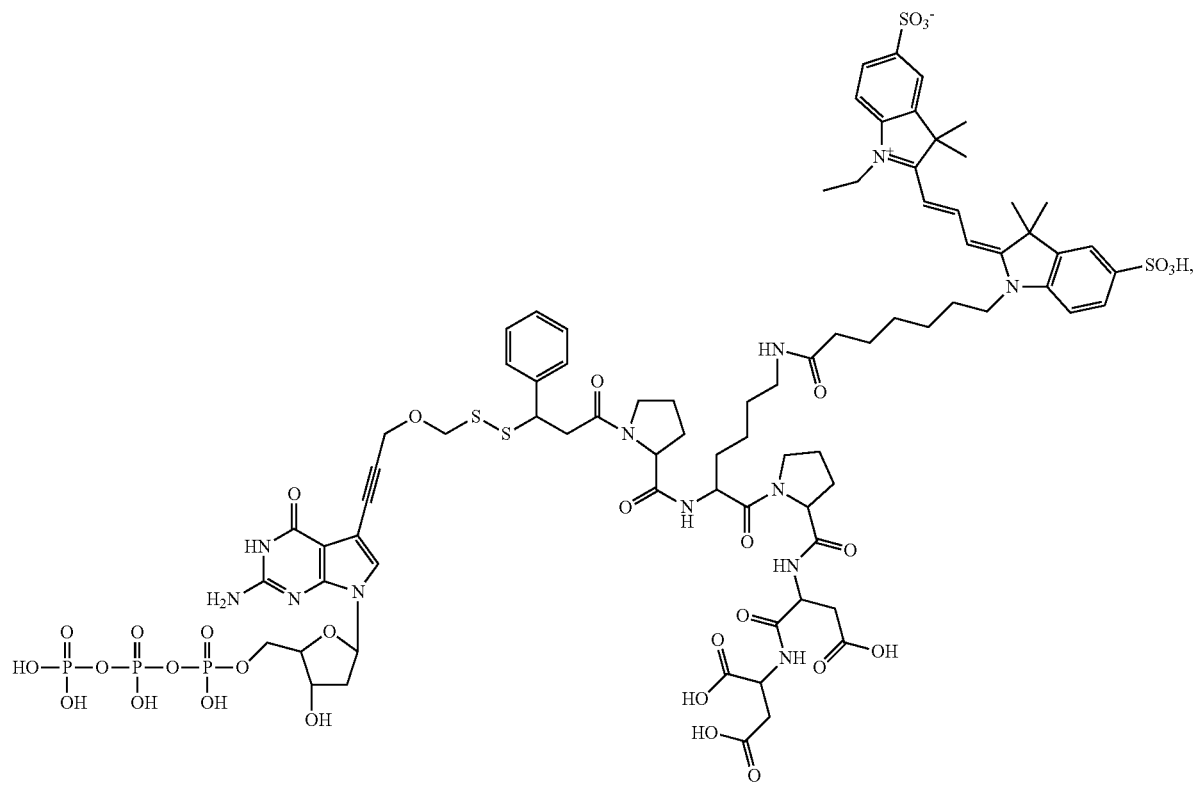
(10)
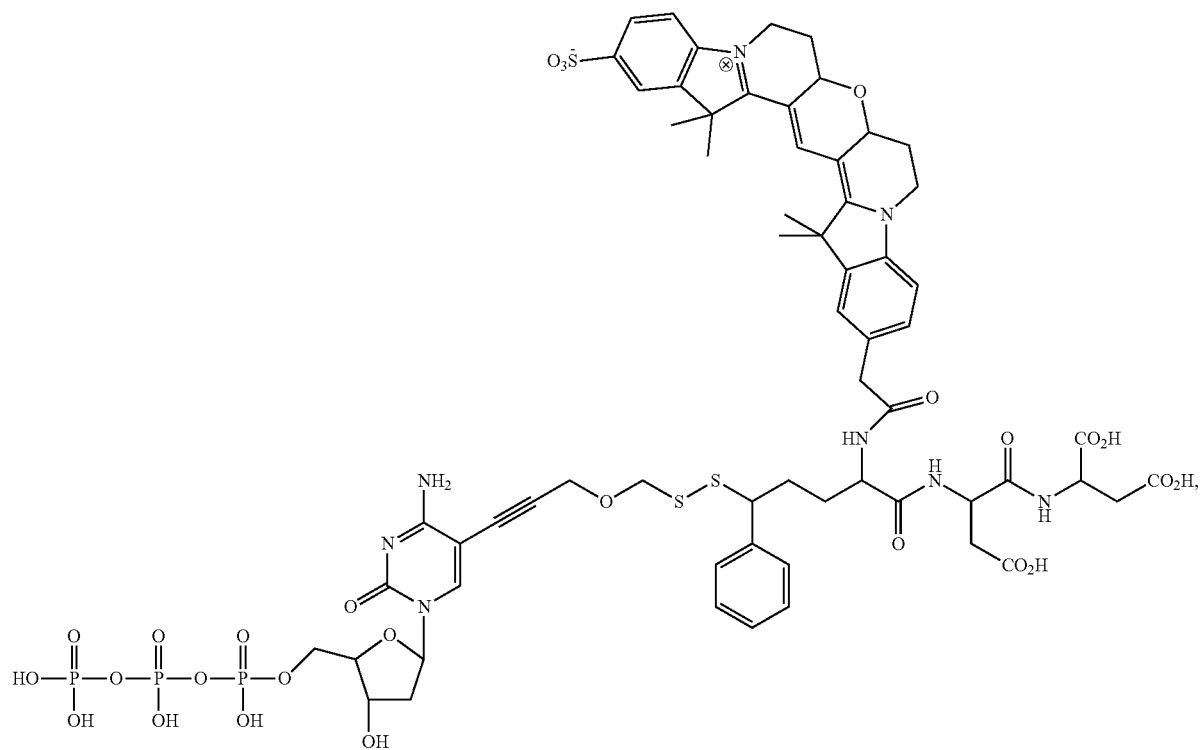

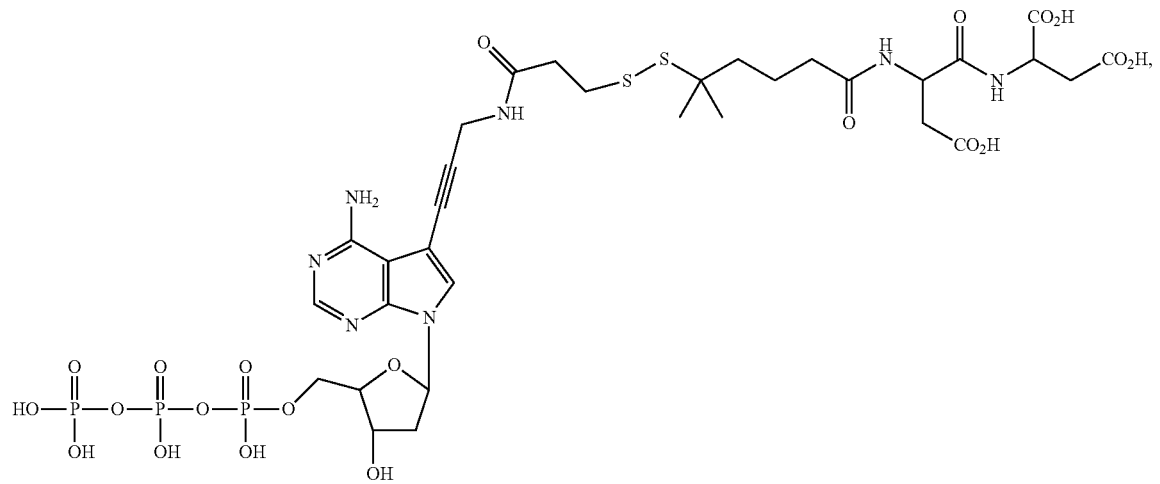
(11)
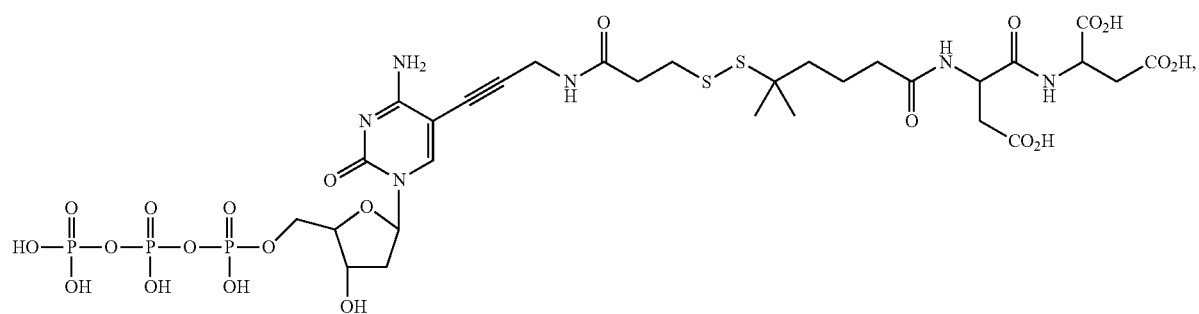
(12)
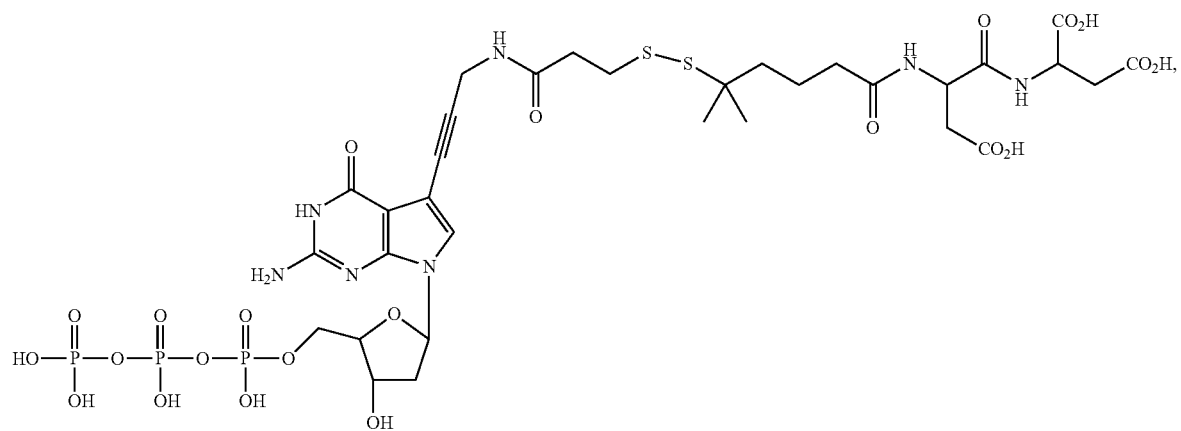
(13)
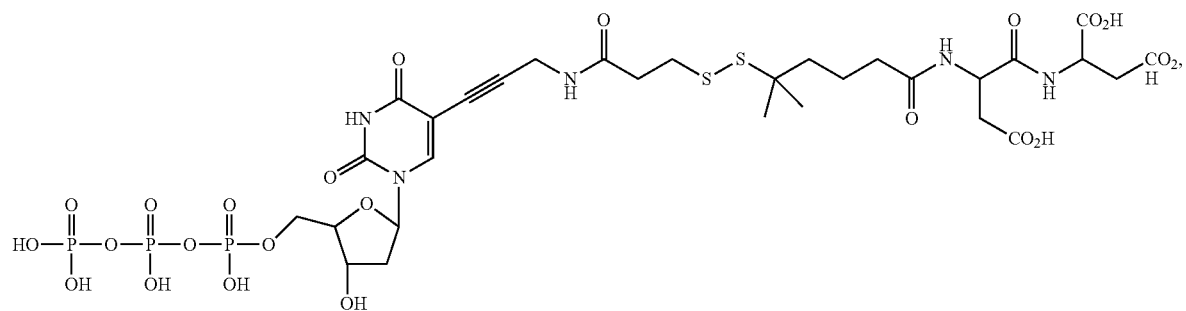
(14)

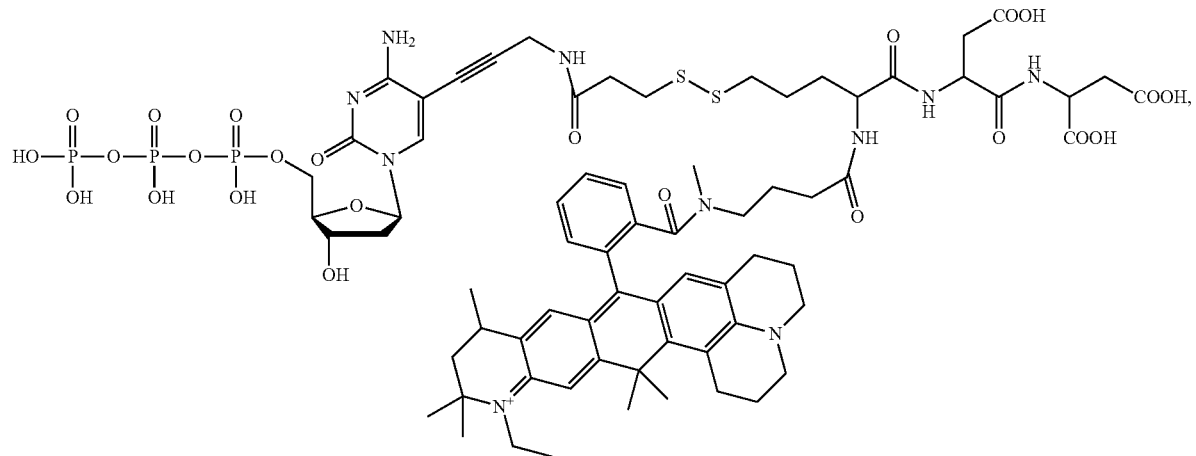
(15)
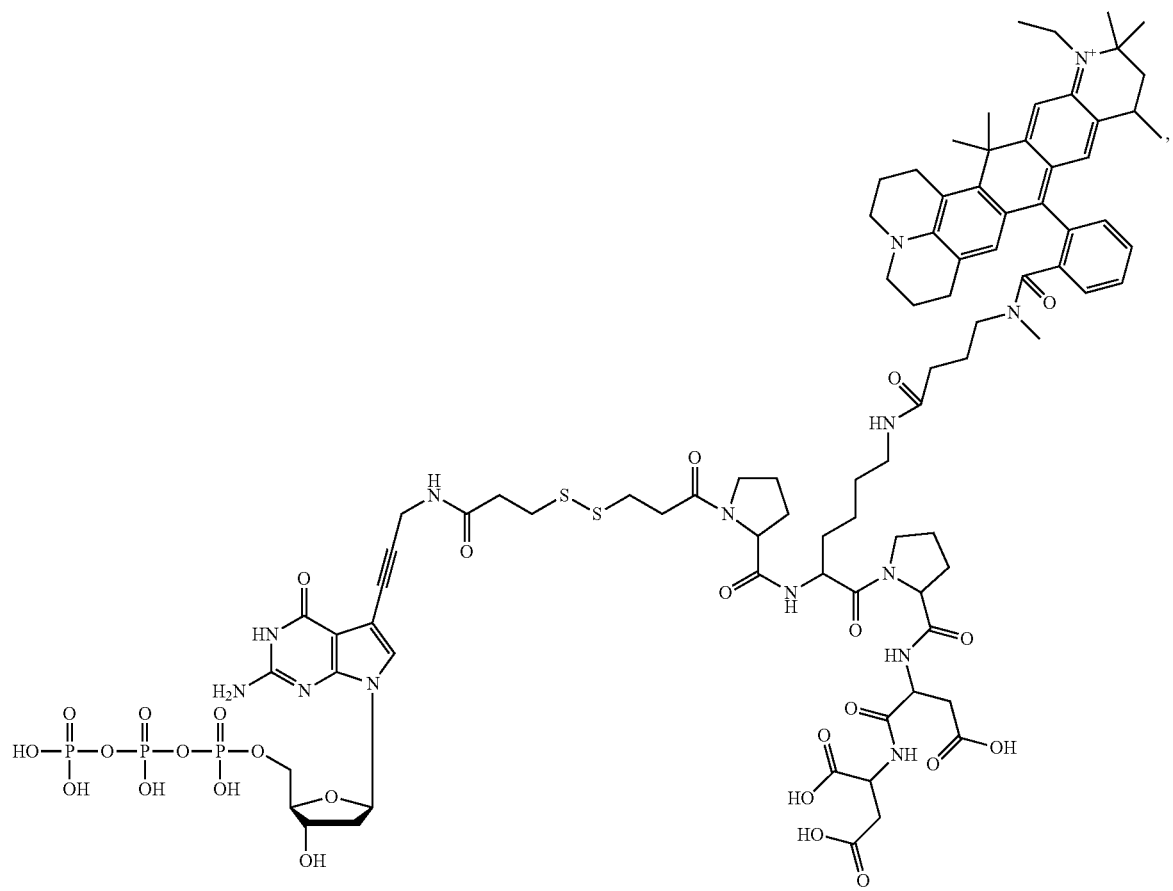
(16)

(17)
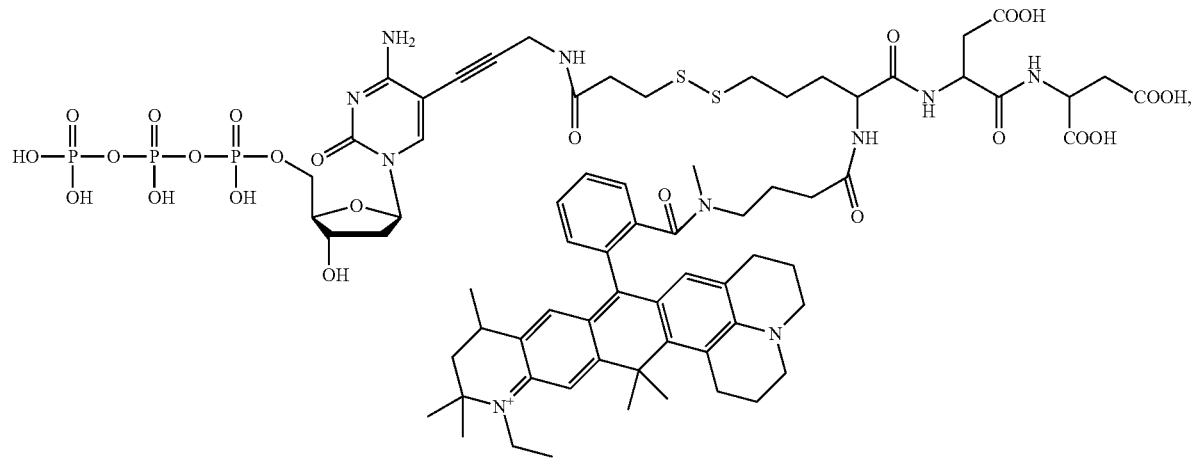
(18)
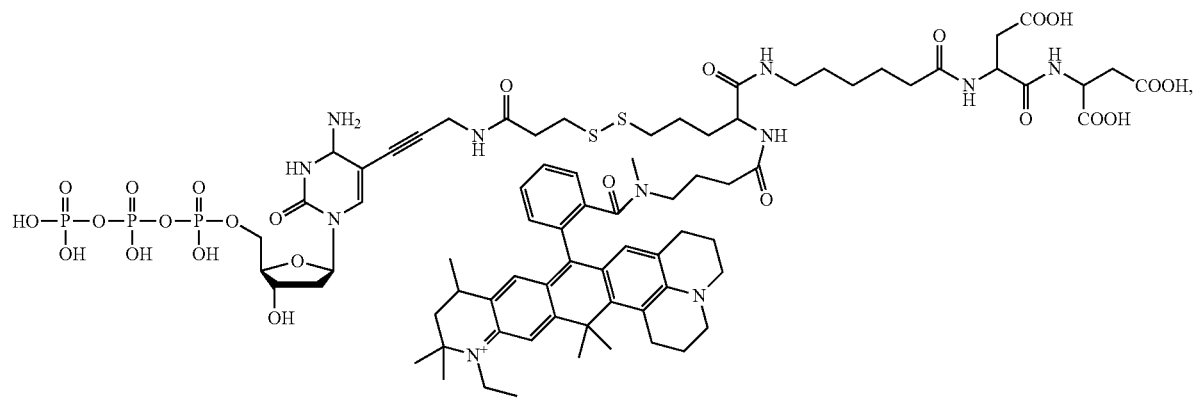
(19)
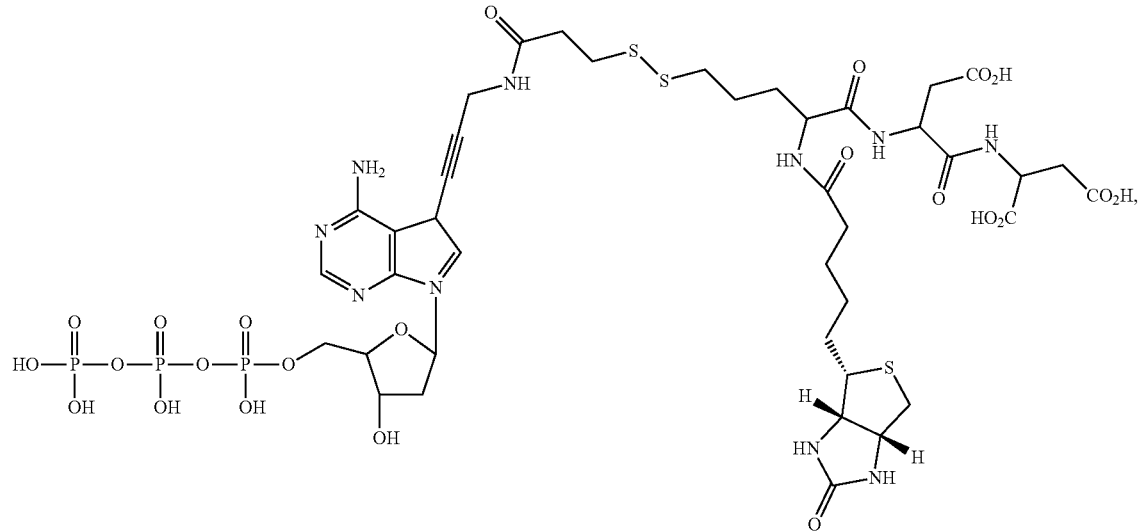

-continued
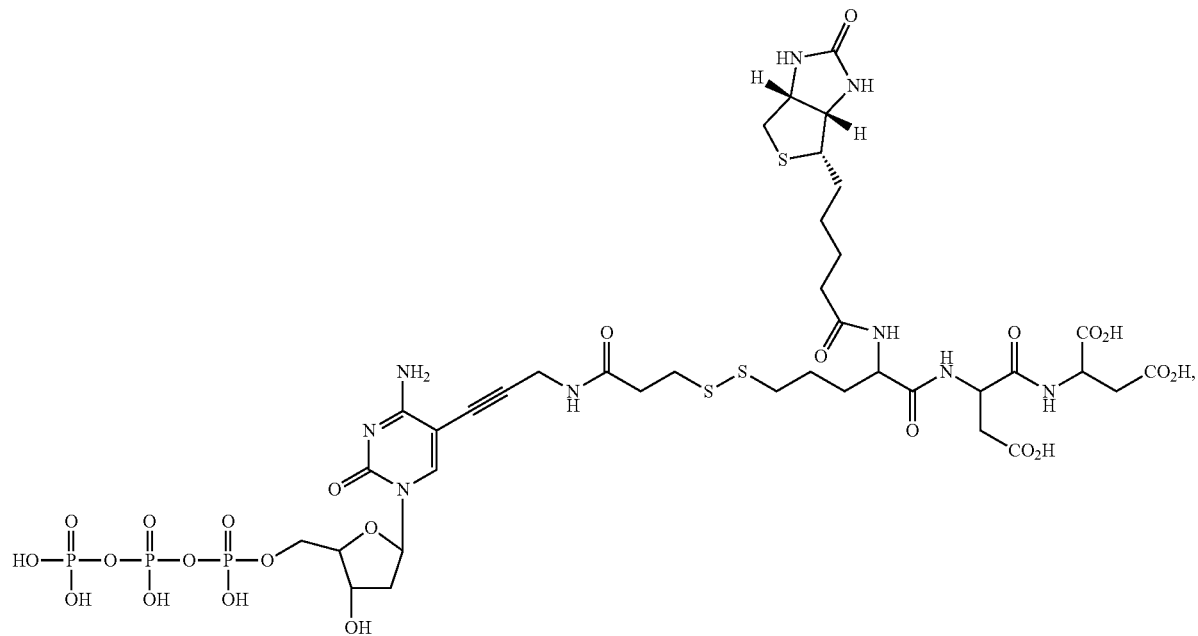
(20)
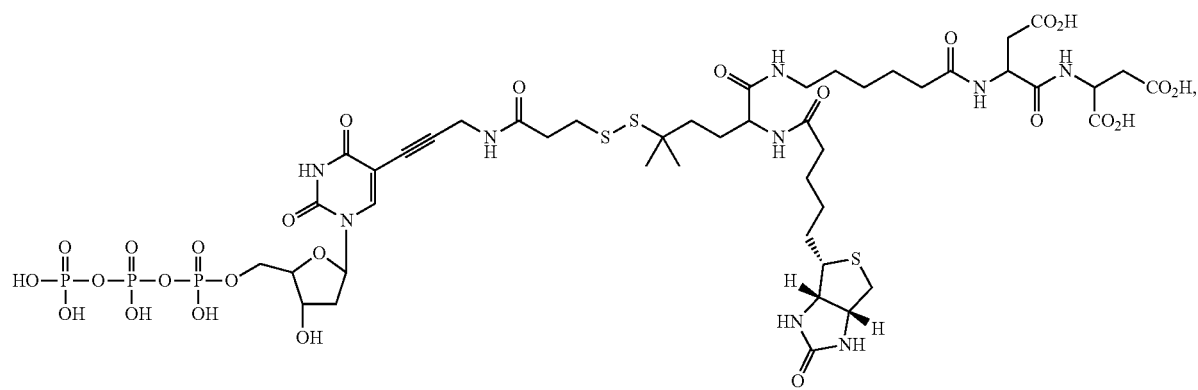
(21)

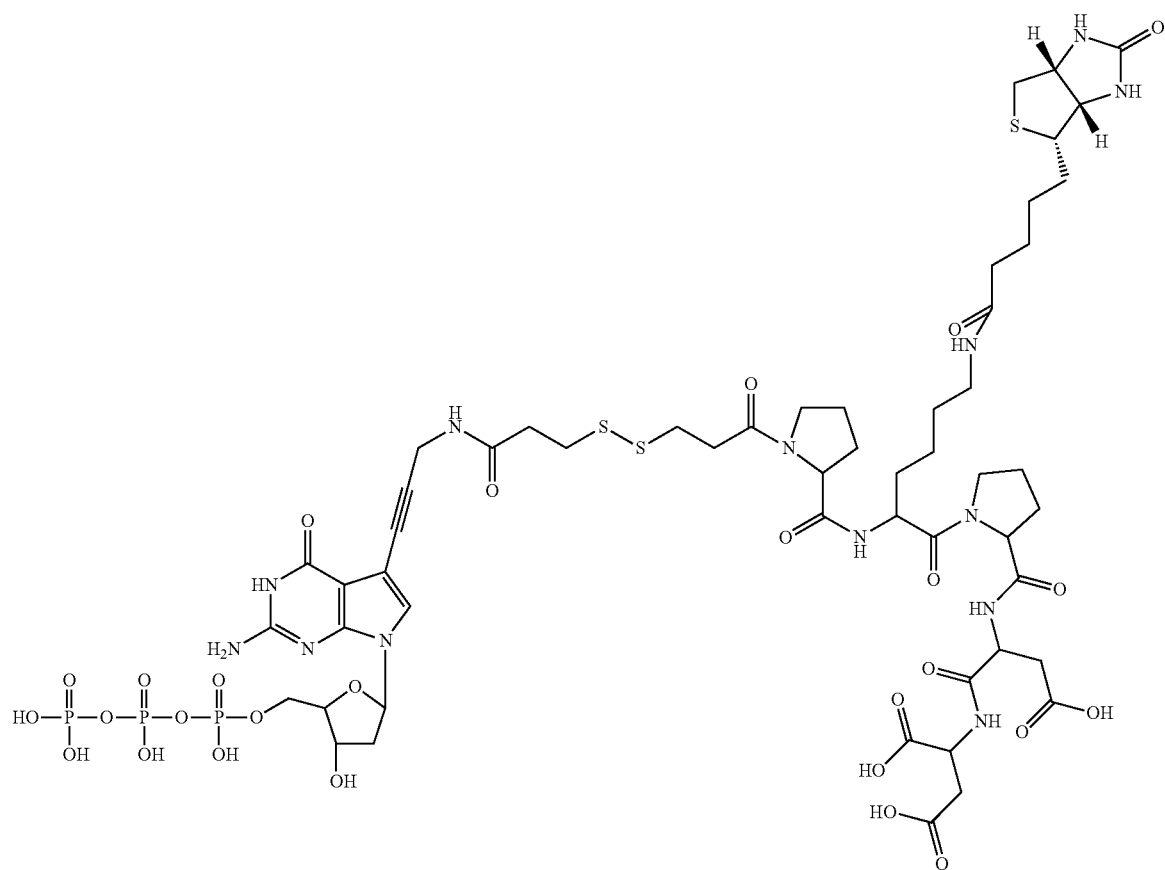
(22)
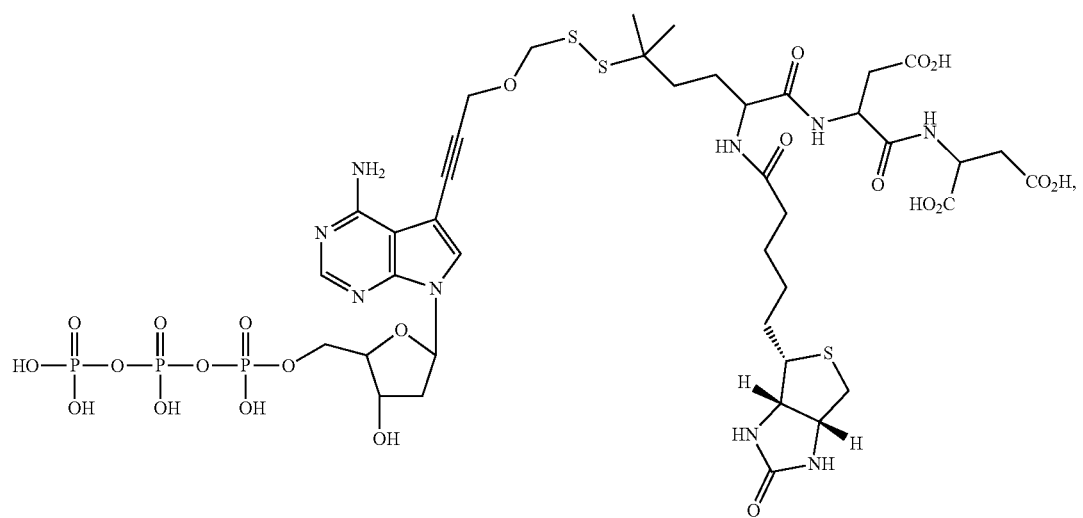
(23)

(24)
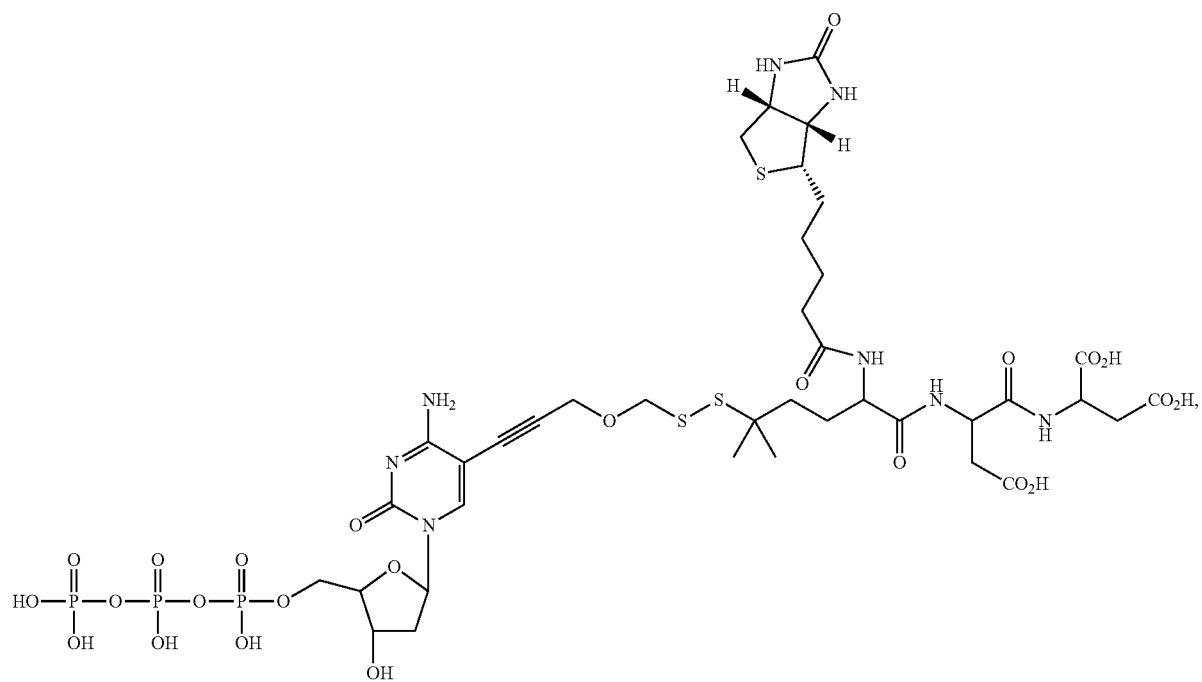
(25)
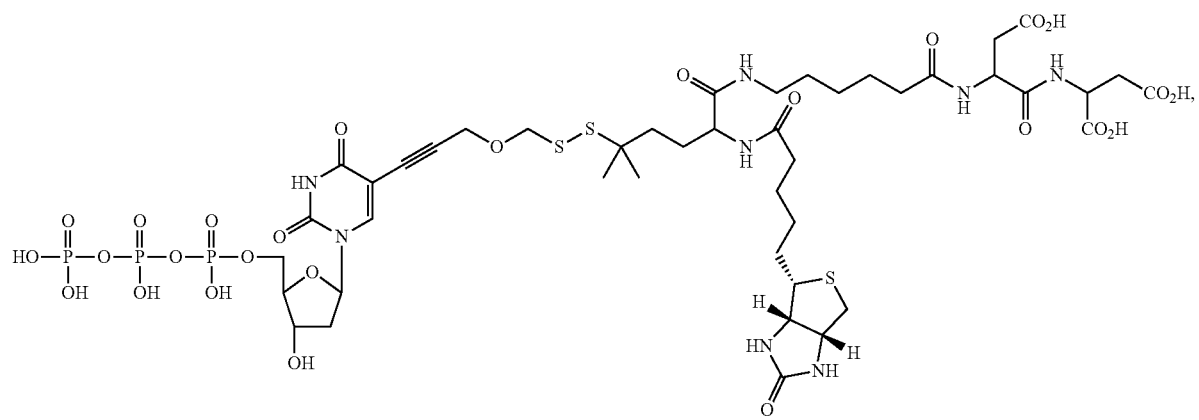

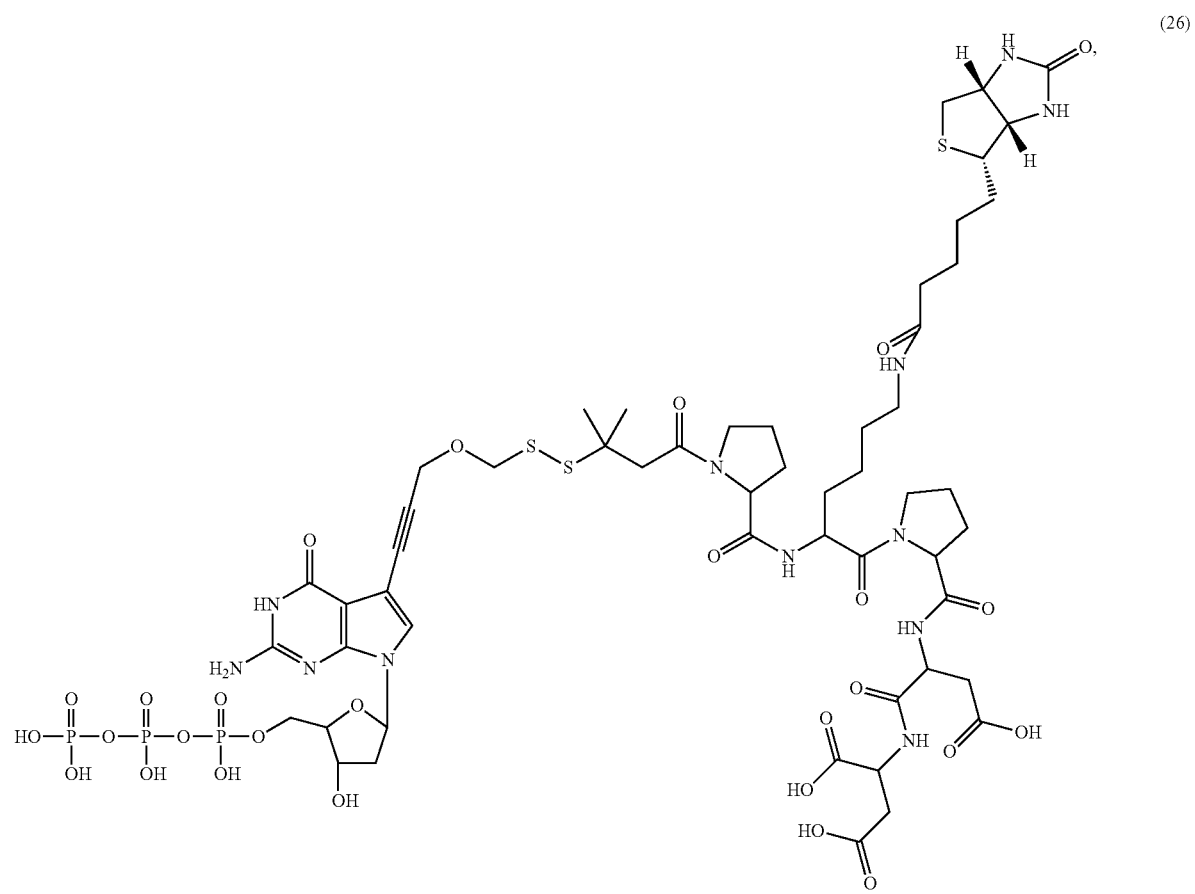
(26)
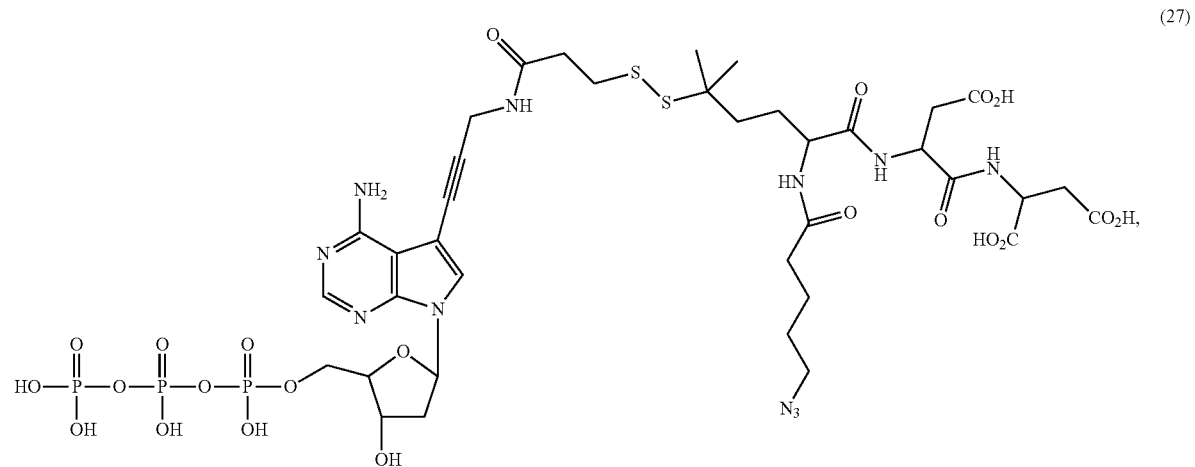
(27)

(28)
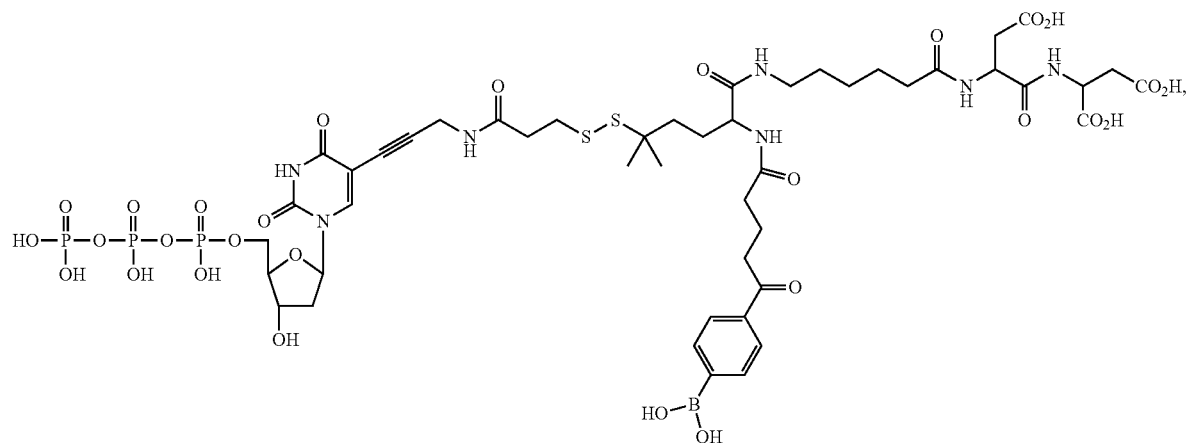
wherein B is a boron atom
(29)
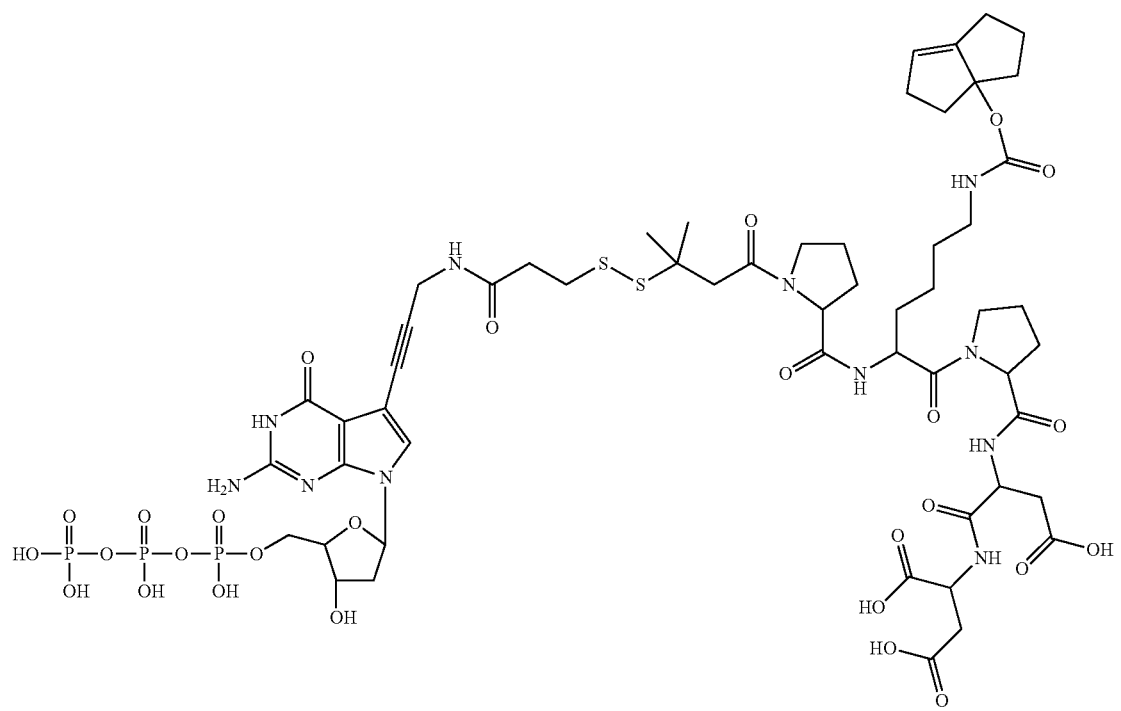

(30)
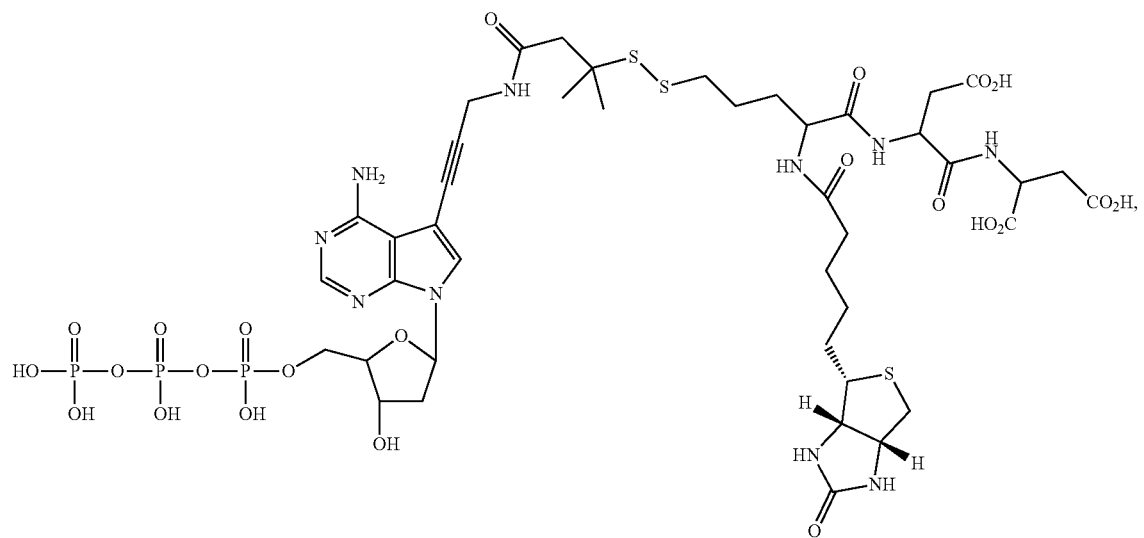
(31)
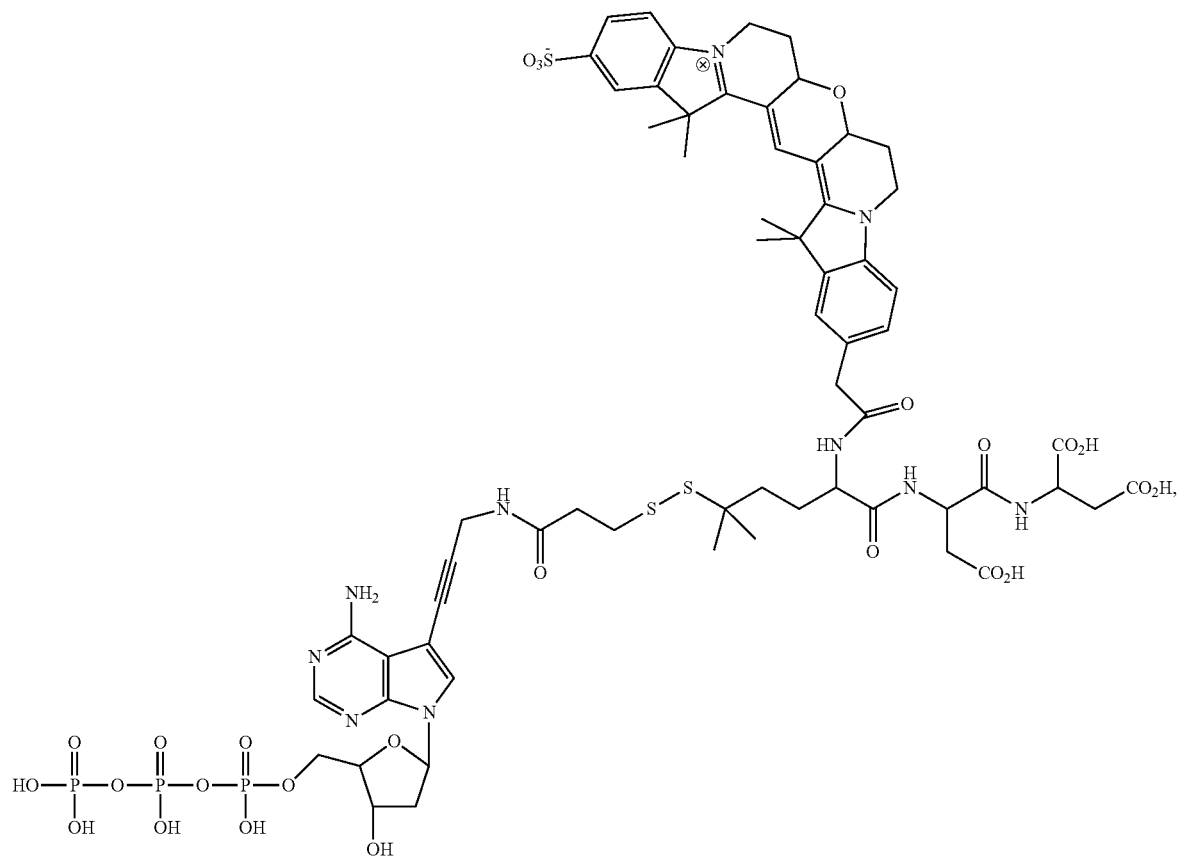

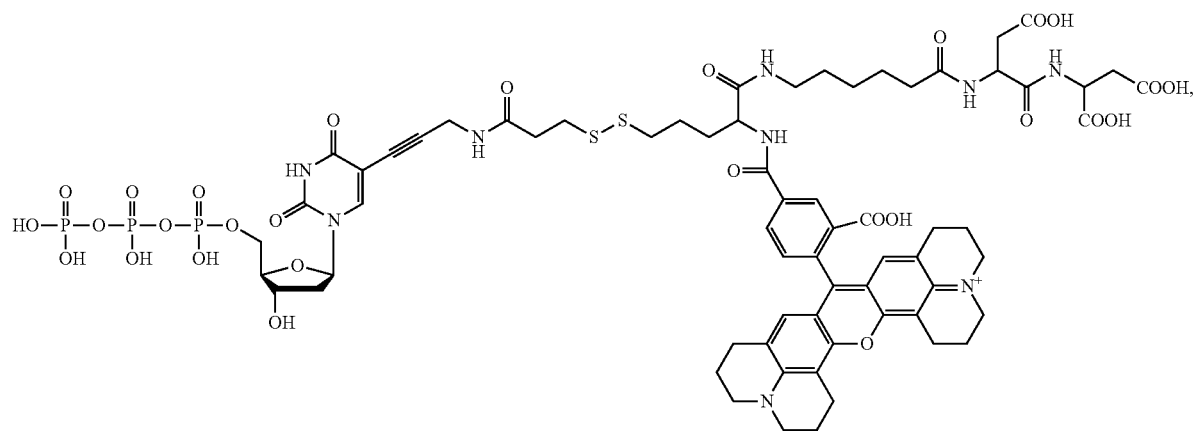
(32)
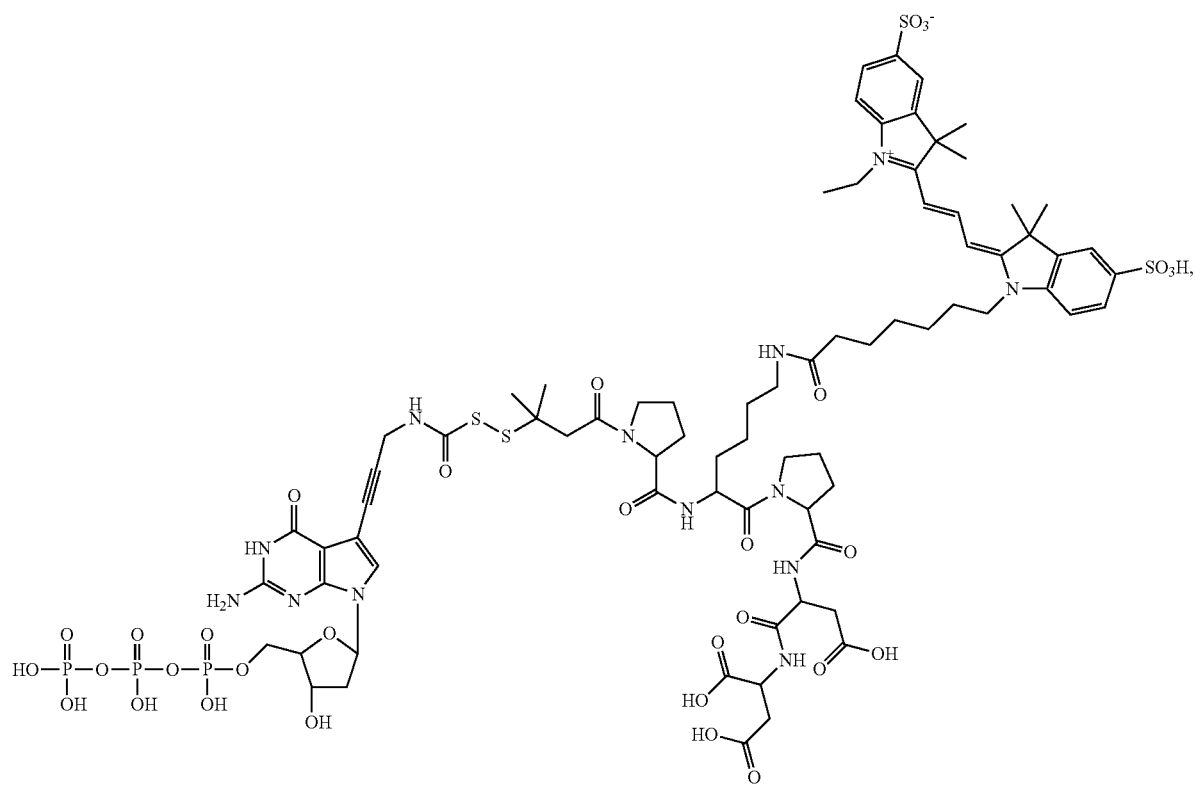
(33)

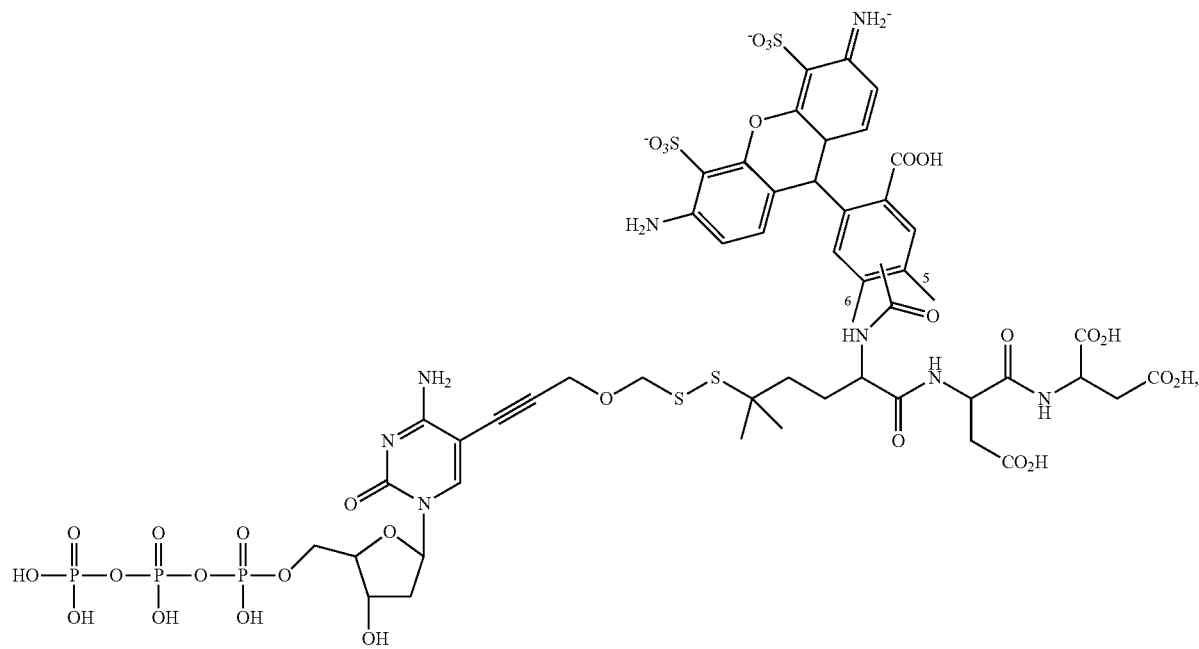
(34)
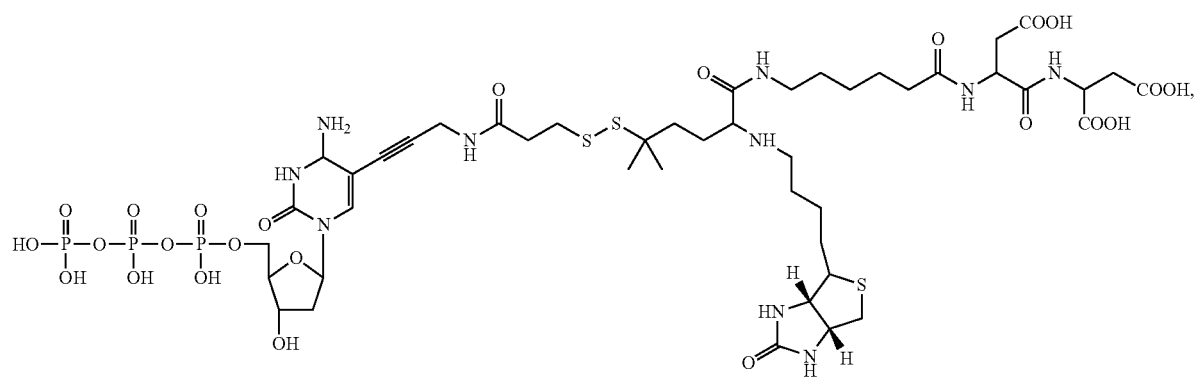
(40)
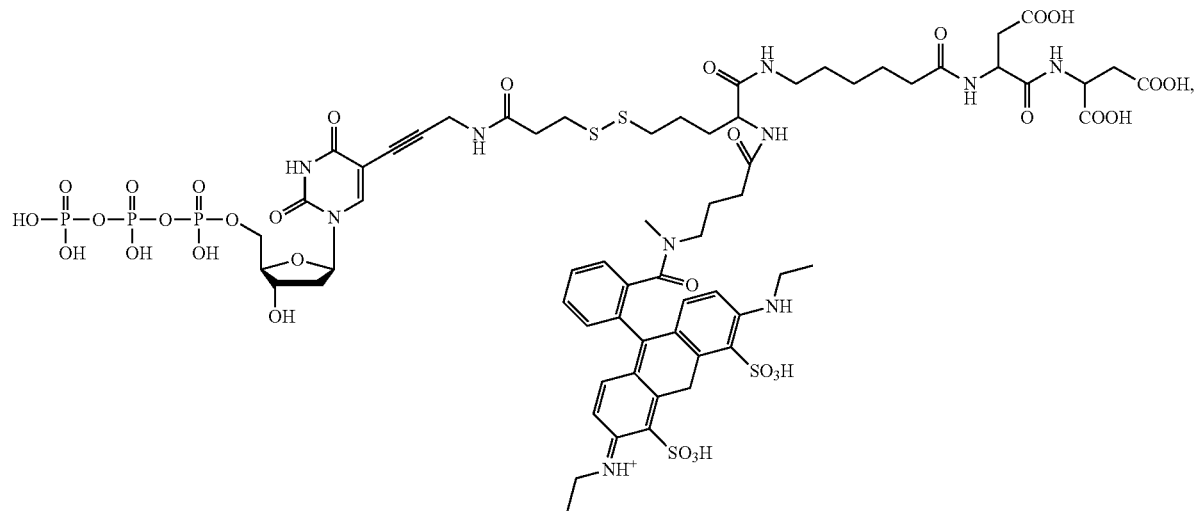
(41)

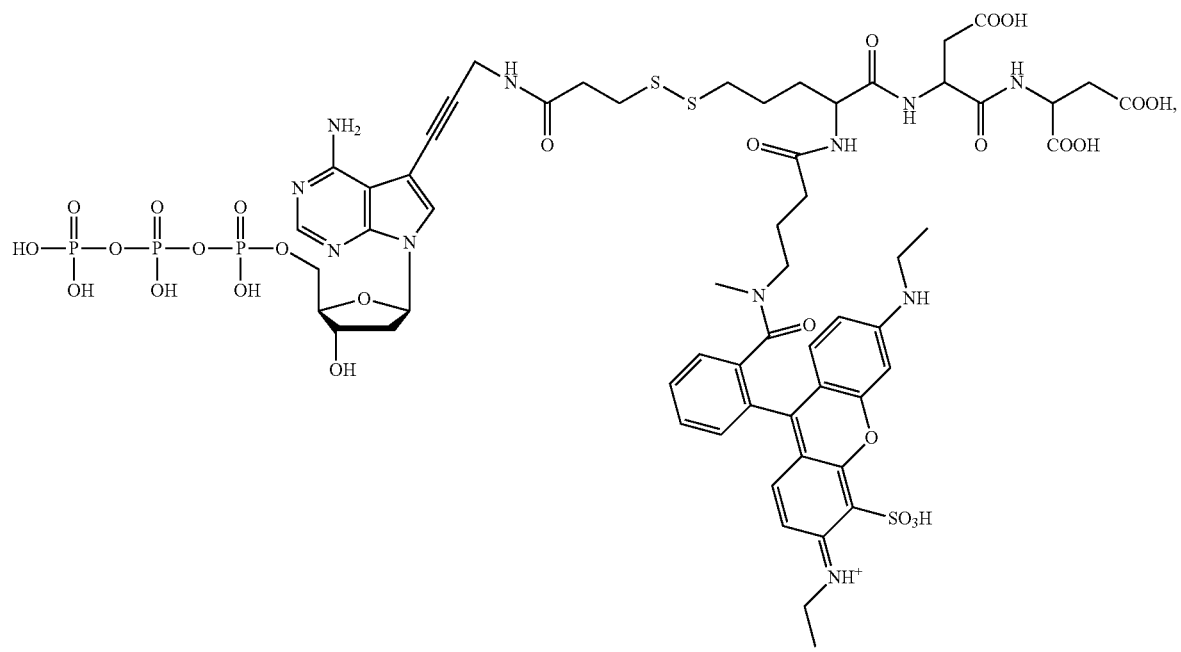
(42)
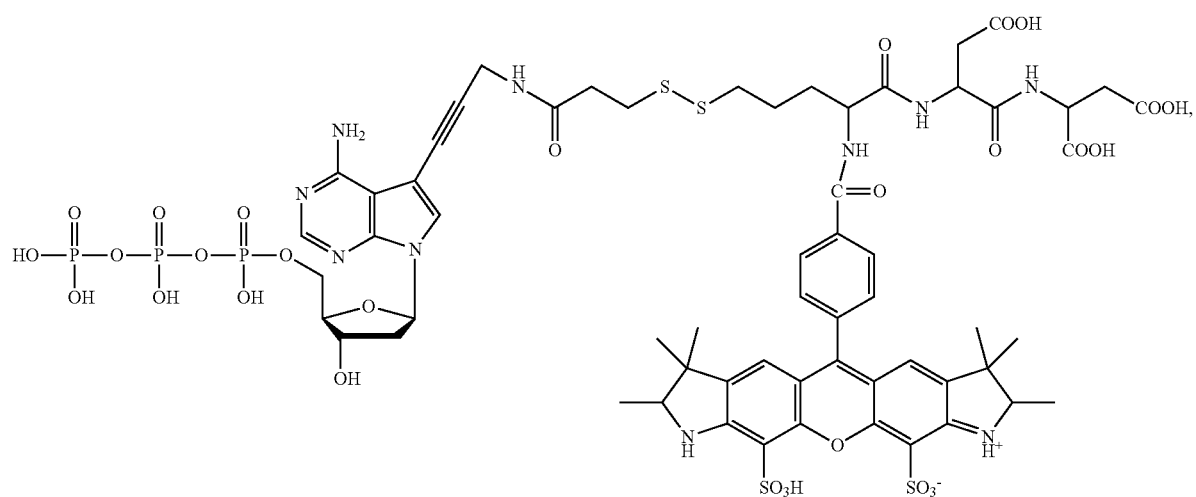
(43)
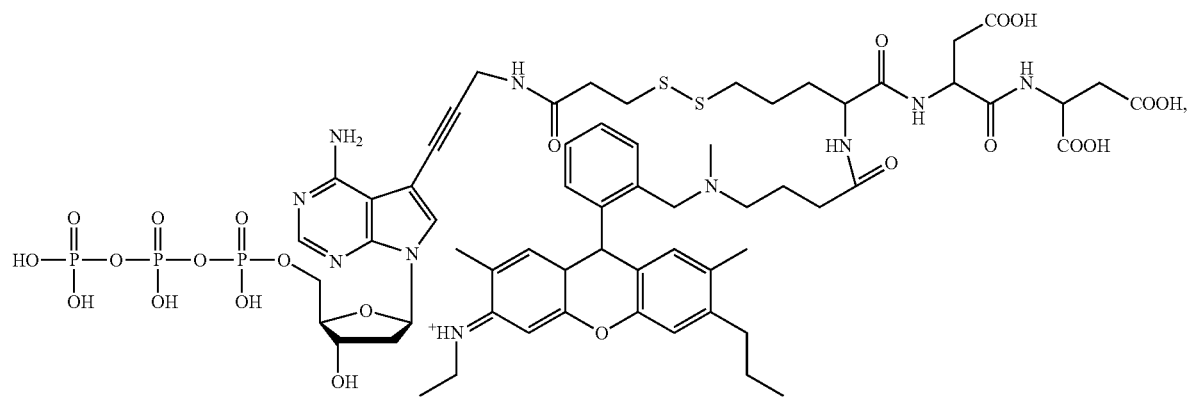
(44)

(45)
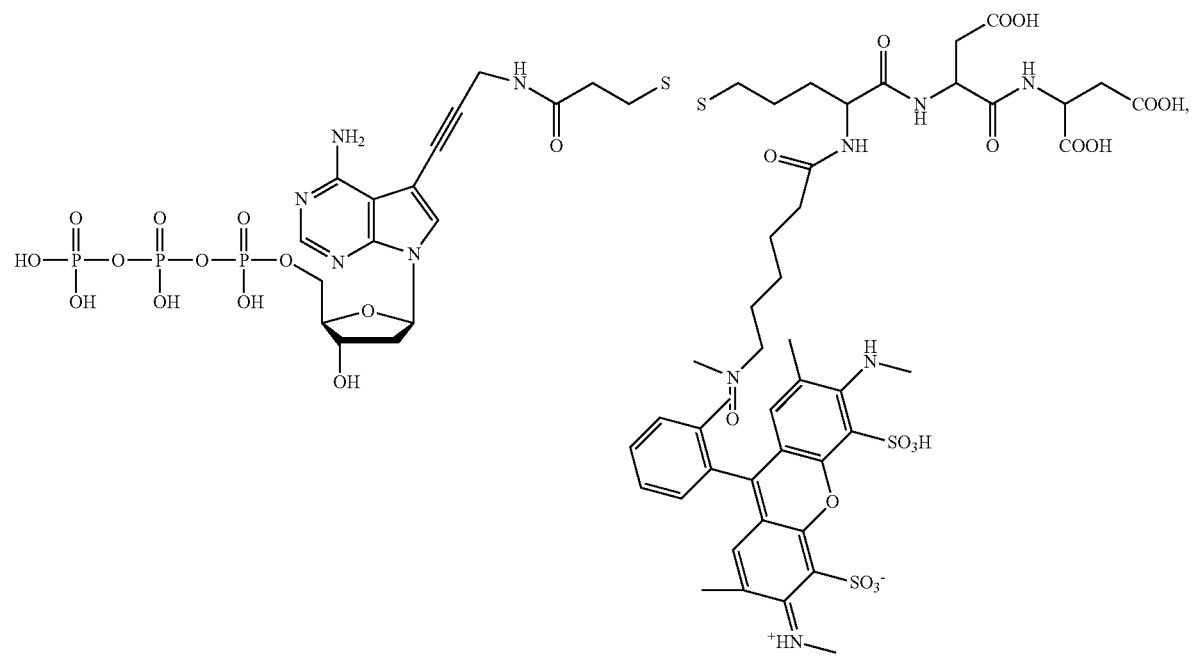
(46)
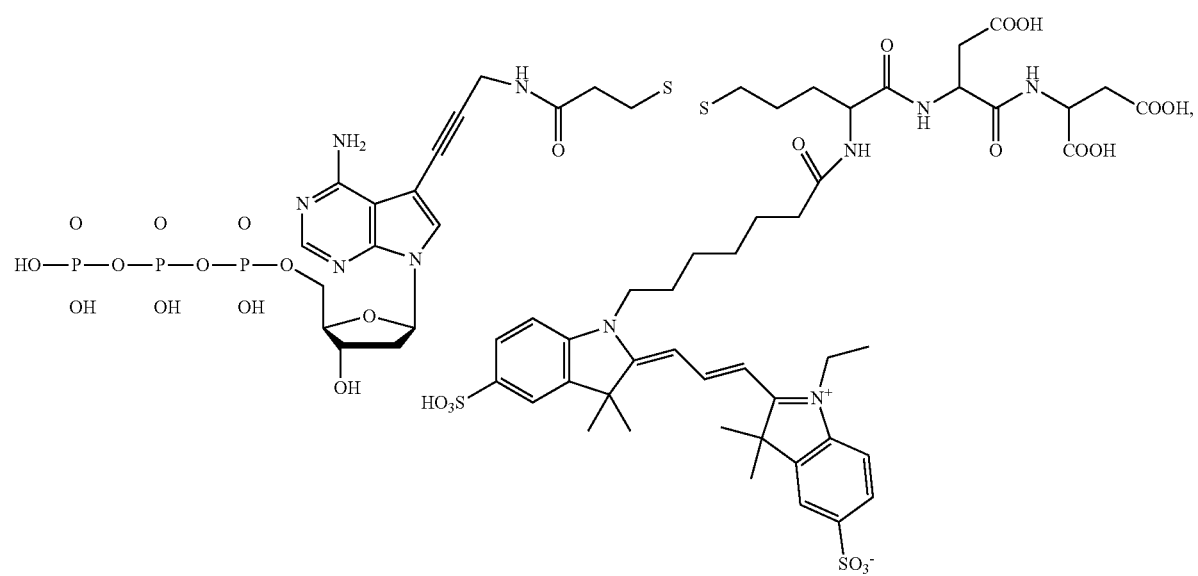

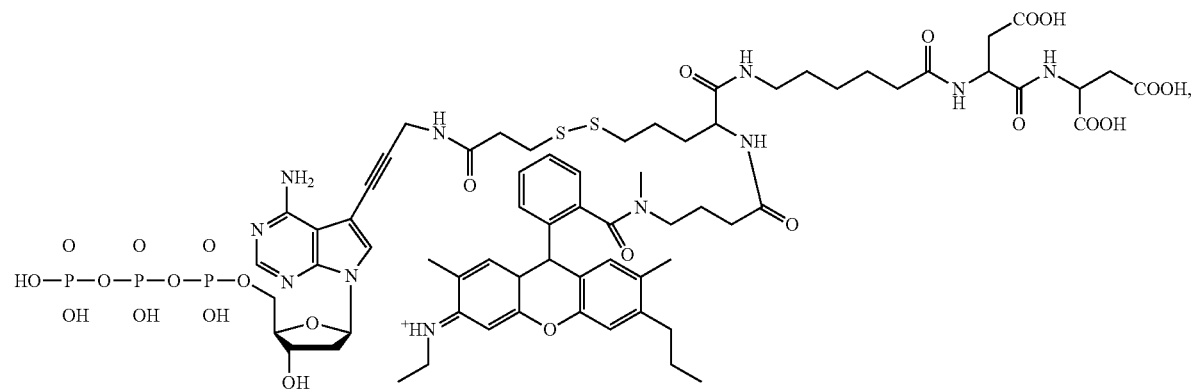
(47)
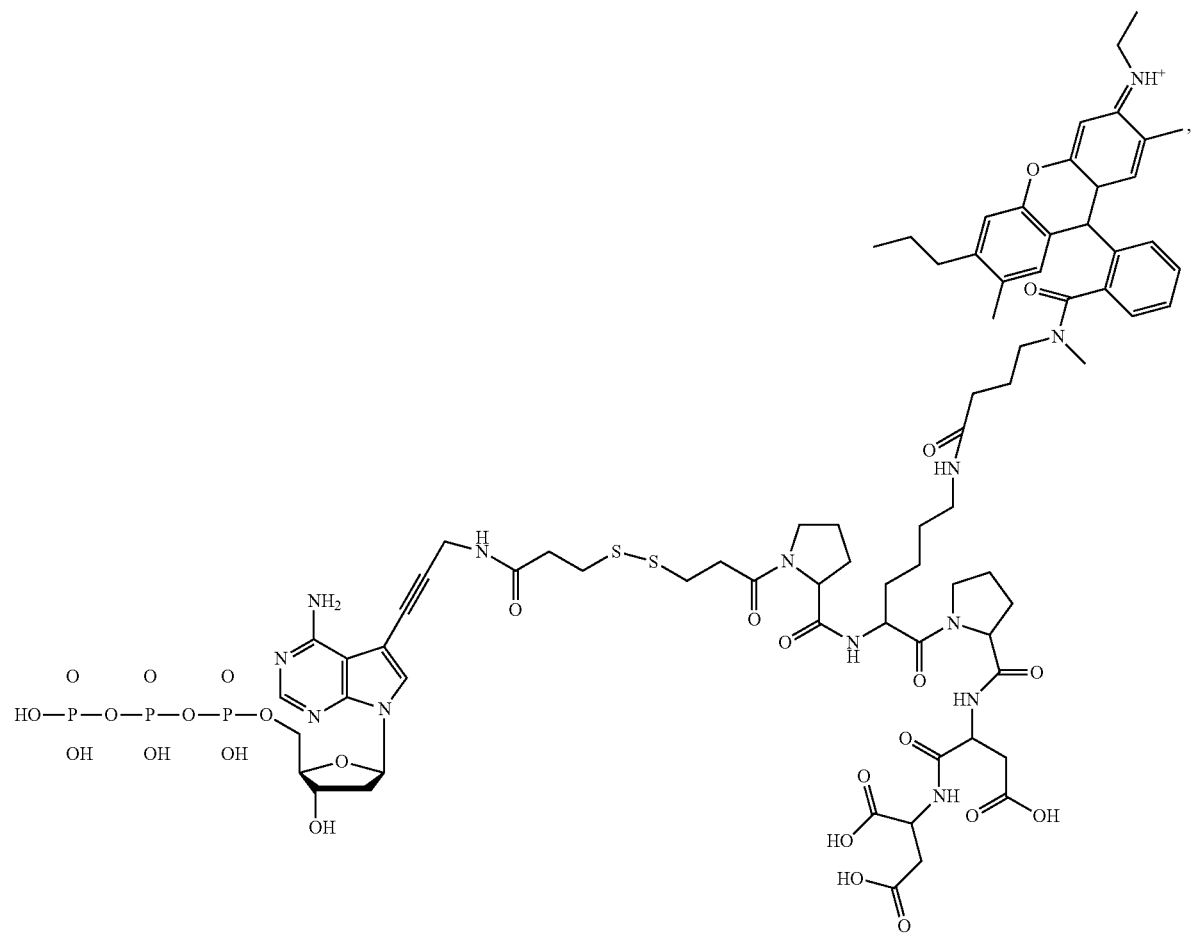
(48)

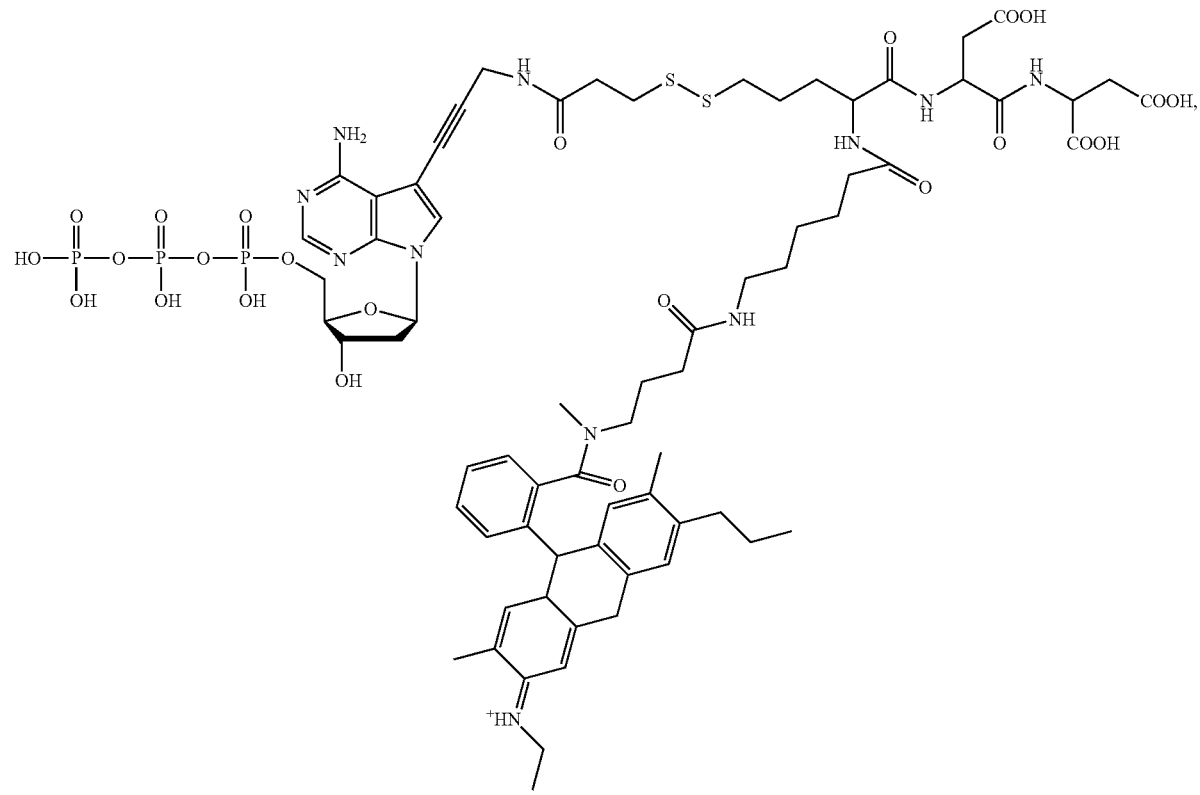
(49)
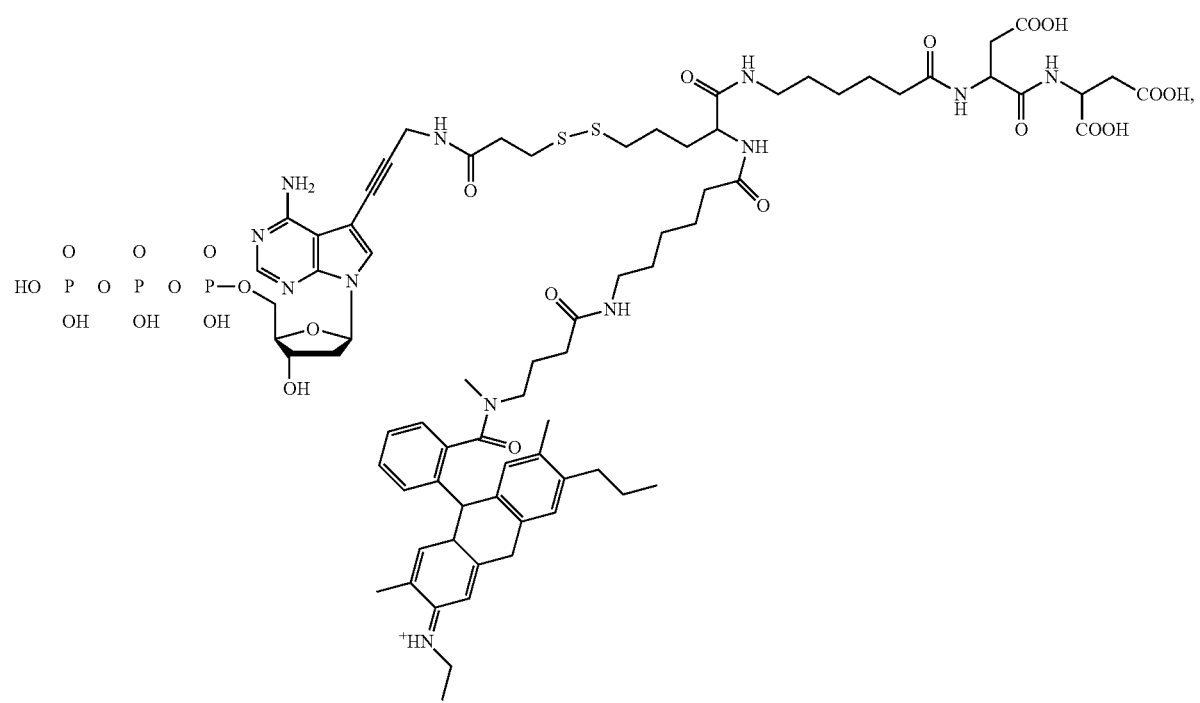
(50)

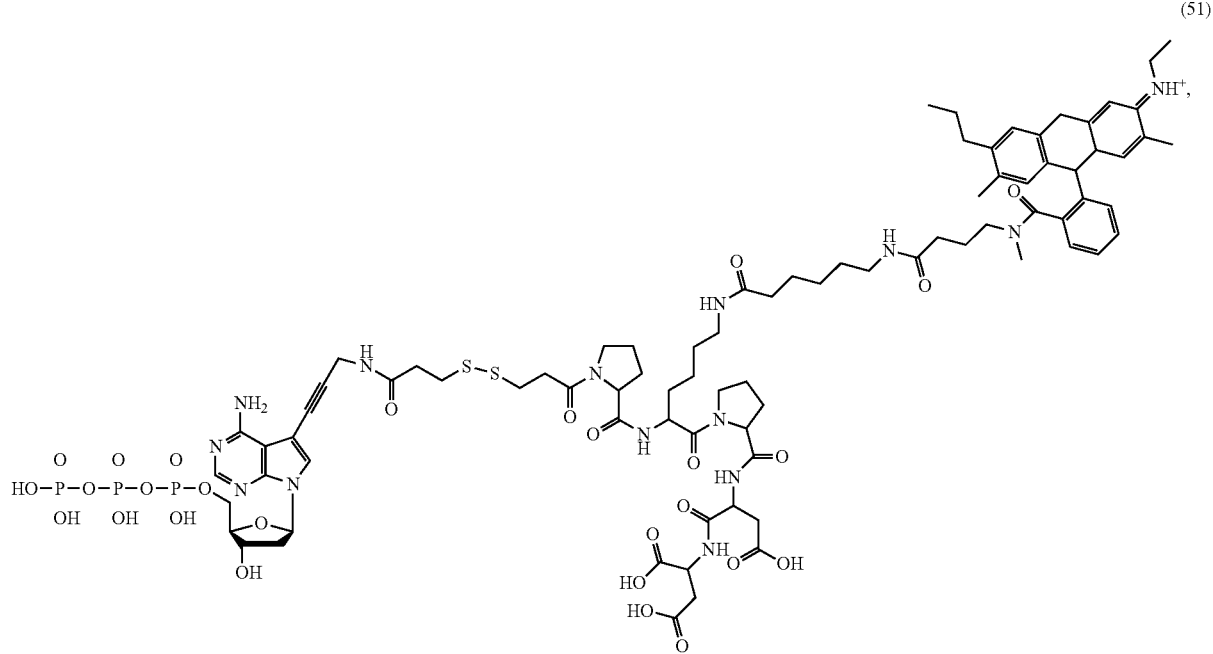
(51)
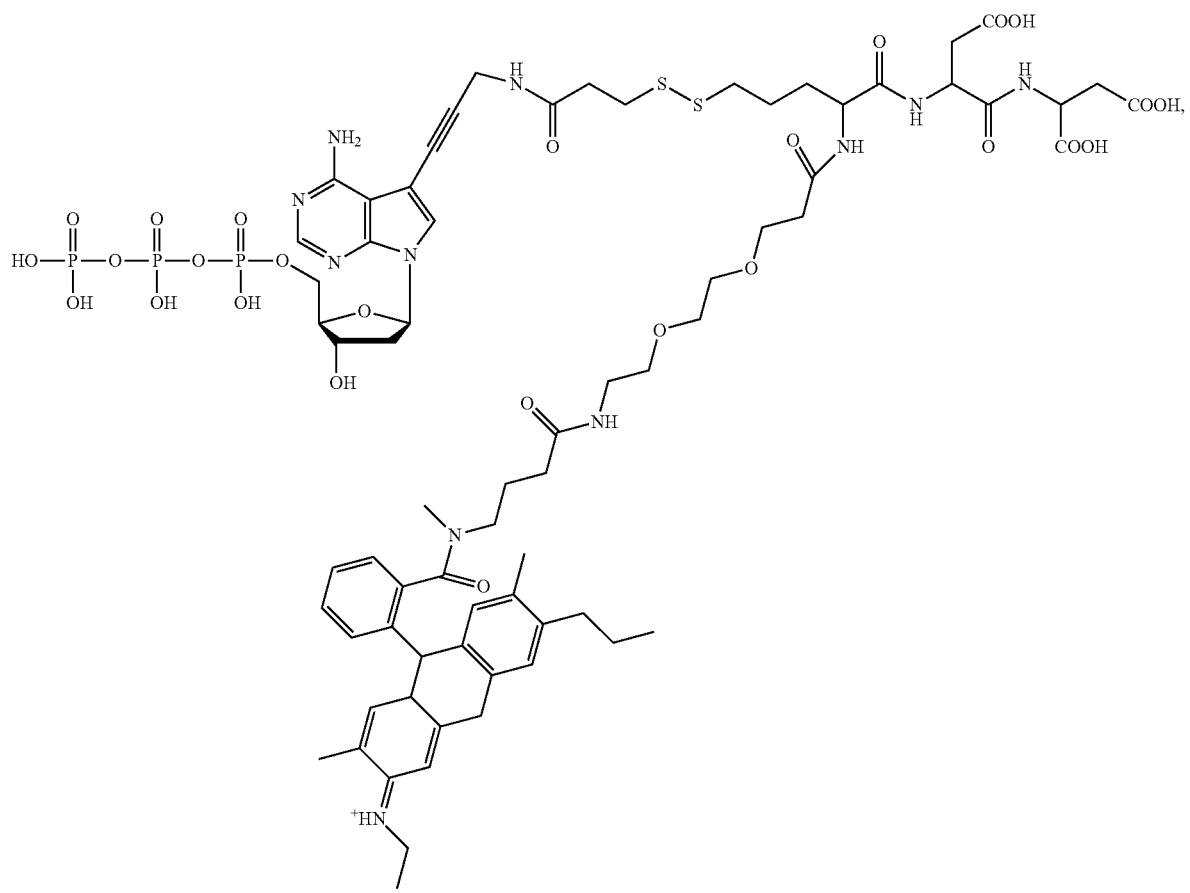
(53)

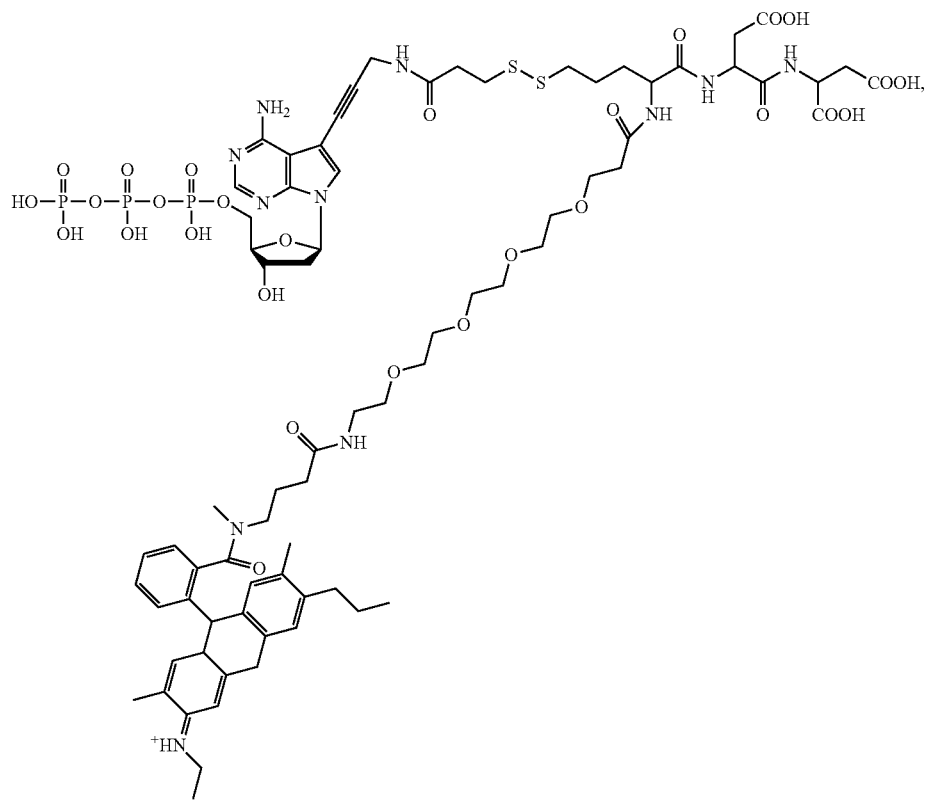
(53)
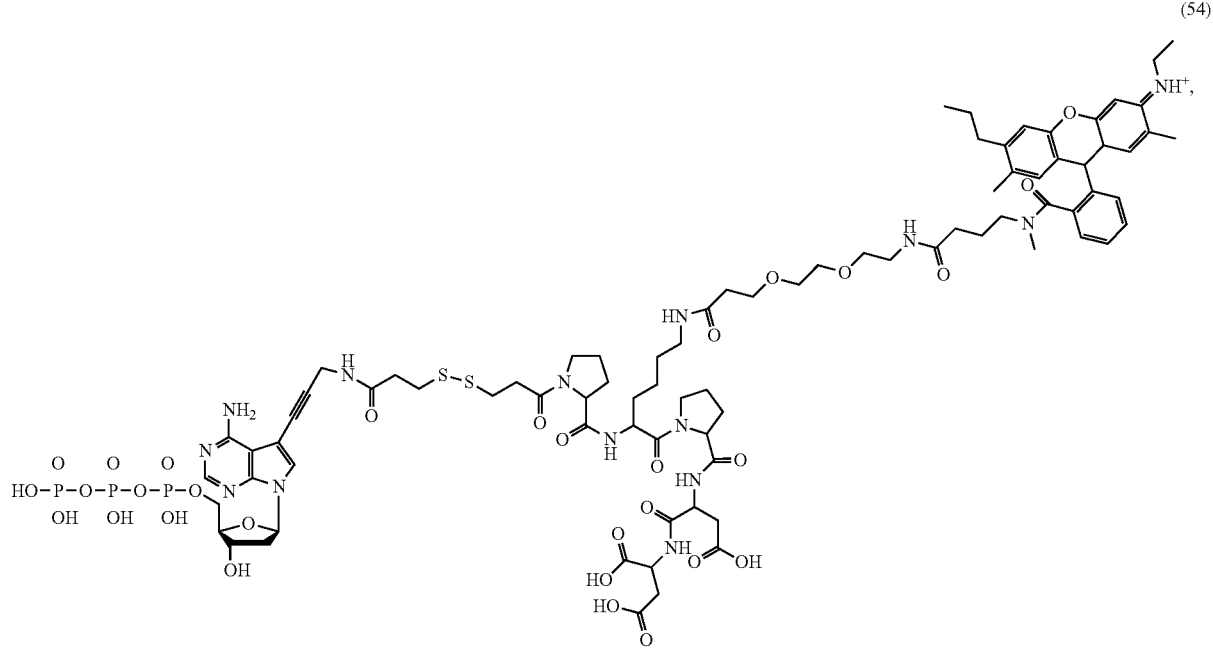
(54)

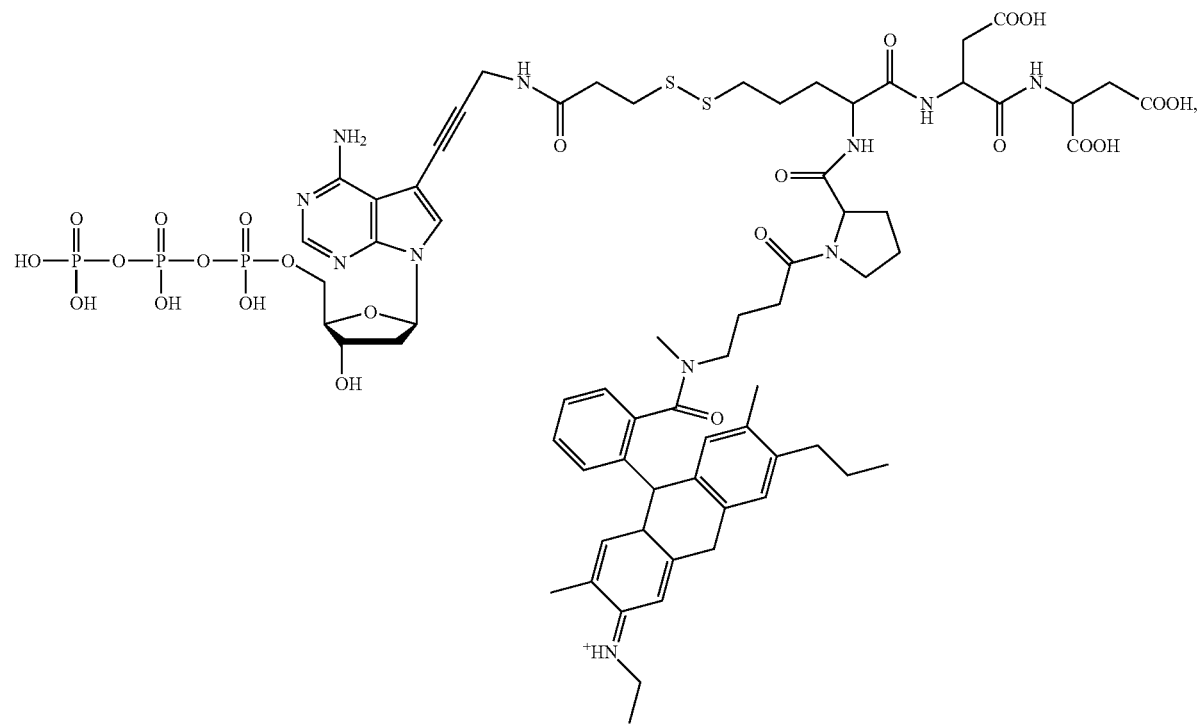
(55)
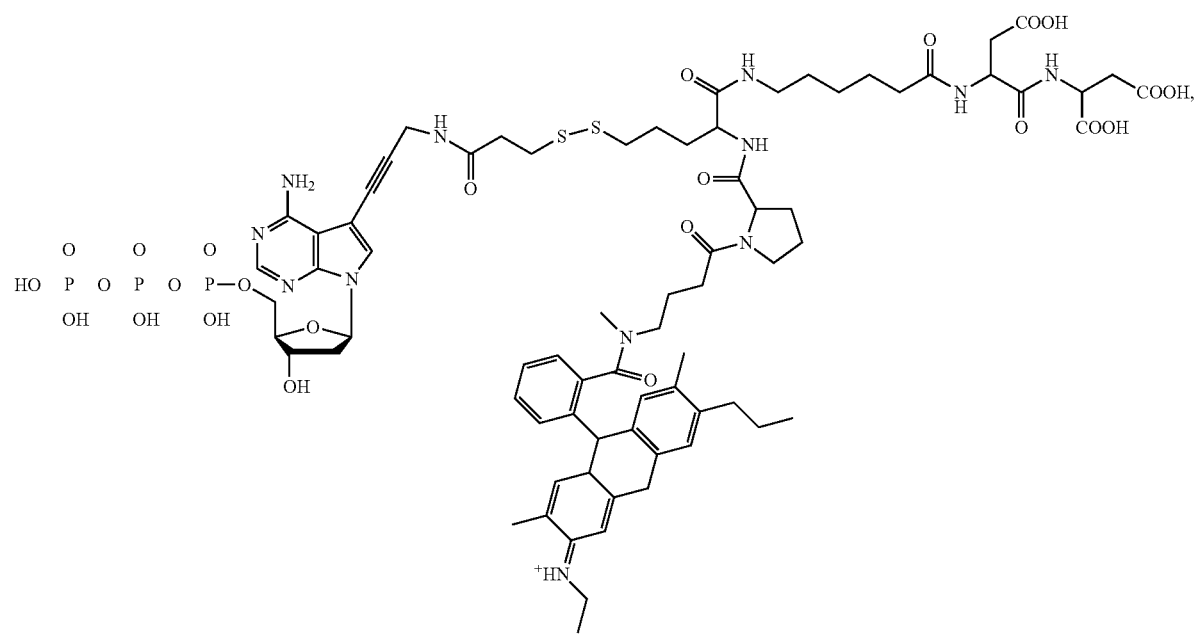
(56)

(57)
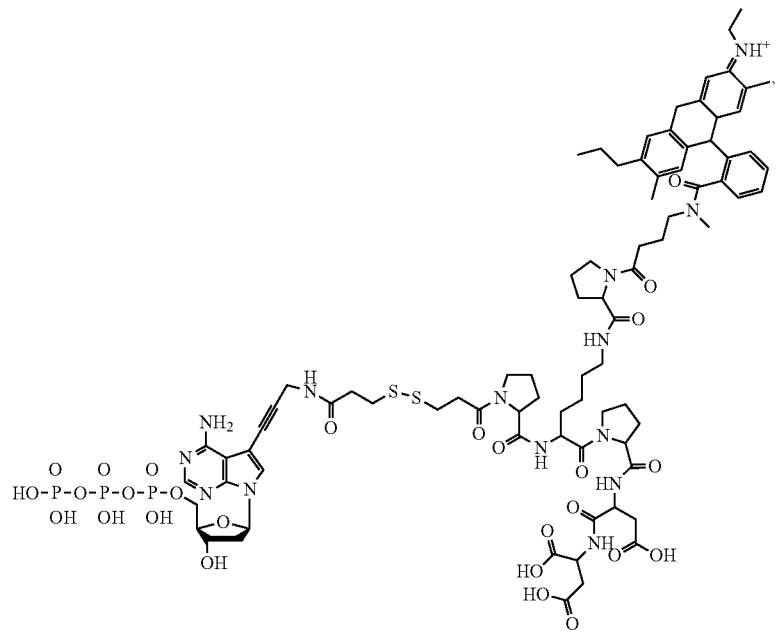
(58)
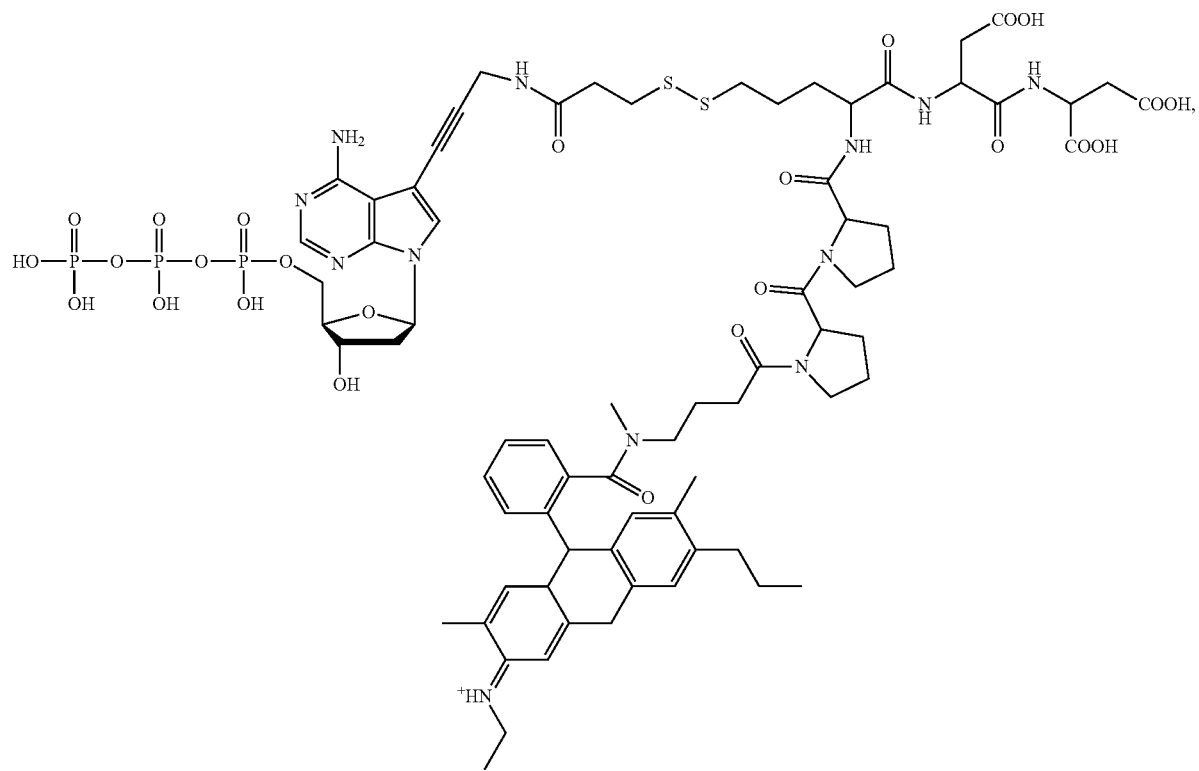

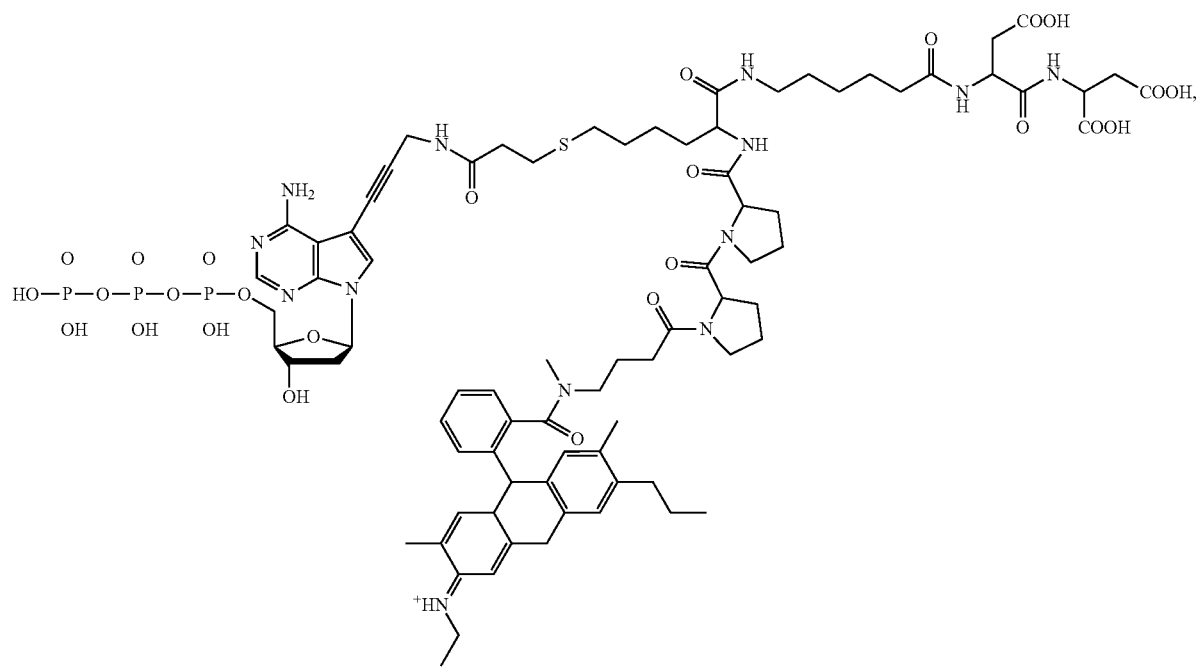
(59)
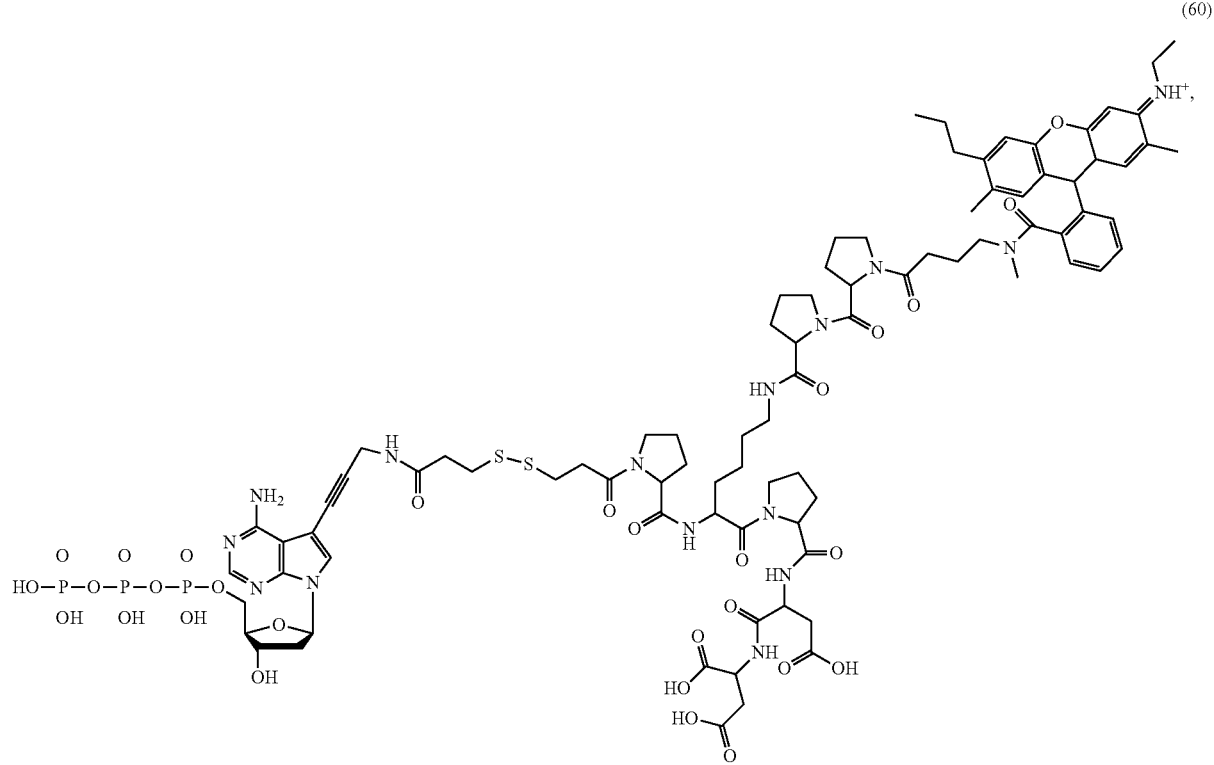
(60)

(61)
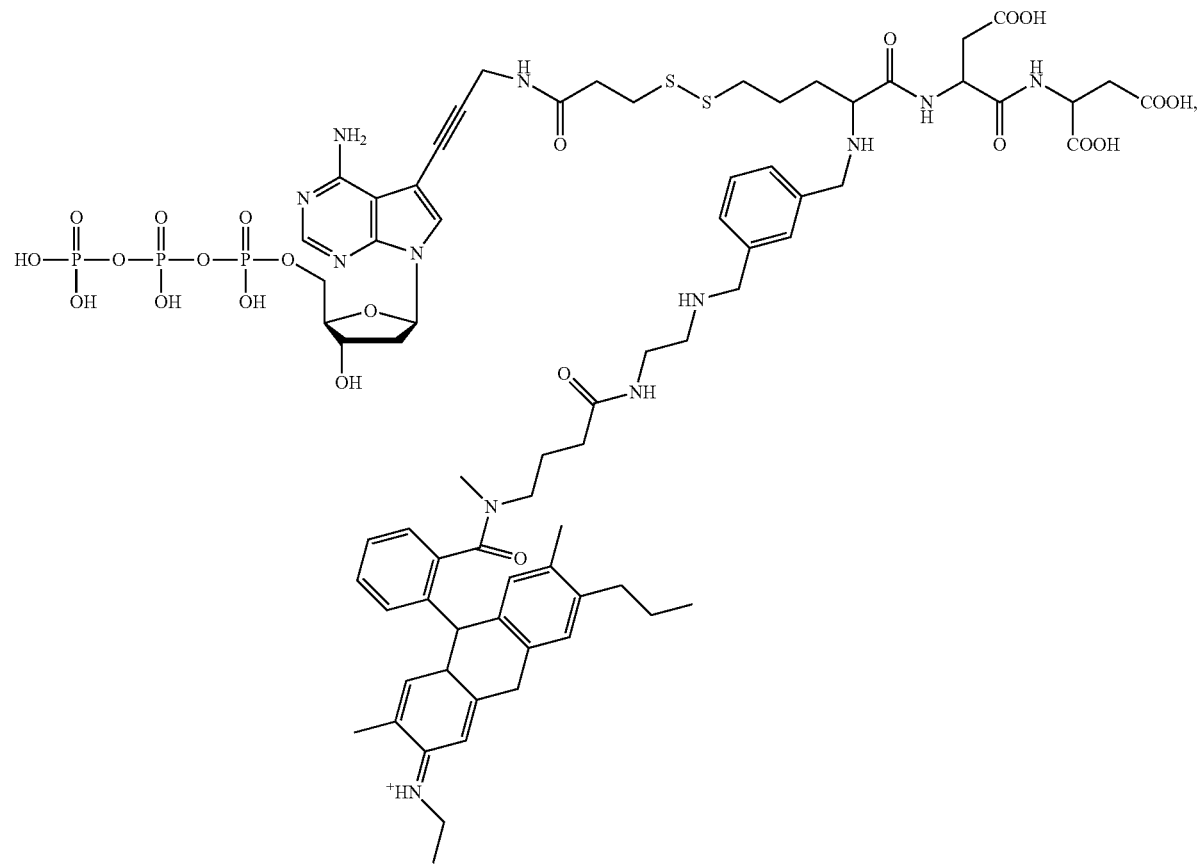
(62)
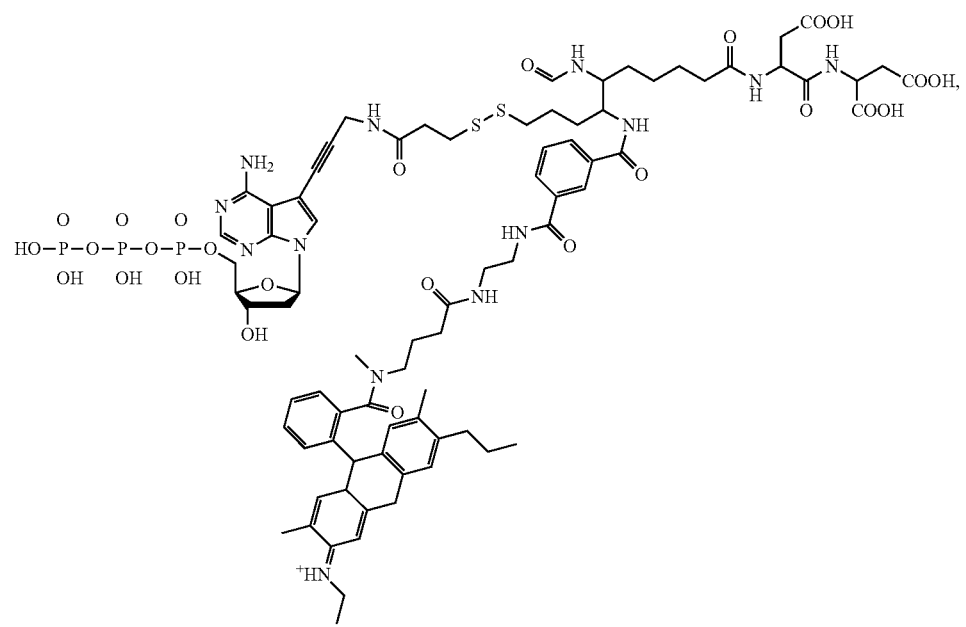

(63)
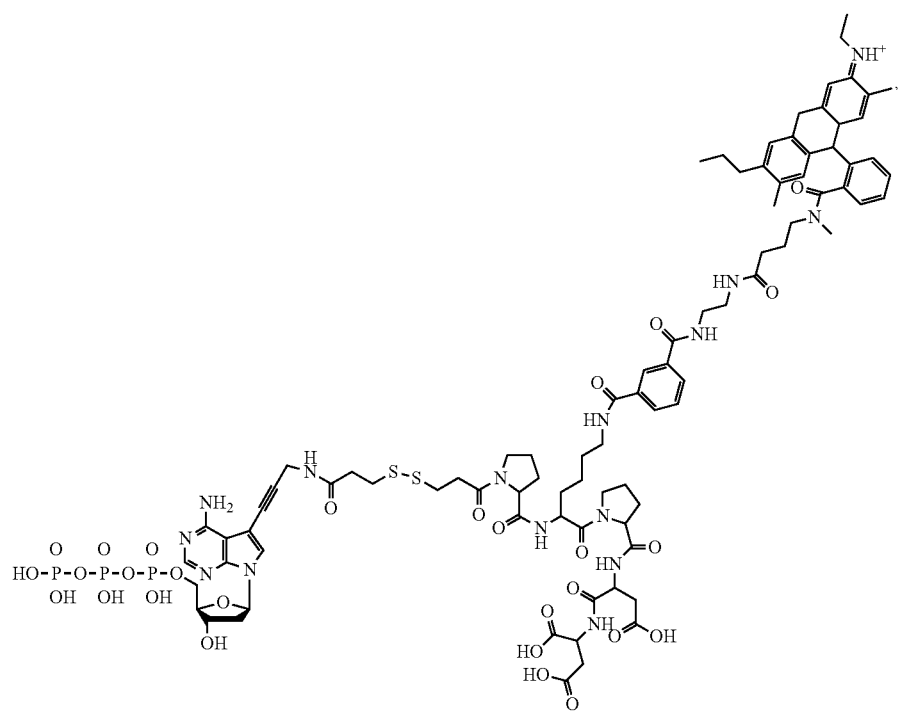
(64)
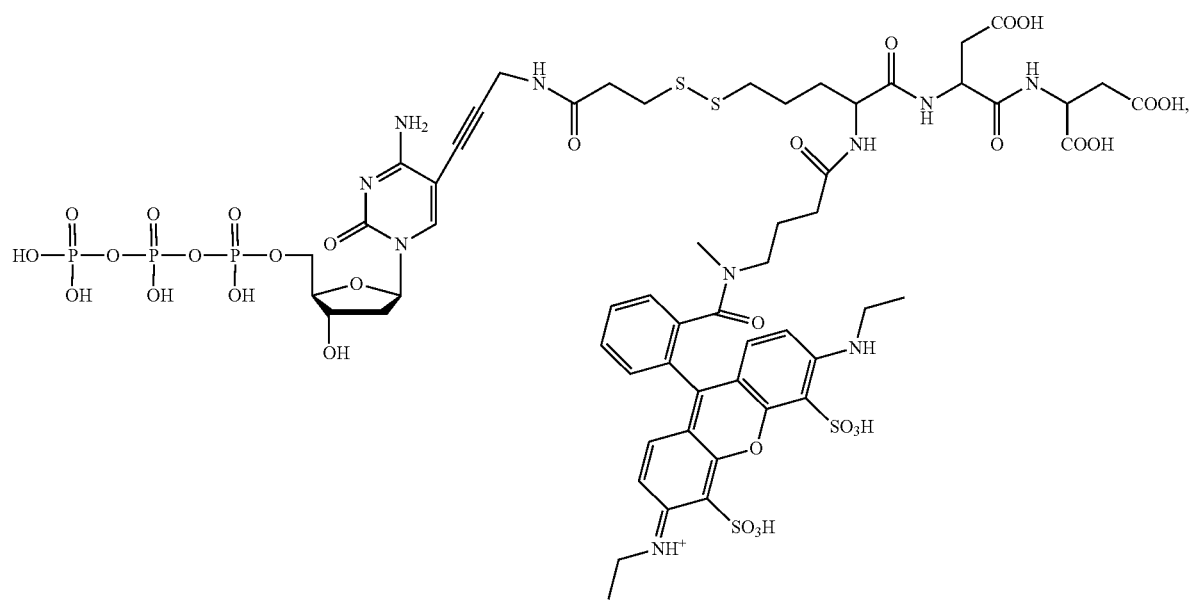

(65)
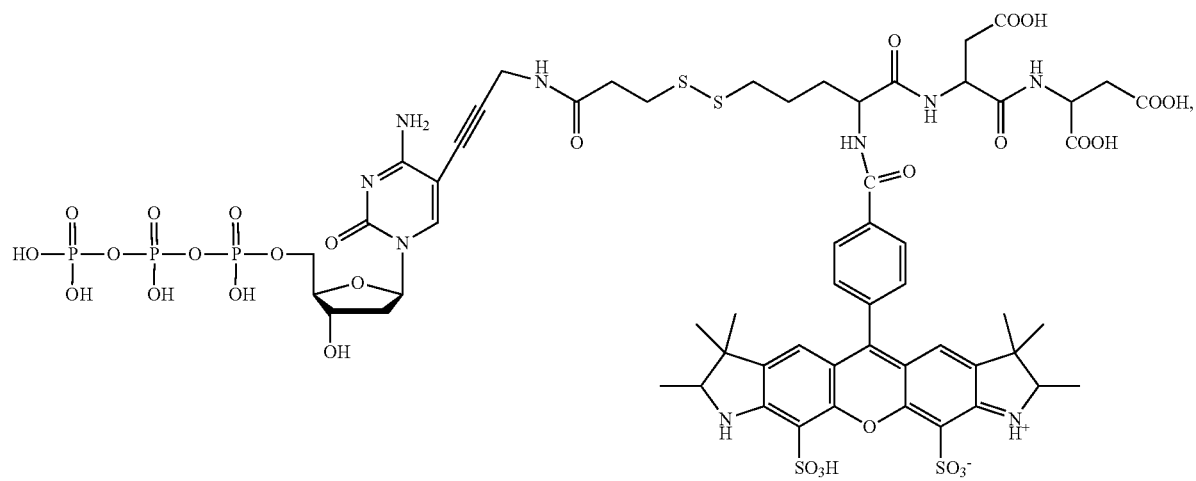
(66)
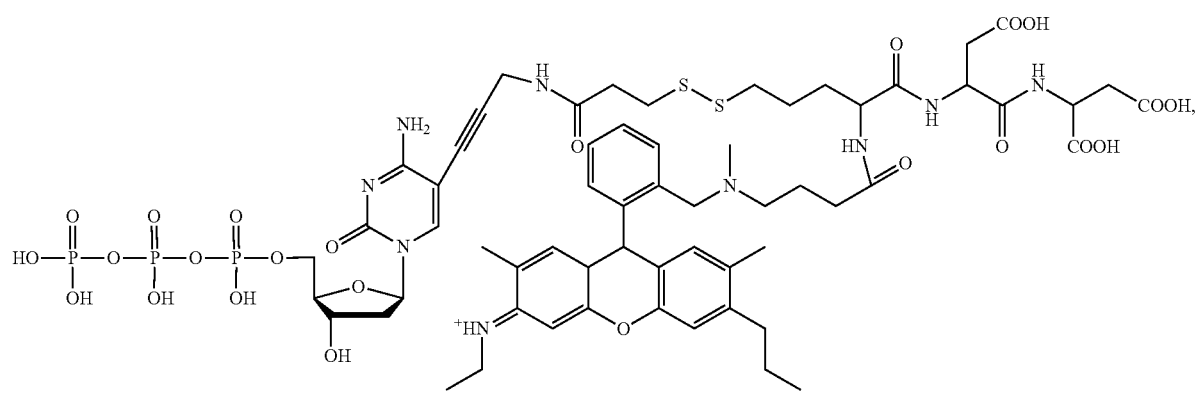
(67)
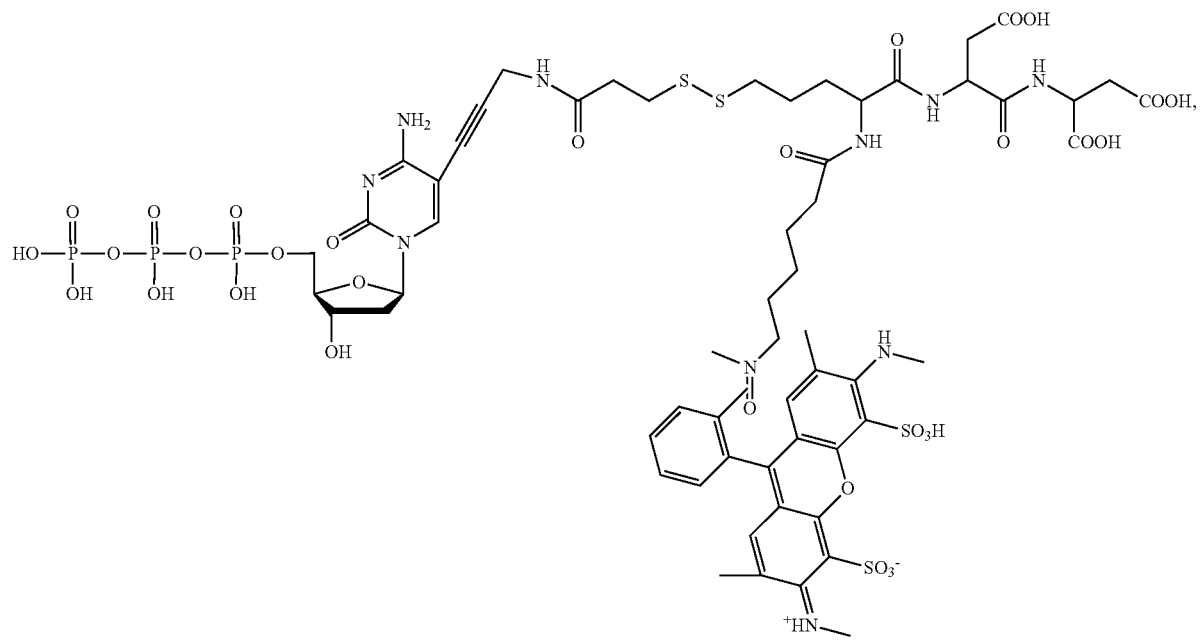

(68)
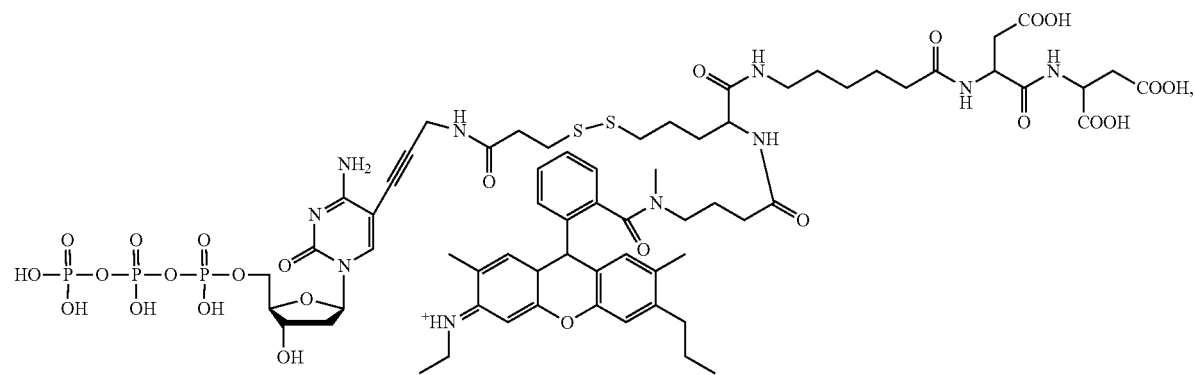
(69)
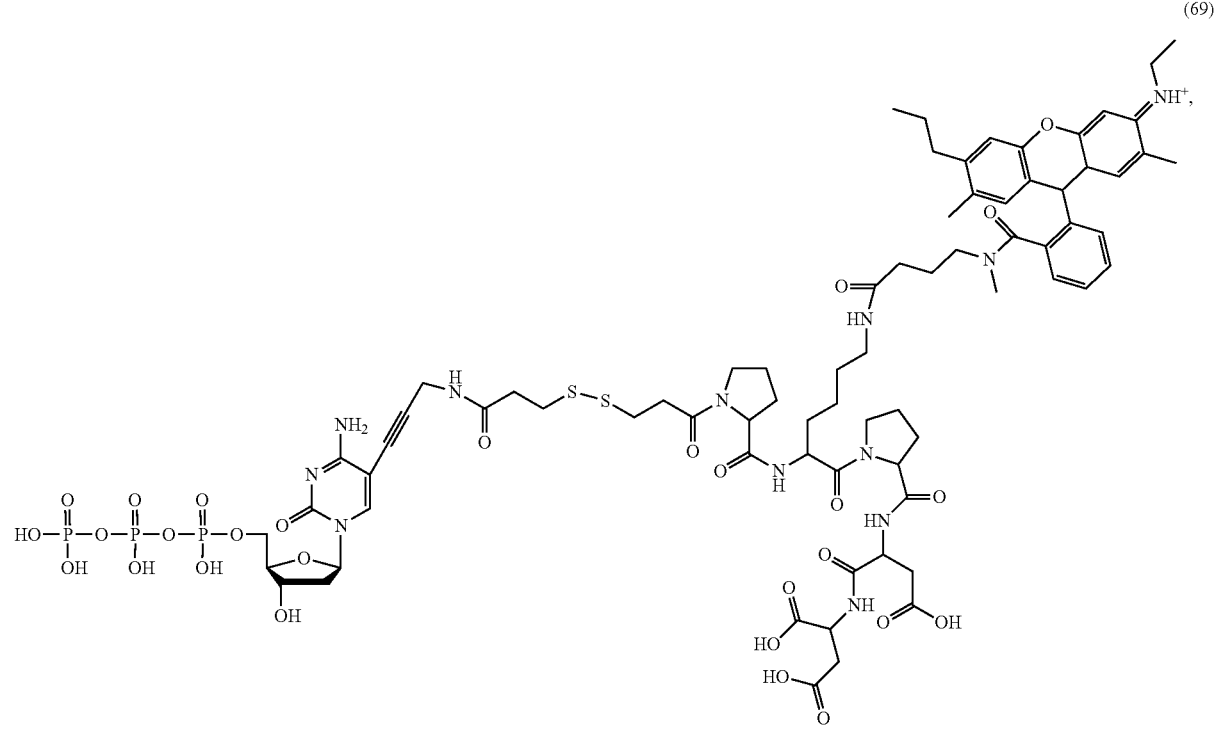

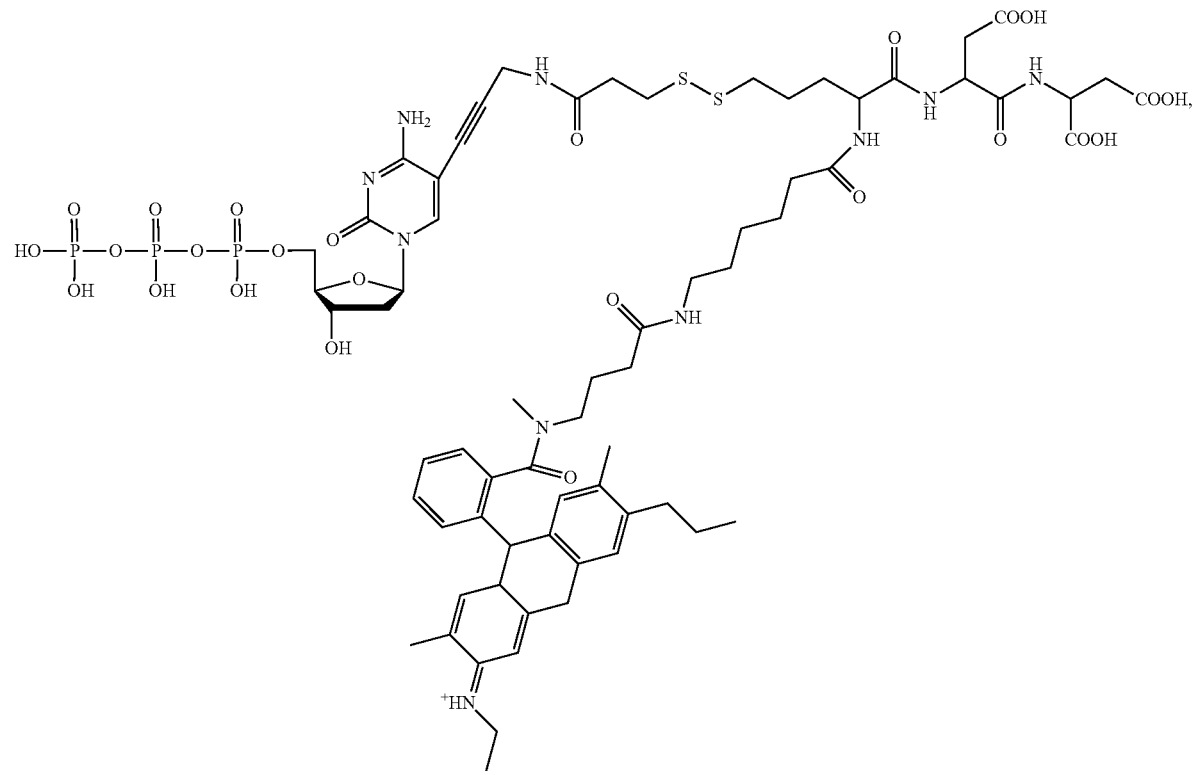
(70)
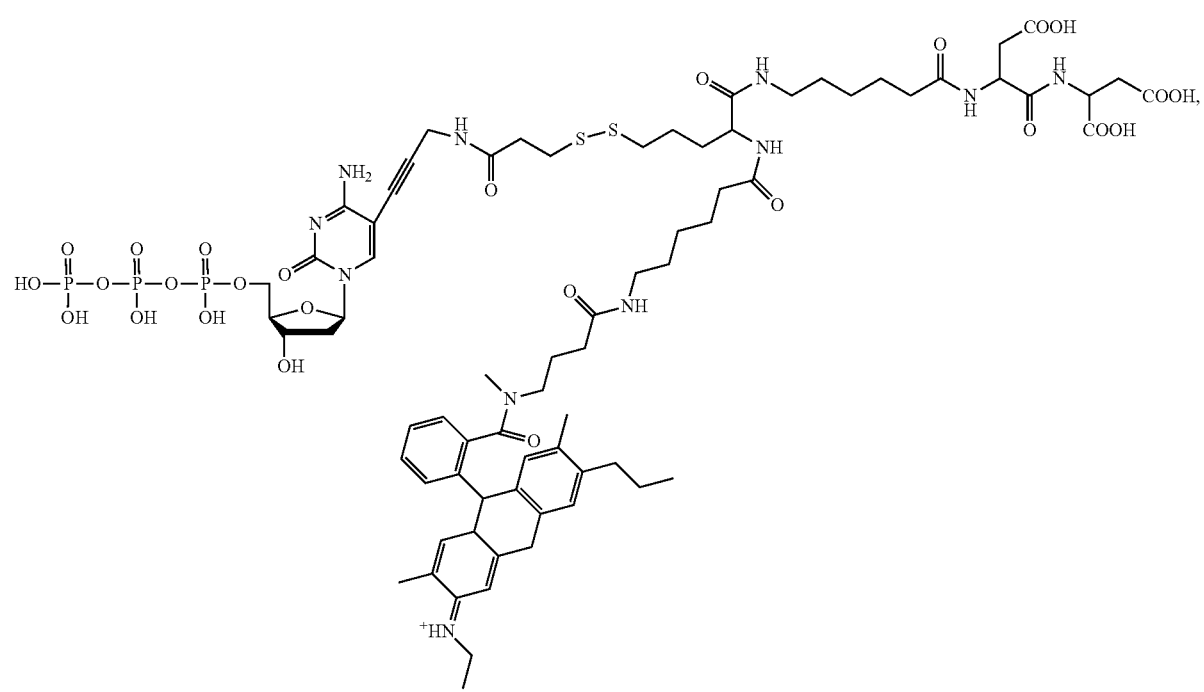
(71)

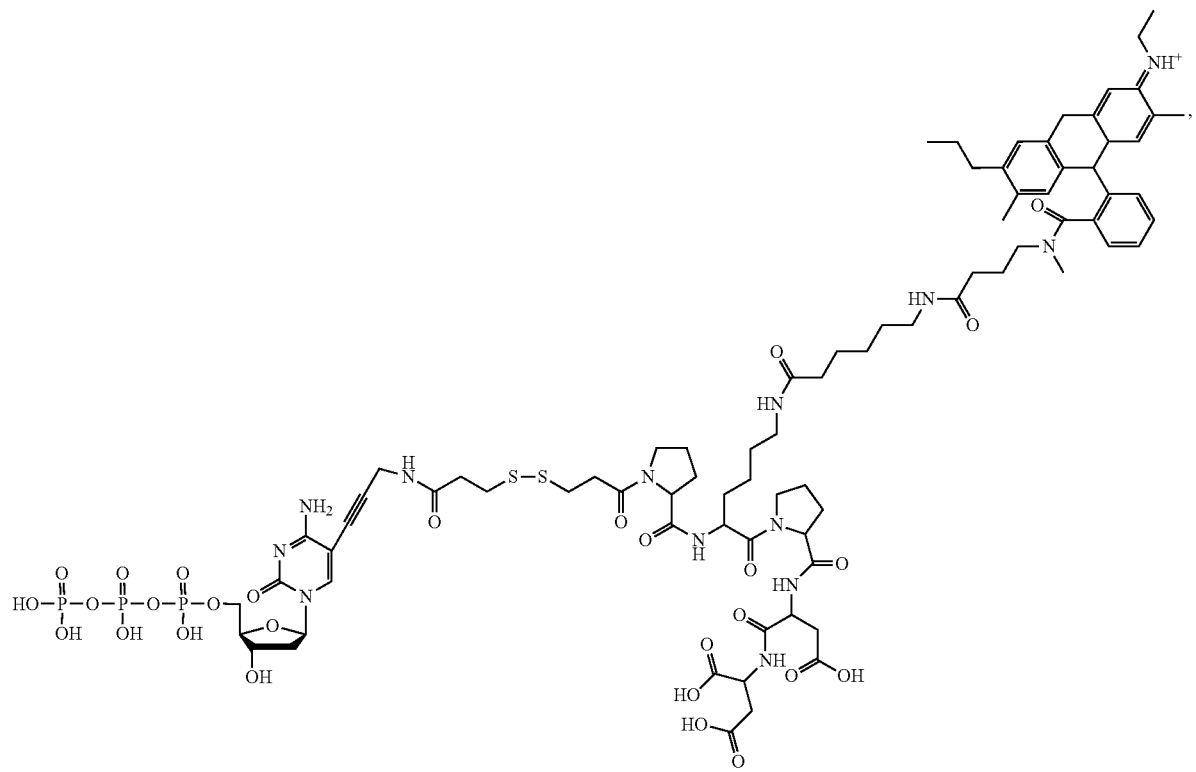
(72)
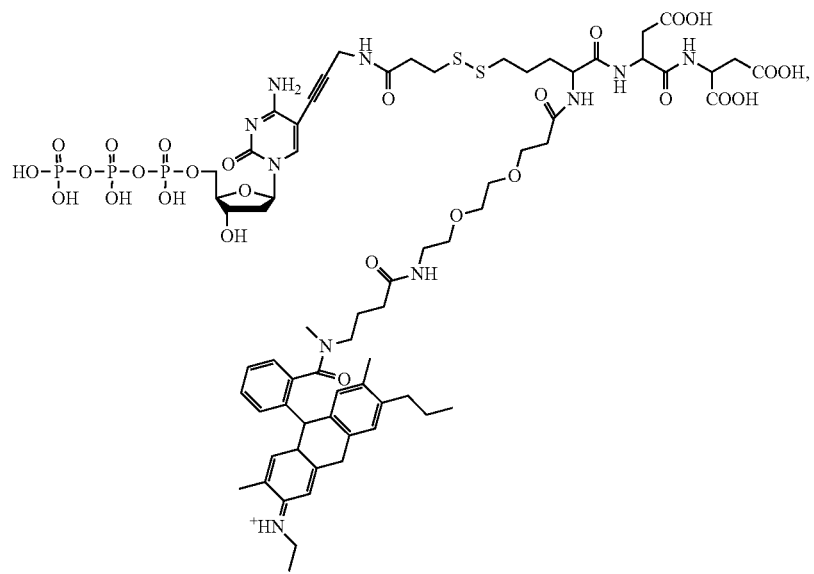
(73)

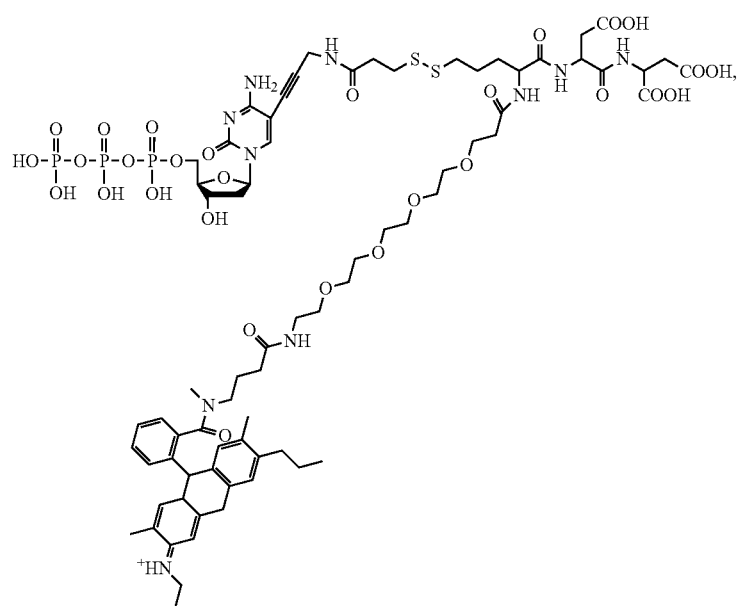
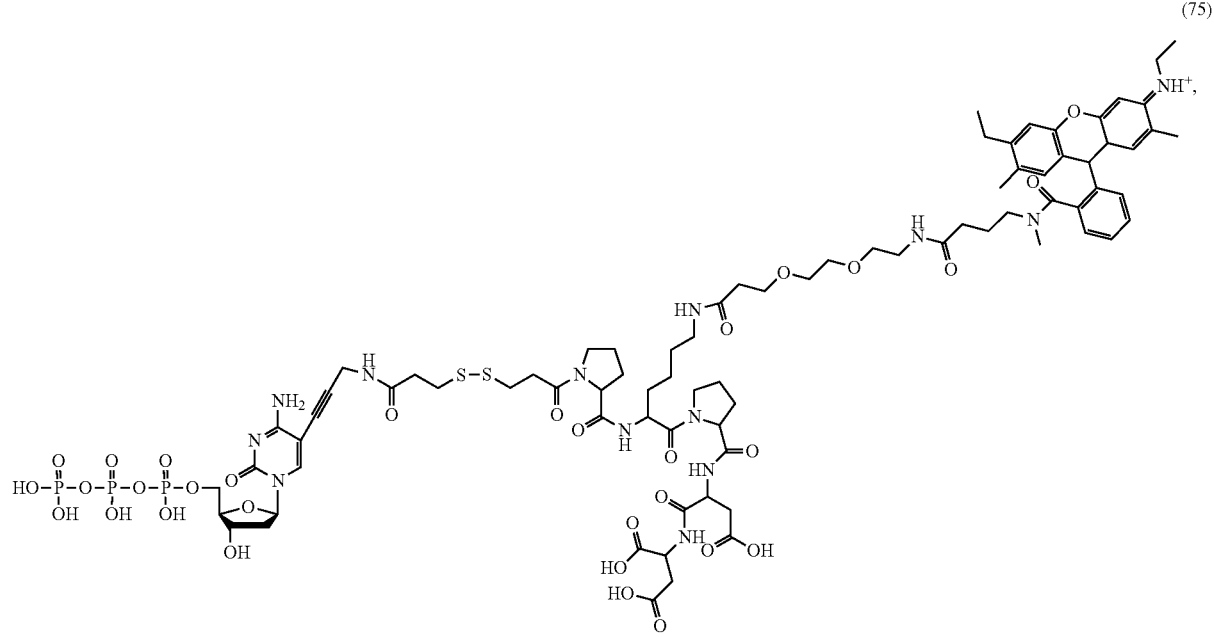

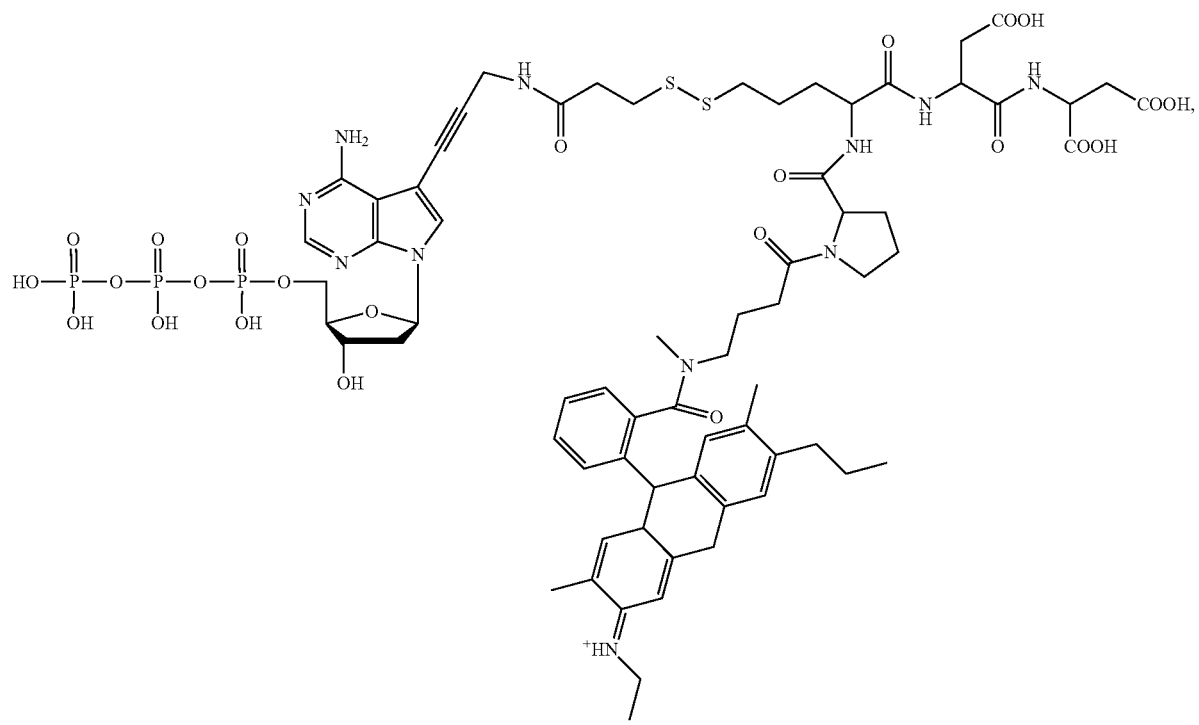
(76)
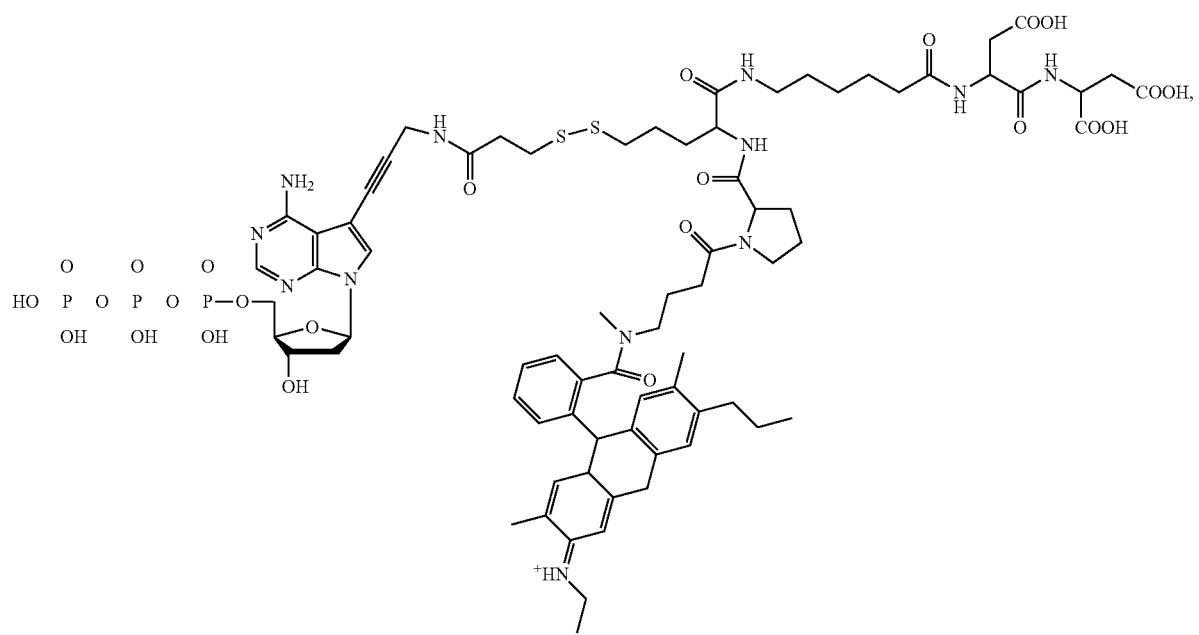
(77)

(78)
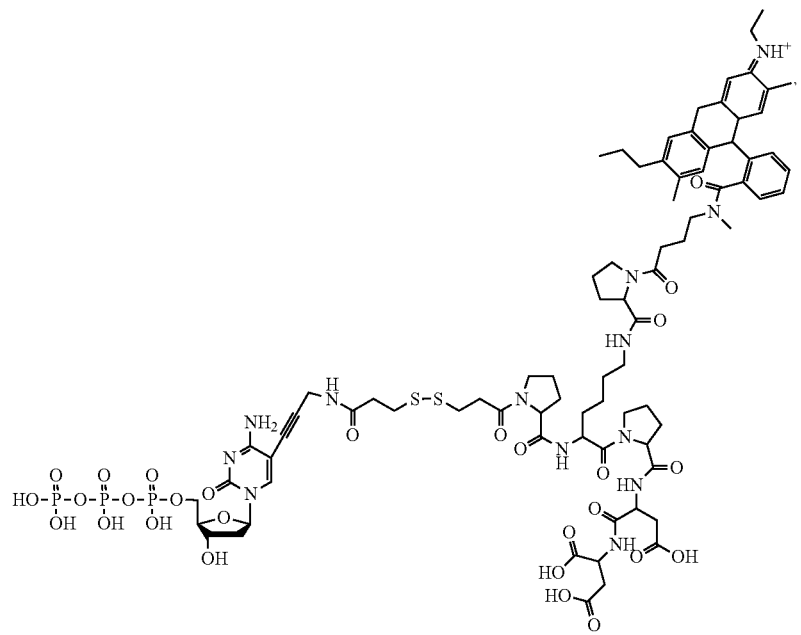
(79)
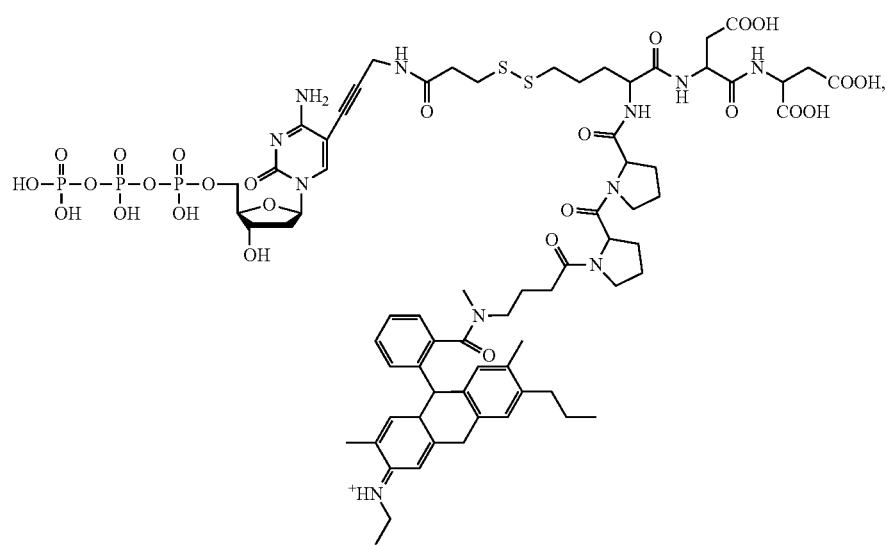

(80)
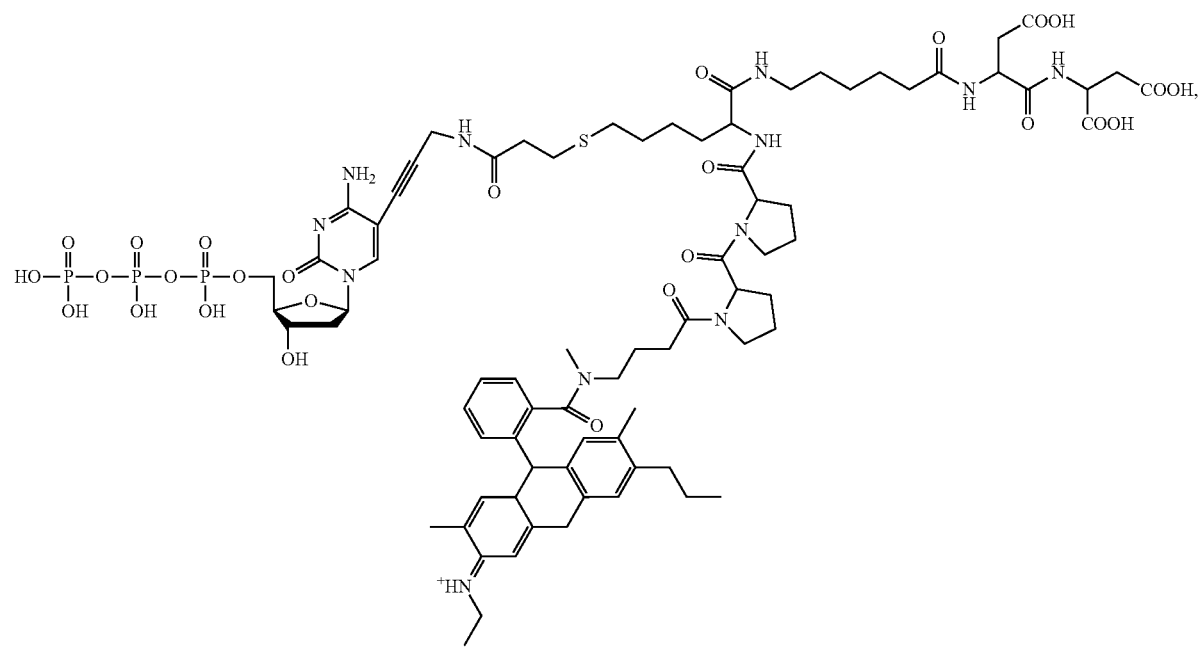
(81)
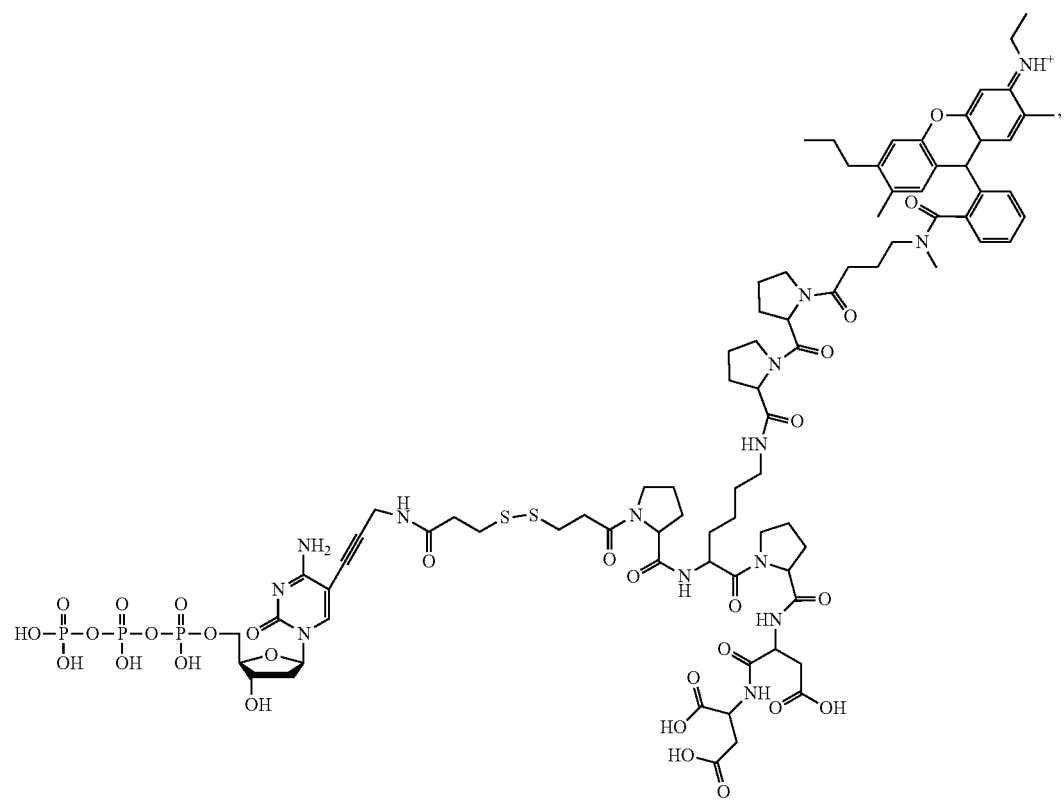

(82)
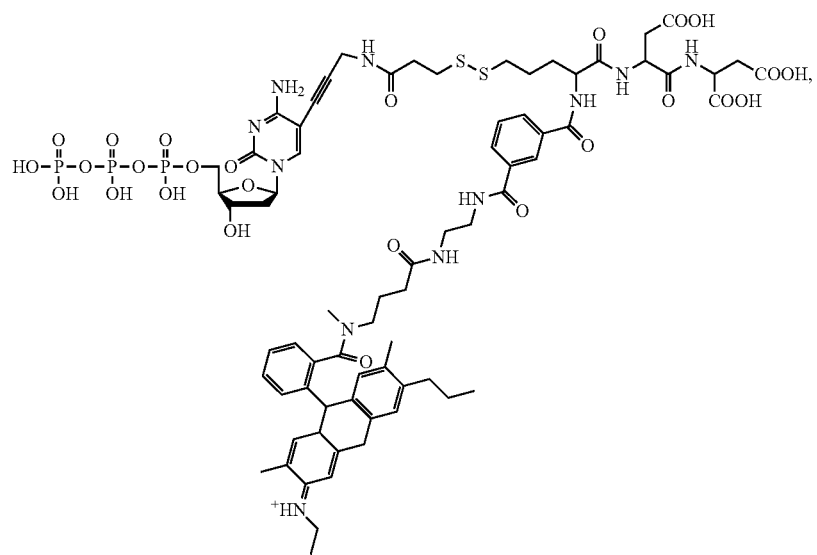
(83)
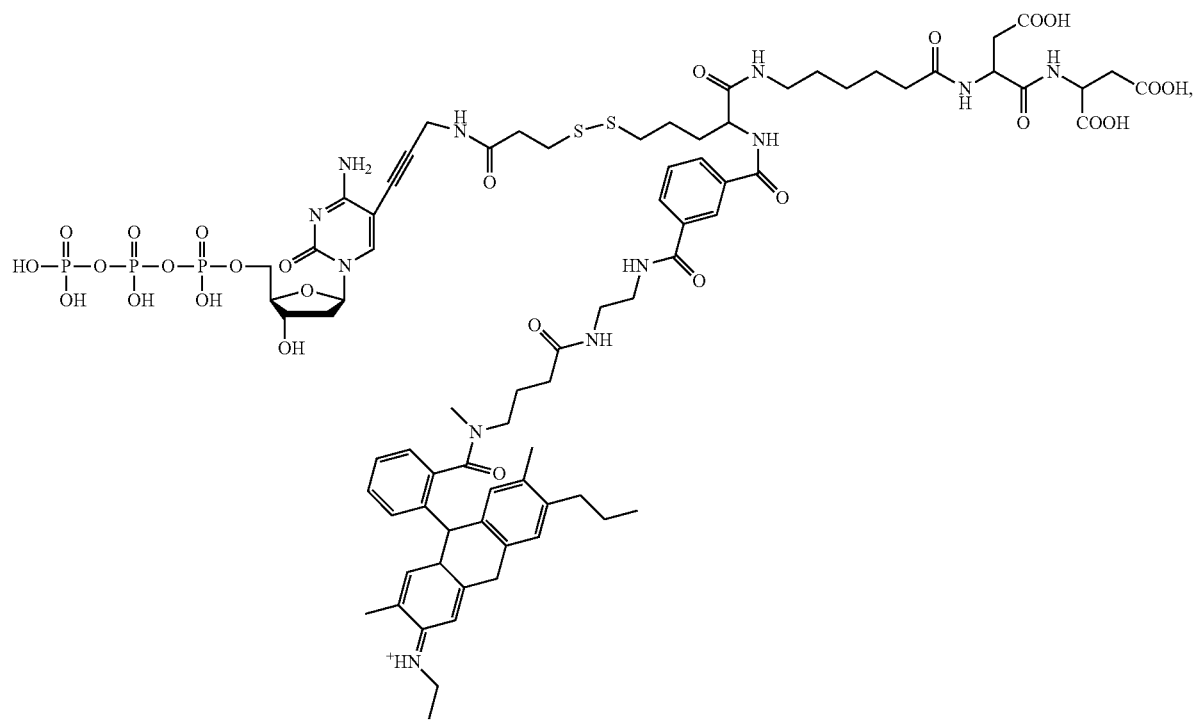

-continued
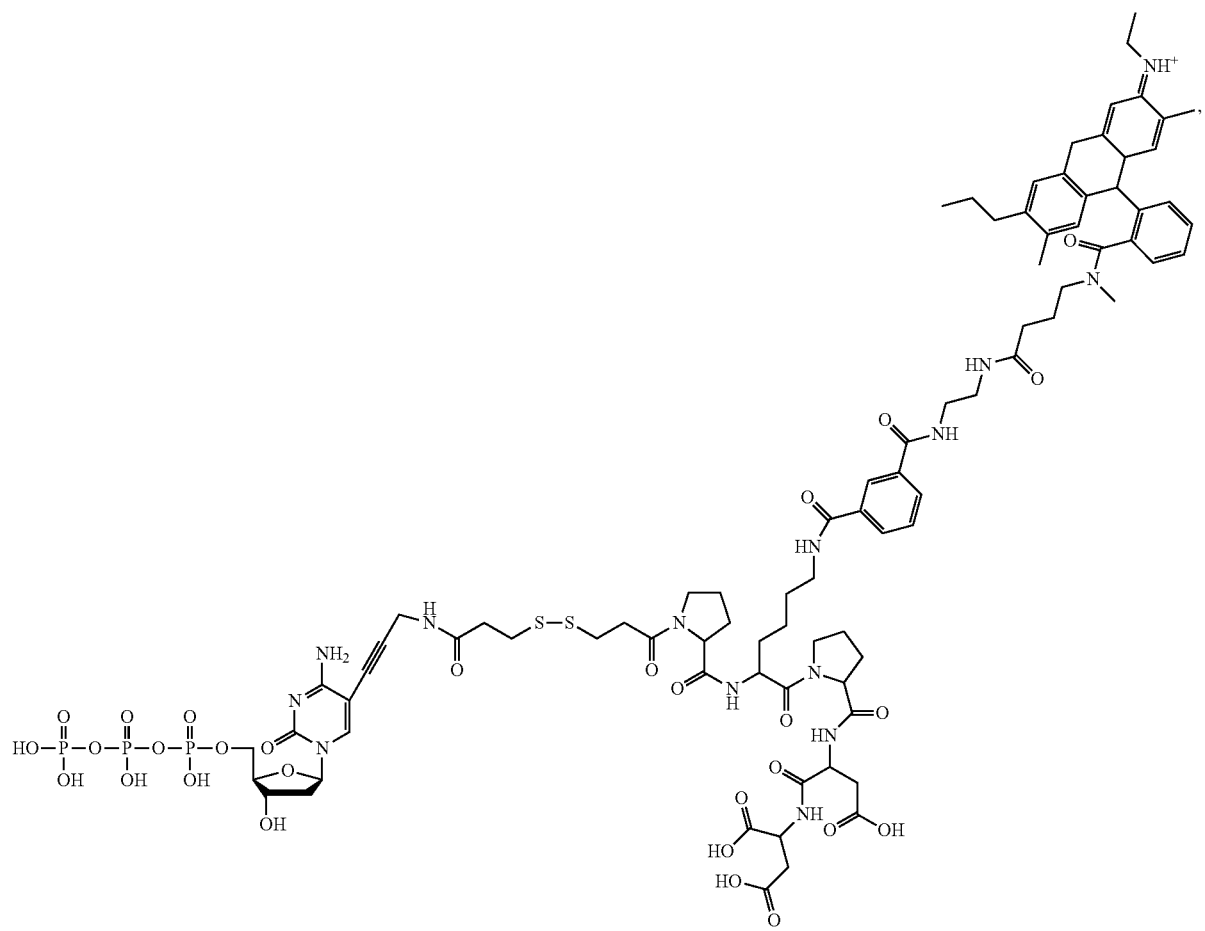
(84)
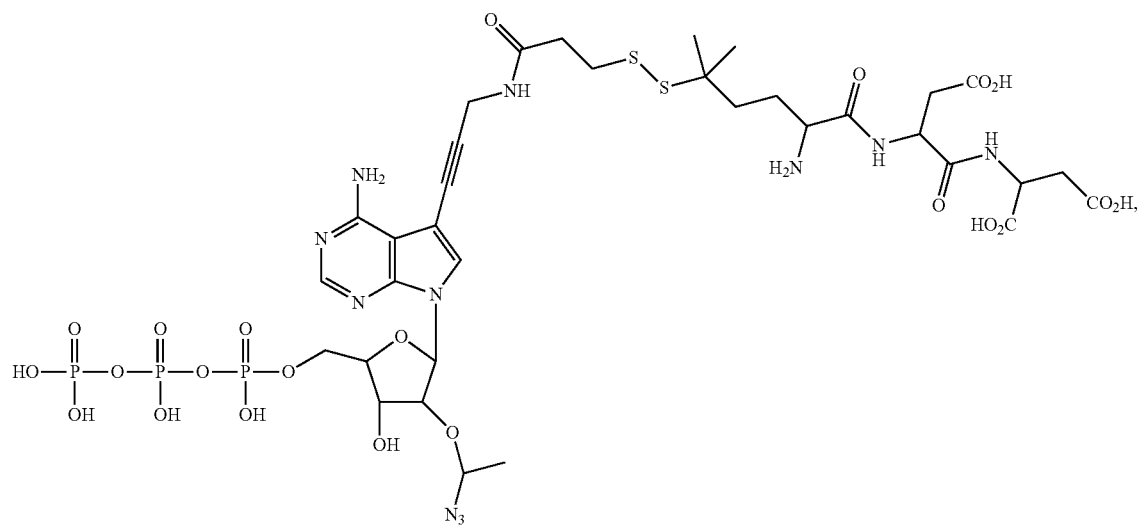
(85)

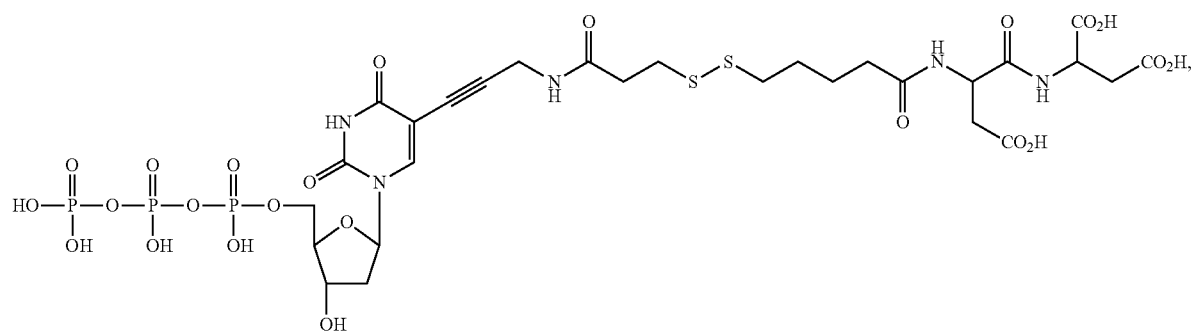
(86)
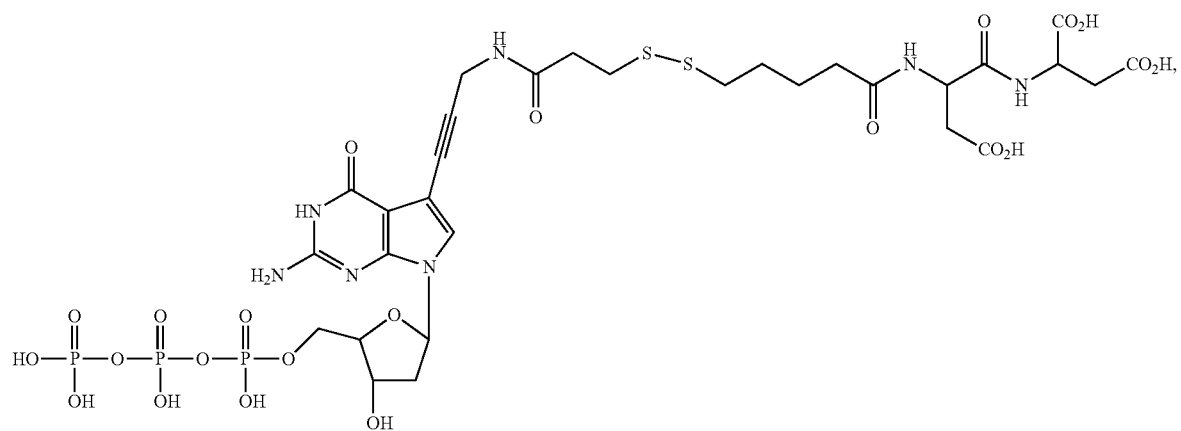
(87)
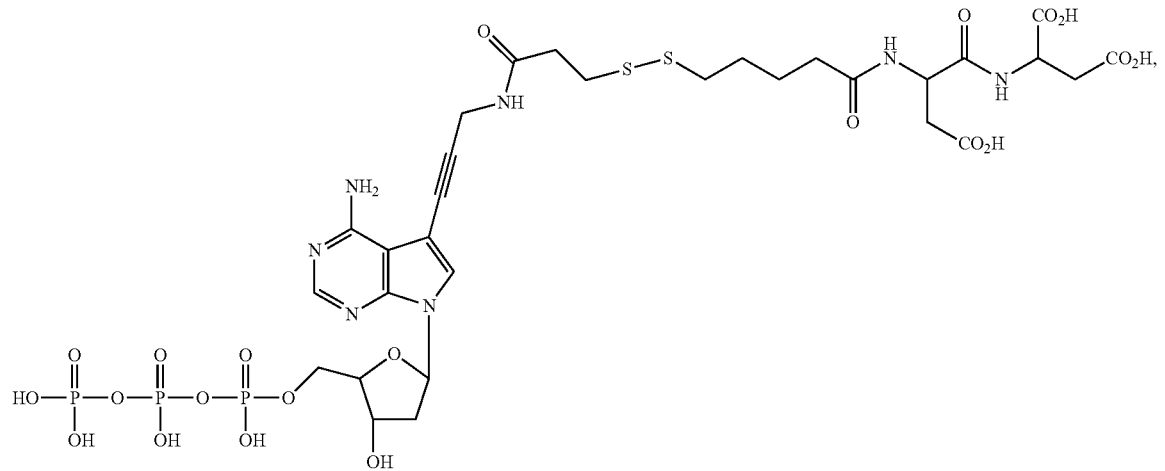
(88)

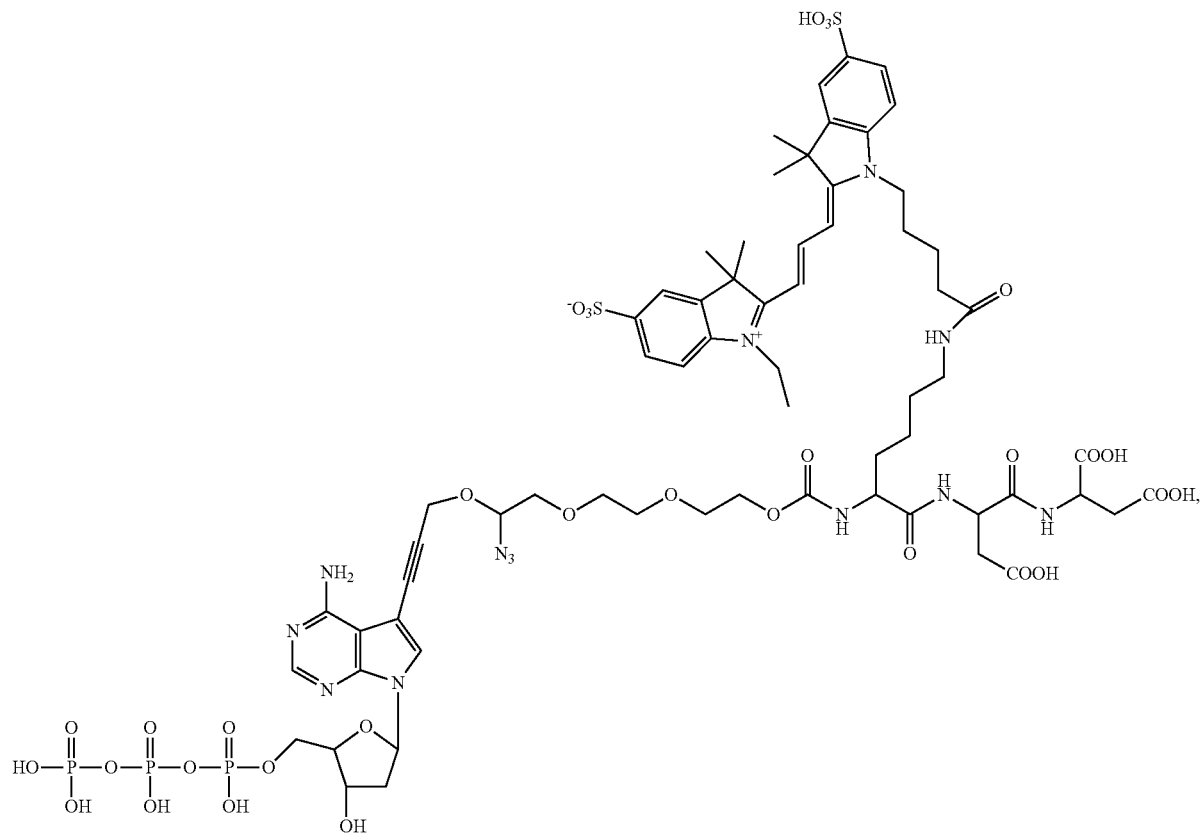
(89)
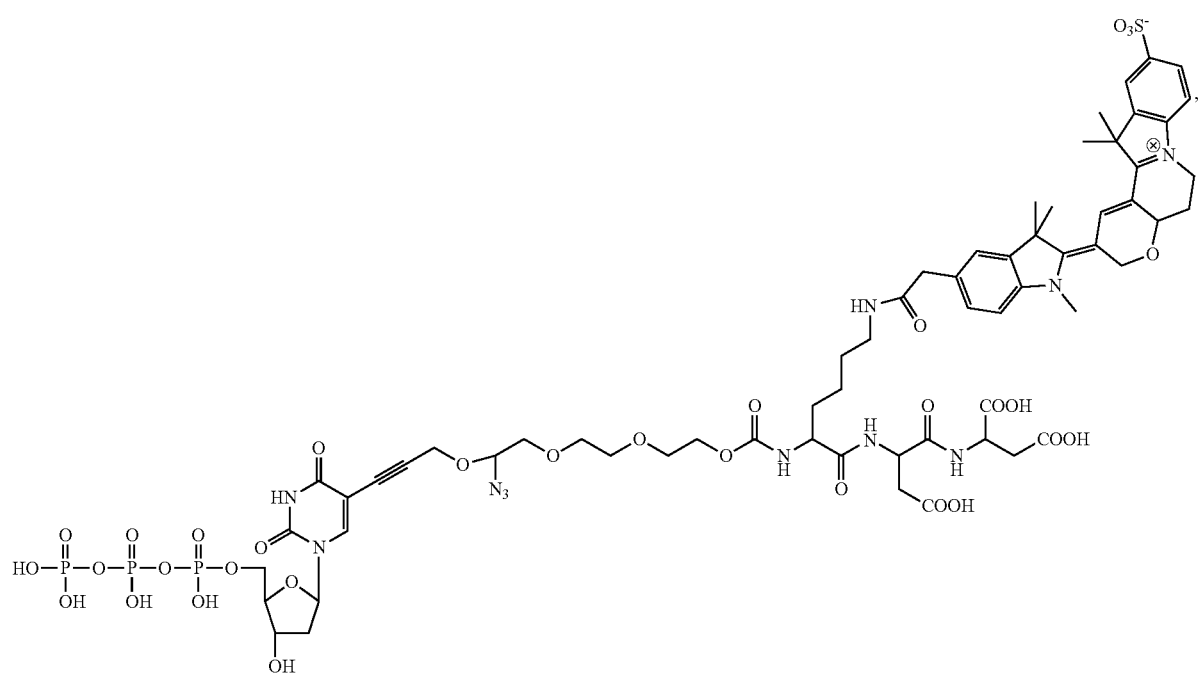
(90)

(91)

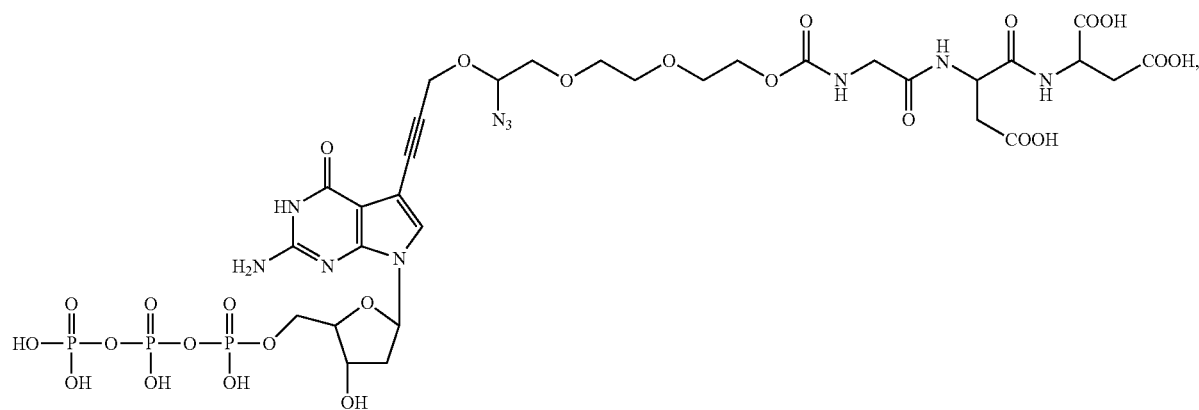

(92)

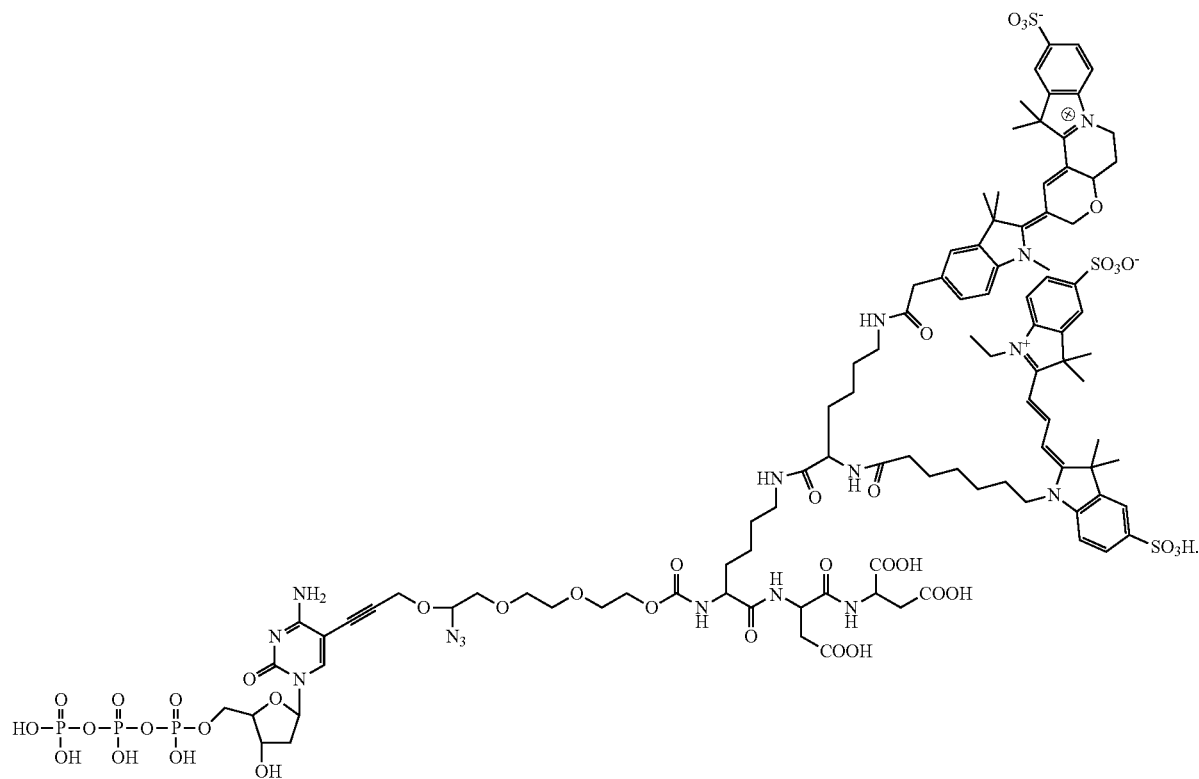

Some tests show that the presence of a long chain of hydrophobic contained in $L_2$ and/or $L_3$ of the compound reduces the intramolecular quenching and/or the intermolecular quenching; in particular, the long chain contains a straight chain or branched chain has no less than four consecutive connected bivalent radicals or no less than four carbon atoms in its backbone, such as compounds (7), (8), (18), (25)-(28), (36), (37), (40), (47) and (49)-(51), any of which contains a —$CH_2$—$CH_2$—$CH_2$—$CH_2$—$CH_2$— at $L_2$ and/or $L_3$.

Some tests show that the presence of a long chain of hydrophilic contained in $L_2$ and/or $L_3$ of the compound may reduce collisions between molecules, which may reduce the intramolecular quenching and increase the stability of molecules/reaction environment; in particular, the long chain comprises a straight chain or branched chain has no less than five consecutive connected bivalent radicals or no less than five atoms in its backbone, such as compounds (35), (52)-(54) and (89)-(92), any of which comprises a —O—$CH_2$—O—$CH_2$—O—$CH_2$—O—$CH_2$— at $L_2$ and/or $L_3$.

Some tests show that the presence of a rigid structure such as one or more cyclic groups contained in $L_2$ and/or $L_3$ of the compound makes the molecular configuration of the compound more controllable, which may reduce the intramolecular quenching and/or the intermolecular quenching and improve the reaction efficiency, such as compounds (55)-(63), (76)-(84), any of which contains one or more cyclic groups at $L_2$ and/or $L_3$.

According to some embodiments, there is provided a dNTP analog, including at least one selected from: a dATP analog, a dCTP analog, a dGTP analog, and dTTP analog. These four kinds of nucleotide analogs are selected from the compounds as described in any embodiment hereinbefore, and their respective bases are a base A, a base C, a base G and a base T, respectively.

According to some embodiments, there is provided an NTP analog. According to some embodiments, the NIT analog includes at least one selected from: an ATP analog, a CTP analog, a GTP analog, and a UTP analog. The ATP analog, the CTP analog, the GTP analog and the UTP analog are compounds of structural formula (I) as described above, and their respective bases are a base A, a base C, a base G and a base U, respectively.

According to some embodiments, there is provided a dNTP analog mixture, including a dATP analog, a dCTP analog, a dGTP analog and a dTTP analog. The dATP analog, the dCTP analog, the dGTP analog and the dTTP analog are compounds of structural formula (I) as described above, and their respective bases are a base A, a base C, a base G and a base T, respectively. Further, at least three of the dATP analog, the dCTP analog, the dGTP analog and the dTTP analog each have a different detectable group or targeting group from each other.

According to some embodiments, the dNTP analog mixture includes a combination of any two nucleotide analogs selected from: a dATP analog, a dCTP analog, a dGTP analog and a dTTP analog. The dATP analog, the dCTP analog, the dGTP analog and the dTTP analog are compounds of structural formula (I) as described above, and their respective bases are a base A, a base C, a base G and a base T, respectively. Further, the two nucleotide analogs in the combination each have a different detectable group or targeting group from each other.

According to some embodiments, there is provided an NTP analog mixture, including an ATP analog, a CTP analog, a GTP analog and a UTP analog. The ATP analog, the CTP analog, the GTP analog and the UTP analog are compounds of structural formula (I) as described above, and their respective bases are a base A, a base C, a base G and a base U, respectively. Further, at least three of the ATP analog, the CTP analog, the GTP analog and the UTP analog each have a different detectable group or targeting group from each other.

According to some embodiments, there is provided an NTP analog mixture, including a combination of any two nucleotide analogs selected from: an ATP analog, a CTP analog, a GTP analog and a UTP analog. The ATP analog, the CTP analog, the GTP analog and the UTP analog are compounds of structural formula (I) as described above, and their respective bases are a base A, a base C, a base G and a base U, respectively. Further, the two nucleotide analogs in the combination each have a different detectable group from each other.

According to some embodiments, there is provided use of the dNTP analog, the NTP analog, the dNTP analog mixture or the NIT analog mixture as described in any embodiment hereinbefore in nucleic acid sequencing, a controlled polymerase chain reaction or a base extension reaction.

According to some embodiments, there is provided a kit for nucleic acid sequencing or a controlled polymerase chain reaction. The kit includes the dNTP analog, the NIT analog, the dNTP analog mixture or the NIT analog mixture as described in any embodiment hereinbefore. The kit may be used in DNA and/or RNA sequencing.

According to some embodiments, the kit further includes: a cleavage agent for acting on a cleavable group or a cleavable bond; and/or a DNA polymerase.

Preparation of Compounds

According to some embodiments, there is provided a method for preparing the nucleotide analog as described in any embodiment hereinbefore, including: synthesizing SPDP using dithiodipyridine and mercaptopropionic acid; synthesizing a first linker using a compound of formula (10-1) and ethyl chloroformate, the first linker being a compound of formula (10-7); connecting a dNTP to the SPDP to obtain dNTP-SPDP; and synthesizing the nucleotide analog using the first linker and the dNTP-SPDP.

Specifically, the dNTP-SPDP may be obtained by a condensation reaction of a compound of formula (31-4) with the dNTP. Further, the dNTP-SPDP is subjected to an exchange reaction with the compound of formula (10-7) to obtain the target compound. The dNTP-SPDP has the following structure:

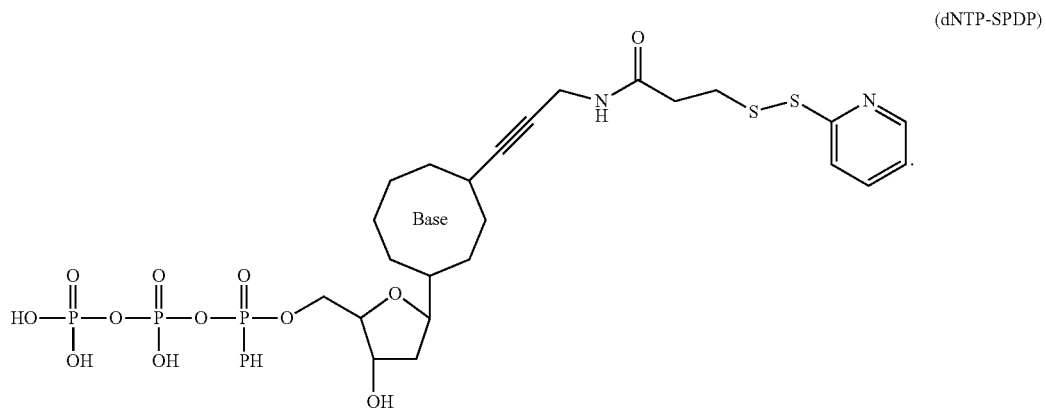

In some examples, the dNTP is a dATP, which may be synthesized or commercially available. In an example, the dATP may be obtained by: 1) subjecting a compound of formula (10-51) to a coupling reaction with trifluoroacetyl propargylamine to obtain a compound of formula (10-52); and 2) subjecting the compound of formula (10-52) to a substitution reaction with pyrophosphate to obtain the dATP.

The compound of formula (31-4) may be customized, or may be obtained by subjecting dithiodipyridine and mercaptopropionic acid to an exchange reaction, followed by an esterification reaction with N-bromosuccinimide (NBS).

The compound of formula (10-7) is commercially available, or may be obtained by transesterification between a compound of formula (10-6) and NH₂OH.

The compound of formula (10-6) is commercially available, or may be obtained by: a) subjecting a compound of formula (10-4) to a condensation reaction with N-hydroxysuccinimide (NHS) to obtain a compound of formula (10-5); and b) subjecting the compound of formula (10-5) to transesterification with H-Asp-Asp-OH to obtain the compound of formula (10-6).

The compound of formula (10-4) is commercially available, or may be obtained by ester hydrolysis of a compound of formula (10-3) in the presence of trifluoroacetic acid.

The compound of formula (10-3) is commercially available, or may be obtained by subjecting a compound of formula (10-2) to an esterification reaction with MsCl, followed by transesterification with KSCOCH₃.

The compound of formula (10-2) is commercially available, or may be obtained by subjecting a compound of formula (10-1) to transesterification with ethyl chloroformate, followed by a reduction reaction with NaBH₄.

The method for synthesizing the compound of formula (I) will be described in detail below, which has no specific order requirements to the following operations (1)-(3).

(1) Synthesis of SPDP

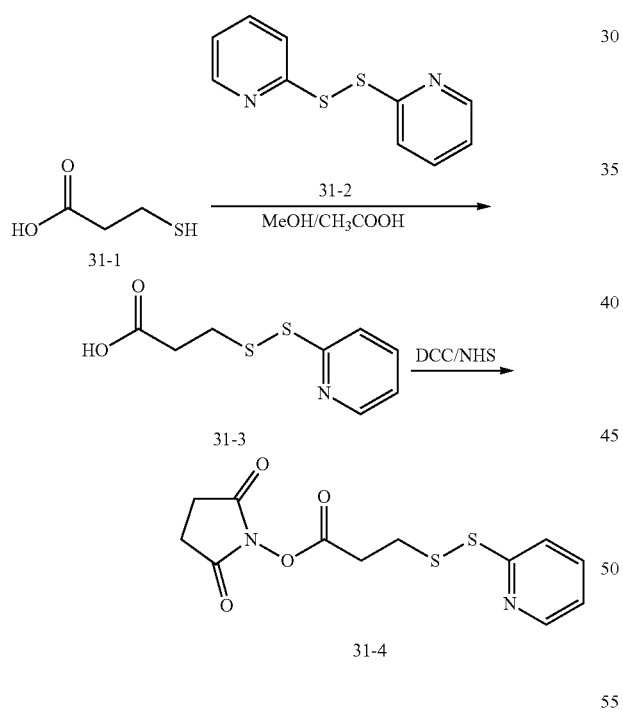

Dithiodipyridine was dissolved in 30 mL of ethanol, followed by addition of 300 µL acetic acid. To the resulting mixture was added dropwise with 636 mg of mercaptopropionic acid (dissolved in 15 mL of ethanol) within 30 min. After stirring overnight at room temperature, the solution was dried by rotary evaporation and then passed through a silica gel column (EA/HX=2/3-1/1) to obtain an intermediate product. After drying by rotary evaporation, the intermediate product was activated by NHS, and then passed through a silica gel column (EA/HX=1/4-1/2). The finally obtained product was a white solid. The H NMR spectrum of SPDP is shown in FIG. 1.

(2) Synthesis of a Structure (V₁-Linker) Between the Base and R₃

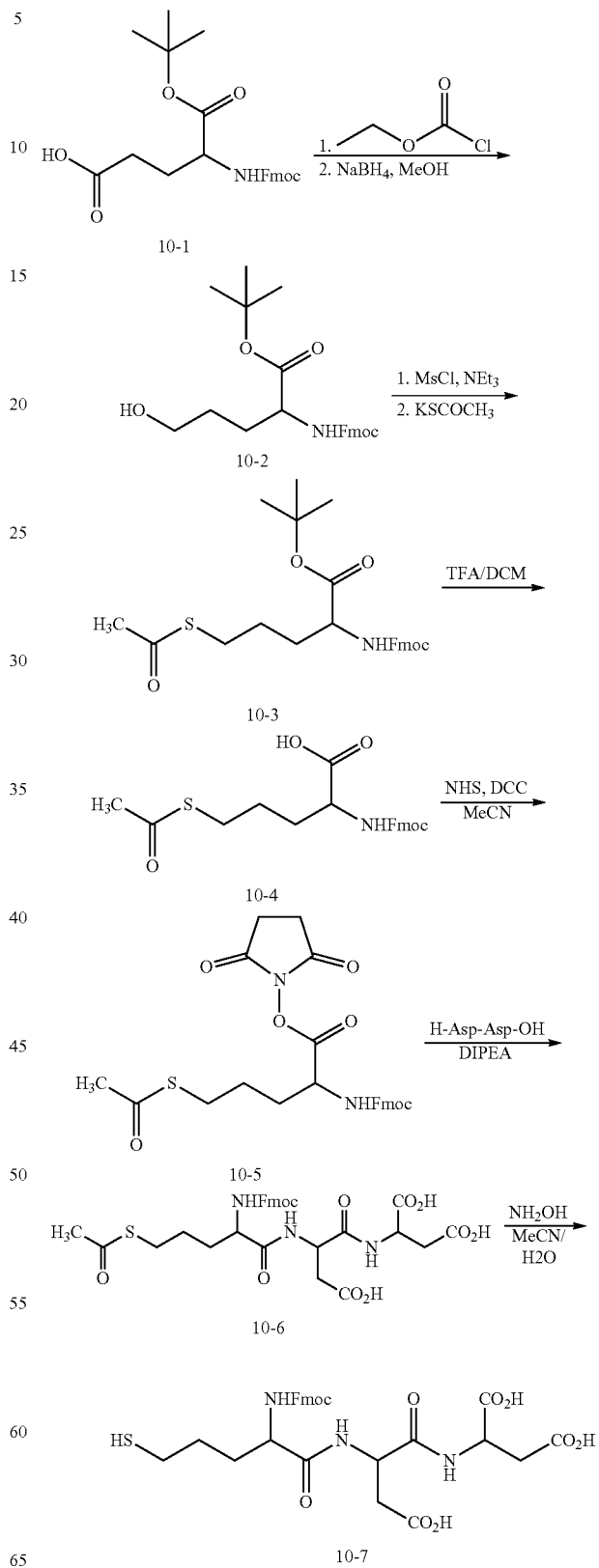

Compound 10-2: 1.02 g of the compound 10-1 (2.35 mmol) was dissolved in 12 mL THF, followed by addition of 0.4 mL triethylamine and 0.3 mL ethyl chloroformate at 0° C. Agitation was performed under an Ar atmosphere for 10 min. 0.27 g of NaBH$_4$ (7.1 mmol) was added in several portions, and 23 mL of ethanol was added slowly within 10 min under stirring. After the reaction solution reaches room temperature under stirring, 10 mL of 10% HCl was added for acidification. The organic phase was dried in vacuum, and then purified by column chromatography to obtain 0.97 g of the compound 10-2.

Compound 10-3: 0.97 g of the compound 10-2 (2.35 mmol) was dissolved in 9 mL CH$_2$Cl$_2$, followed by addition of 0.7 mL triethylamine (5.0 mmol), and then the reaction system was cooled to 0° C. 0.28 mL of MsCl (3.6 mmol) was added dropwise slowly in 15 min. After the detection with the TLC plate showed that the starting material was depleted, the reaction mixture was washed with water (2/25 mL), dried with anhydrous Na$_2$SO$_4$, and then further dried to a solid. Afterwards, 0.54 g of KSCOCH$_3$ (4.7 mmol) was added to a solution of the said solid in 6 mL acetonitrile to react at room temperature for 12 h. The obtained crude product was purified by column chromatography with a solvent system of 5%-20% EtOAc/n-hexane to obtain 0.57 g brown oily solid compound 10-3.

Compound 10-4: 0.29 g of the compound 10-3 (0.61 mmol) was dissolved in 2 mL CH$_2$Cl$_2$, followed by addition of 2 mL trifluoroacetic acid to react at room temperature for 30 min. Afterwards, the solution was washed with a saturated salt solution (2×20 mL), and the organic layer was dried with anhydrous Na$_2$SO$_4$ to obtain the compound 10-4 (0.22 g, yield: 88%).

Compound 10-6: the compound 10-4 (0.22 g, 0.53 mmol) was dissolved in 3 mL acetonitrile, followed by addition of N,N'-dicyclohexylcarbodiimide (DCC, 0.12 g, 0.58 mmol) and NHS (0.07 g, 0.63 mmol) to react at the room temperature under stirring for 1 h. After filtering out the white solid N,N'-dicyclohexylurea (DCU) generated by the reaction, the filtrate was combined with H-Asp-Asp-OH (0.13 g, 0.52 mmol) dissolved in a mixture of 2.4 mL (0.25M) K$_2$HPO$_4$ and 1 mL acetonitrile, and then combined with 0.15 mL N,N-diisopropylethylamine (DIPEA) to ensure a pH of about 8. After purification by HPLC, the compound 10-6 (0.25 g, yield: 75%) was obtained.

Compound 10-7: 0.023 mg of the compound 10-6 was dissolved in 0.5 mL of 50% MeCN/H$_2$O mixture. The mixture was treated with 0.5 mL of 1M NH$_2$OH, and stirred at room temperature for 10 min. Afterwards, purification was performed by HPLC to obtain the compound 10-7.

(3) Synthesis of the Compound dATP-SPDP

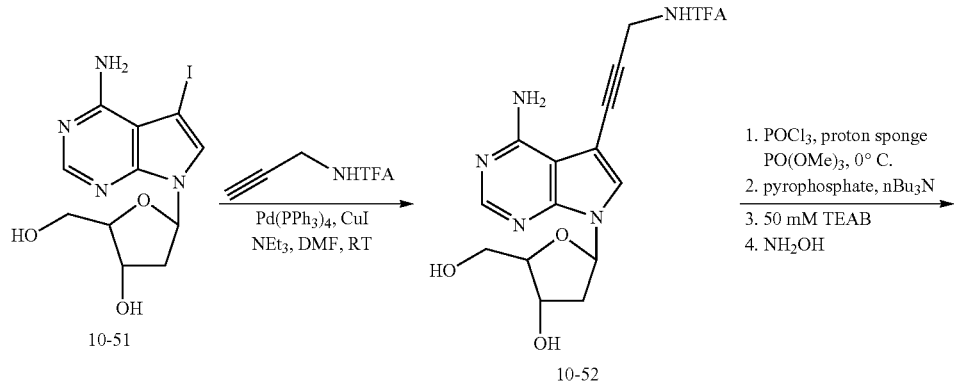

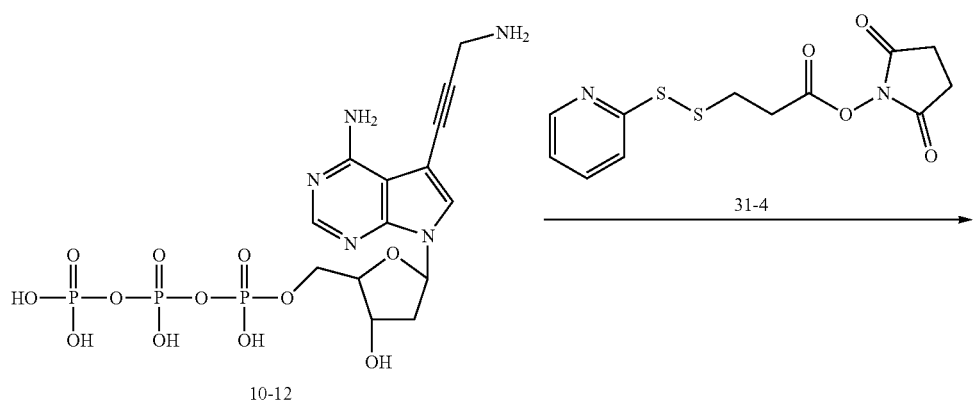

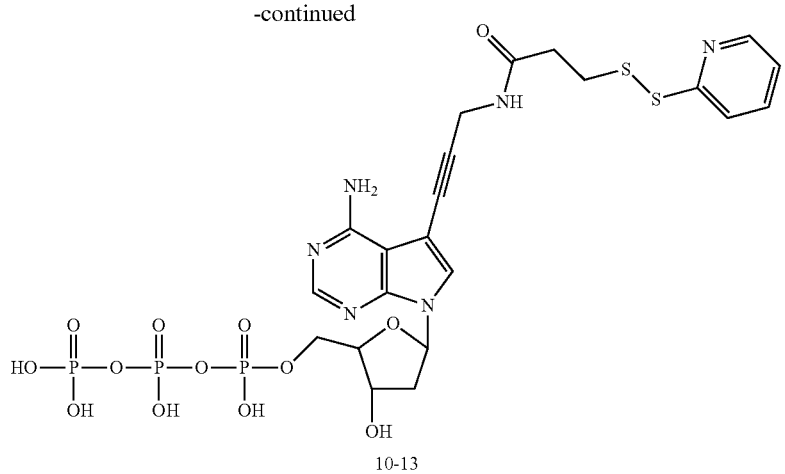

10-13

Compound 10-52: the compound 10-51 (70 g), N,N-dimethylformamide (DMF) (700 mL), trifluoroacetyl propargylamine (21.5 g), TEA (35.8 g), Pd(PPh₃)₄ (13.7 g), and CuI (4.6 g) were successively added to a 1 L three-necked flask Atmosphere of the reaction system was replaced with nitrogen three times, and stirred at 35 V for 3 to 4 h under the protection of nitrogen gas. The reaction was monitored by TLC with a developing solvent of EA (ethyl acetate):Hex (hexane)=1:1. The reaction solution was poured into 1.2 L water, and then extracted with EA (500 mL×2). The combined oil layer was washed successively with a saturated solution of ammonium chloride (500 mL×2) and a saturated solution of sodium chloride (500 mL×2), dried with anhydrous sodium sulfate, and then dried by rotary evaporation to obtain 99 g dark brown solid as a crude product. The crude product was dissolved in 300 mL dichloromethane (DCM), and then added slowly with 200 mL Hex. The resulting system was allowed to stand overnight at 0° C. for recrystallization. After filtration, a light-yellow solid product was obtained, which was washed and rinsed with a mixed solvent (100 mL, EA/Hex=1/5, v/v), and then dried in vacuum at 35° C. The mother liquor was combined for further recrystallization. Finally, 43.6 g of light-yellow solid product was obtained, with a molar yield of 60%.

Compound 10-12: the compound 10-52 (500 mg) and proton sponge (431 mg) were mixed in a 100 mL round bottom flask, which were completely dissolved by anhydrous acetonitrile (10 mL), followed by removal of acetonitrile with a rotary evaporator, and these operations were repeated 3 times. The resulting mixture was concentrated with a high vacuum oil pump overnight. The next day, the mixture was dissolved by PO(OMe)₃ (10 mL) under magnetic stirring, followed by concentrating with the high vacuum oil pump for 5 min, the atmosphere was replaced by argon via a three-way pipe, and these operations were repeated 3 times. Afterwards, the reaction system was placed in an ice-water bath and stirred for 5-10 min, followed by addition of POCl₃ (0.14 mL) in about 1 min, and then further stirred for 3 h in the ice-water bath, obtaining a first reaction solution.

(Bu₃N)₂PPi (tributylammonium pyrophosphate, 1383 mg) was dissolved in anhydrous DMF (10 mL) in a round bottom flask under magnetic stirring, the resulting mixture was concentrated with the high vacuum oil pump for 5 min, the atmosphere was replaced by argon via a three-way pipe, and these operations were repeated 3 times. Afterwards, Bu₃N (1.17 mL) was added, and the resulting mixture was placed in an ice-water bath and stirred for 5-10 min, obtaining a second reaction solution. The first reaction solution prepared in step 2 and its residual liquid washed by a small amount of PO(OMe)₃ off the round bottom flask were added dropwise into the second reaction solution prepared in step 3 within 2-3 min. Subsequently, the reaction system was kept in the ice-water bath and stirred for 2 h. After the reaction was completed, the reaction system was added with the prepared triethylammonium bicarbonate (TEAB)(1 mol, 10 mL) under the ice-water bath and further stirred for 1 h. The diethylaminoethyl cellulose (DEAE) resin soaked in deionized water was loaded into a flash chromatographic column (about 10 cm long), and then the reaction solution, after dilution with deionized water (120 mL), was transferred to the flash chromatographic column. The flash chromatographic column was successively rinsed with 300 mL deionized water and TEAB solutions (300 mL for each concentration of 0.1 M, 0.2 M, 0.4 M, 0.6 M, 0.8 M, and 1 M), and the eluate was monitored by UV. The product began to come out when using the 0.4 M FLAB solution. The FLAB buffer and water were removed from the product at 27° C. using a rotary evaporator. The dry mixture obtained by the rotary evaporation was added with stronger ammonia water (100 mL) and magnetically stirred for 24 h. Afterwards, the ammonia water was removed using the rotary evaporator at 27° C.

Compound 10-13: SPDP (0.5 mL, 0.1 M in anhydrous DMF, 1.25 eq) was added to the aqueous solution of the compound 10-12, the pH was adjusted to about 8.5, and the reaction was carried out for 10 min. The product was purified by HPLC (Buffer A: 0.1 M TEAB; Buffer B: acetonitrile). The mass spectrum of the compound 10-13 shows M/Z=739.15.

(4) Synthesis of Compound dATP-V₁—S—S-ATTO647N

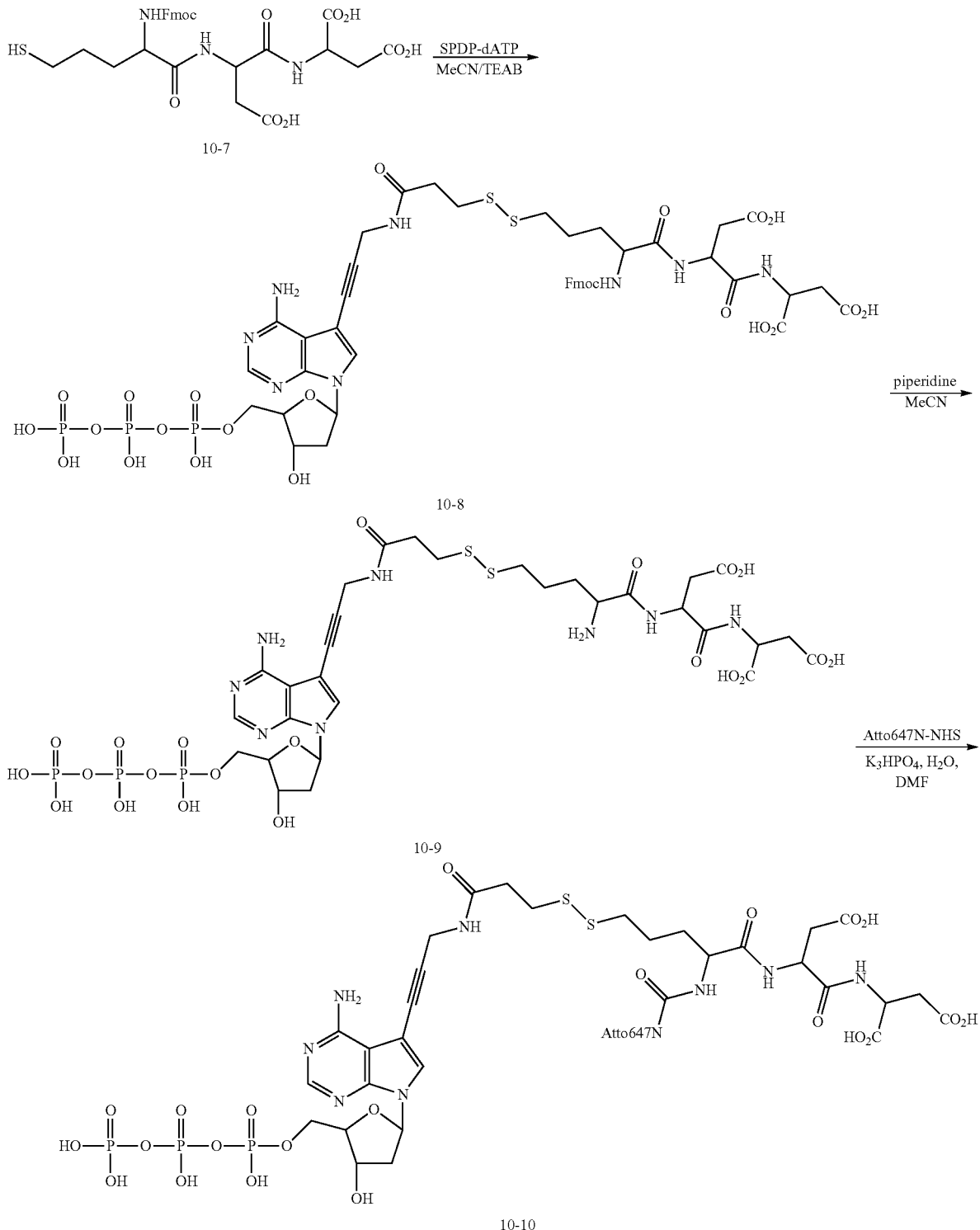

Compound 10-8: the HPLC component of the compound 10-7 and the HPLC component of the compound 10-13 were mixed and stirred at room temperature for 15 min, followed by concentration and HPLC purification (Buffer A: 0.1 M TEAB; Buffer B: acetonitrile), obtaining the compound 10-8.

Compound 10-9: the compound 10-8 (about 16 μmop was treated with 2 mL of 20% piperidine/MeCN and 1 mL of 20% piperidine/MeCN for 15 minutes to remove the Fmoc protecting group. Then, the product was purified by HPLC (Buffer A: 0.1 M TEAB; Buffer B: acetonitrile) to obtain the HPLC component of compound 10-9.

131

Compound 10-10: ATTO647N-NHS (0.36 mL, 36 mmol, 0.1 M in anhydrous DMF) was added to a solution of the compound 10-9 (17.6 mL) in a mixture of water and DMF, and the reaction was monitored by HPLC. After the raw material was exhausted, the resulted product was purified by HPLC (Buffer A: 0.1 M TEAB; Buffer B: acetonitrile) to obtain the compound 10-10.

According to some embodiments, there is provided another method for preparing the nucleotide analog as described in any embodiment hereinbefore, including: synthesizing dNTP-MPSSK; synthesizing a second linker using a compound of formula (31-4) and a hexapeptide, the second linker being the compound of formula (11-10), and the hexapeptide being H-Pro-Lys(Fmoc)-Pro-Asp-Asp-OH; and mixing the second linker and the dNTP-MPSSK to obtain the target compound.

A specific example of this method will be described in detail below, which has no order requirements to the following operations (1) and (2).

(1) Synthesis of dNTP-MPSSK

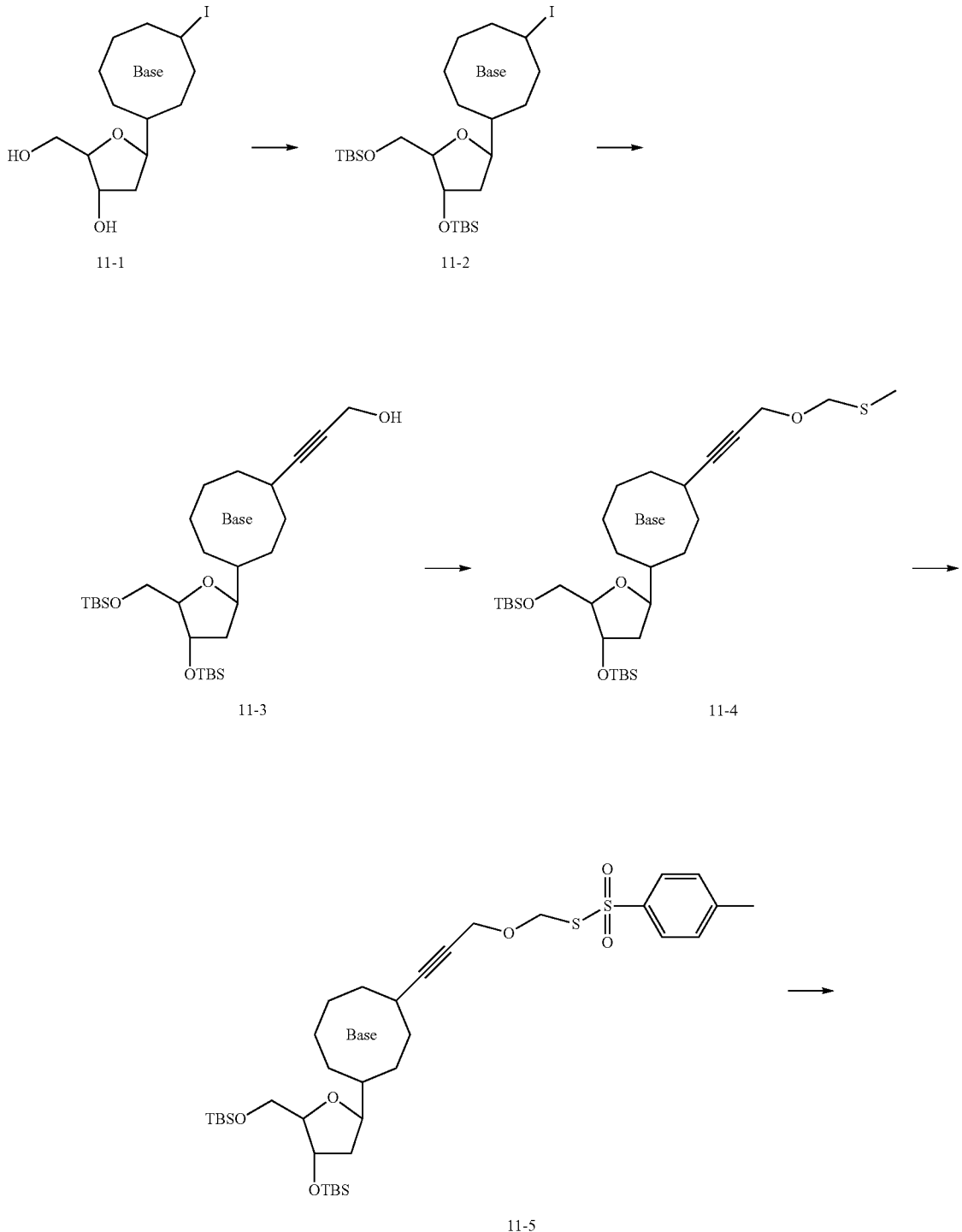

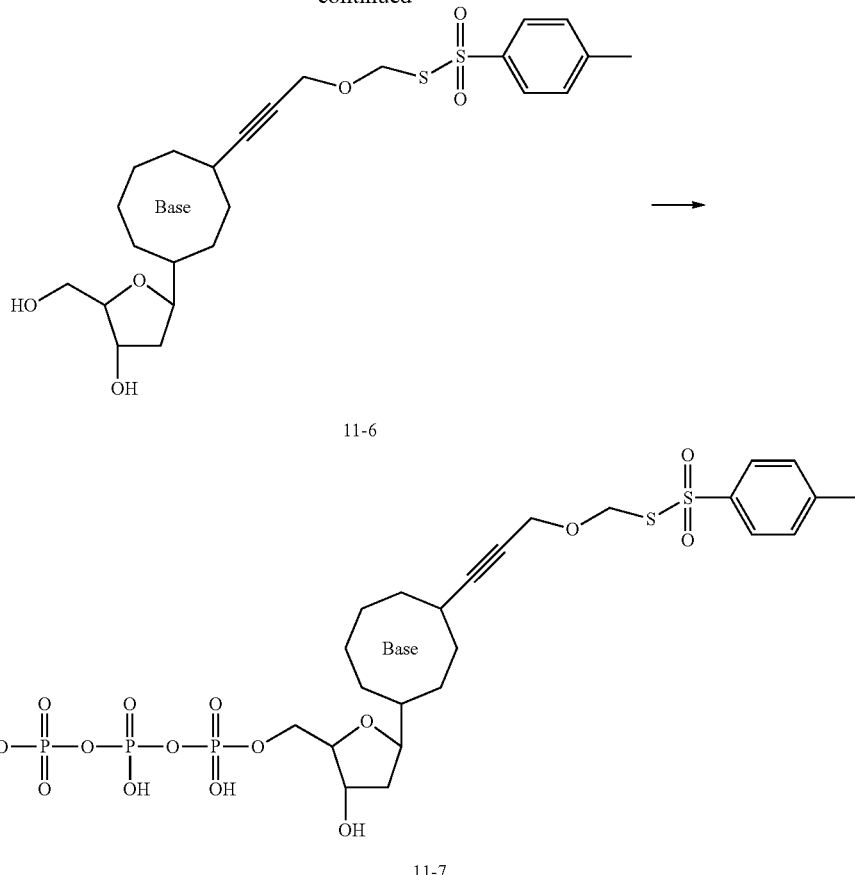

11-6

11-7

Compound 11-2: under the protection of nitrogen, the compound 11-1 (10.2 g, 29.2 mmol, 1.0 eq) was dissolved in pyridine (80 mL), tert-butyldimethylchlorosilane (TBSCl, 9.8 g, 35.1 mmol, 2.2 eq) was dissolved in pyridine (30 mL), and then the TBSCl solution was added dropwise to the solution of compound 11-1 in the ice-water bath at 0 V (significantly less by-product with double-protection will be generated at 0 V). After completion of the addition, the mixture was stirred at 20° C. for 12 h, and the reaction was monitored by TLC. After the reaction was completed, 100 mL of water was added to quench the reaction. The mixture was rotary evaporated at 45 V to remove pyridine until a volume of 80 mL, which was then poured into 800 mL of water to precipitate out a white solid. The obtained solid/liquid mixture was filtrated by suction, the residue was rinsed with n-hexane/ethyl acetate (50 mL, V (hexane):V (ethyl acetate)=8:1) 3 times and then dried by air-blowing at 50° C. for 10 h to obtain the white solid of the compound 11-2 (10.8 g, 80%).

Compound 11-3: the compound 11-2 (10.8 g), DMF (200 mL), propargyl alcohol (21.5 g), LEA (35.8 g), Pd(PPh$_3$)$_4$ (13.7 g) and CuI (4.6 g) were successively added to a 1 L three-necked flask, the reaction system was purged with nitrogen gas three times, and stirred at 35 V for 3 to 4 h under the protection of nitrogen gas. The reaction was monitored by TLC with a developing solvent of EA:Hex=1:1. The reaction solution was poured into 1.2 L water, and then extracted with EA (500 mL×2). The combined oil layer was washed successively with a saturated solution of ammonium chloride (500 mL×2) and a saturated solution of sodium chloride (500 mL×2), dried with anhydrous sodium sulfate, and then dried by rotary evaporation to obtain 99 g dark brown solid as a crude product. The crude product was dissolved in 300 mL DCM, and then added slowly with 200 mL Hex. The resulting system was allowed to stand overnight at 0° C. for recrystallization. After filtration, a light-yellow solid product was obtained, which was washed and rinsed with a mixed solvent (100 mL, EA/Hex=1/5, v/v), and then dried in vacuum at 35° C. The mother liquor was combined for further recrystallization. Finally, 12.6 g light-yellow solid product of the compound 11-3 was obtained.

Compound 11-4: the compound 11-3 (10.8 g, 23.1 mmol, 1.0 eq) was dissolved in 60 mL dimethyl sulfoxide (DMSO), followed by addition of 30 mL acetic acid and 60 mL acetic anhydride in sequence. The mixture was stirred at 25° C. for 12 h, and the reaction was monitored by TLC. After the reaction was completed, 50 mL of water was added to quench the reaction, and the mixture was extracted with EtOAc two times (40 mL×2). The combined organic phase was washed with water two times (50 mL×2), and the organic phase was washed with a saturated NaHCO$_3$ solution to a pH of about 7. The organic phase was separated, washed with a saturated NaCl solution (100 mL), and dried over anhydrous Na$_2$SO$_4$, and the solvent was removed by rotary evaporation at 38° C., thereby obtaining a yellow oily crude product of the compound 11-4.

Compound 11-5: the compound 11-4 (0.48 mmol) was dissolved in 5 mL DCM, followed by addition of cyclohexane (2.88 mmol) and SO$_2$Cl (0.96 mmol). The mixture was stirred at room temperature for 1 h, and the reaction system was monitored by TLC. Afterwards, the system was dried, and then dissolved in 4 mL DMF, followed by addition of p-MePhSO₂SK (1.44 mL) to react at room temperature for 1 h. The reaction solution was extracted with EA, washed with a saturated salt solution, and then passed through a chromatographic column to obtain the compound 11-5.

Compound 11-6: the compound 11-5 (7.39 mmol, 1.0 eq) was dissolved in 40 mL tetrahydrofuran, followed by addition of triethylamine trihydrofluoride (7.14 g, 44.4 mmol, 6 eq) to react at 25° C. for 12 h under stirring. The reaction was monitored by TLC. The solvent was removed by rotary evaporation at 25° C. 25 mL of ethyl acetate and 15 mL of water were added, the organic phase was separated, and the aqueous phase was further extracted for three times with EtOAc (10 mL×3) until there was no product in the aqueous phase. The combined organic phase was rotary evaporated at 38° C. to remove the solvent, giving 4 g crude product. The crude product was passed through a chromatographic column with DCM and mixtures of DCM and MeOH (DCM: MeOH:100:1/90:1/80:1/60:1/50:1/40:1/30:1/20:1) as the eluent successively to obtain the compound 11-6 as a brown-yellow solid (2.0 g, 63%).

Compound 11-7: the compound 11-6 (500 mg) and proton sponge (431 mg) were mixed in a 100 mL round bottom flask, which were completely dissolved by anhydrous acetonitrile (10 mL), followed by removal of acetonitrile with a rotary evaporator, and these operations were repeated 3 times. The resulting mixture was concentrated with a high vacuum oil pump overnight. The next day, the mixture was dissolved in PO(OMe)₃ (10 mL) under magnetic stirring, followed by concentrating with the high vacuum oil pump for 5 min, the atmosphere was replaced by argon via a three-way pipe, and these operations were repeated 3 times. Afterwards, the reaction system was placed in an ice-water bath and stirred for 5-10 min, followed by addition of POCl₃ (0.14 mL) in about 1 min, and then further stirred for 3 h in the ice-water bath, obtaining a first reaction solution.

(Bu₃N)₂PPi (1383 mg) was dissolved in anhydrous DMF (10 mL) in a round bottom flask under magnetic stirring, the resulting mixture was concentrated with the high vacuum oil pump for 5 min, the atmosphere was replaced by argon via a three-way pipe, and these operations were repeated 3 times. Afterwards, Bu₃N (1.17 mL) was added, and the resulting mixture was placed in an ice-water bath and stirred for 5-10 min, obtaining a second reaction solution. The first reaction solution prepared in step 2 and its residual liquid washed by a small amount of PO(OMe)₃ off the round bottom flask were added dropwise into the second reaction solution prepared in step 3 within 2-3 min. Subsequently, the reaction system was kept in the ice-water bath and stirred for 2 h. After the reaction was completed, the reaction system was added with the prepared FLAB (1 mol, 10 mL) under the ice-water bath and further stirred for 1 h. The DEAE resin soaked in deionized water was loaded into a flash chromatographic column (about 10 cm long), and then the reaction solution, after dilution with deionized water (120 mL), was transferred to the flash chromatographic column. The flash chromatographic column was successively rinsed with 300 mL deionized water and FLAB solutions (300 mL for each concentration of 0.1 M, 0.2 M, 0.4 M, 0.6 M, 0.8 M, and 1 M), and the eluate was monitored by UV. The product began to come out when using the 0.4 M FLAB solution. The TEAB buffer and water were removed from the product at 27° C. using a rotary evaporator. The dry mixture obtained by the rotary evaporation was added with stronger ammonia water (100 mL) and magnetically stirred for 24 h. Afterwards, the ammonia water was removed using the rotary evaporator at 27° C. to obtain the compound 11-7.

(2) Synthesis of a Structure (V₃-Linker) Between the Base and R₃

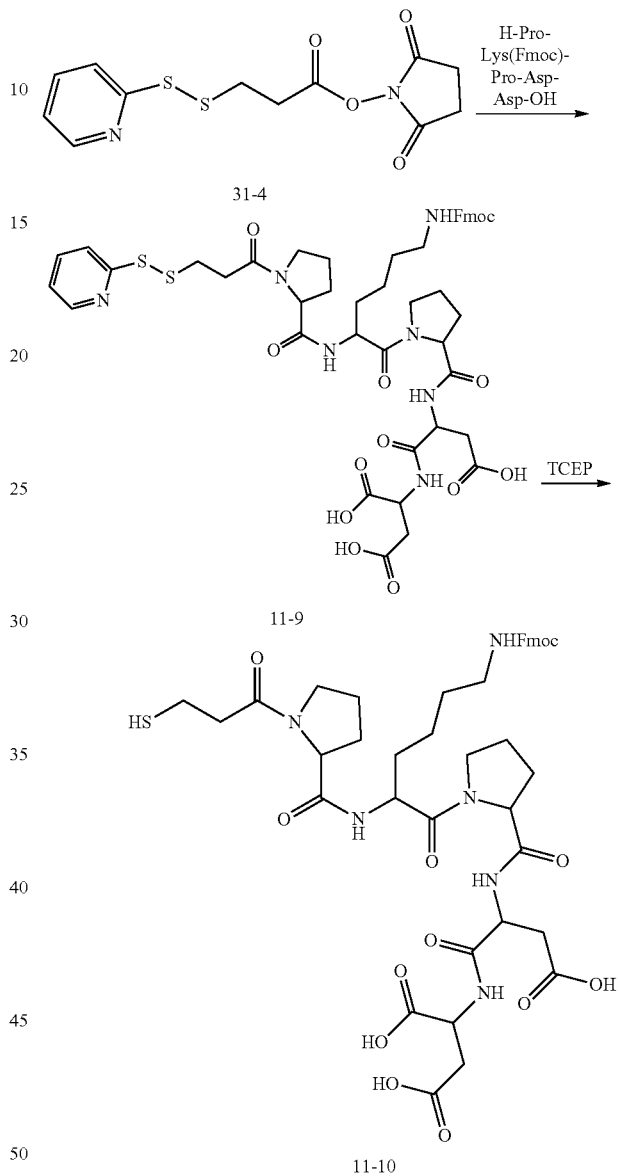

Compound 11-9: 0.178 mg (0.2 mmol) of hexapeptide was dissolved in 0.1M K₂HPO₄ (5 mL), followed by addition of 327 mg SPDP (0.4 mmol, in 4 mL DMF) to react at room temperature for 2 h. The reaction is monitored by HPLC until the hexapeptide is completely reacted. The product, after purification by HPLC, was lyophilized. The mass spectrum of the compound 11-9 shows that M/Z=1087.3929.

Compound 11-10: 0.046 mg of the compound 11-9 was dissolved in 0.5 mL of 50% MeCN/H₂O mixture, and the solution was treated with 1 mL of 1 M NH₂OH. The reaction was performed at room temperature for 10 min under stirring, and then the product was purified by HPLC to obtain the compound 11-10.

(3) Synthesis of dNTP-5-O—S—S—V$_3$-Dye
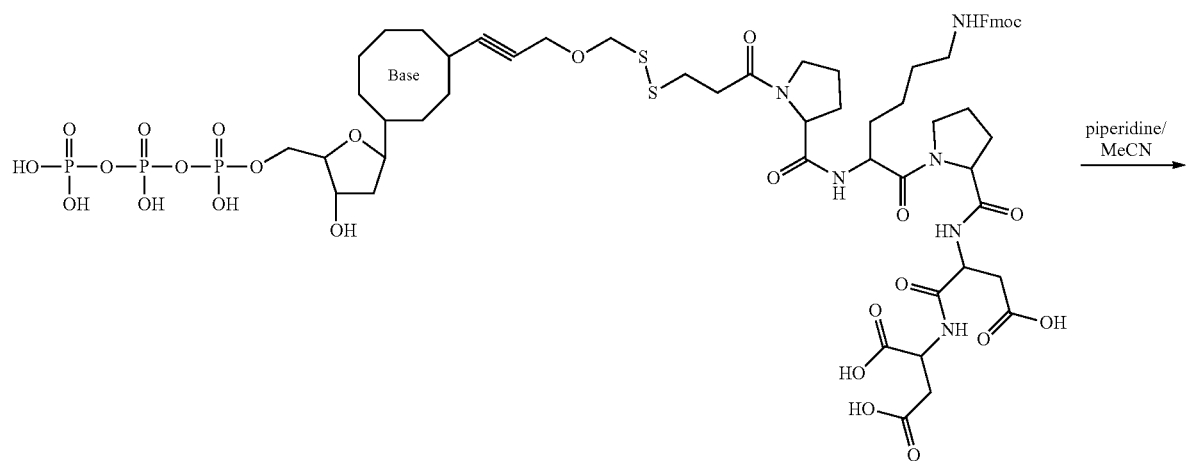
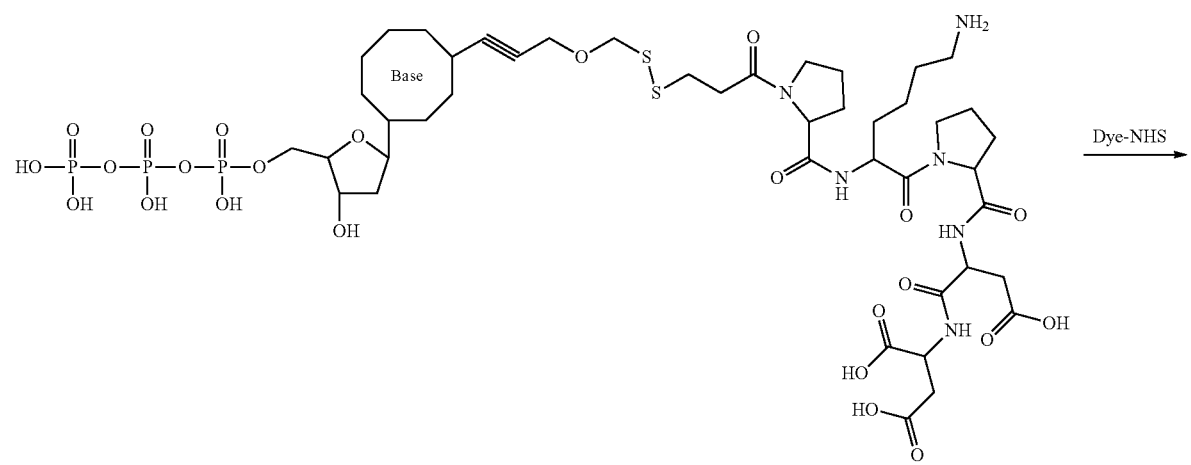
11-12
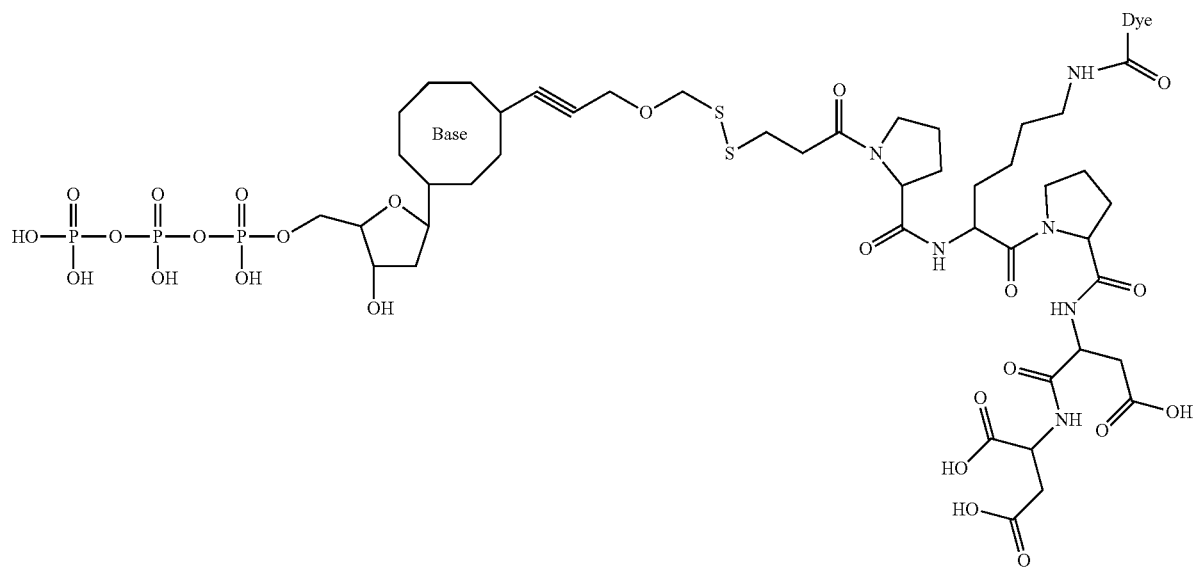
11-13

Compound 11-11: the HPLC component of the compound 11-10 and the HPLC component of the compound 11-7 were mixed and stirred at room temperature for 15 min, followed by concentration and HPLC purification (Buffer A: 0.1 M FLAB; Buffer B: acetonitrile), obtaining the compound 11-11.

Compound 11-12: the compound 11-11 (about 16 μmol) was treated with 2 mL of 20% piperidine/MeCN and 1 mL of 20% piperidine/MeCN for 15 minutes to remove the Fmoc protecting group. Then, the product was purified by HPLC (Buffer A: 0.1 M FLAB; Buffer B: acetonitrile) to obtain the HPLC component of the compound 11-12.

Compound 11-13: Dye-NHS (0.36 mL, 36 μmol, 0.1 M in anhydrous DMF) was added to a solution of the compound 11-12 (17.6 mL) in a mixture of water and DMF, and the reaction was monitored by HPLC. After the raw material was exhausted, the resulting product was purified by HPLC (Buffer A: 0.1 M TEAB; Buffer B: acetonitrile) to obtain the compound 11-13.

The following example relates to synthetic routes of nucleotide analogs that do not need to be capped during use, i.e., capless nucleotide analogs. Those skilled in the art are able to prepare the capless nucleotide analog according to the following illustrated synthesis processes, the specific reaction conditions described in above examples, and in combination with the general knowledge including such as test means. The term "capless" means that no capping step or no capping reagent is needed during use of the compound.

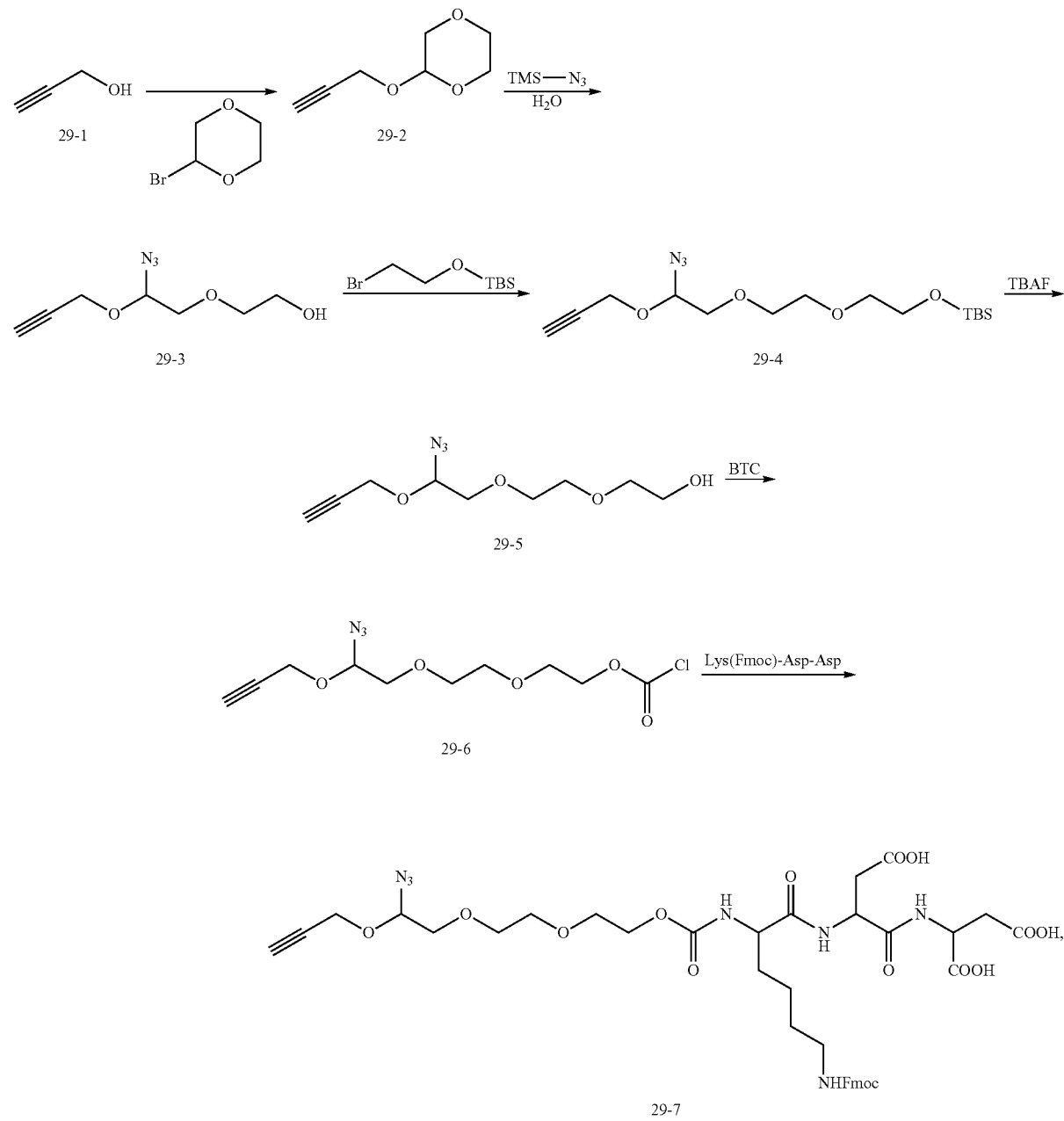

Scheme 1 wherein the compound of formula (29-7) may be further reacted with a base, a nucleic acid, a deoxynucleic acid or their respective derivatives to obtain the compound of formula (I), an example of which is as follows:
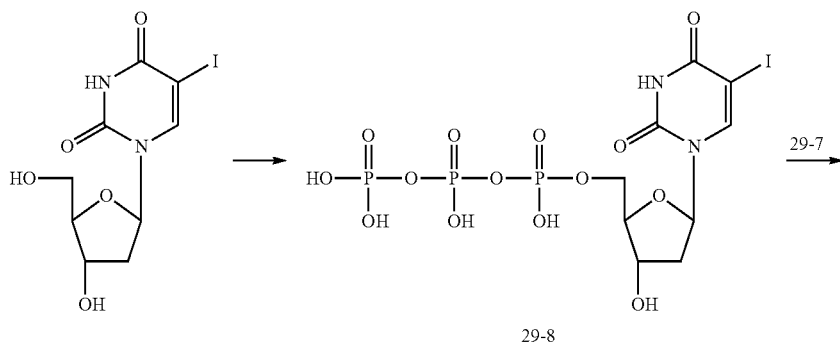
29-8
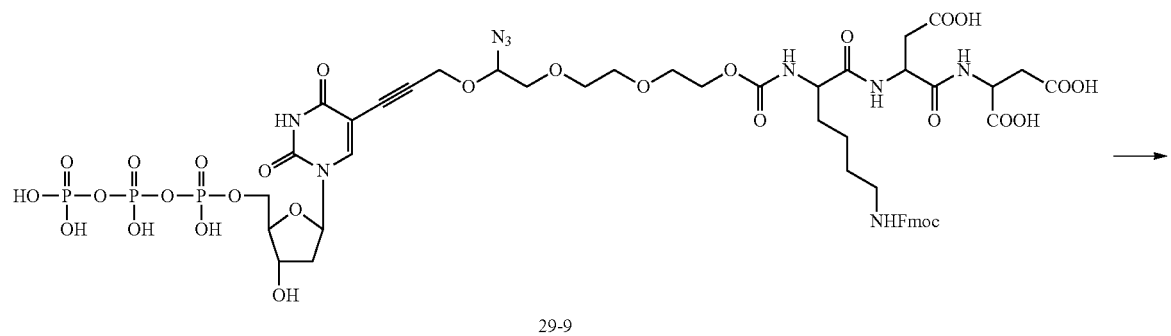
29-9
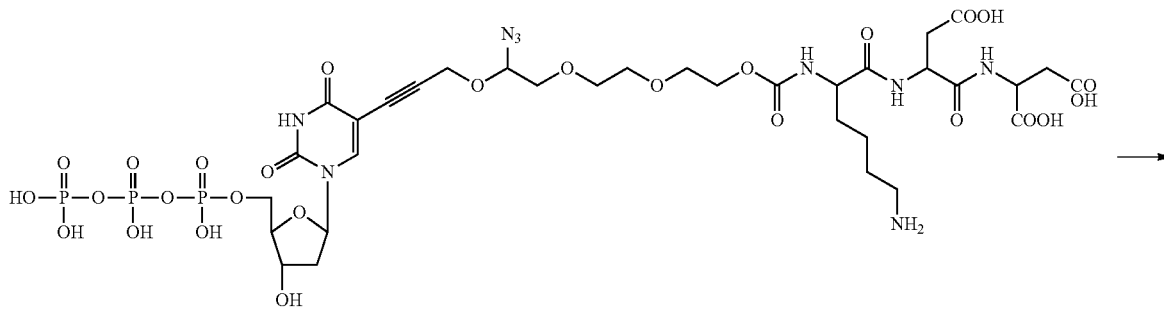
29-10
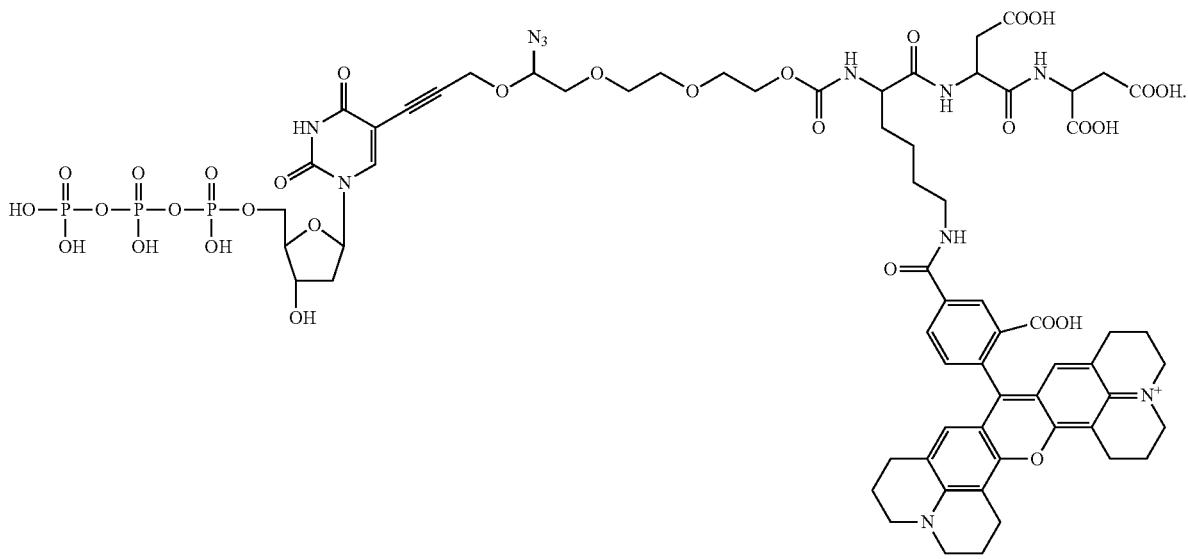
29-11

Scheme 2
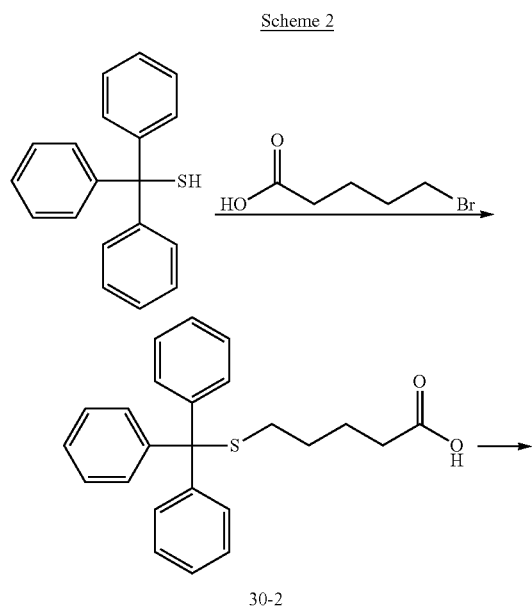
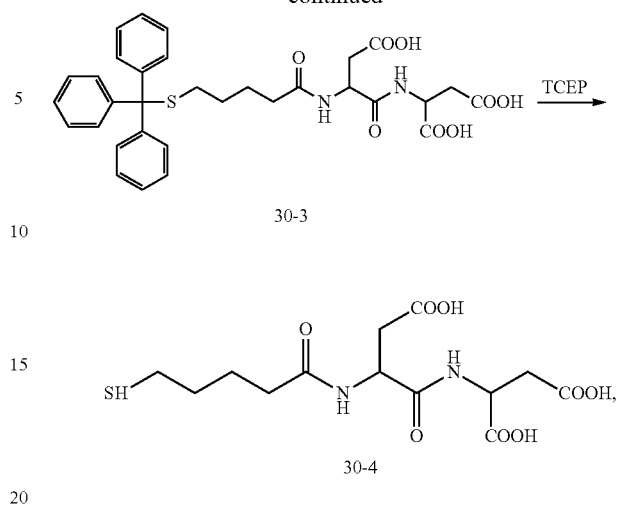
wherein the compound of formula (30-4) may be further reacted with a base, a nucleic acid, a deoxyribonucleic acid or their respective derivatives to obtain the compound of formula (I), an example of which is as follows:
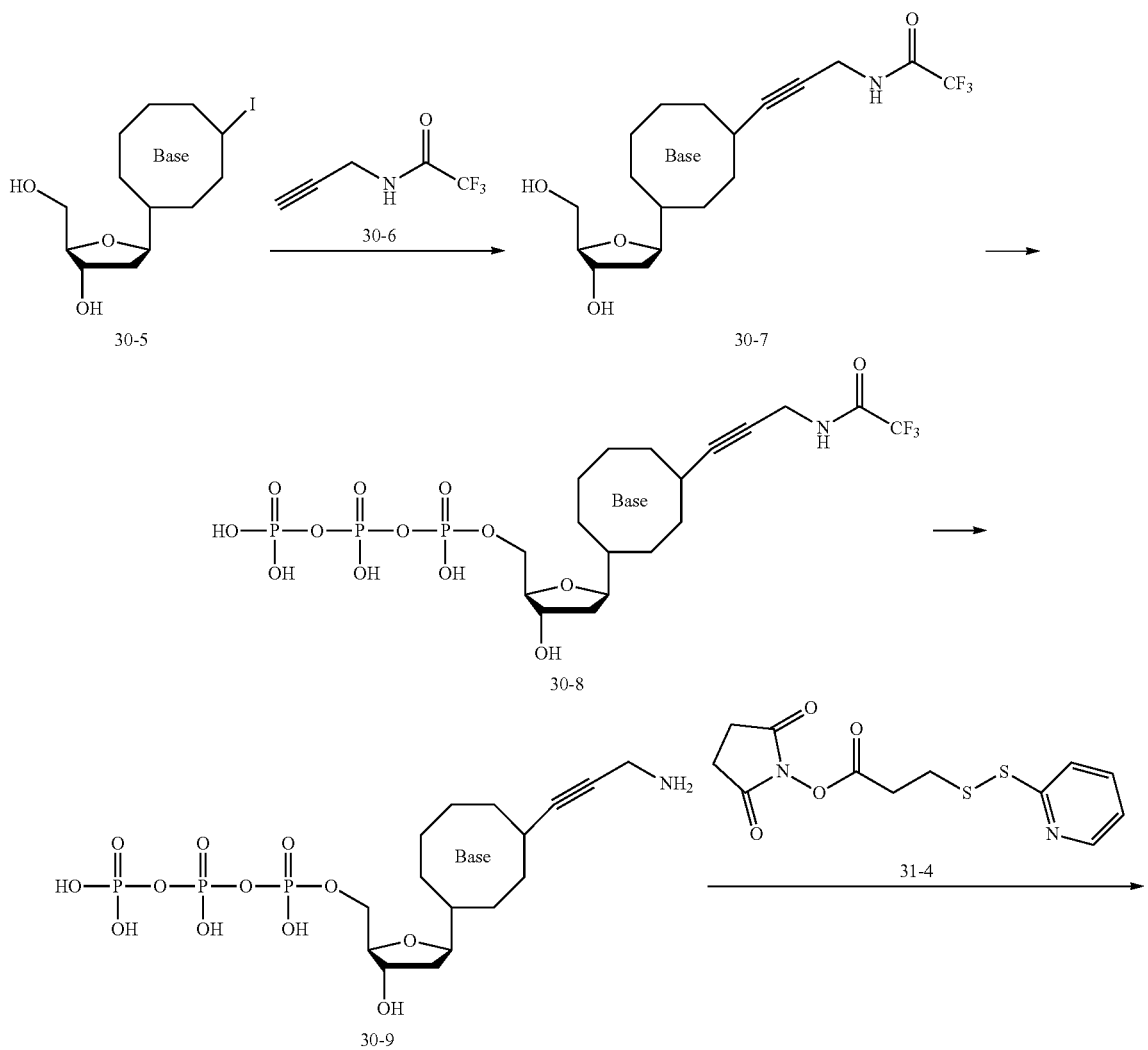

-continued
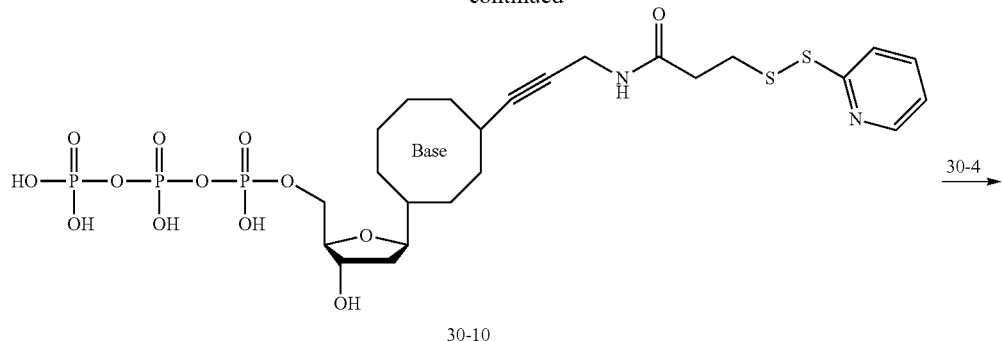
30-10
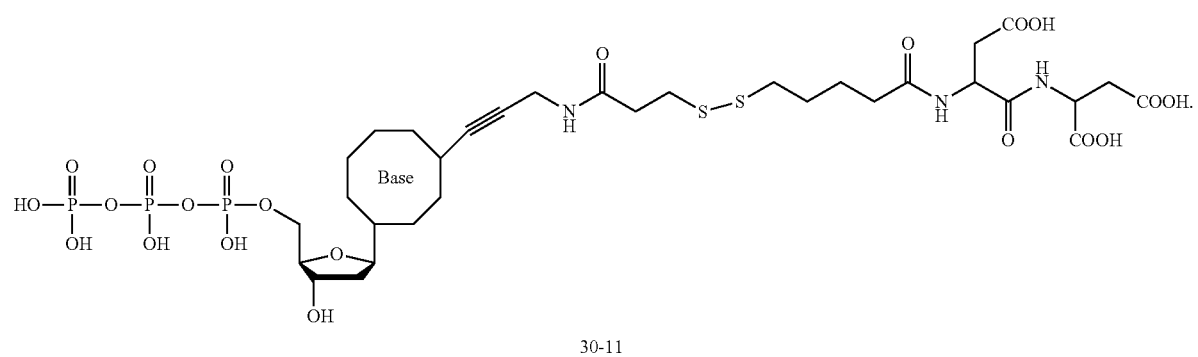
30-11
Scheme 3
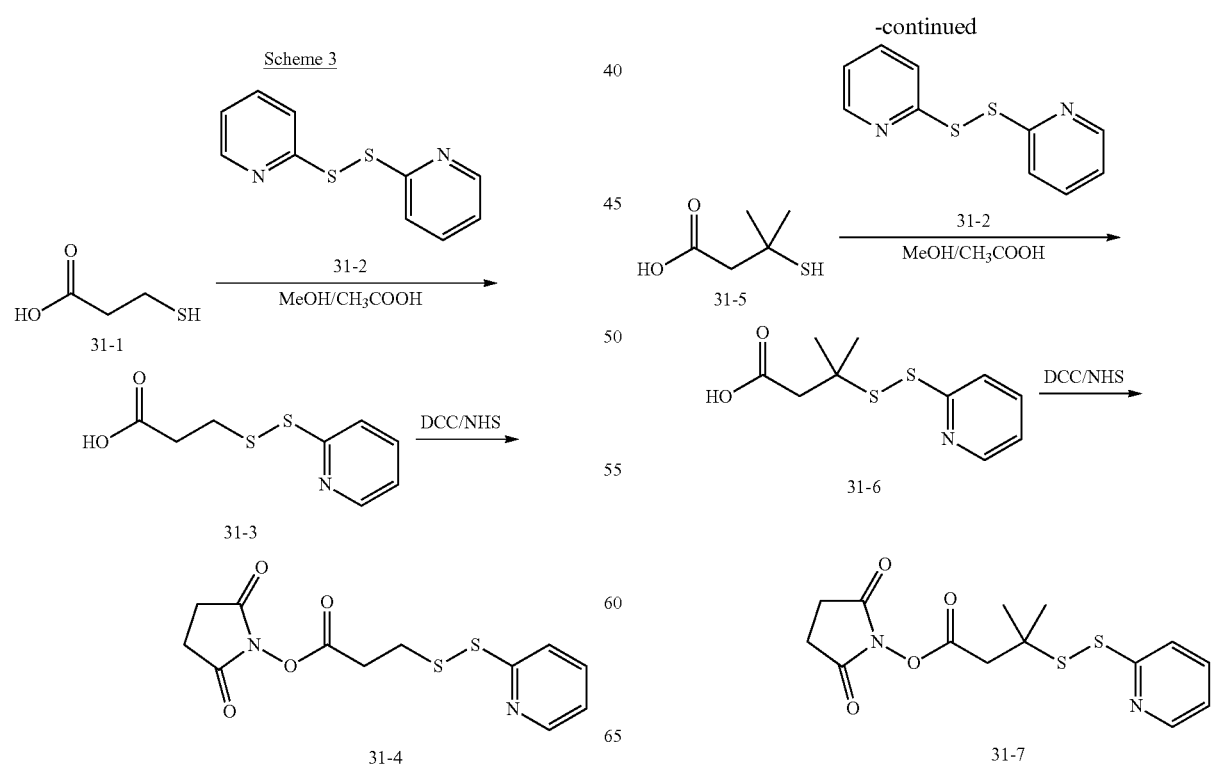

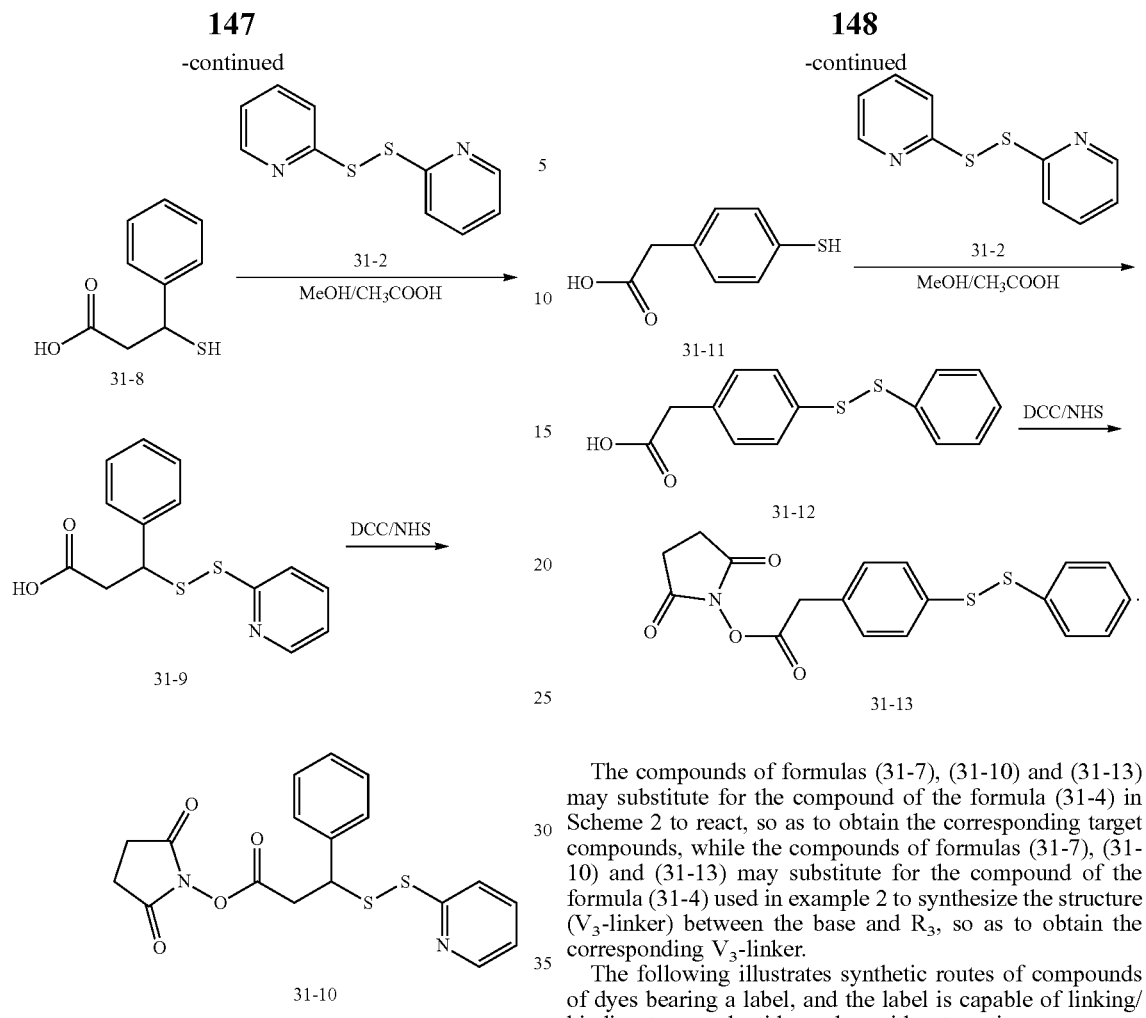

The compounds of formulas (31-7), (31-10) and (31-13) may substitute for the compound of the formula (31-4) in Scheme 2 to react, so as to obtain the corresponding target compounds, while the compounds of formulas (31-7), (31-10) and (31-13) may substitute for the compound of the formula (31-4) used in example 2 to synthesize the structure ($V_3$-linker) between the base and $R_3$, so as to obtain the corresponding $V_3$-linker.

The following illustrates synthetic routes of compounds of dyes bearing a label, and the label is capable of linking/binding to a nucleotide analog with a targeting group.

Scheme 1

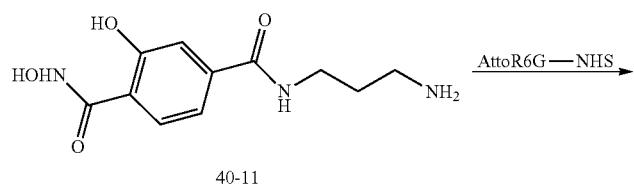

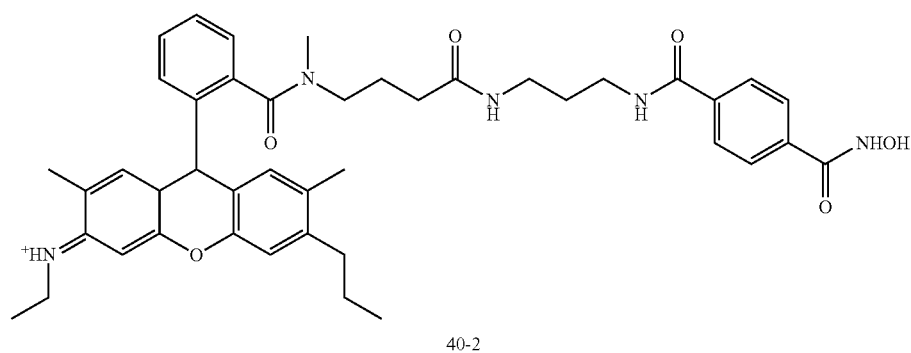

Scheme 2

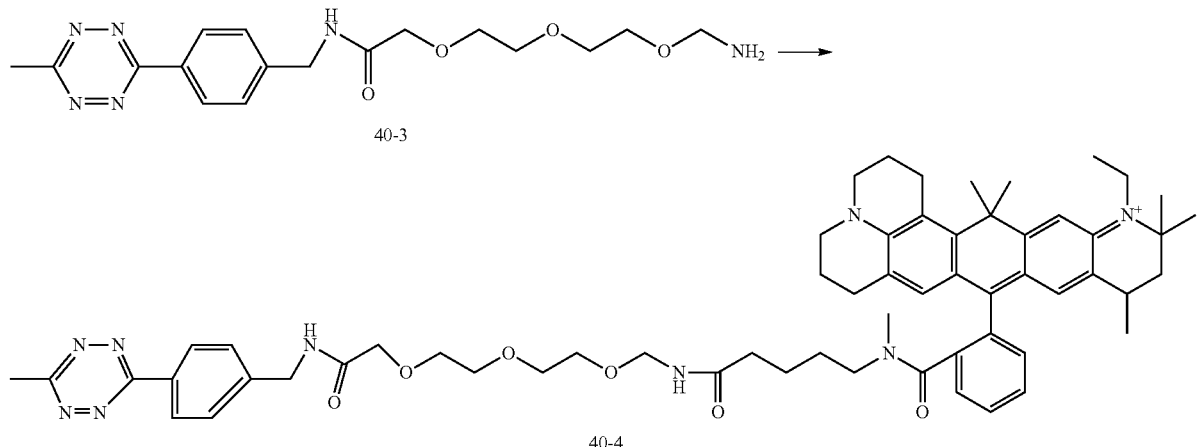

Application of Compounds

According to some embodiments of the present disclosure, there is provided a nucleic acid sequencing method, including: (a) placing a mixture of a first template-primer complex, one or more nucleotide analogs and a DNA polymerase under a condition suitable for base extension to enable the nucleotide analog to bind to the first nucleic acid template-primer complex, obtaining an extension product; in which the nucleotide analog is selected from the dNTP analog, the NTP analog, the dNTP analog mixture, and the NTP analog mixture as described hereinbefore. The method according to embodiments of the present disclosure can quickly and accurately determine the nucleic acid sequence of a sample. By using the compounds as described in any embodiments hereinbefore for the base extension, this method can realize the nucleic acid sequencing.

The first template-primer complex may be free in a liquid phase environment or may be fixed at a specific position. In some examples, the first nucleic acid template-primer complex is connected to a solid phase carrier. For example, the first template-primer complex is immobilized/fixed to a chip or a microsphere.

In some examples, the nucleic acid sequencing method further includes: (b) acting on a cleavable group or a cleavable bond of the extension product to obtain a second nucleic acid template-primer complex; and (c) replacing the first nucleic acid template-primer complex with the second nucleic acid template-primer complex, and performing operations (a) and (b) at least once; in other words, (c) is: repeating a cycle of reaction comprising (a) to (b) one or more times, wherein in each repetition of (a) the mixture further comprises the second template-primer complex produced in (b) of a previous cycle of reaction.

In some examples, the operation (a) further includes: detecting the extension product to obtain a signal corresponding to a nucleotide analog bound to the first nucleic acid template-primer complex.

In some examples, the nucleic acid sequencing method further includes: determining a nucleic acid sequence according to the signal.

In some examples, the nucleotide analog used includes a targeting group, and the operation (a) includes: adding a detectable compound to obtain the extension product, wherein the detectable compound bears a specific group, which is capable of specifically binding with the targeting group. In a specific example, the $R_3$ group of the nucleotide analog is the targeting group, such as a compound (31), and the operation (a) includes: binding the nucleotide analog to the first nucleic acid template-primer complex under the action of polymerase, and adding a fluorescent molecule labeled with dibenzocyclooctyne (DBCO) to enable the extension product (a template-primer complex bound with the nucleotide analog) to be labeled with the fluorescent molecule, thereby capable of generating a detectable signal.

In an example, a cleavage site of the operation (b) is at a position of the C group in any above nucleotide analogs. For example, with respect to the compound of formula (3) whose C group includes a disulfide bond, 3'-OH of the base of this compound is unexposed or difficult to bind to the nucleotide (virtual inhibition) due to the space folding of $L_2$-$R_5$ in solution or due to charges, while by breaking the disulfide bond, the 3'-OH of the base will be exposed to bind with the next nucleotide.

According to some embodiments, there is provided a primer extending method, including: placing a polymerase, a nucleic acid template-primer complex and one or more nucleotide analogs into a reactor to enable the nucleotide analog to bind to the nucleic acid template-primer complex, obtaining an extension product; wherein the nucleotide analog is selected from the compounds as described hereinbefore. The method according to embodiments of the present disclosure can accurately and quickly extend the primer.

According to some embodiments, there is provided a mixture, including: a template to be tested; a primer paired with at least a part of a strand of the template to be tested; a DNA polymerase; and the dNTP analog, the NTP analog, the dNTP analog mixture, or the NTP analog mixture as described hereinbefore. The said primer paired with at least a part of a strand of the template to be tested may be in a separated state from or a binding state with the template to be tested.

According to some embodiments, the template, the primer, the polymerase, and the dNTP analog, the NTP analog, the dNTP analog mixture, or the NIT analog mixture as described herein before are contained in a buffer.

In some examples, an application method of the nucleotide analog is as follows. The nucleotide analog contains an inhibitory group capable of virtually blocking the 3' end of the base and is fluorescently labeled, which is applicable to the second- or third-generation (single molecule) SB S. Fluorescent bases G and A bear ATTO647N, and fluorescent bases C and T bear Cy3B, the base G is combined with the base T, the base A is combined with the base C, and the two combinations are added separately.

In some examples, an application method of the nucleotide analog is as follows. The nucleotide analog contains an inhibitory group capable of virtually blocking the 3' end of the base and is fluorescently labeled, which is applicable to the second- or third-generation (single molecule) SBS. The base G does not bear a fluorescent dye, the base A bears ATTO647N, the base C bears Cy3B, and the base T bears both ATTO647N and Cy3B. The bases A, T, G and C are mixed and added together.

In some examples, an application method of the nucleotide analog is as follows. The nucleotide analog contains an inhibitory group capable of virtually blocking the 3' end of the base and is fluorescently labeled, which is applicable to the second- or third-generation (single molecule) SBS. The base G bears ATTO647N/Cy5, the base A bears Texred/ROX, the base T is linked to Alex Fluor 488, and the base C is linked to Cy3/ATTO532. The bases A, T, G and C are mixed and added together.

In some examples, an application method of the nucleotide analog is as follows. The nucleotide analog contains an inhibitory group capable of virtually blocking the 3' end of the base and is fluorescently labeled, which is applicable to the second- or third-generation (single molecule) SBS. The bases A, T, G and C are linked to biotin, ATTO647N is linked to streptomycin. The bases A, T, G and C are added separately, one base at a time, with each addition followed by the addition of ATTO647N-streptomycin.

In some examples, an application method of the nucleotide analog is as follows. The nucleotide analog contains an inhibitory group capable of virtually blocking the 3' end of the base, which is applicable to the second- or third-generation (single molecule) SBS. The base A bears azido, ROX is linked to dibenzocyclooctyne, the base T bears PBA, ATTO Rho6G is linked to SHA, the base G bears a TCO group, ATTO647N is linked to tetrazine, the base C is linked to biotinyl, and Alexa Flour 488 is linked to a streptomycin group. The bases A, T, G and C are mixed and added together. Next, the ROX-dibenzocyclooctyne, ATTO Rho6G-SHA, ATTO647N-tetrazine, and Alexa Flour488-streptomycin are added together. Using signals acquired from the targeted pairing between the azido and the dibenzocyclooctyne, the targeted pairing between PBA and SHA, the targeted pairing between the TCO group and tetrazine, and the targeted pairing between biotinyl and the streptomycin group, base recognition is achieved, so as to achieve sequencing.

In some examples, an application method of the nucleotide analog is as follows. The nucleotide analog contains an inhibitory group capable of virtually blocking the 3' end of the base, which is applicable to the second- or third-generation (single molecule) SBS. The bases G and A are linked to biotinyl, ATTO647N is linked to streptomycin, the bases C and T are linked to PBA, and ATTORho6G is linked to SHA. The base G is combined with the base T, the base A is combined with the base C, and the two combinations are added separately, following each addition of the base combinations, a mixture of ATTO647N-streptomycin and ATTO Rho6G-SHA is added. Using signals obtained from the targeted pairing between PBA and SHA and the targeted pairing between biotinyl and the streptomycin group, and due to two repetitions proceeded in each cycle, base recognition is achieved, so as to achieve sequencing. One cycle is defined to include once extension of the four kinds of bases.

Using the above examples, dNTP-5-O—S—S—$V_3$-Atto532 containing the $V_3$-linker is prepared, such as a specific compound of formula (11-13), in which the Dye is Atto532. In order to verify an extending ability of the base, the base extension reaction is performed in solution and detected using capillary electrophoresis (first generation sequencer, ABI3100).

Reaction process: hybridization of a primer with a template to be sequenced—addition of a reaction buffer, bases and an enzyme—extension reaction—termination of the reaction—addition of the product to 3100 for detection.

Figure 2:
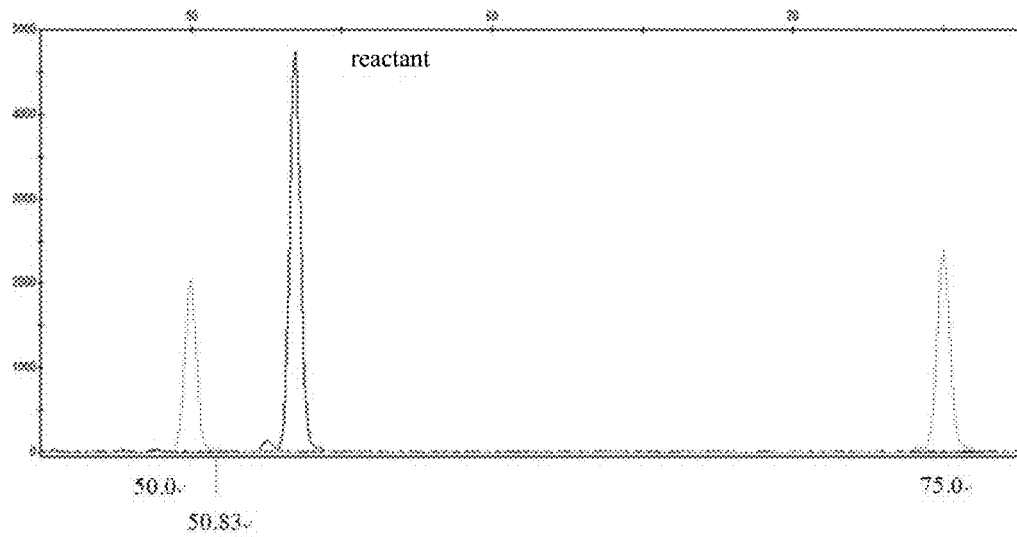
FIG. 2 is a graph showing a detection result of an extension product according to an embodiment of the present disclosure.
Figure 2:
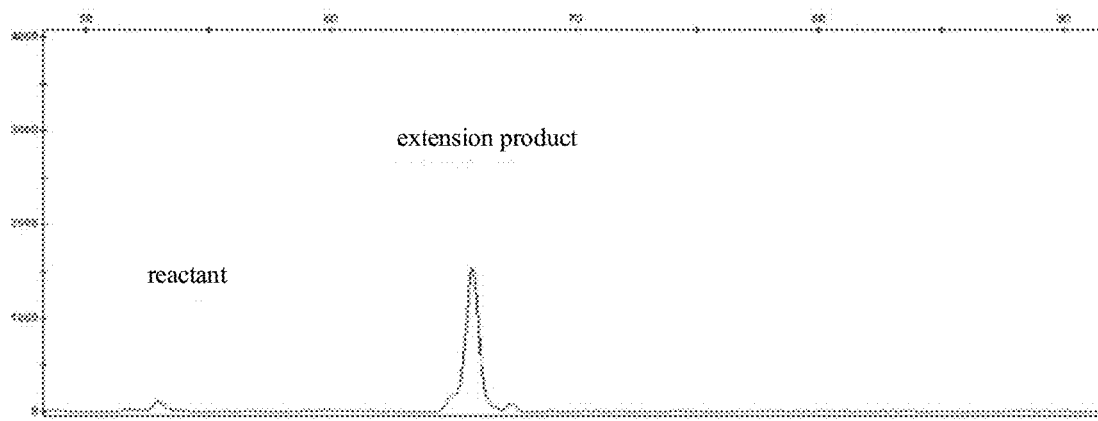

Depending on the nucleotide analog to be detected, a first base of the template for extension is a complementary base to the corresponding compound to be tested. The primer is labeled with fluorescence, and a reaction efficiency is quantificationally estimated by measuring the migration of the primer in capillary electrophoresis before and after the reaction and the intensity of the fluorescent signals. Reaction efficiency=peak area of a corresponding product/(peak area of residual reactants+peak area of the corresponding product). FIG. 2 shows the reaction results of the compound according to an embodiment. By calculation, the reaction efficiency under the solution verified reaction conditions is >90%.

Figure 3:
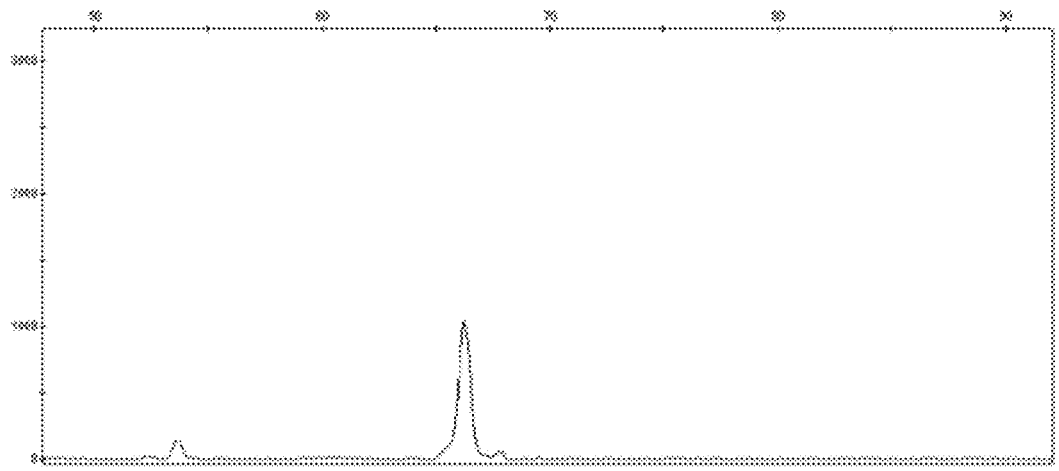
FIG. 3 is a graph showing a detection result of an extension product according to an embodiment of the present disclosure.

Further, in order to detect the performance of the nucleotide analog when the template is or contains a homopolymer, the first three bases in the template strand are made the same, and by adding the nucleotide analog to be tested to verify the condition of continuous addition and to determine the ability of the compound to block the next base from binding to the template strand. FIG. 3 illustrates the result of the blocking effect of the compound according to an embodiment of the present disclosure on the homopolymer, which shows that no extension of two or more bases in one reaction is found under the experimental conditions, indicating that the compound has a better inhibiting/terminating ability.

Figure 4:
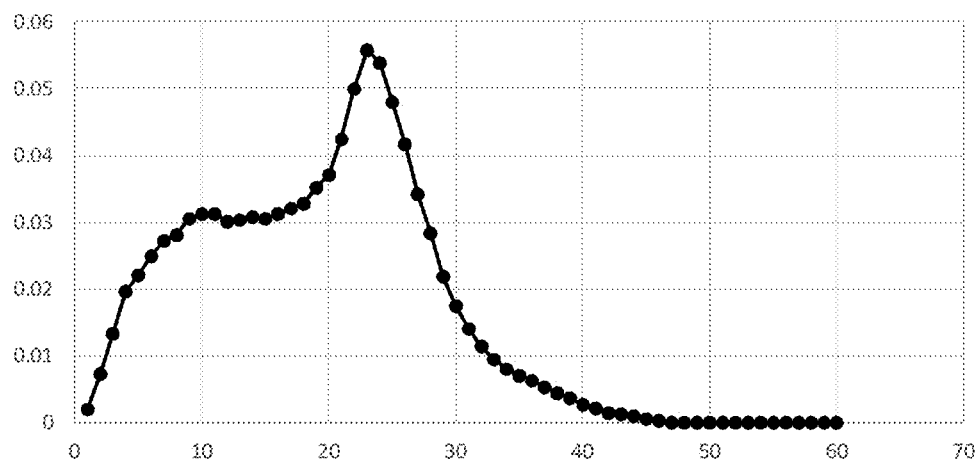
FIG. 4 is a graph showing read length distribution of reads obtained by applying a compound according to an embodiment of the present disclosure in sequencing.

In order to verify the performance of the nucleotide analog to be tested on a single-molecule platform, the inventors hybridize an artificially synthesized multi-target (a mixture of 20 kinds of template nucleic acids) to a sequencing chip for the performance evaluation. 60 cycles are performed, and each cycle includes four base extension reactions (repetitions) with the base adding order being C, T, A, G. Each repetition includes: base extension, photographing, cleavage of a side chain including a dye (acting on the cleavable group/bond), and cleaning. Through data processing (including image processing) and base recognition, the extension condition of an immobilized strand on the chip is calculated, and the reaction performance of the compound is determined. FIG. 4 shows the read length distribution of reads obtained by sequencing with the compound of the present disclosure. As can be seen, the compound of the present disclosure has the function of reversible termination, which can effectively prevent the binding of the next base in one reaction, but does not hinder the binding/extension of the next base in the next reaction, and thus can be used for the nucleic acid sequencing. It should be illustrated that the abscissa of FIGS. 2-3 refers to base size, and the ordinate refers to fluorescence intensity; and the abscissa of FIG. 4 is the read length, and the ordinate is proportion.

Using the above method, other compounds are tested by the inventor, including compounds of formulas (41), (42), (44)-(52) and (54)-(74), and results show that these compounds can be used for the sequencing individually. The reaction efficiencies of the compounds of formulas (41), (42), (44)-(52) and (54)-(74) are 94.5%, 96.2%, 100.4%, 96.4%, 83.5%, 13.8%, 16.8%, 68.9%, 76.2%, 64.0%, 80.6%, 94.1%, 88.9%, 80.8%, 40.6%, 92.1%, 86.1%, 93.2%, 94.6%, 87.8%, 95.7%, 50.2%, 103.2%, 91.5%, 58.6%, 107.3%, 90.5%, 97.1%, 98.4%, 98.4%, 86.0% and 93.0%, respectively.

Figure 5:
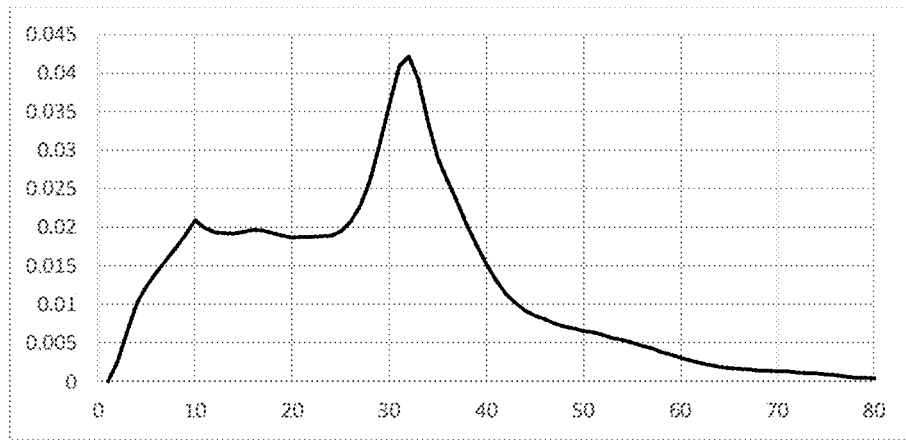
FIG. 5 is a graph showing read length distribution of reads obtained by applying two fluorescent-labeled nucleotide analogs according to an embodiment of the present disclosure in sequencing verification.

The inventors also performed sequencing verification using two fluorescently labeled bases. One cycle includes two repetitions/twice additions of nucleotide analogs mixture. The combination of the mixture and the detectable label includes a combination of A-Atto647N and T-AttoRho6 g and a combination of C-Atto532 and G-Atto647N. For example, with respect to the specific compound of formula (11-13), the base may be replaced with base A, T, C or G as needed, and sequencing is performed by hybridization with a synthesized multi-target (template) with a length of 33 nt. The AT mixture and the CG mixture are added in this order for 76 cycles, and after each cycle, pictures are taken with a 640 nm laser first, and then with a 532 nm laser. The original read length distribution obtained finally is shown in FIG. 5, indicating that a main peak of read lengths of reads obtained after 76 cycles is 32 bp.

Examples of the application of specific compounds to single- or multi-color sequencing are illustrated in the following, and the sequencing results are similar to that of the above examples (not shown).

Figure 6:
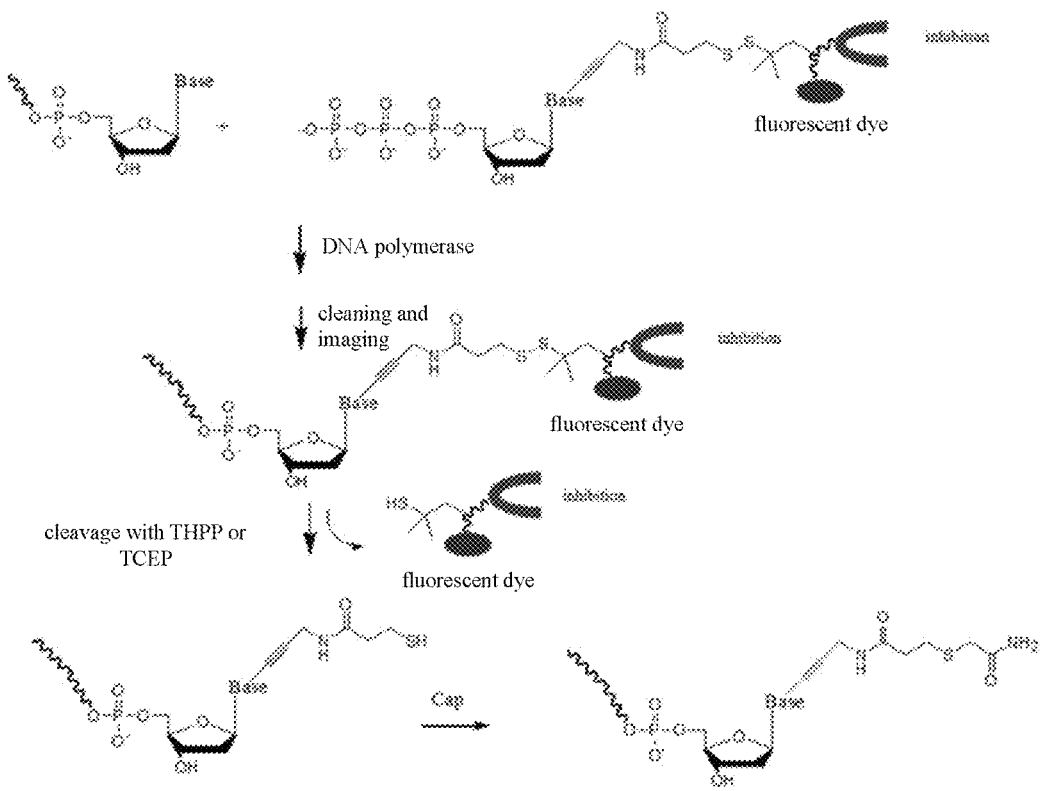
FIG. 6 is a flowchart of applying a nucleotide analog in base extension/sequencing according to an embodiment of the present disclosure, in which a capping step is included.

As shown in FIG. 6, a single-color sequencing method includes (a) the following elements: i) a set of nucleic acids (primer/probe); ii) a nucleotide polymerase; iii) a sample template strand which can hybridize with nucleic acids or nucleic acid analogs; iv) a set of labeled nucleotide analogs, each of which includes a base, a ribose or deoxyribose, a cleavable —S—S— bond, an inhibitory group which blocks the 3' end, and a detectable label linked to the base through the —S—S-linker, and a specific example of which may be such as the compound of formula (3), where the Base is a base A, a base T, a base G or a base C; and (b) the following specific steps: 1) fixing the template strand to be tested to a chip, adding the DNA polymerase, and then adding dNTPs-S—S-linker-Dye (A, T, G, C; the linker is not limited, which for example may be a $V_1$-linker, a $V_3$-linker, etc., and the same is true for the following cases), so that the dNTPs-SS-linker-Dye (A, T, G, C) are incorporated with the template strand; 2) washing away non-incorporated molecules, and detecting the incorporated fluorescent molecules; 3) adding TCEP or THPP to cleave the —S—S— bond, so as to remove the fluorescent group attached to the template strand and expose the 3'-OH to prepare for the next cycle/repetition of nucleotide incorporation; 4) adding a capping reagent to capture a thiol group on the template, and then washing away the excess capping reagent, followed by the next cycle/repetition of extension; then, repeating the steps 1) to 4) for 30 times, 100 times, or even 1000 times.

Figure 7:
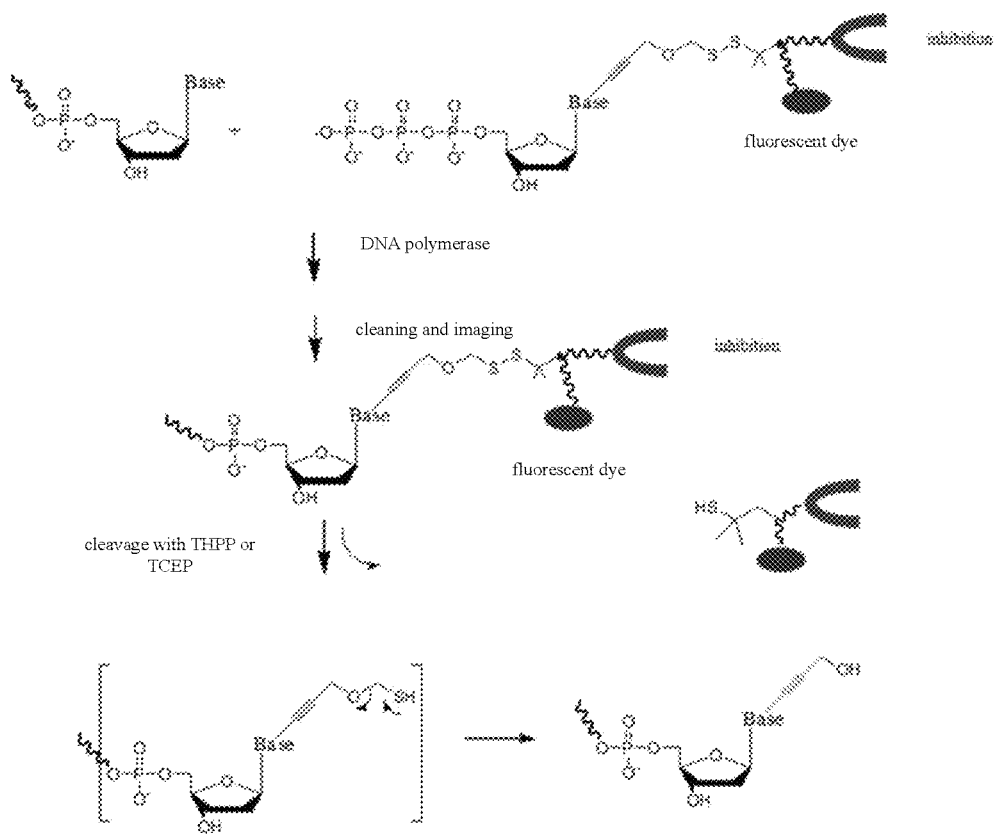
FIG. 7 is a flowchart of applying a nucleotide analog with a virtual blocking group in pairing according to an embodiment of the present disclosure, in which no capping step is needed.
Figure 8:
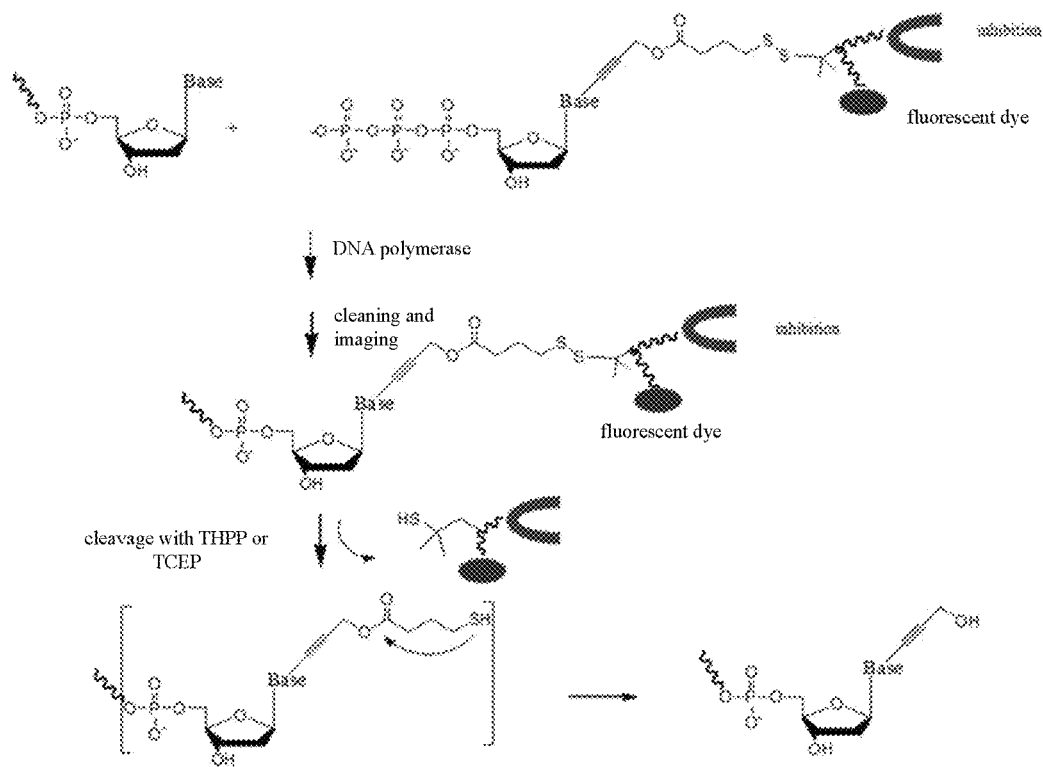
FIG. 8 is a flowchart of applying a nucleotide analog with a virtual blocking group in pairing according to an embodiment of the present disclosure, in which no capping step is needed.

As shown in FIG. 7 or FIG. 8, a single-color sequencing method includes (a) the following elements: i) a set of nucleic acids; ii) a nucleotide polymerase; iii) a template strand which can hybridize with nucleic acids or nucleic acid analogs; iv) a set of labeled nucleotide analogs, each of which includes a base, a ribose or deoxyribose, a cleavable —S—S— bond, an inhibitory group which blocks the 3' end, and a detectable label linked to the base through the —S—S— linker, and a specific example of which may be such as the compound of formula (11-13), where the Base is a base A, a base T, a base C or a base G.

The single-color sequencing method includes: (b) the following specific steps: 1) fixing the template strand to be tested to a chip, adding the DNA polymerase, and then adding dNTPs-S—S-linker-Dye (A, T, G, C), so that the dNTPs-SS-linker-Dye (A, T, G, C) are incorporated with the template strand; 2) washing away non-incorporated molecules, and detecting incorporated fluorescent molecules; 3) adding TCEP or THPP to cleave the —S—S— bond, so as to remove the fluorescent group attached to the template strand and expose the 3'-OH to prepare for the next cycle/repetition of extension; then, repeating the steps 1) to 3) for 30 times, 100 times, or even 1000 times.

Figure 9:
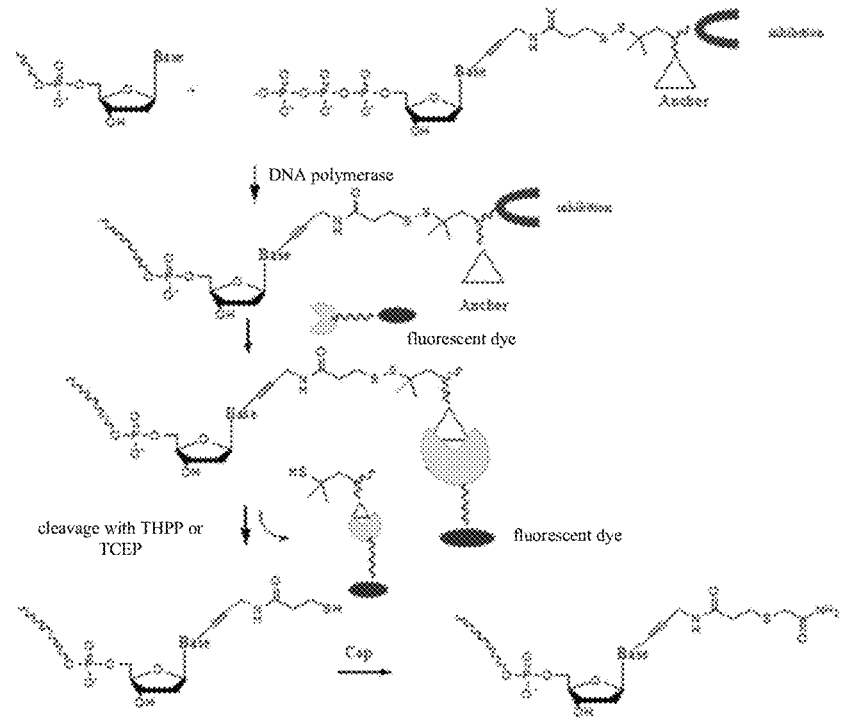
FIG. 9 is a flowchart of targeted pairing of a virtually blocked base according to an embodiment of the present disclosure.

As shown in FIG. 9, a single-color sequencing method includes (a) the following elements: i) a set of nucleic acids; ii) a nucleotide polymerase; iii) a sample template strand which can hybridize with nucleic acids or nucleic acid analogs; iv) a set of labeled nucleotide analogs, each of which includes a base, a ribose or deoxyribose, a cleavable —S—S— bond, an inhibitory group which blocks the 3' end, and a detectable label linked to the base through the —S—S-linker, and a specific example of which may be such as the compound of formula (19), which is expressed as dNTPs-S—S-linker-biotin hereinafter.

The single-color sequencing method includes: (b) the following specific steps: 1) adding the DNA polymerase to enable one of the four kinds of dNTPs-5-S—S-linker-biotin to be incorporated to an end of the template strand to be tested; 2) adding ATTO647N-labeled streptomycin, in which the ATTO647N will be labeled to the dNTPs-S—S-linker-biotin of the template strand to be tested due to the interaction between streptomycin and the biotin, followed by washing and photographing (this process is the same for different kinds of bases); 3) adding TCEP or THPP to cleave the —S—S— bond, so as to remove the fluorescent group attached to the template strand and expose the 3'-OH to prepare for the next cycle of extension; 4) adding a capping reagent to capture the thiol group on the template, and washing away the excess capping reagent, followed by the next cycle/repetition of extension; then, repeating the steps 1) to 4) for 30 times, 100 times, or even 1000 times. The capping reagent may be a compound or a composition containing at least one of I—O=NH and I—O—OH.

Figure 10:
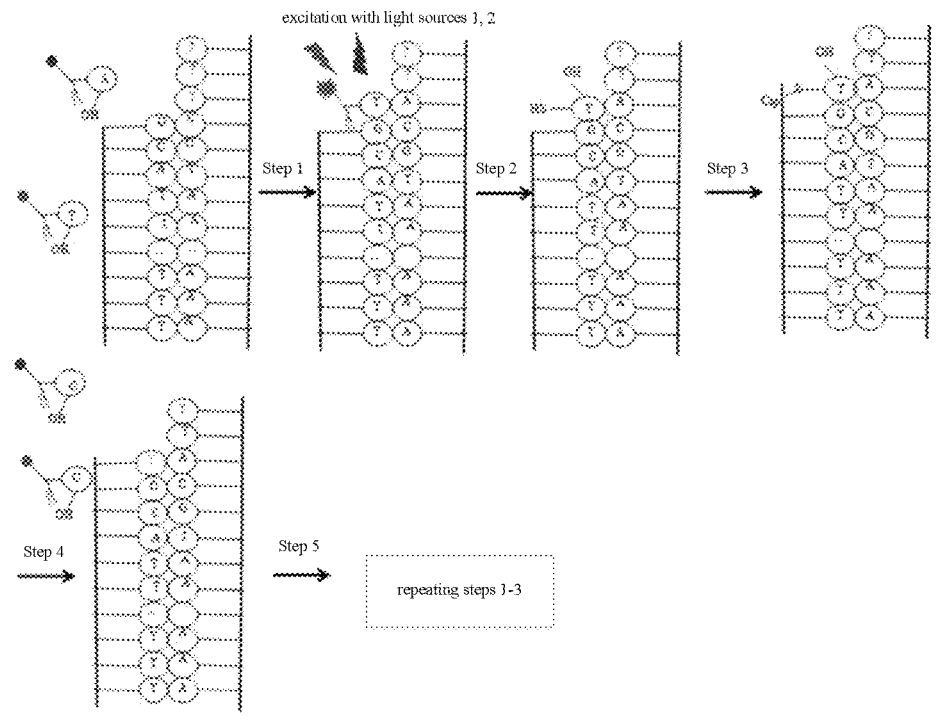
FIG. 10 is a flowchart of applying a double-color virtual blocked nucleotide analog in SBS sequencing according to an embodiment of the present disclosure.

As shown in FIG. 10, a double-color (two-color) sequencing method includes (a) the following elements: i) a set of nucleic acids; ii) a nucleotide polymerase; iii) a sample template strand which can hybridize with nucleic acids or nucleic acid analogs; iv) a set of labeled nucleotide analogs, each of which includes a base, a ribose or deoxyribose, a cleavable —S—S— bond, an inhibitory group which blocks the 3' end, and a detectable label linked to the base through the —S—S-linker, and a specific example of which may be such as the compound of formula (4), which is expressed as dNTP-5-S—S-linker-Dye hereinafter.

The double-color sequencing method includes the following specific steps: 1) adding the DNA polymerase, dATP-5-S—S-linker-Dye and dTTP-5-S—S-linker-Dye to enable one or both of the two kinds of dNTPs-5-S—S-linker-Dye to be incorporated to an end of the template strand to be tested, and then washing away the unincorporated nucleotide analogs, followed by 2) excitation with lasers 1, 2, and photographing; 3) adding TCEP or THPP to cleave the —S—S— bond, so as to remove the fluorescent group attached to the template strand and expose the 3'-OH to prepare for the next cycle/repetition of extension; 4) adding a capping reagent to cap the thiol group; 5) adding dGTP-5-S—S-linker-Dye, dCTP-5-S—S-linker-Dye and the DNA polymerase; 6) repeating the steps 2) to 4); then, repeating the above steps for 1 time, 10 times, 50 times, 100 times, or 1000 times.

Figure 11:
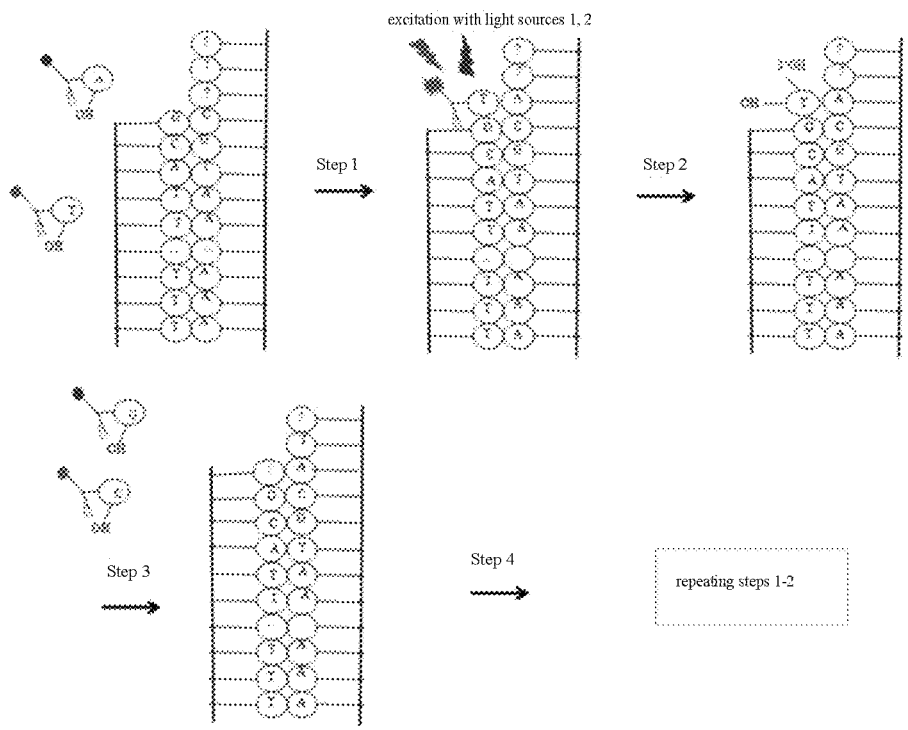
FIG. 11 is a flowchart of applying a double-color virtual blocked capless nucleotide analog in SBS sequencing according to an embodiment of the present disclosure.

As shown in FIG. 11, a double-color sequencing method includes (a) the following elements: i) a set of nucleic acids; ii) a nucleotide polymerase; iii) a sample template strand which can hybridize with nucleic acids or nucleic acid analogs; iv) a set of labeled nucleotide analogs, each of which includes a base, a ribose or deoxyribose, a cleavable —S—S— bond, an inhibitory group which blocks the 3' end, and a detectable label linked to the base through the —S—S— linker, and a specific example of which may be such as the compound of formula (7), which is expressed as dNTP-5-O—S—S-linker-Dye hereinafter.

The double-color sequencing method includes: (b) the following specific steps: 1) adding the DNA polymerase, dATP-5-O—S—S-linker-Dye and dTTP-5-O—S—S-linker-Dye to enable one or both of the two kinds of dNTPs-5-O—S—S— linker-Dye to be incorporated to an end of the template strand to be tested, and then washing away the unincorporated nucleotide analogs, followed by 2) excitation with lasers 1, 2, and photographing; 3) adding TCEP or THPP to cleave the —S—S— bond, so as to remove the fluorescent group attached to the template strand and expose the 3'-OH to prepare for the next cycle of extension; 4) adding dGTP-5-O—S—S-linker-Dye, dCTP-5-O—S—S-linker-Dye and the DNA polymerase, and repeating the steps 2) to 3); then, repeating the above steps for at least 1 time, 10 times, 50 times, 100 times, or 1000 times.

Figure 12:
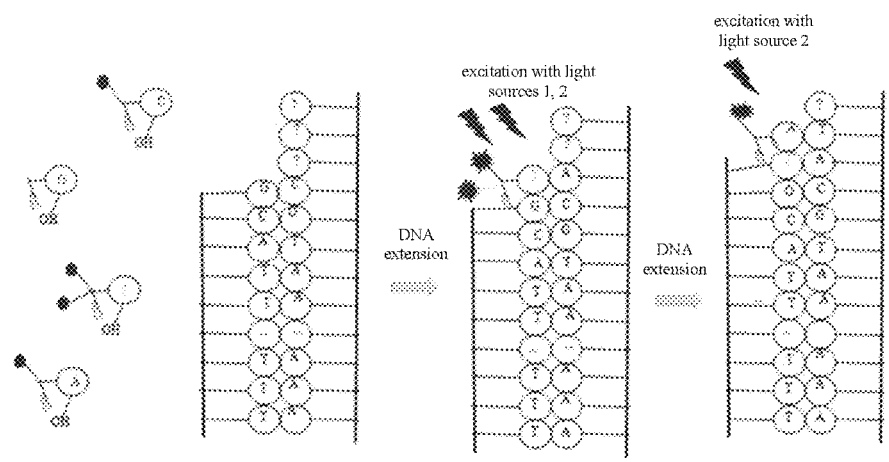
FIG. 12 is a flowchart of a double-color sequencing method according to an embodiment of the present disclosure.

A double-color sequencing (fluorescence resonance energy transfer, FRET) method is shown in FIG. 12, which uses a mixture of nucleotide analogs without a detectable label and nucleotide analogs with a detectable label for sequencing, and includes: (a) the following elements: i) a set of nucleic acids; ii) a nucleotide polymerase; iii) a sample template strand which can hybridize with nucleic acids or nucleic acid analogs; iv) a set of labeled nucleotide analogs, specific examples of which are such as the compounds of formulas (89), (90), (91) and (92), in which the compounds of formulas (89), (90) and (92) are expressed as dNTP-5-O—$N_3$—$V_{10}$-Dye hereinafter, and the compound of formula (91) without a detectable label is expressed as cold dGTP hereinafter.

The double-color sequencing method includes: (b) the following specific steps: 1) adding the DNA polymerase, dATP-5-O—$N_3$—$V_{10}$-Cy5, dTTP-5-O—$N_3$—$V_{10}$-Cy3b, cold dGTP, dTTP-5-O—$N_3$—$V_{10}$-Cy3b (Cy5) to enable at least one of the four kinds of nucleotide analogs to be incorporated to an end of the template strand to be tested, and then washing away the unincorporated nucleotide analogs, followed by 2) excitation with lasers 1, 2, and photographing; 3) adding TCEP or THPP to cleave the —O—C— bond adjacent to the azide, so as to remove the fluorescent group attached to the template strand and expose the 3'-OH to prepare for the next cycle of extension; 4) repeating the steps 1) to 3); and then repeating the above steps for at least 1 time, 10 times, 50 times, 100 times, or 1000 times.

Figure 13:
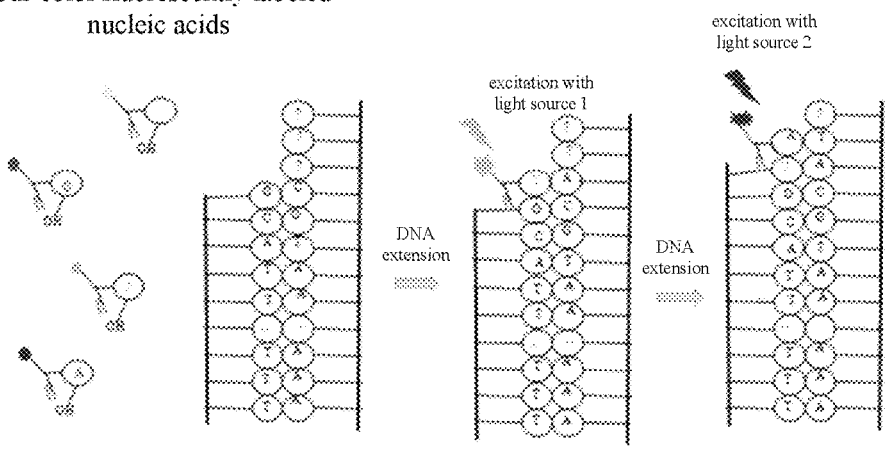
FIG. 13 is a flowchart of a four-color sequencing method according to an embodiment of the present disclosure.

As shown in FIG. 13, a four-color sequencing method includes (a) the following elements: i) a set of nucleic acids; ii) a nucleotide polymerase; iii) a sample template strand which can hybridize with nucleic acids or nucleic acid analogs; iv) a set of labeled nucleotide analogs, each of which includes a base, a ribose or deoxyribose, a cleavable —S—S— bond, an inhibitory group which blocks the 3' end, and a detectable label linked to the base through the —S—S-linker, a specific example of which may be the compound of formula (1), where the Base may be replaced with base A, T, C or G as needed, Dye may be replaced with Cy3b, Rox, Cy5 or Alexa488 as needed, and which may be expressed as dNTP-5-S—S-linker-Dye, where the linker may be the same or different for different nucleotide analogs.

The four-color sequencing method includes: (b) the following specific steps: 1) adding the DNA polymerase, dATP-5-S—S-linker-Cy3b, dTTP-5-S—S-linkerRox, dGTP-5-S—S-linker-Cy5 and dCTP-5-S—S-linker-Alexa488 to enable at least one of the four kinds of dNTPs-5-S—S-linker-Dye to be incorporated to an end of the template strand to be tested, and then washing away the unincorporated nucleotide analogs, followed by 2) photographing; 3) adding TCEP or THPP to cleave the —S—S— bond, so as to remove the fluorescent group attached to the template strand and expose the 3'-OH to prepare for the next cycle of extension; 3) adding a capping reagent to protect the thiol group to prepare for the next cycle of extension; 4) repeating the steps 1) to 3) for at least 1 time, 10 times, 50 times, 100 times, or 1000 times.

A four-color sequencing method includes (a) the following elements: i) a set of nucleic acids; ii) a nucleotide polymerase; iii) a sample template strand which can hybridize with nucleic acids or nucleic acid analogs; iv) a set of labeled nucleotide analogs, each of which includes a base, a ribose or deoxyribose, a cleavable bond/group, an inhibitory group which blocks the 3' end, and a detectable label linked to the base through a linker, a specific example of which may be the compound of formula (27), which may be expressed as dNTP-5-O—S—S-linker-targeting group, where the azido in this structure is the targeting group, which may be substituted by other targeting group as needed, and the base in this structure may be substituted by a corresponding base as needed.

The four-color sequencing method includes: (b) the following specific steps: 1) adding four kinds of dNTPs-5-O—S—S-linker-targeting group, at least one of which is incorporated to an end of the template strand to be tested, and then washing away the unincorporated nucleotide analogs; 2) adding a mixture of ROX-labeled dibenzocyclooctyne, ATTO Rho6G-labeled SHA, ATTO647N-labeled tetrazine and Alexa488-labeled streptomycin to make the mixture target to the nucleotide analogs with a targeted group on the template strand to be tested, washing away unincorporated nucleotide analogs with a targeted label, and photographing; 3) adding TCEP or THPP to cleave the —S—S— bond, so as to remove the fluorescent group of the nucleotide analogs incorporated to the template strand and expose the 3'-OH to prepare for the next cycle of extension; 4) repeating the steps 1) to 3) for at least 1 time, 10 times, 50 times, 100 times, or 1000 times.

Reference throughout this specification to "an embodiment", "one embodiment", "another embodiment", "some embodiments", "an example", "a specific example", "another example", or "some examples", means that a particular feature, structure, material, or characteristic described in connection with the embodiment or example is included in at least one embodiment or example of the present disclosure. Thus, the appearances of the phrases such as "in an embodiment", "in one embodiment", "in another embodiment", "in some embodiments", "in an example", "in a specific example", "in another example", or "in some examples", in various places throughout this specification are not necessarily referring to the same embodiment or example of the present disclosure. Furthermore, the particular features, structures, materials, or characteristics may be combined in any suitable manner in one or more embodiments or examples. In addition, in the absence of contradiction, those skilled in the art can combine the different embodiments or examples described in this specification, or combine the features of different embodiments or examples.

Although embodiments of the present disclosure have been shown and described above, it would be appreciated by those skilled in the art that the above embodiments are illustrative, cannot be construed to limit the present disclosure, and changes, alternatives, modifications and variants can be made in the embodiments within the scope of the present disclosure.

What is claimed is:

1. A nucleotide or nucleoside analog compound, having a structural formula (I):

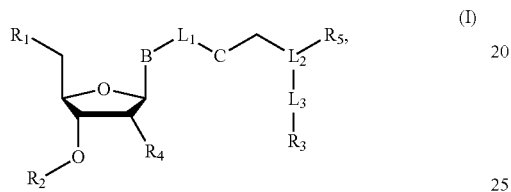

wherein $L_1$ is a covalent bond, $L_2$ comprises at least one member selected from:

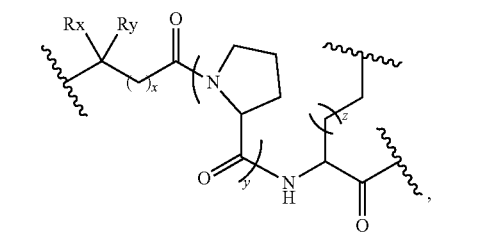

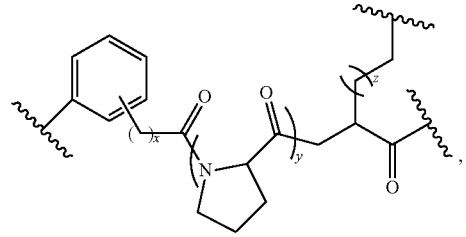

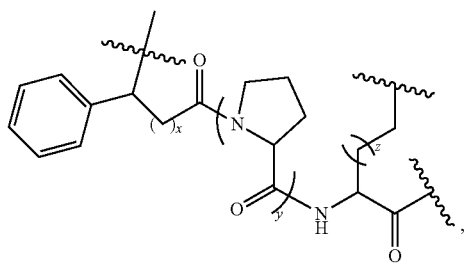

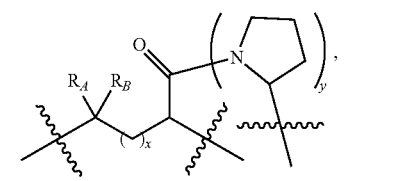

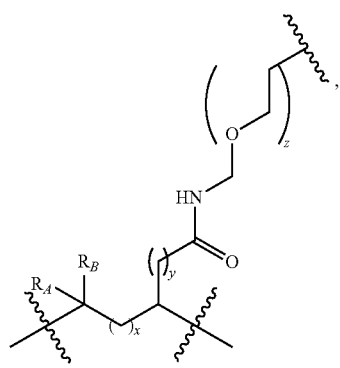

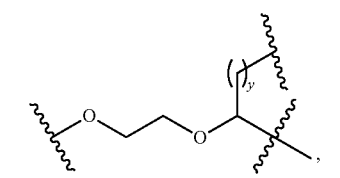

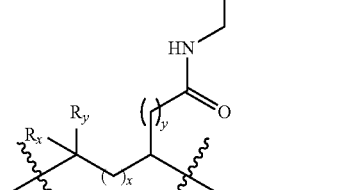

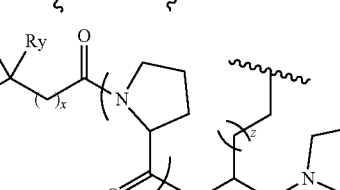

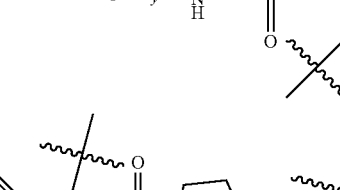

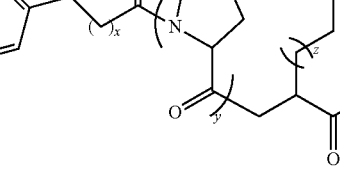

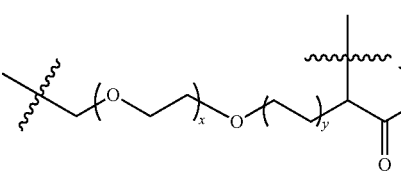

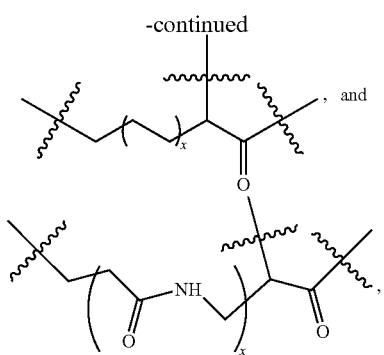, and

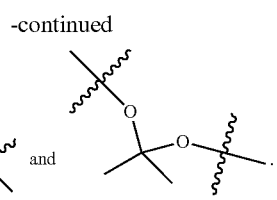 and 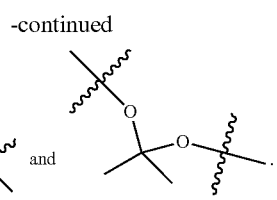.

wherein $R_x$, $R_y$, $R_A$, and $R_B$ are each independently H, $C_{1-6}$ alkyl chain, $C_{3-10}$ cycloalkyl, or $C_{5-10}$ aryl, and x, y, and z are each independently an integer of 0 to 6;

$L_3$ is a covalent bond or a covalently linked group;

B is a base or a base derivative;

$R_1$ is —OH, a phosphate group or a nucleotide;

$R_2$ is H or a cleavable group;

$R_3$ is a detectable group or a targeting group;

$R_5$ is an inhibitory group;

$R_4$ is H or —$OR_6$, wherein $R_6$ is H or a cleavable group; and

C comprises a trivalent radical having a structural formula (II) or a quadrivalent radical having a structural formula (III):

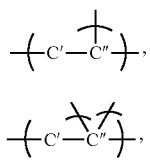 (II)

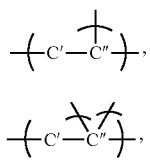 (III)

wherein C' is a bivalent radical comprising a disulfide bond and a carbon-oxygen bond, a disulfide bond, or a carbon-oxygen bond; and C" is an optionally substituted branched alkyl or an optionally substituted aryl;

wherein B is selected from the group consisting of a purine, a pyrimidine, and analogs thereof; and wherein L1 is covalently bonded to a non-nitrogen or non-oxygen position of B.

2. The compound as claimed in claim 1, wherein $R_2$ comprises at least one group selected from

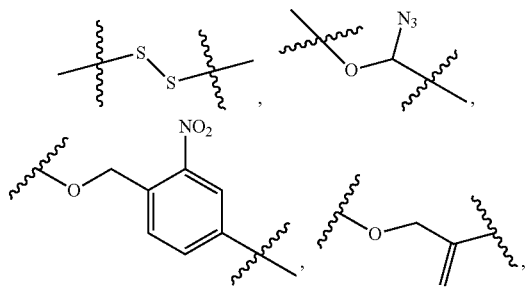

3. The compound as claimed in claim 1, wherein when C' comprises a carbon-oxygen bond but no disulfide bond, C" comprises an azido or a nitroso.

4. The compound as claimed in claim 1, wherein C' further comprises at least one selected from the group consisting of: an optionally substituted ethynyl, an optionally substituted amido alkyl, and an optionally substituted straight or branched alkyl.

5. The compound as claimed in claim 1, wherein C" further comprises at least one selected from the group consisting of: an optionally substituted amido alkyl, and an optionally substituted straight or branched alkyl.

6. The compound as claimed in claim 1, wherein $L_2$ is selected from the group consisting of:

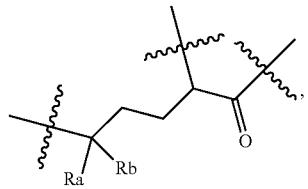

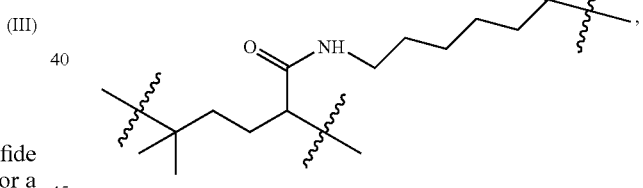

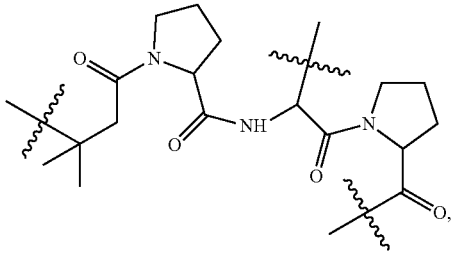

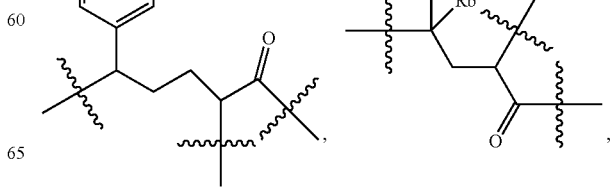

-continued

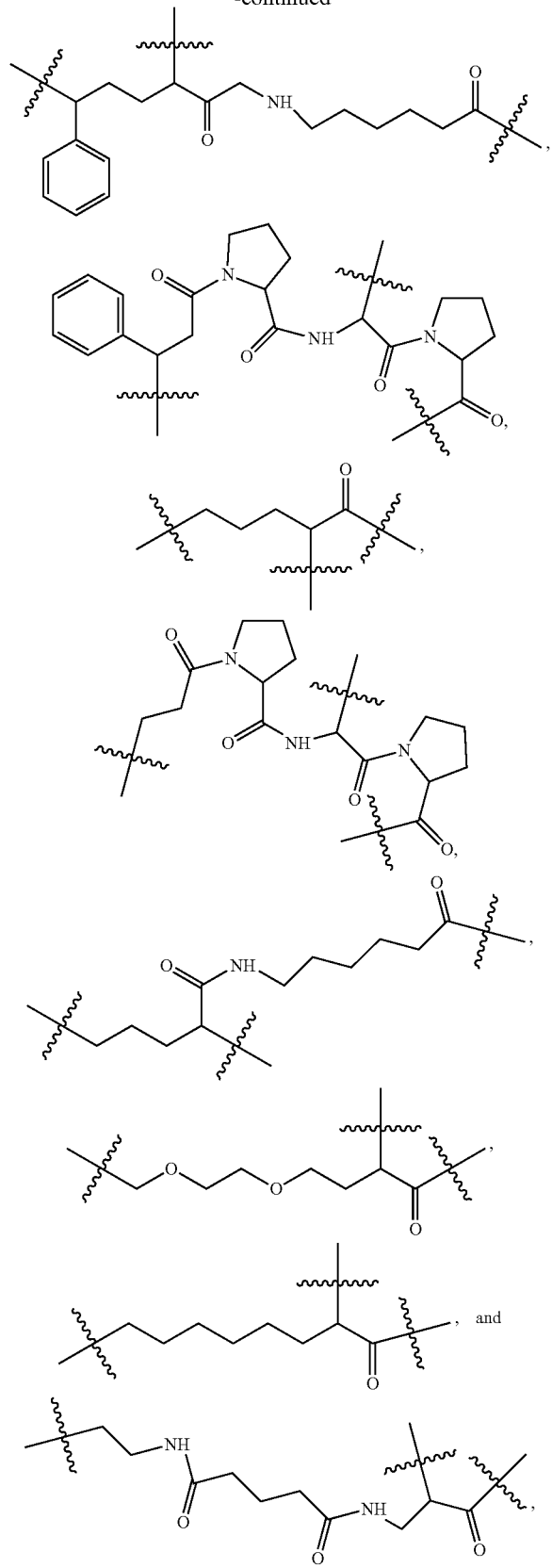

wherein Ra and Rb are each independently H, substituted or unsubstituted alkyl, substituted or unsubstituted heteroalkylene, substituted or unsubstituted cycloalkyl, substituted or unsubstituted isocycloalkyl, or substituted or unsubstituted aryl, at least one of Ra and Rb is not H.

7. The compound as claimed in claim 1, wherein $L_3$ is selected from the group consisting of a covalent bond, an optionally substituted $C_{1-8}$ alkyl, an optionally substituted $C_{1-8}$ alkylene, an optionally substituted $C_{2-8}$ heteroalkylene, an optionally substituted $C_{3-8}$ cycloalkylene, an optionally substituted $C_{3-8}$ isocycloalkylene, and an optionally substituted $C_{6-8}$ aryl alkenyl.

8. The compound as claimed in claim 7, wherein $L_3$ is $L_3^A$-$L_3^B$-$L_3^C$-$L_3^D$-$L_3^E$,
wherein $L_3^A$, $L_3^B$, $L_3^C$, $L_3^D$ and $L_3^F$ are each independently selected from the group consisting of a covalent bond, substituted or unsubstituted alkylene, substituted or unsubstituted heteroalkylene, substituted or unsubstituted cycloalkylene, substituted or unsubstituted isocycloalkylene, substituted or unsubstituted aryl alkenyl,
at least one of $L_3^A$, $L_3^B$, $L_3^C$, $L_3^D$ and $L_3^E$ is not the covalent bond.

9. The compound as claimed in claim 8, wherein $L_3^A$, $L_3^B$, $L_3^C$, $L_3^D$ and $L_3^E$ are each independently selected from the group consisting of a covalent bond, $C_{2-6}$ alkylene, heteroalkylene with 2 to 6 skeleton atoms, $C_{3-6}$ cycloalkylalkenyl, heterocycloalkylalkenyl with 2 to 6 skeleton atoms, and $C_{6-10}$ aryl alkenyl, wherein the $C_{2-6}$ alkylene, heteroalkylene with 2 to 6 skeleton atoms, $C_{3-6}$ cycloalkylene, heterocycloalkylene with 2 to 6 skeleton atoms, and $C_{6-10}$ aryl alkenyl are each independently unsubstituted or substituted with 1 to 5 $C_{1-6}$ alkyl, halogen, nitro, or $C_{1-6}$ haloalkyl.

10. The compound as claimed in claim 7, wherein $L_3$ is selected from the group consisting of:

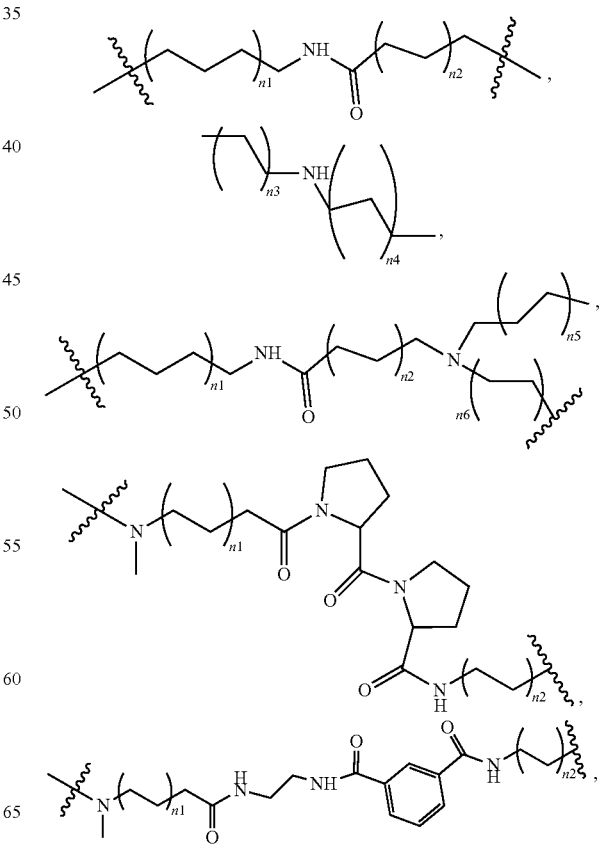

-continued

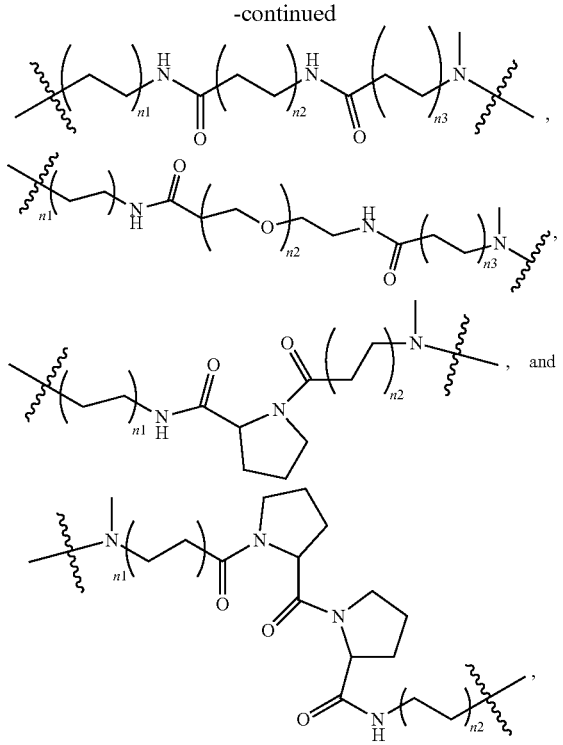

wherein n1, n2, n3, n4, n5, and n6 are each independently an integer of 0 to 7.

11. The compound as claimed in claim 1, wherein $R_5$ has a following structure:

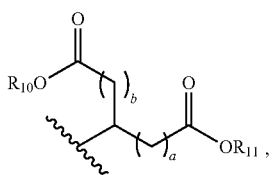

wherein $R_{10}$ and $R_{11}$ are each independently H or $C_{1-6}$ alkyl, and a and b are each independently an integer of 0 to 5.

12. A method for sequencing a nucleic acid, comprising:
(a) placing a mixture of a first template-primer complex, one or more nucleotide analogs as claimed in claim 1, and a DNA polymerase under a condition suitable for base extension to enable the nucleotide analog to bind to the first template-primer complex and thereby obtain an extension product.

13. The method as claimed in claim 12, further comprising:
(b) acting on the cleavable group of the extension product to obtain a second template-primer complex;
(c) repeating a cycle of reaction comprising (a) to (b) one or more times, wherein in each repetition of (a) the mixture further comprises the second template-primer complex produced in (b) of a previous cycle of reaction.

14. The compound as claimed in claim 1, wherein B is

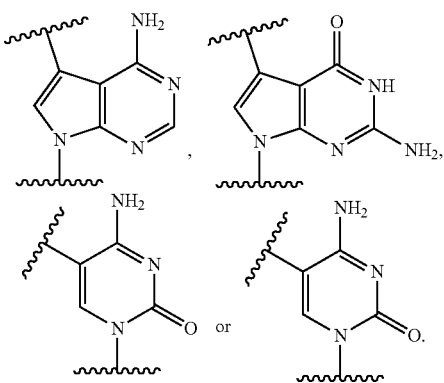

15. The compound as claimed in claim 1, wherein $R_3$ is at least one selected from the group consisting of a dye, a reactive group of click chemistry, azido and biotinyl.

16. The compound as claimed in claim 1, wherein $R_5$ comprises at least one charged group, and the charged group comprises —COOH, —$PO_4$, —$SO_4$, —$SO_3$, and —$SO_2$.

* * * * *